(12) United States Patent
Yen et al.

(10) Patent No.: US 10,622,566 B2
(45) Date of Patent: *Apr. 14, 2020

(54) POLYHETEROAROMATIC COMPOUND AND ORGANIC ELECTROLUMINESCENCE DEVICE USING THE SAME

(71) Applicants: Feng-Wen Yen, Taipei (TW); Li-Chieh Chuang, Hsinchu (TW)

(72) Inventors: Feng-Wen Yen, Taipei (TW); Li-Chieh Chuang, Hsinchu (TW)

( * ) Notice: Subject to any disclaimer, the term of this patent is extended or adjusted under 35 U.S.C. 154(b) by 277 days.

This patent is subject to a terminal disclaimer.

(21) Appl. No.: 15/790,038

(22) Filed: Oct. 22, 2017

(65) Prior Publication Data

US 2019/0123284 A1 Apr. 25, 2019

(51) Int. Cl.
| | |
|---|---|
| *H01L 51/00* | (2006.01) |
| *C09K 11/06* | (2006.01) |
| *C07D 495/22* | (2006.01) |
| *C07D 491/20* | (2006.01) |
| *C07D 491/22* | (2006.01) |
| *C07F 7/08* | (2006.01) |
| *C07D 517/20* | (2006.01) |
| *C07D 517/22* | (2006.01) |
| *C07D 495/20* | (2006.01) |
| *H01L 51/50* | (2006.01) |
| *C09K 11/02* | (2006.01) |

(52) U.S. Cl.
CPC ........ *H01L 51/0071* (2013.01); *C07D 491/20* (2013.01); *C07D 491/22* (2013.01); *C07D 495/20* (2013.01); *C07D 495/22* (2013.01); *C07D 517/20* (2013.01); *C07D 517/22* (2013.01); *C07F 7/0816* (2013.01); *C09K 11/025* (2013.01); *C09K 11/06* (2013.01); *H01L 51/0067* (2013.01); *H01L 51/0068* (2013.01); *H01L 51/0069* (2013.01); *H01L 51/0072* (2013.01); *H01L 51/0073* (2013.01); *H01L 51/0074* (2013.01); *C09K 2211/1018* (2013.01); *H01L 51/001* (2013.01); *H01L 51/006* (2013.01); *H01L 51/0052* (2013.01); *H01L 51/0056* (2013.01); *H01L 51/0085* (2013.01); *H01L 51/0094* (2013.01); *H01L 51/5012* (2013.01); *H01L 51/5072* (2013.01)

(58) Field of Classification Search
CPC .. C07D 491/20; C07D 491/22; C07D 495/20; C07D 495/22; C07D 517/20; C07D 517/22; C07F 7/0816; C09K 11/025; C09K 11/06; C09K 2211/1018; H01L 51/001; H01L 51/0073; H01L 51/0074; H01L 51/0085; H01L 51/0094; H01L 51/5012; H01L 51/5072; H01L 51/0052; H01L 51/0056; H01L 51/006; H01L 51/0067; H01L 51/0068; H01L 51/0069; H01L 51/0071; H01L 51/0072
See application file for complete search history.

(56) References Cited

U.S. PATENT DOCUMENTS

| | | | |
|---|---|---|---|
| 8,062,769 B2 | 11/2011 | Kai et al. | |
| 8,632,893 B2 | 1/2014 | Lin et al. | |
| 8,993,130 B2 | 3/2015 | Yen et al. | |
| 9,190,619 B2 | 11/2015 | Yen et al. | |
| 10,249,828 B2* | 4/2019 | Stoessel | C09K 11/06 |
| 2013/0240796 A1 | 9/2013 | Parham et al. | |
| 2014/0138669 A1* | 5/2014 | Nakagawa | H05B 33/14 257/40 |
| 2016/0093823 A1* | 3/2016 | Seo | H01L 51/5016 257/40 |

FOREIGN PATENT DOCUMENTS

KR 10-2011-0110508 A 10/2011

* cited by examiner

*Primary Examiner* — Dawn L Garrett

(57) ABSTRACT

The present invention discloses a novel polyheteroaromatic compound derived from 7',7'-dimethyl-5',7'-dihydrospiro[cyclopenta[1,2-b:5,4-b'-dithiophene-4,13'-indeno[1,2-b] acridine] core structures. The polyheteroaromatic compound can be used as organic electroluminescence materials for use in an organic electroluminescence device and electronic equipment.

13 Claims, 1 Drawing Sheet

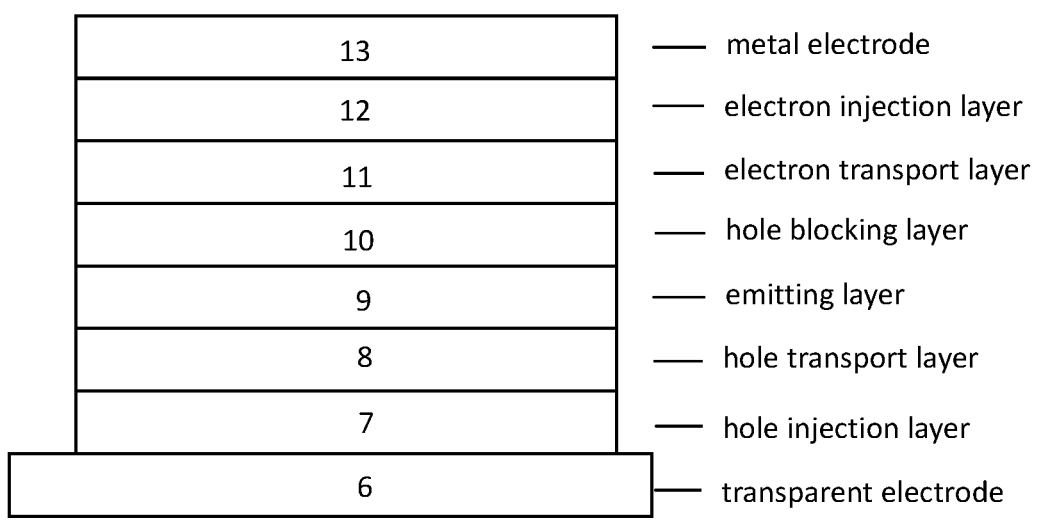

POLYHETEROAROMATIC COMPOUND AND ORGANIC ELECTROLUMINESCENCE DEVICE USING THE SAME

FIELD OF INVENTION

The present invention relates to a polyheteroaromatic compound having a 7',7'-dimethyl-5',7'-dihydrospiro[cyclopenta[1,2-b:5,4-b']dithio-phene-4,13'-indeno[1,2-b]acridine] core structure and, more particularly, to an organic electroluminescence device using the polyheteroaromatic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

The first diode device was reported by Ching W. Tang and Steven Van Slyke at Eastman Kodak in 1987. The device used a two-layer structure with separate hole transporting and electron transporting layers such that recombination and light emission occurred in the middle of the organic layer. This resulted in reduction of operating voltage and improvement of the efficiency, thereby leading to the current area of organic EL device research and device production.

Typically, the organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light outcoupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

In 2012, a new type of fluorescent organic EL device was developed by Adachi and coworkers. The new organic EL device incorporated the mechanism of thermally activated delayed fluorescence (TADF), which was a promising way to obtain a high percentage of singlet exciton formation by converting spin-forbidden triplet excitons up to the singlet level through the mechanism of reverse intersystem crossing (RISC).

1e;2qThe phosphorescent organic EL device utilizes both triplet and singlet excitions. Cause of longer lifetime and diffusion length of triplet excitions compared to those of singlet excitions, the phosphorescent organic EL device generally needs an additional hole blocking layer (HBL) between the emitting layer (EML) and the electron transporting layer (ETL) or the electron transporting layer with hole blocking ability (HBETL) instead of the typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block holes transport from the EML to the ETL and to pass electrons from the ETL to the EML. In addition, good thermal and electrochemical stability of the phosphorescent emitting host material is also needed.

The compounds with a 10H-spiro[acridine-9,9'-fluorene] structure have found their applications in organic EL devices, which can be found in U.S. Pat. No. 8,632,893. In addition, the compounds having a structure of 7',7'-dimethyl-5',7',10,11-tetrahydrospiro[dibenzo[a,d][7]annulene-5,13'-inde no[1,2-b]acridine] were used in OLEDs, which was disclosed in KR Appl. No. 1020100029865. In the present invention, we develop a novel polyhetero-aromatic compound having a core structure of 7',7'-dimethyl-5',7'-dihydrospiro[cyclopenta-[1,2-b:5,4-b']dithiophene-4,13'-indeno[1,2-b]acridine to improve the performance of the organic EL devices.

SUMMARY OF THE INVENTION

Accordingly, an object of the invention is to provide a polyheteroaromatic compound and an organic EL device using the same, which can operate under reduced voltage and exhibit high light-emitting efficiency.

Another object of the present invention is to provide a polyheteroaromatic compound, which can be used as a phosphorescent host material, a fluorescenct host material, a fluorescent dopant material, a TADF host material, or a TADF dopant material in the emitting layer, and/or an electron transport layer (ETL) material for an organic EL device to improve the power consumption and luminous efficiency.

According to the present invention, a polyheteroaromatic compound which can be used for organic EL devices is disclosed. The polyheteroaromatic compound is represented by the following formula (1):

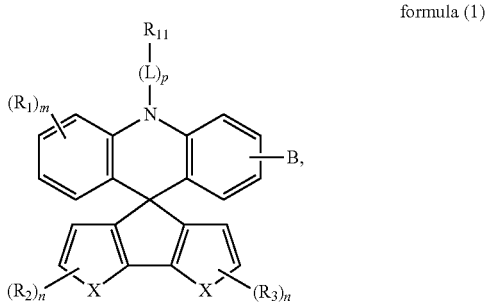

formula (1)

wherein X is O, S, or Se; each n and p is independently an integer of 0 to 2; L represents formula (2) below:

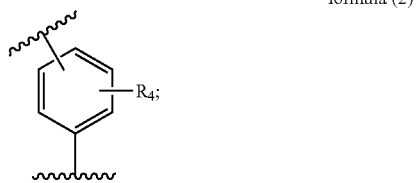

formula (2)

and B represents formula (3) below:

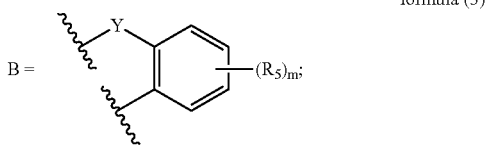

formula (3)

wherein m is an integer of 0 to 4; Y is O, S, Se, $CR_6R_7$, $NR_8$, or $SiR_9R_{10}$; and $R_1$ to $R_{11}$ are independently selected from the group consisting of a hydrogen atom, a halide, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, and a substituted or unsubstituted arylamine group having 6 to 60 carbon atoms.

The present invention further discloses an organic electroluminescence device. The organic electroluminescence device comprises a pair of electrodes composed of a cathode and an anode, and a light emitting layer and one or more organic thin film layers between the pair of electrodes. At least one of the light emitting layer and the organic thin film layer comprises the polyheteroaromatic compound of formula (1).

BRIEF DESCRIPTION OF THE DRAWINGS

The FIGURE shows one embodiment of the organic EL device of the present invention. In the device, hole injection layer 7 is deposited onto transparent electrode 6, hole transport layer 8 is deposited onto hole injection layer 7, fluorescence or phosphorescence emitting layer 9 is deposited onto hole transport layer 8, hole blocking layer 10 is deposited onto emitting layer 9, electron transport layer 11 is deposited onto hole blocking layer 10, electron injection layer 12 is deposited onto electron transport layer 11, and metal electrode 13 is deposited onto electron injection layer 12.

DESCRIPTION OF THE PREFERRED EMBODIMENTS

What probed into the invention is the polyheteroaromatic compound and organic EL device using the polyheteroaromatic compound. Detailed descriptions of the production, structure and elements will be provided as follows such that the invention can be fully understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a polyheteroaromatic compound which can be used as the host material, the fluorescent dopant material, the thermally activated delayed fluorescence host material, or the thermally activated delayed fluorescence dopant material of the light emitting layer, and/or the electron transporting material for the organic EL device is disclosed. The polyheteroaromatic compound is represented by the following formula (1):

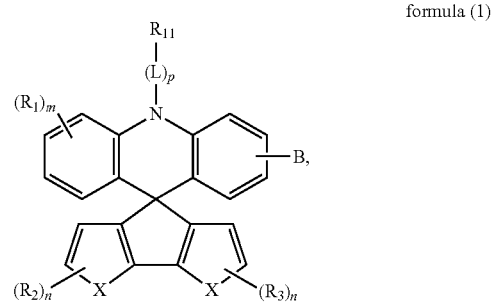

formula (1)

wherein X is O, S, or Se; each n and p is independently an integer of 0 to 2; L represents formula (2) below:

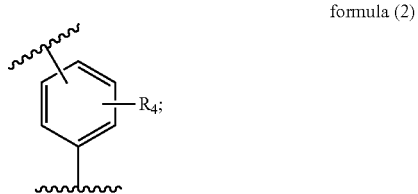

formula (2)

and B represents formula (3) below:

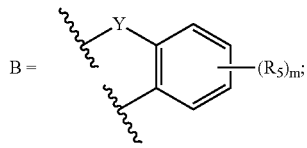

formula (3)

wherein m is an integer of 0 to 4; Y is O, S, Se, $CR_6R_7$, $NR_8$, or $SiR_9R_{10}$; and $R_1$ to $R_{11}$ are independently selected from the group consisting of a hydrogen atom, a halide, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, and a substituted or unsubstituted arylarnine group having 6 to 60 carbon atoms.

In some embodiments, $R_8$ or $R_{11}$ represents one of the following substituents:

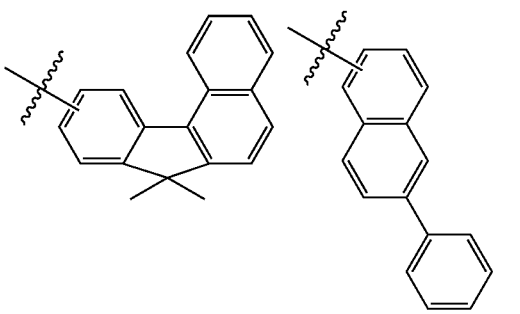
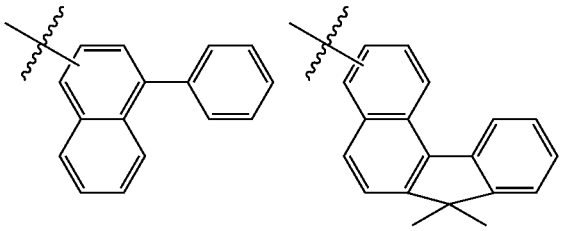
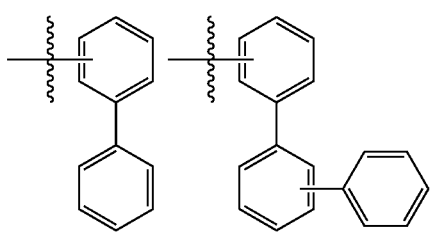
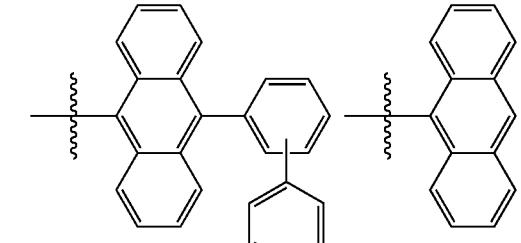
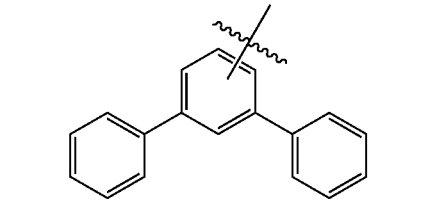
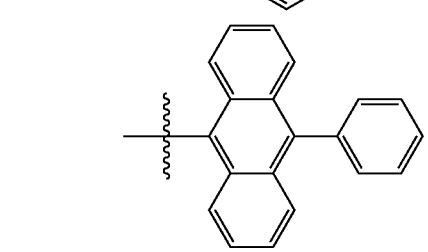
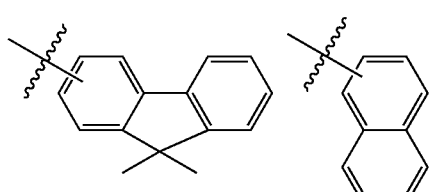
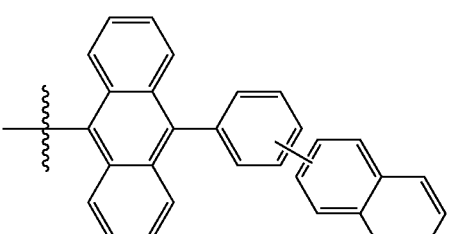
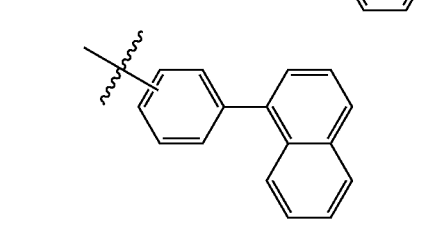
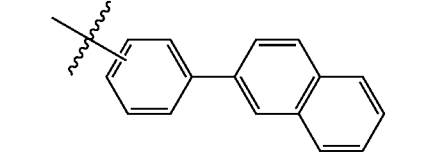
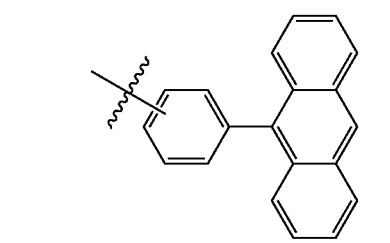

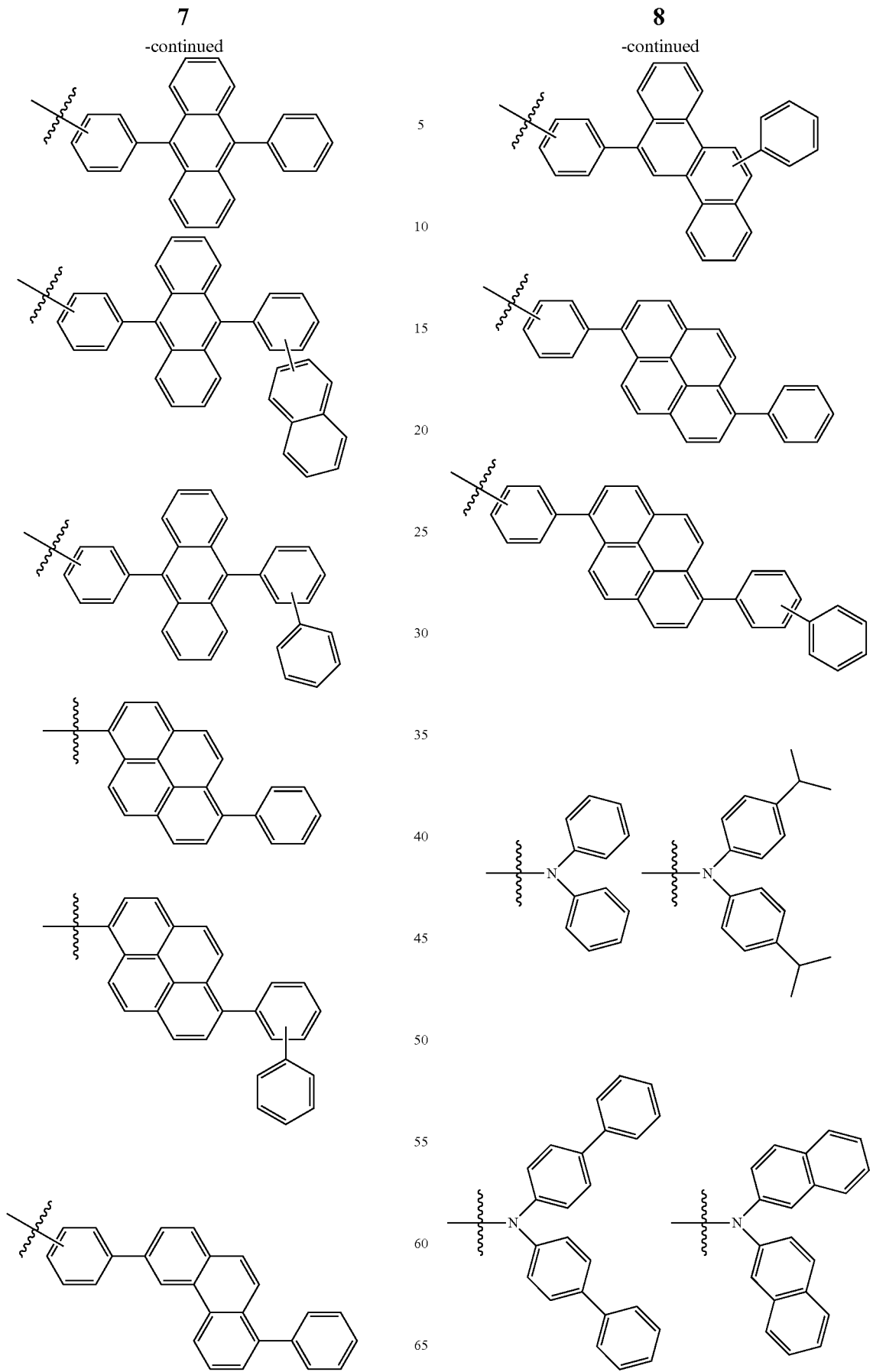

-continued
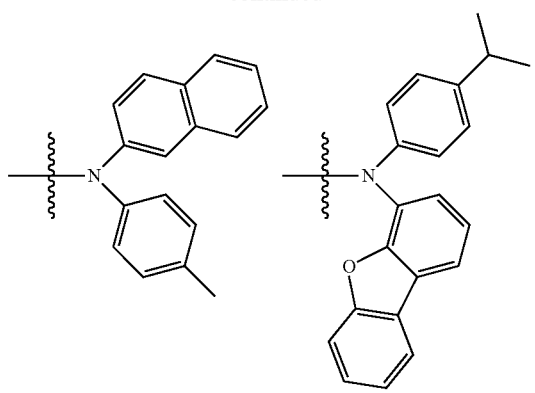
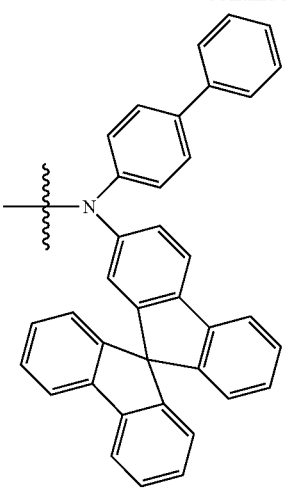
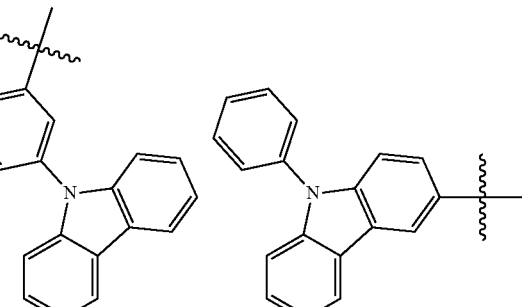
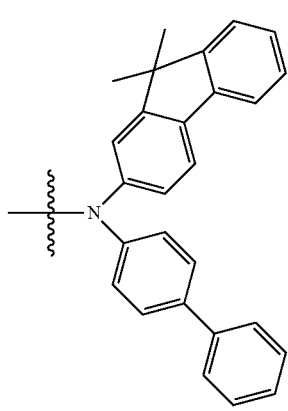
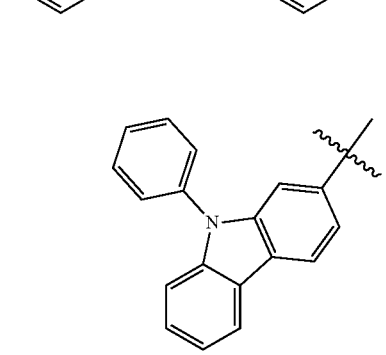
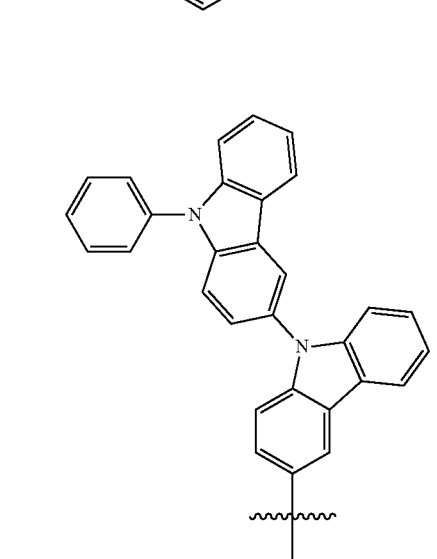

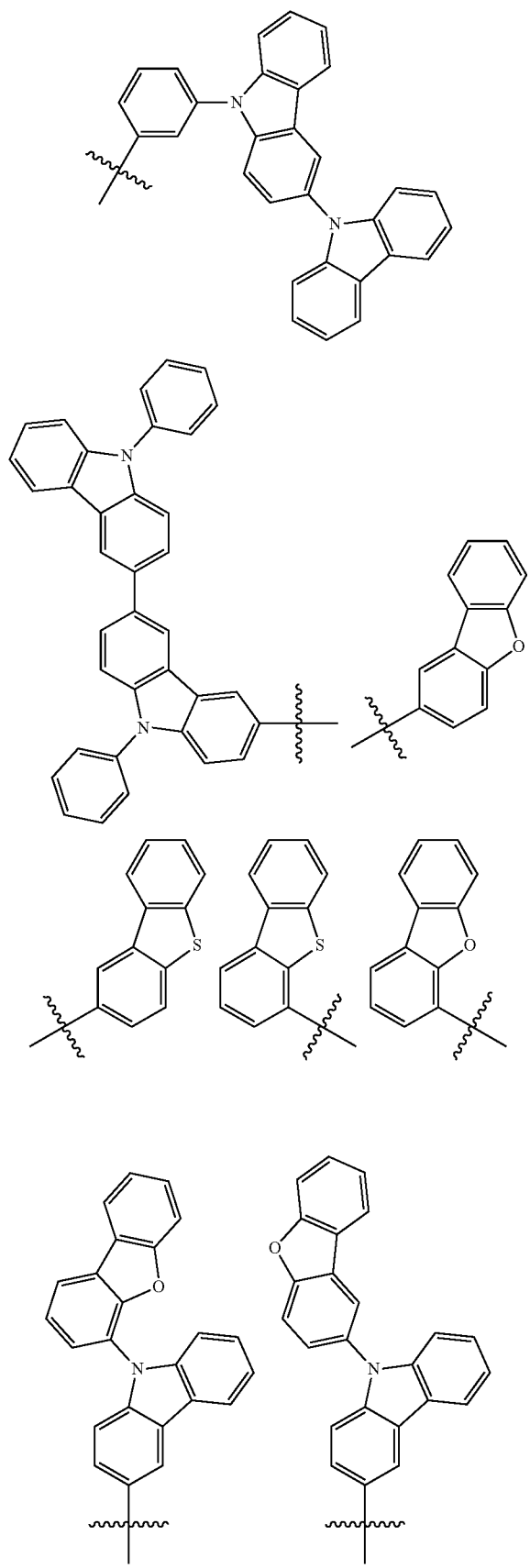
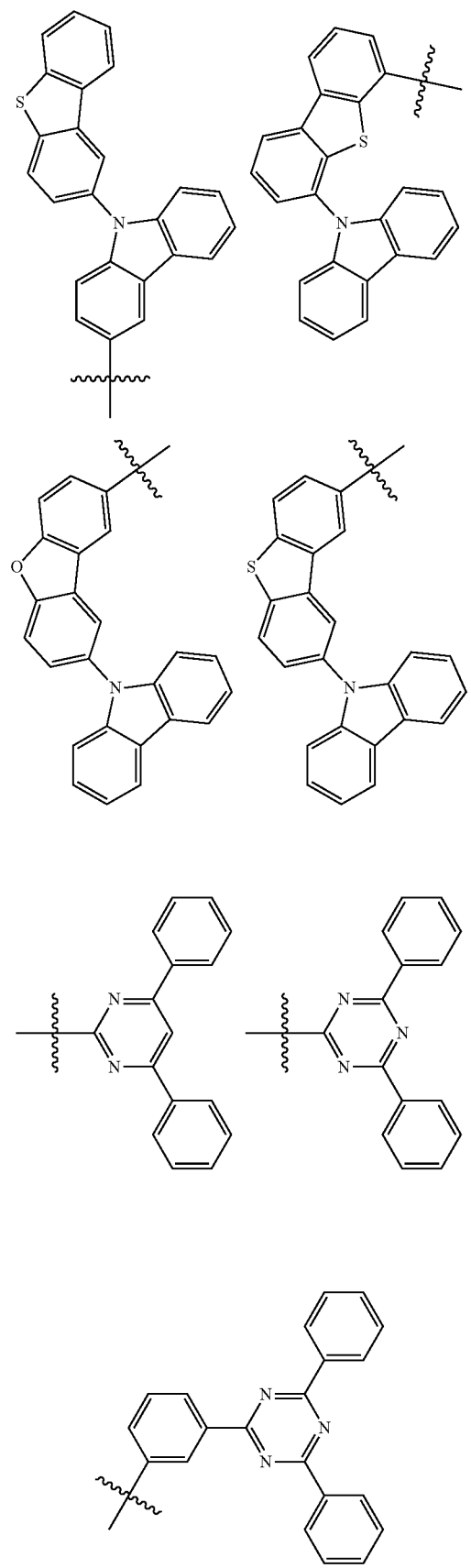

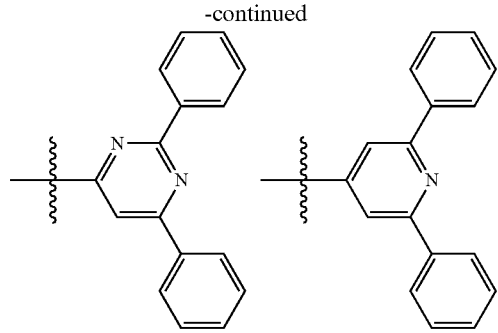
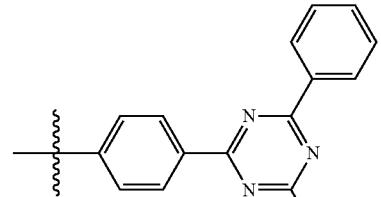
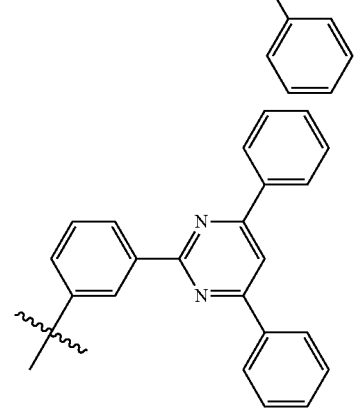
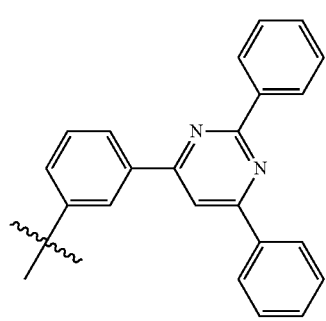
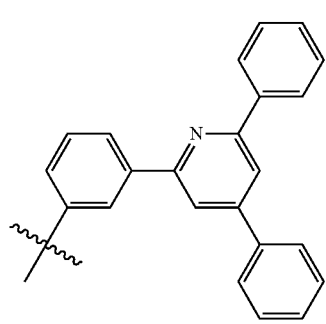
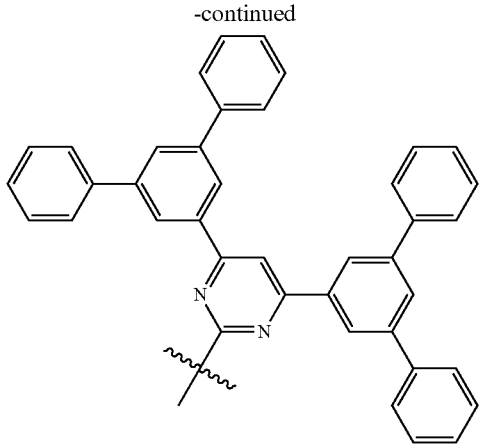
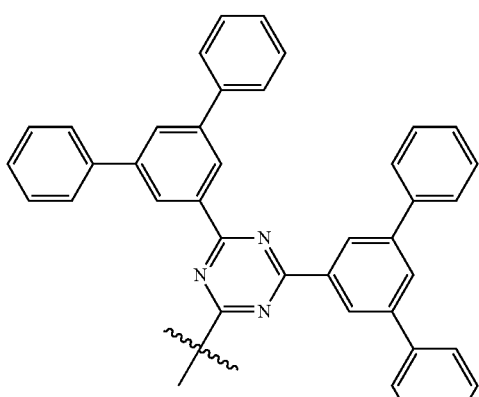
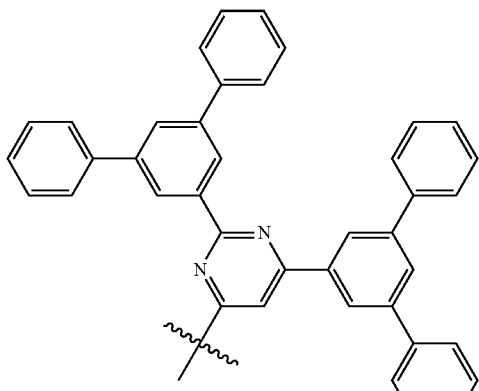
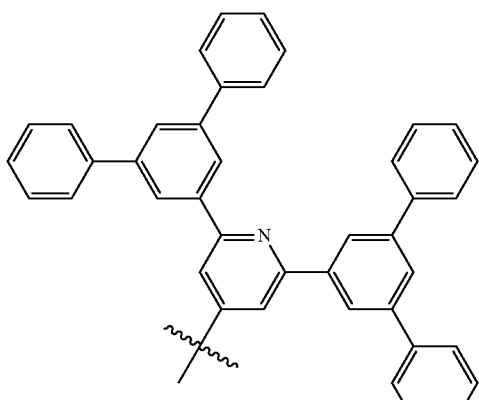

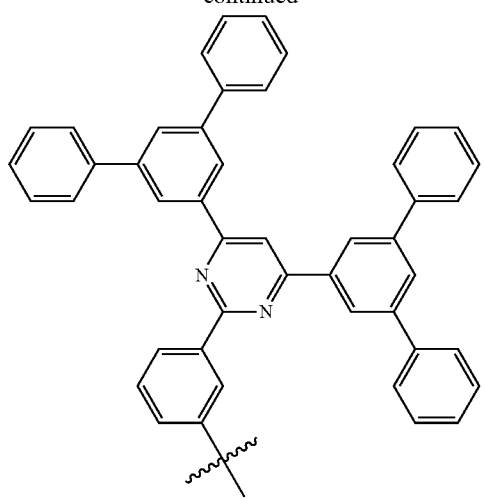
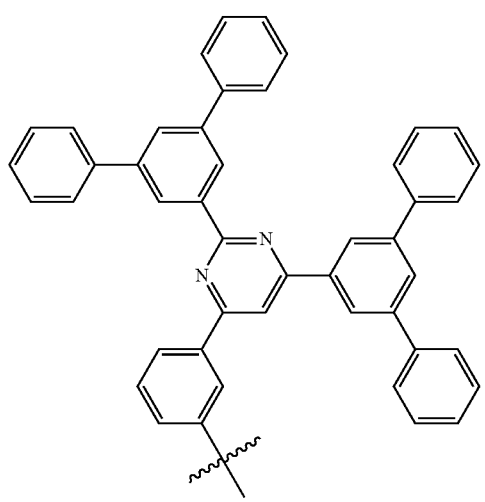
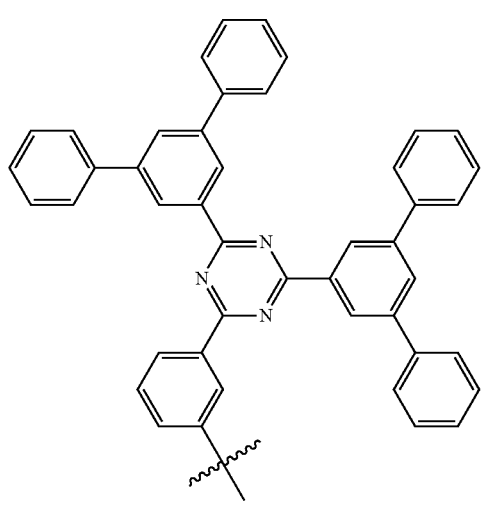
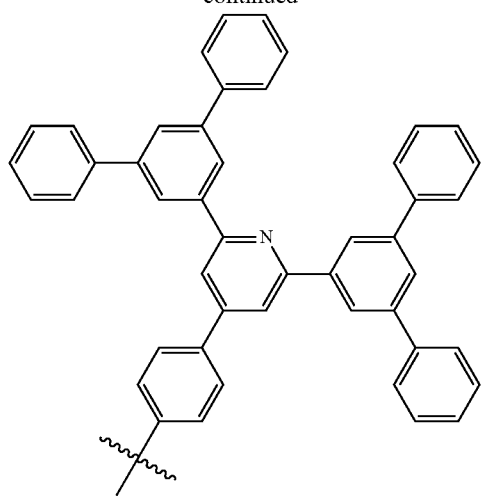
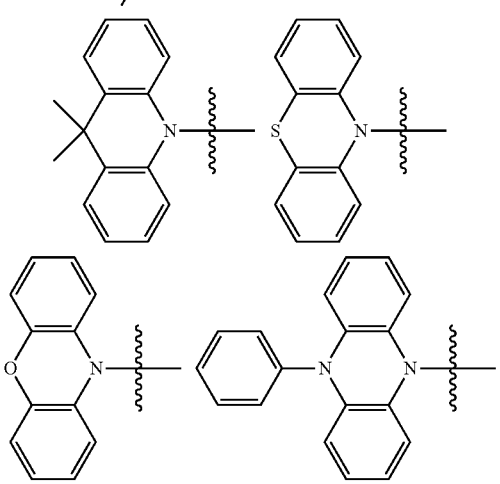
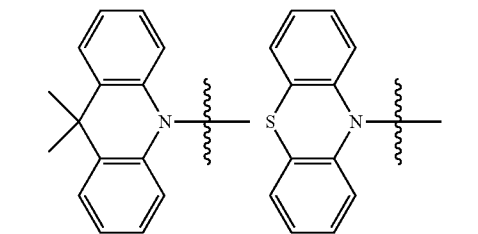
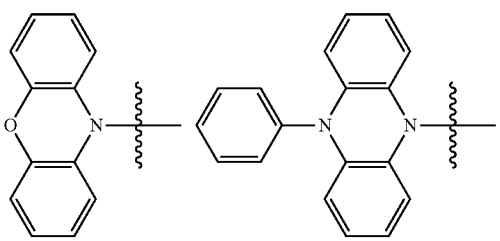
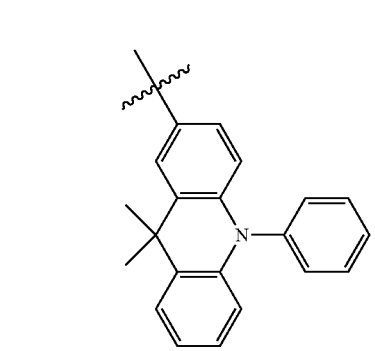
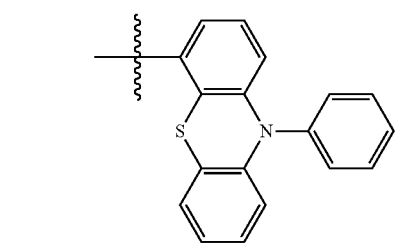

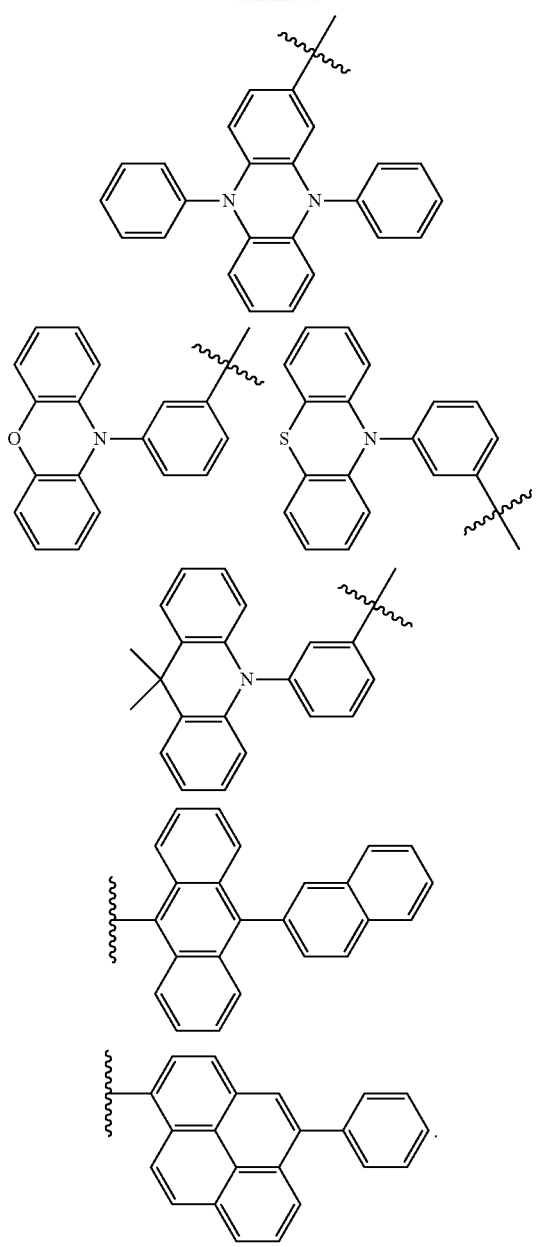
Preferably, the polyheteroaromatic compound is represented by one of the following formula (4) to formula (9):
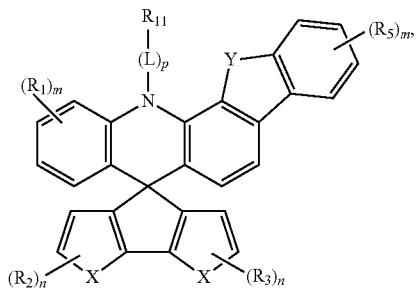
formula (4)
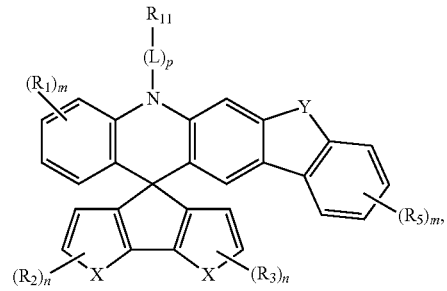
formula (5)
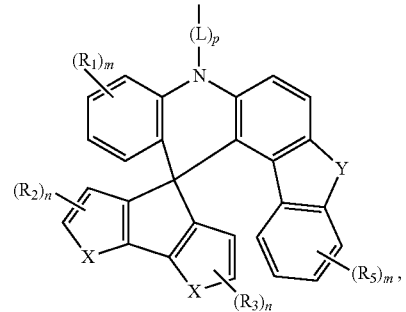
formula (6)
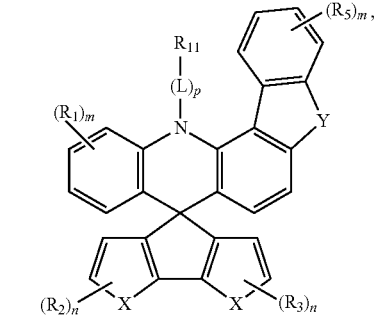
formula (7)
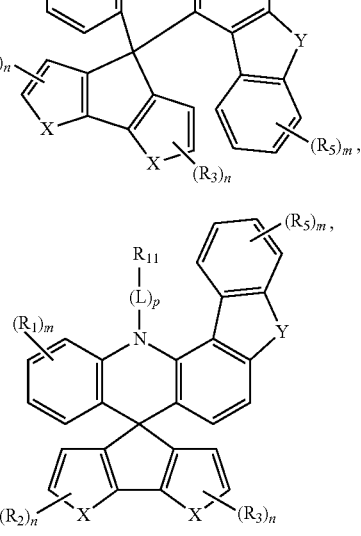
formula (8)
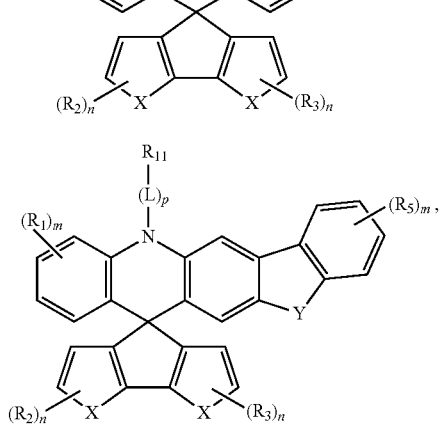
formula (9)
wherein X, n, p, L, m, Y and $R_1$ to $R_{11}$ have the same meaning as defined above.

Preferably, the polyheteroaromatic compound is one of the following compounds:
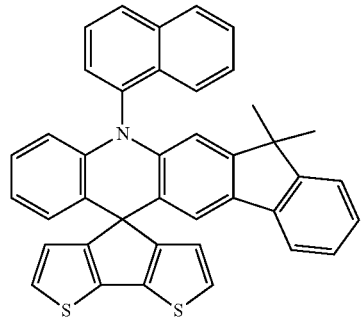
C1
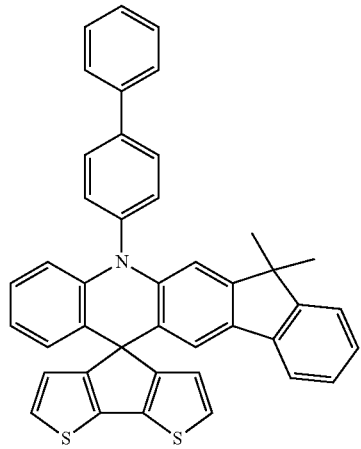
C2
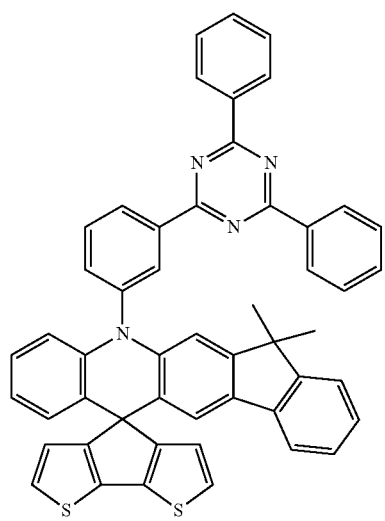
C3
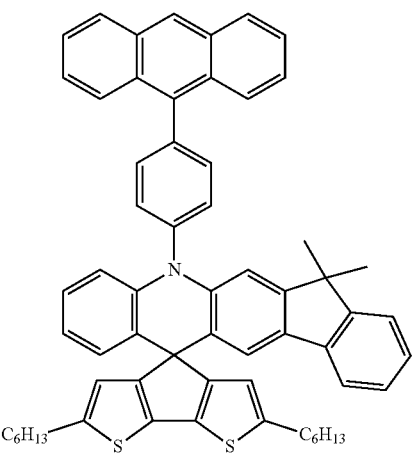
C4
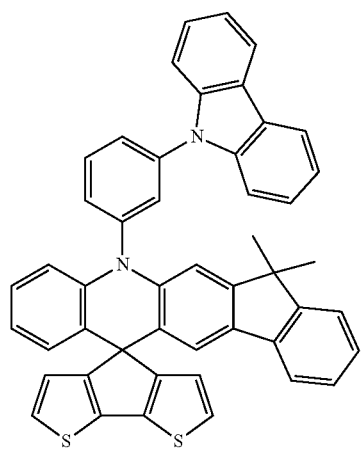
C5
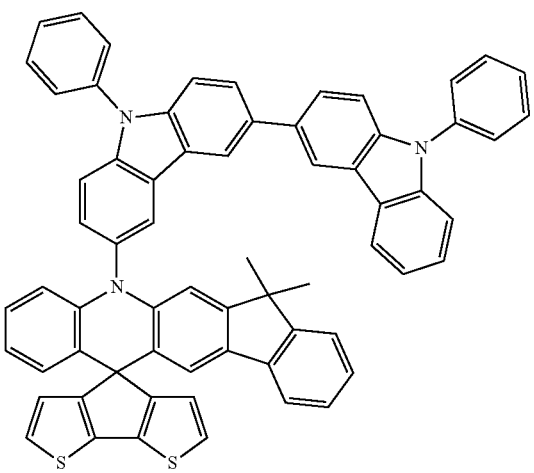
C6

-continued
C7
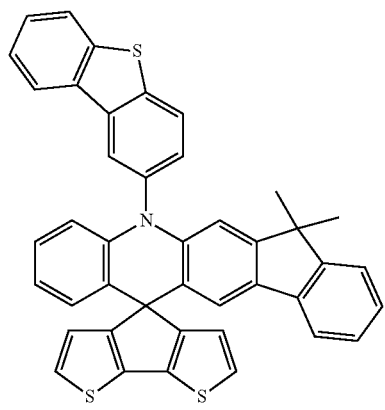
C8
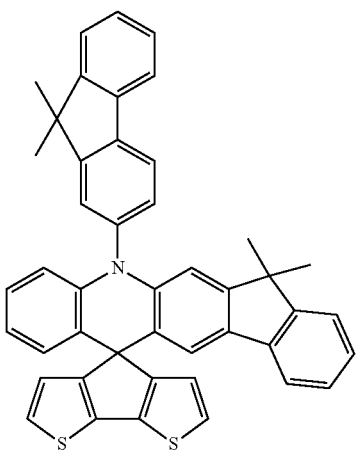
C9
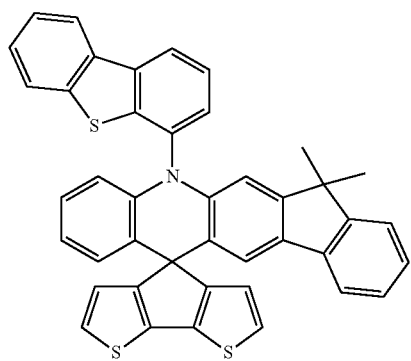
C10
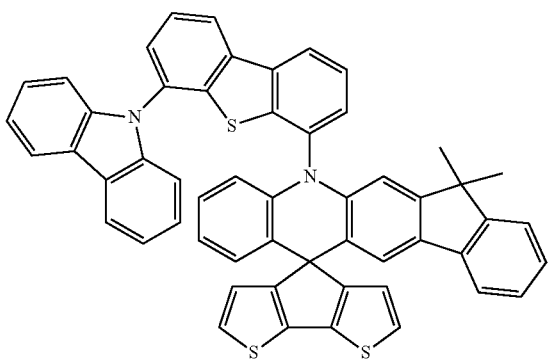
C11
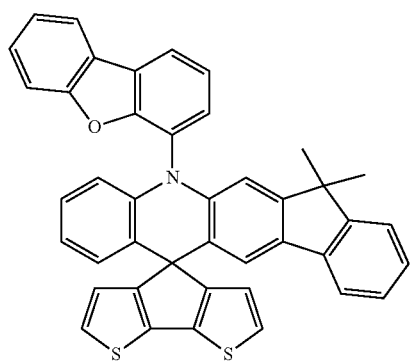
C12
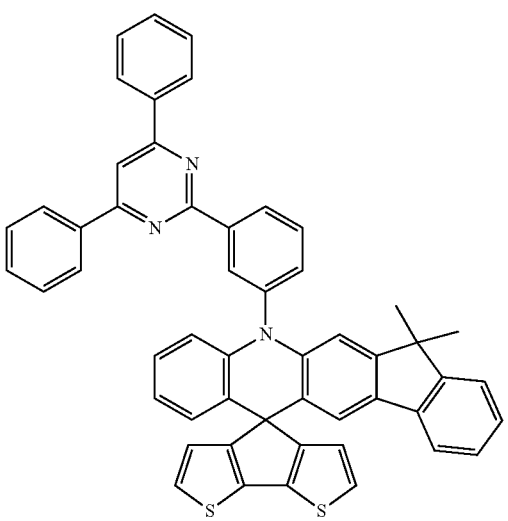

-continued
C13
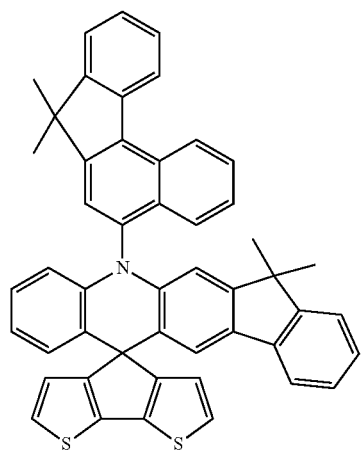
C14
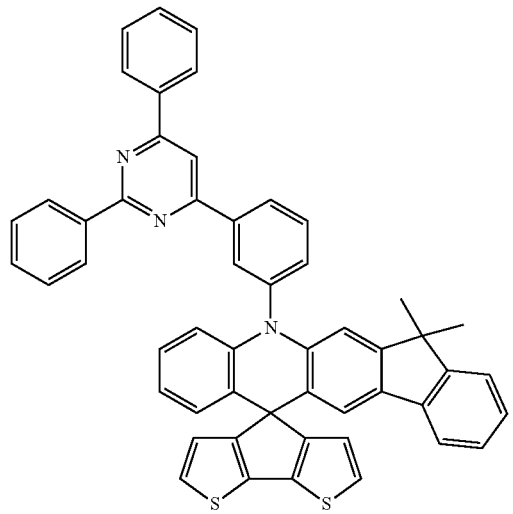
C15
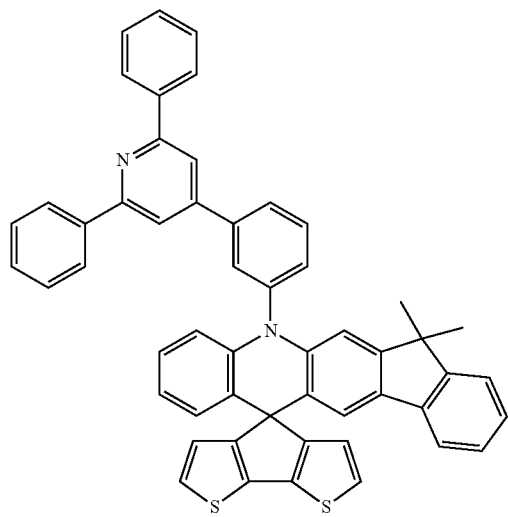
C16
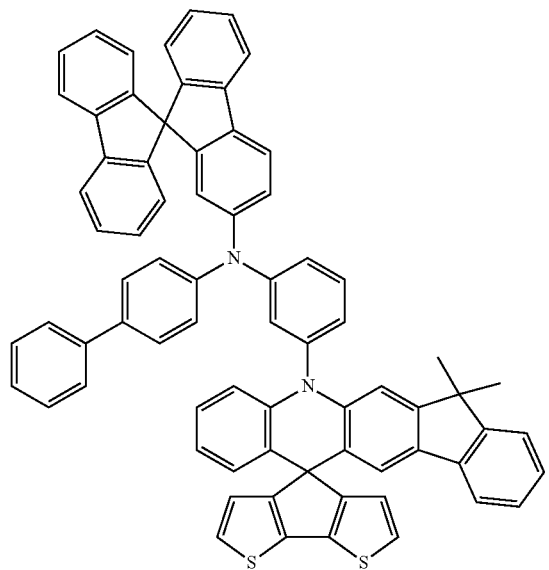
C17
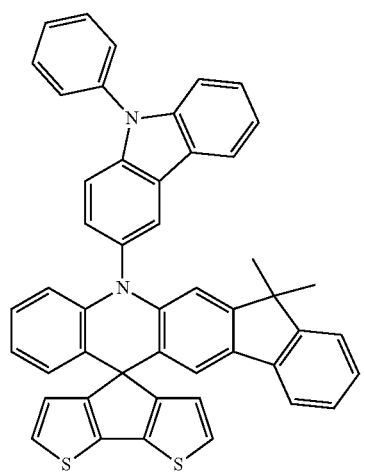
C18
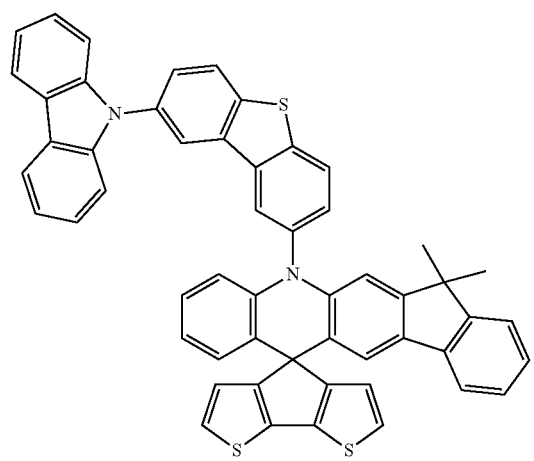

-continued
C19
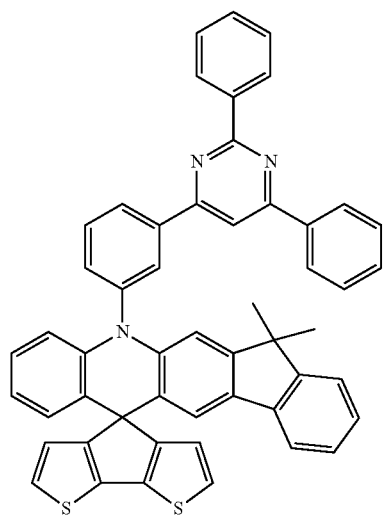
C20
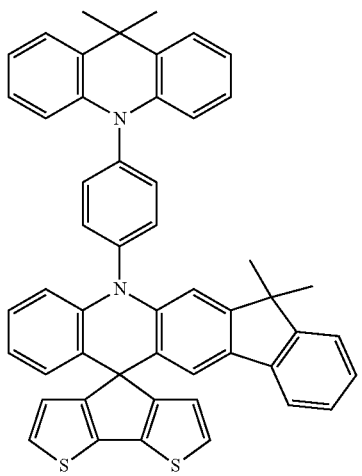
C21
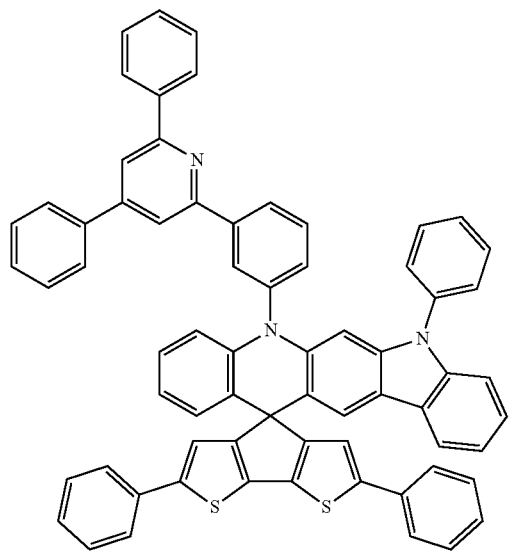
C22
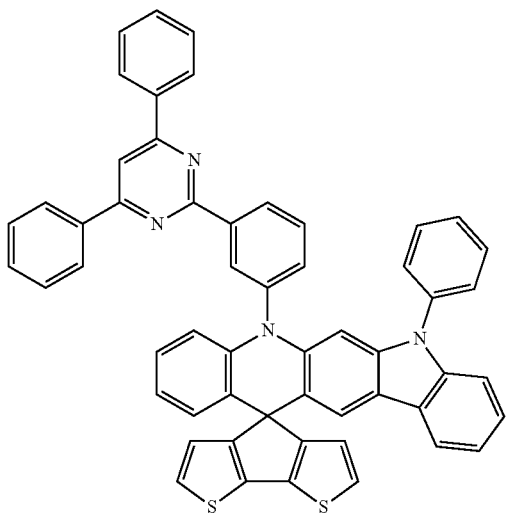
C23
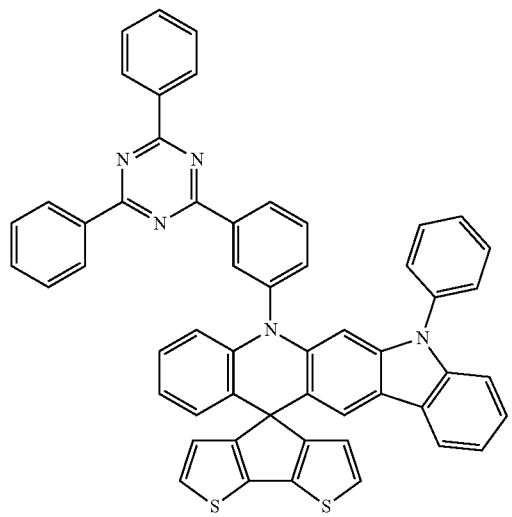
C24
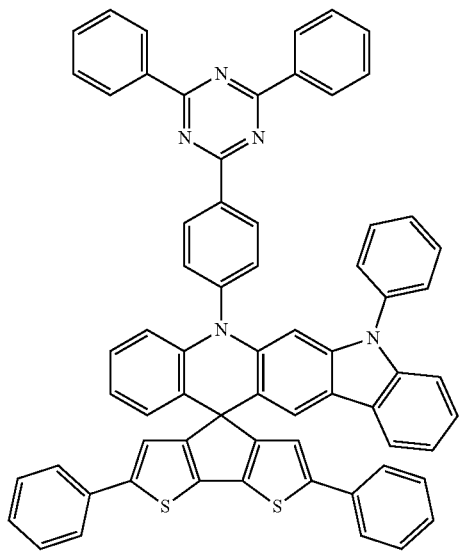

-continued
C25
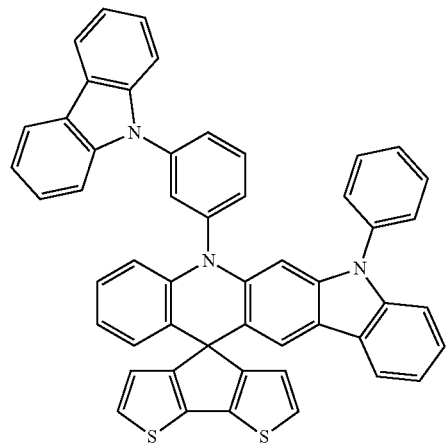
C26
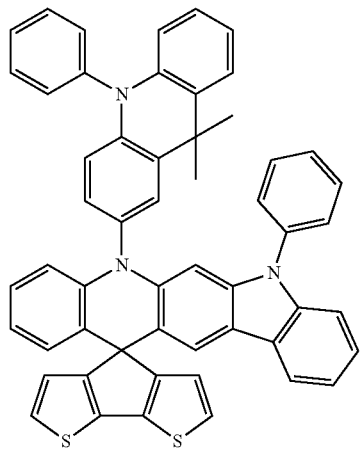
C27
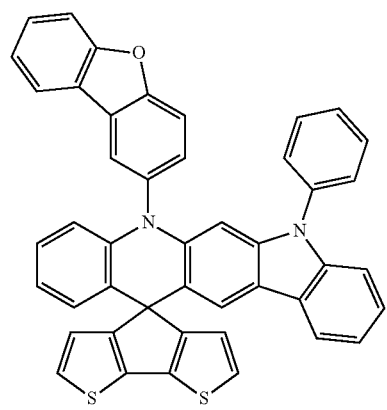
C28
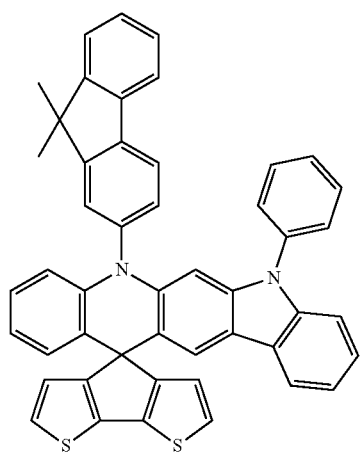
C29
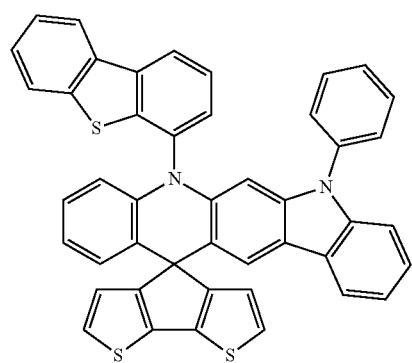
C30
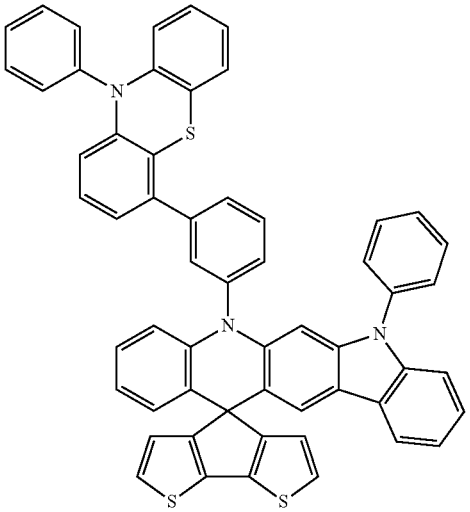

-continued
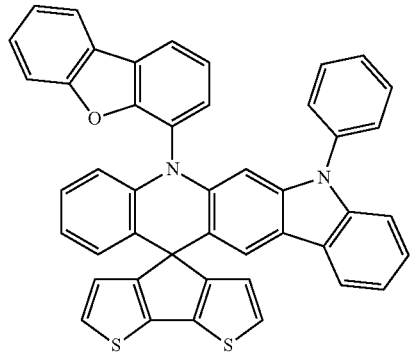
C31
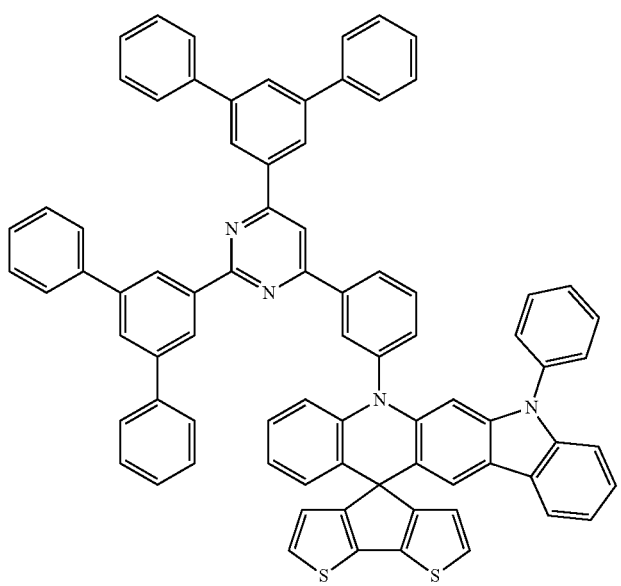
C32
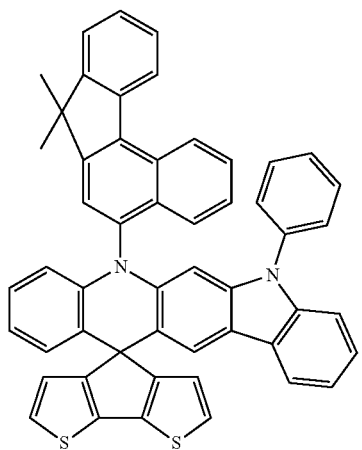
C33
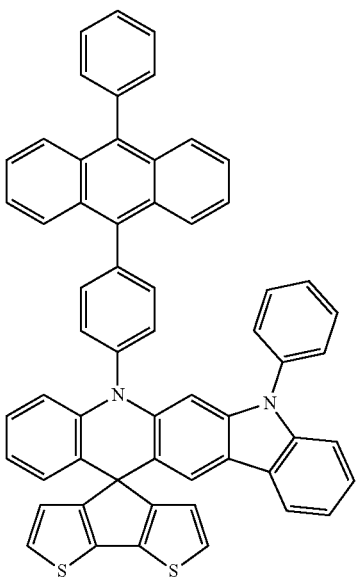
C34

-continued
C35
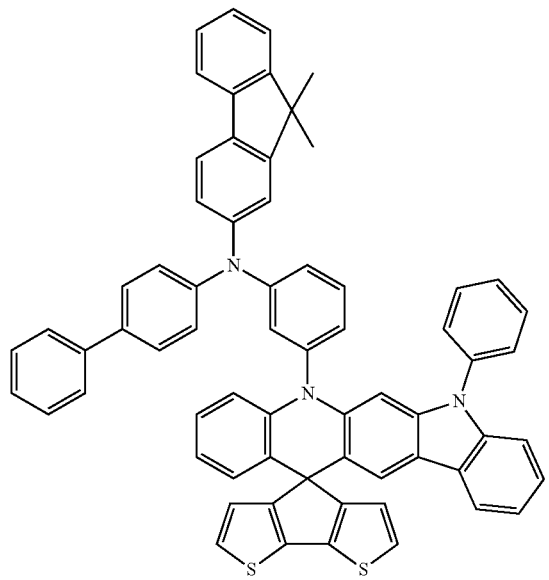
C36
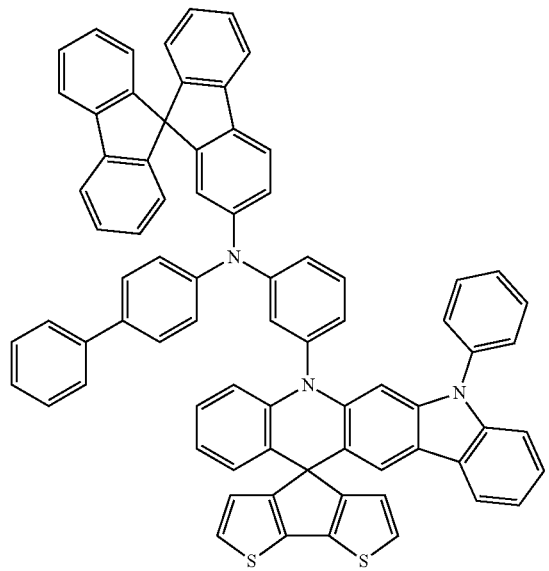
C37
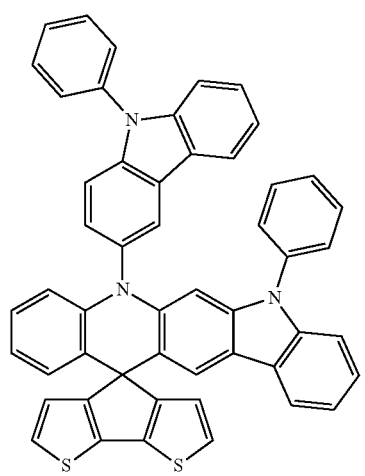
C38
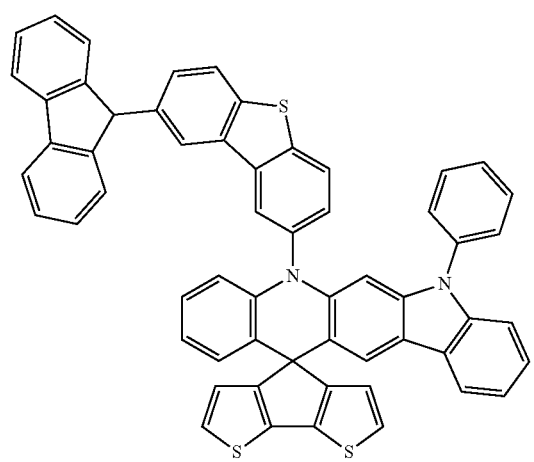
C39
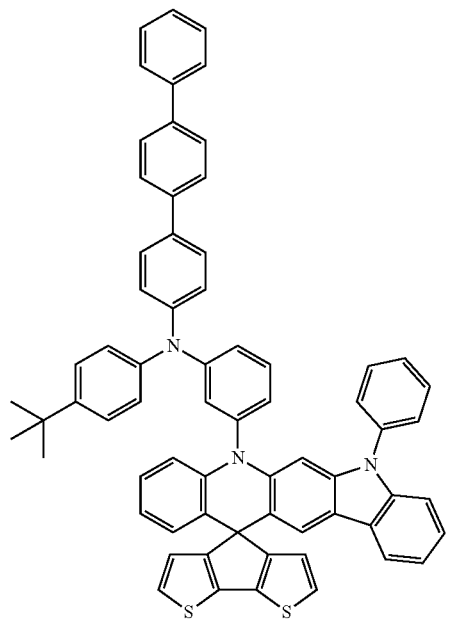
C40
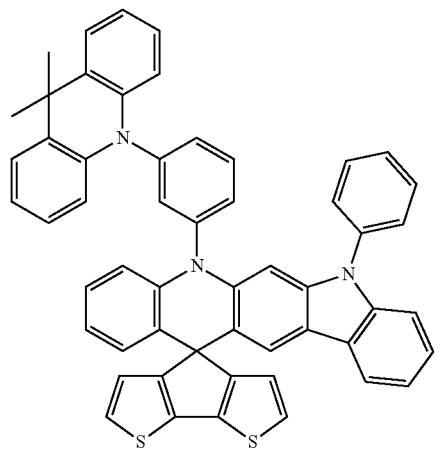

-continued
C41
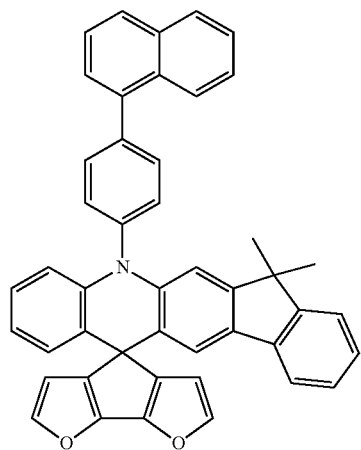
C42
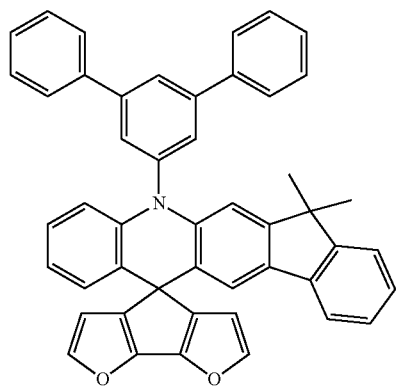
C43
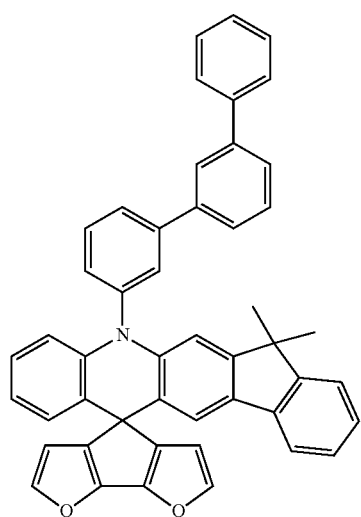
C44
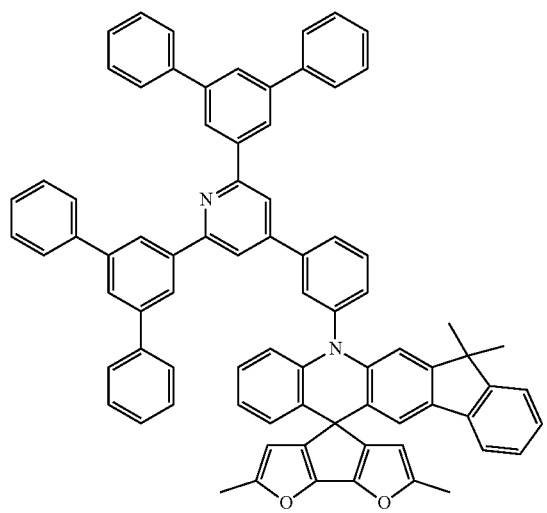
C45
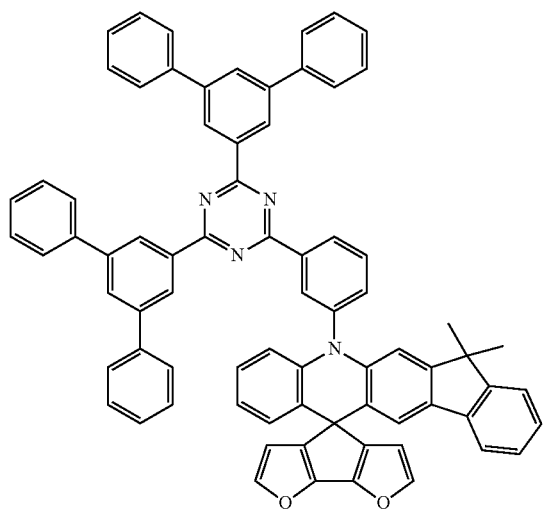

-continued
C46
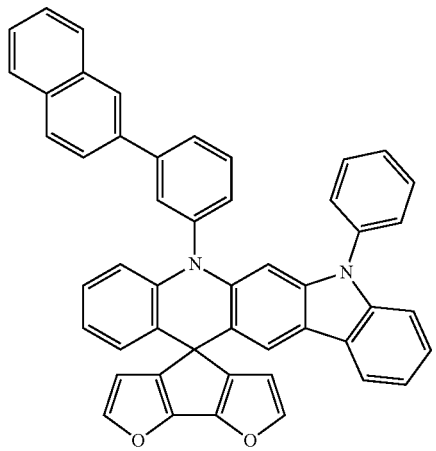
C47
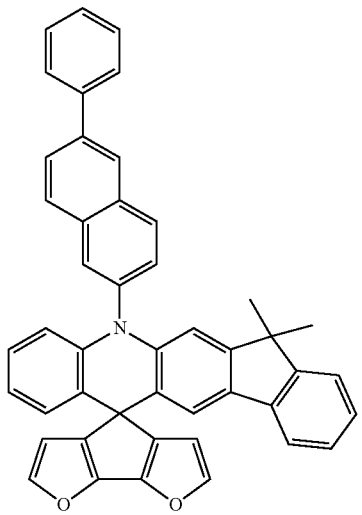
C48
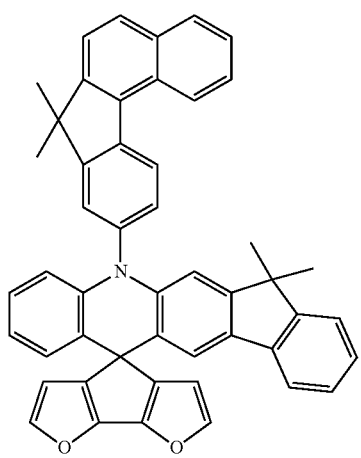
C49
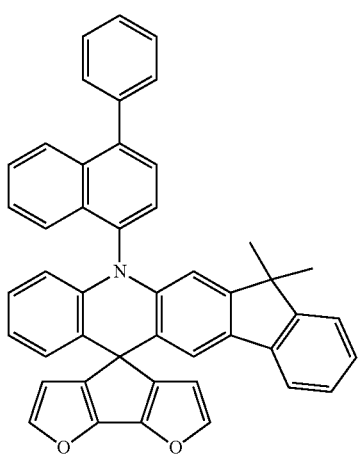
C50
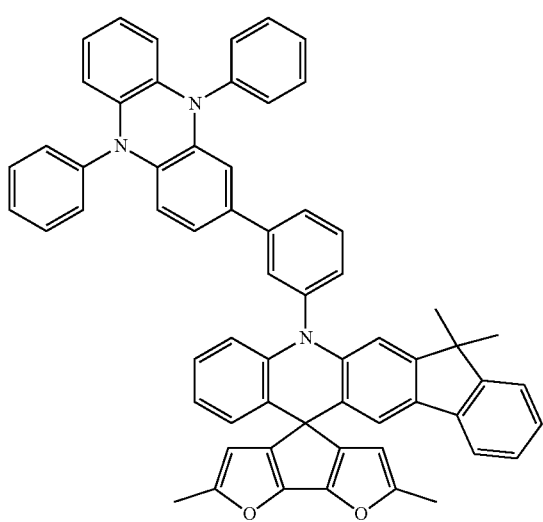
C51
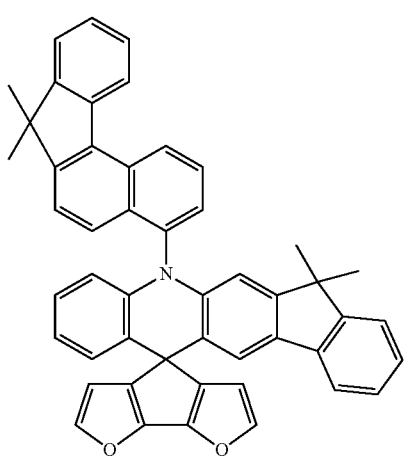

-continued
C52
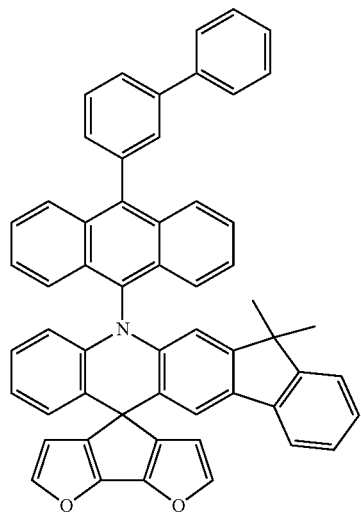
C53
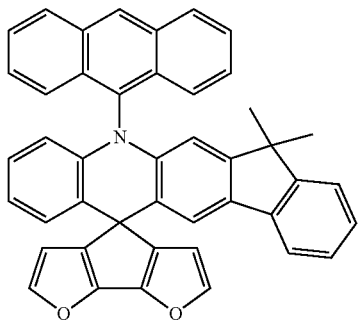
C54
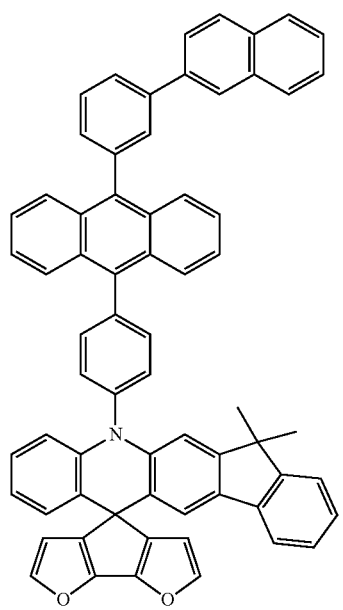
C55
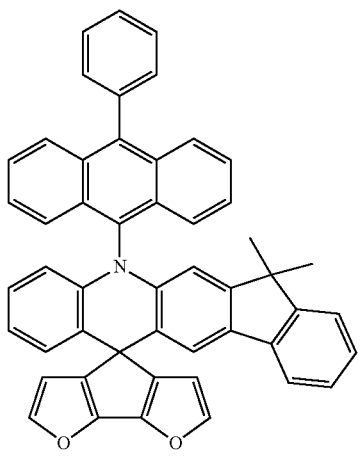

-continued
C56
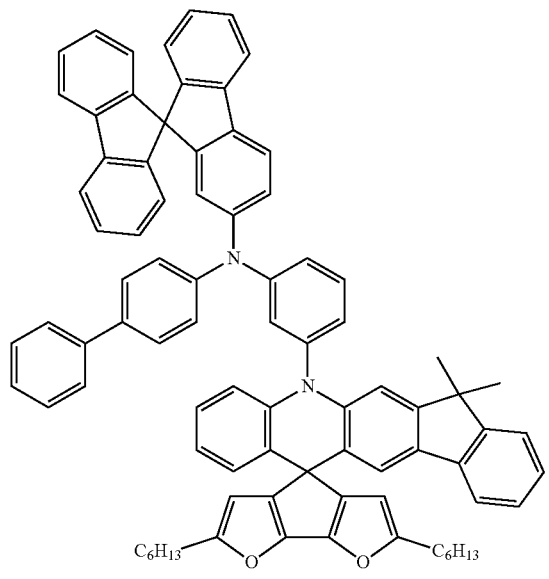
C57
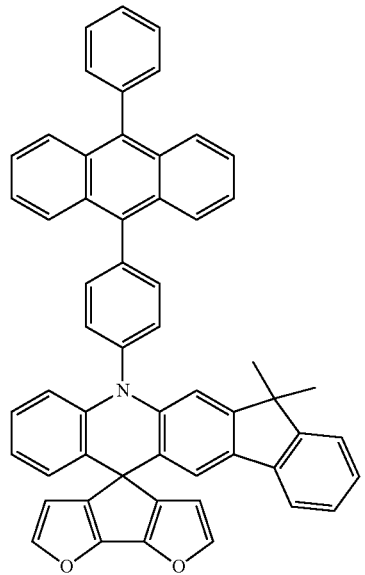
C58
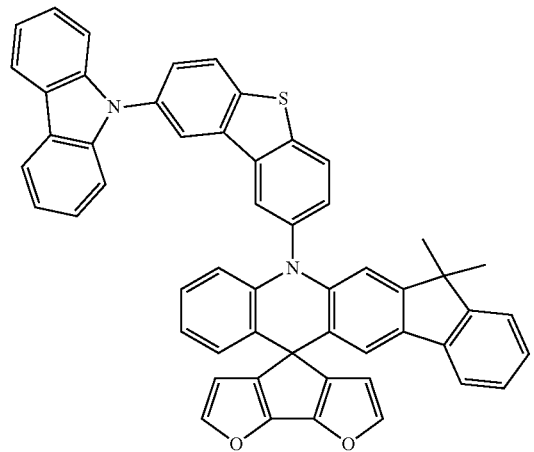
C59
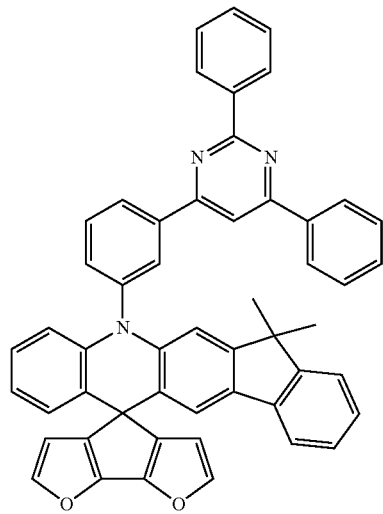

C60
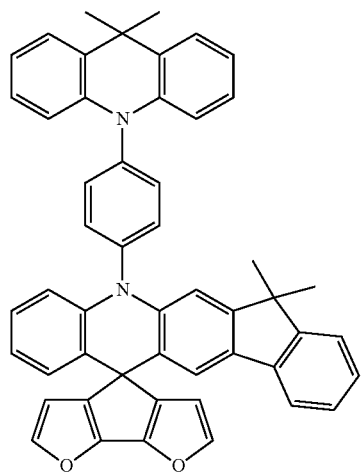
C61
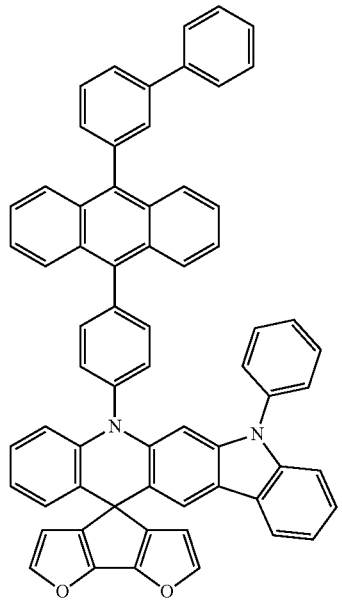
C62
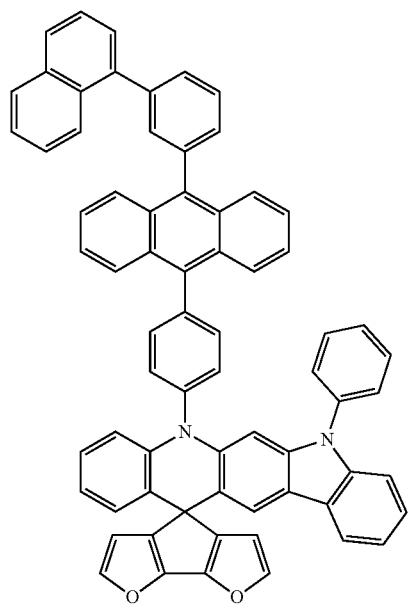
C63
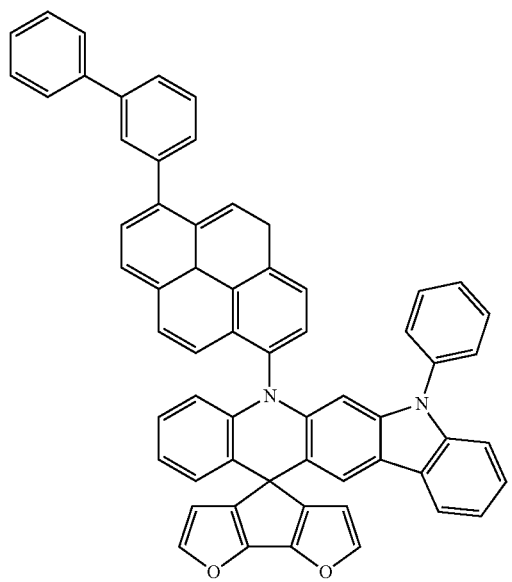

-continued
C64
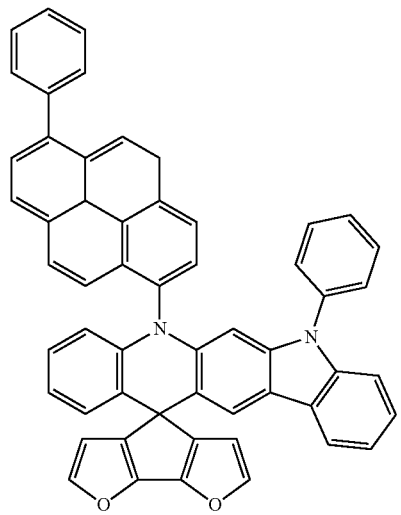
C65
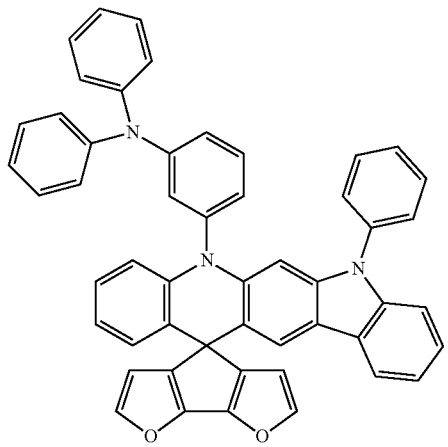
C66
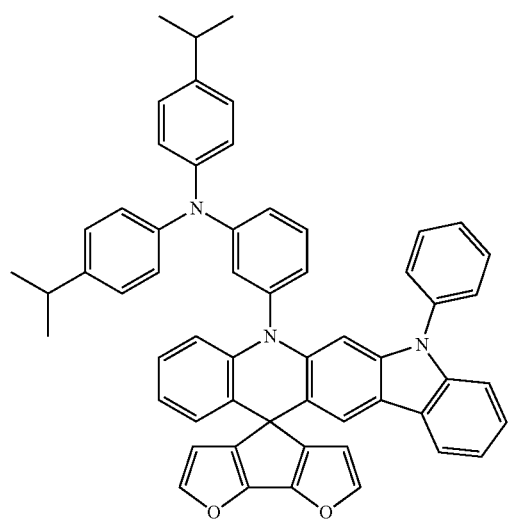
C67
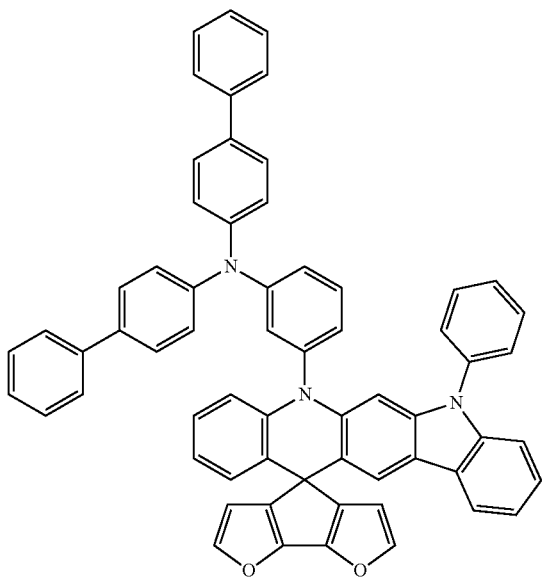
C68
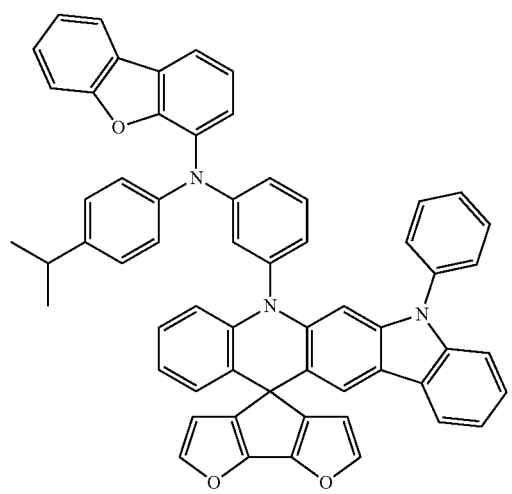
C69
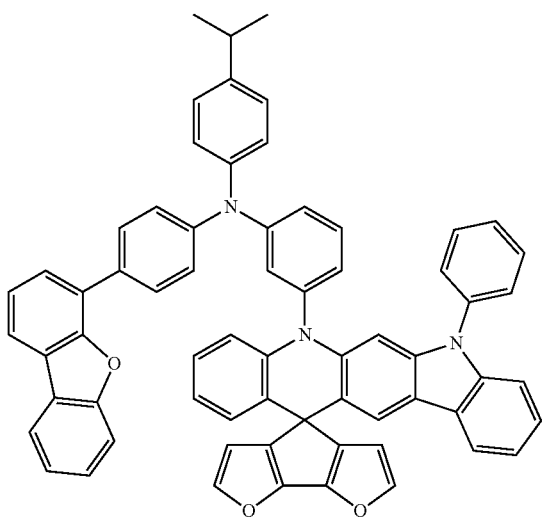

-continued
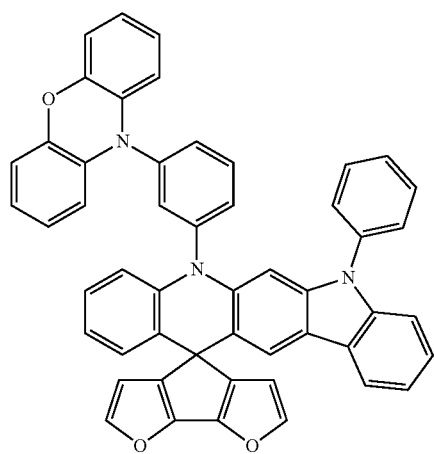
C70
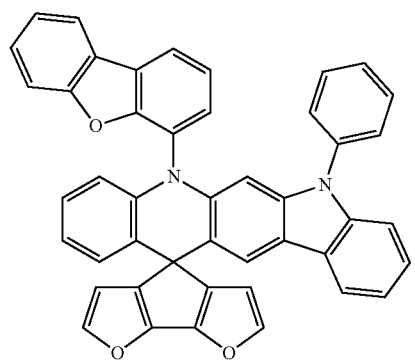
C71
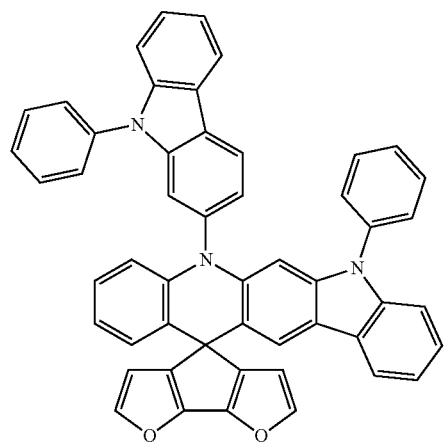
C72
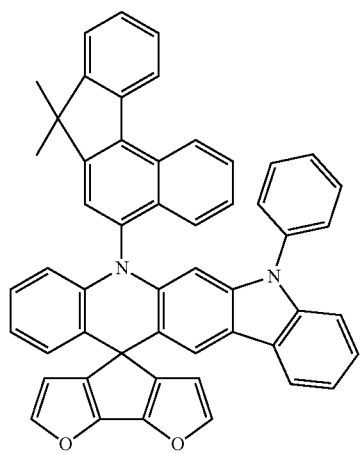
C73
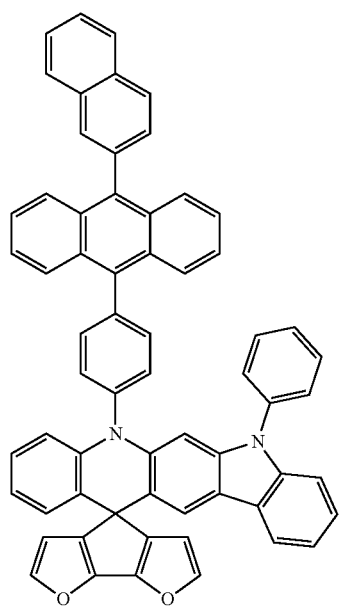
C74
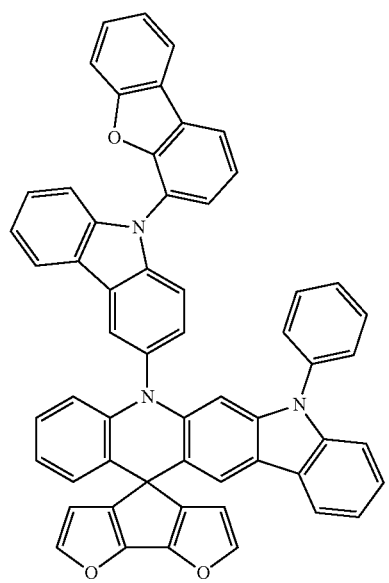
C75

-continued
C76
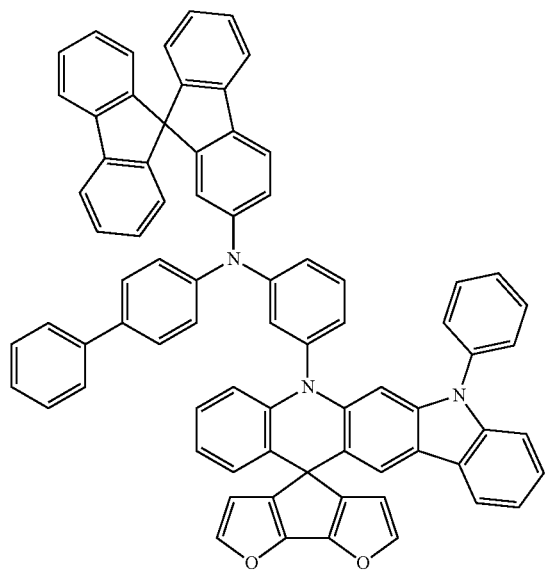
C77
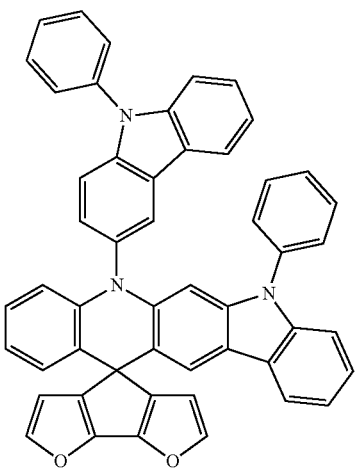
C78
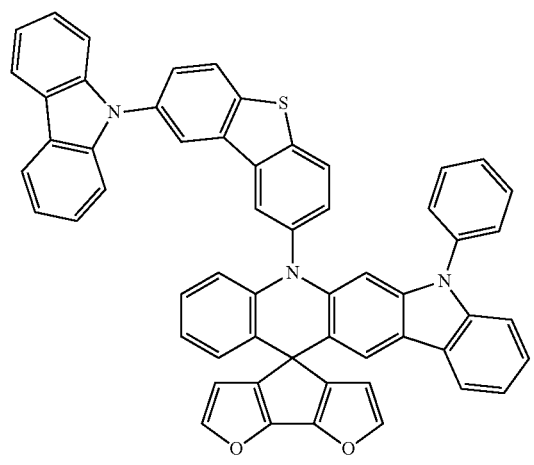
C79
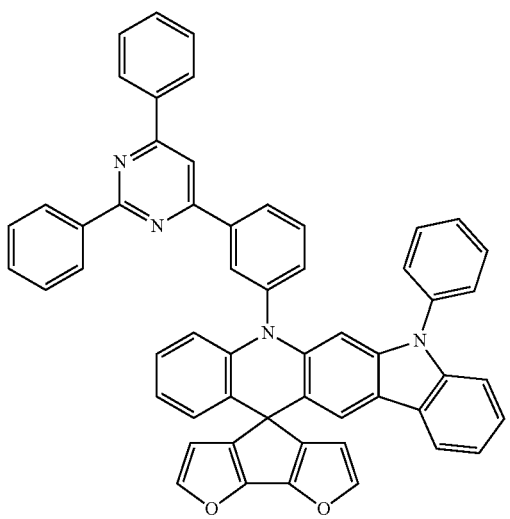
C80
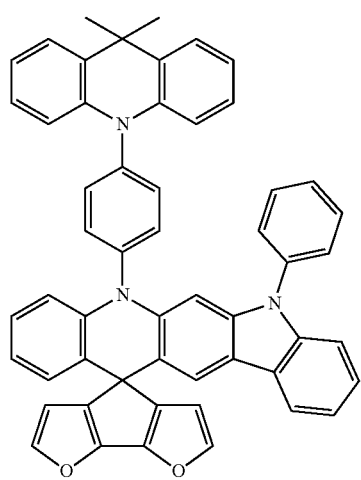
C81
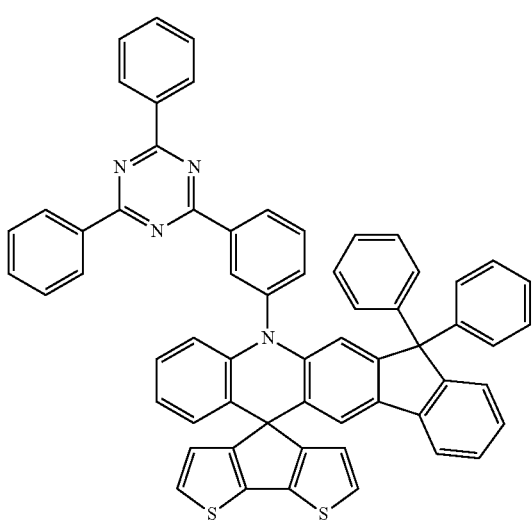

-continued
C82
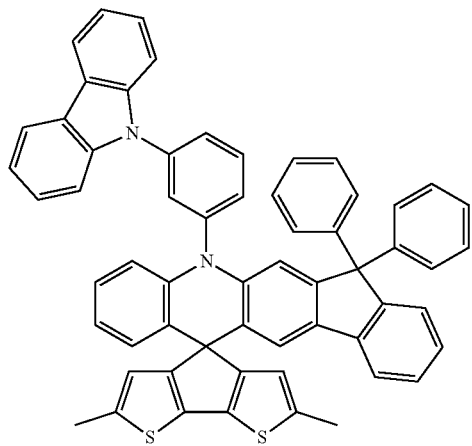
C83
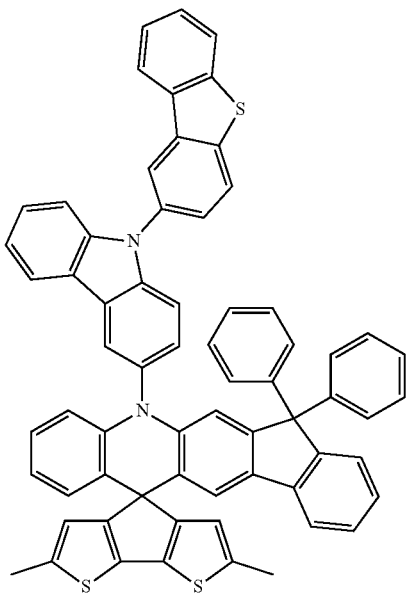
C84
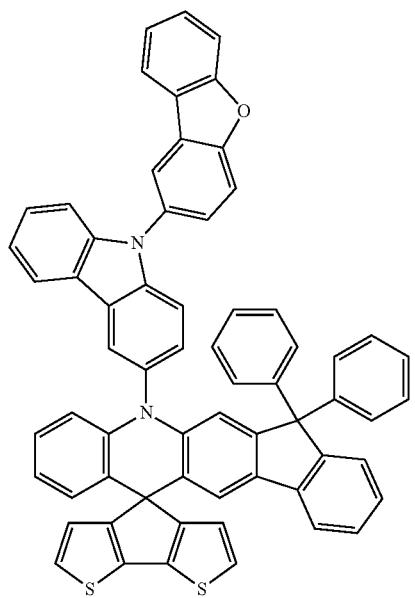
C85
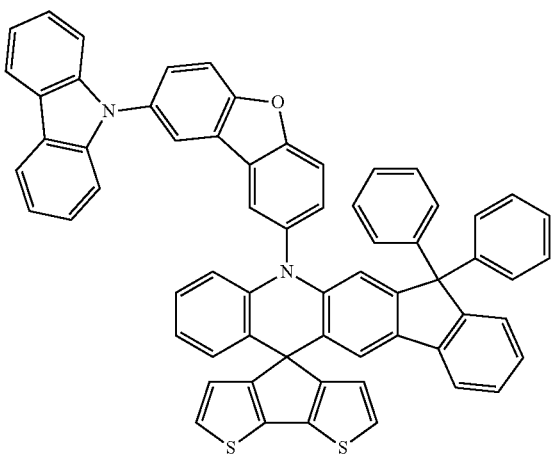

-continued
C86
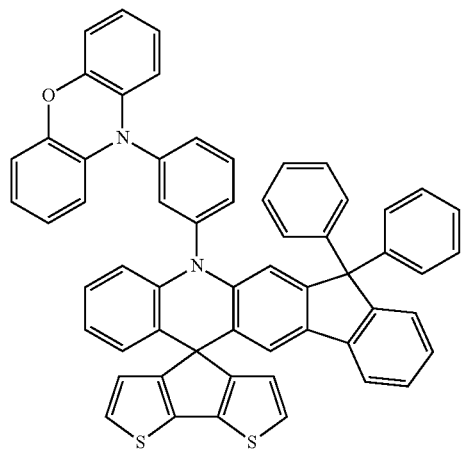
C87
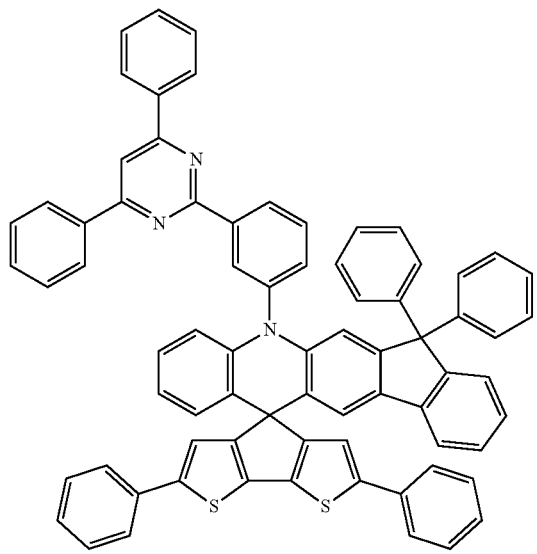
C88
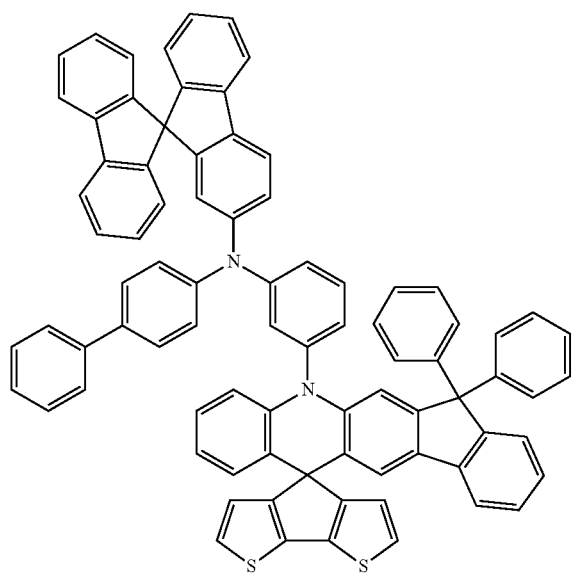
C89
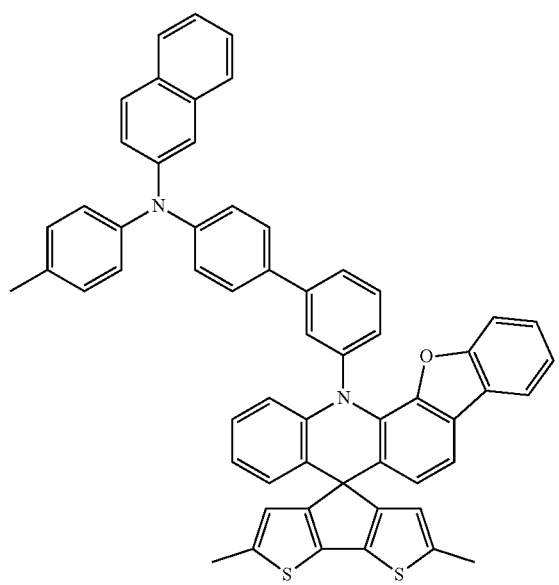
C90
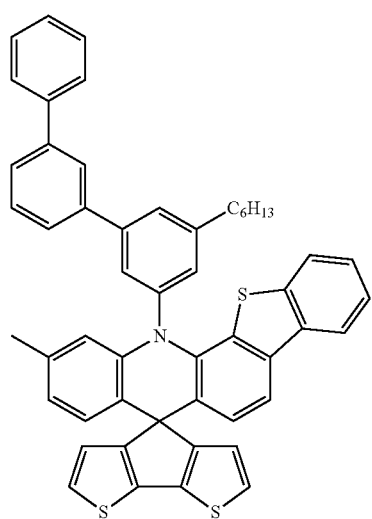
C91
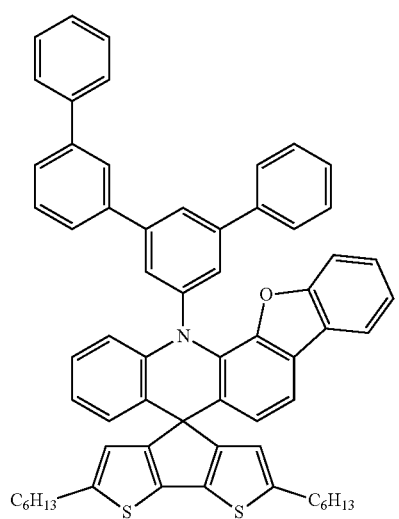

-continued
| | |
|---|---|
| C92 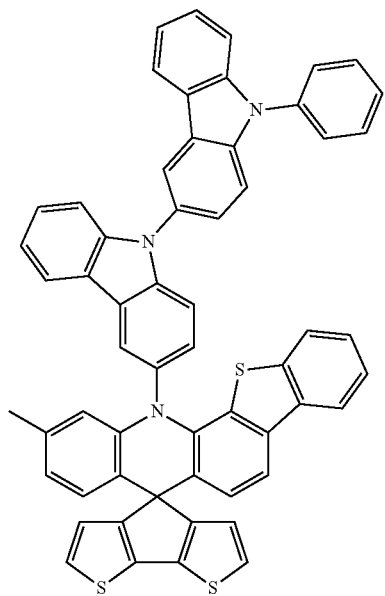 | C93 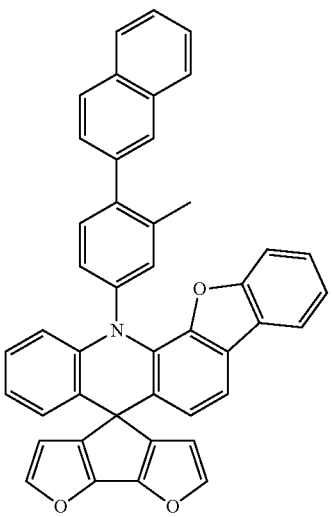 |
| C94 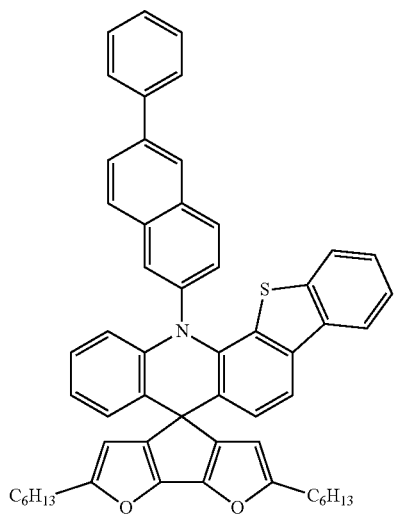 | C95 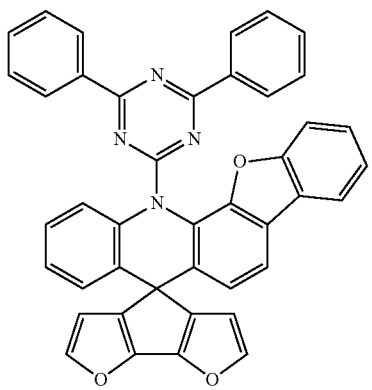 |
| C96 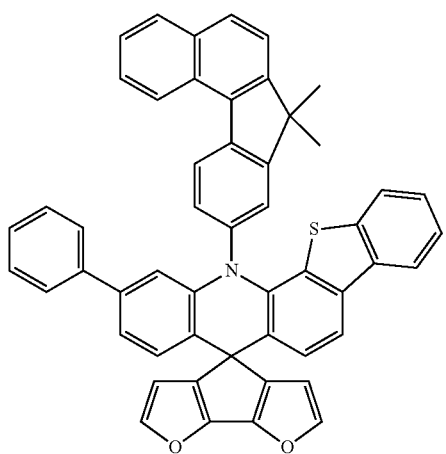 | C97 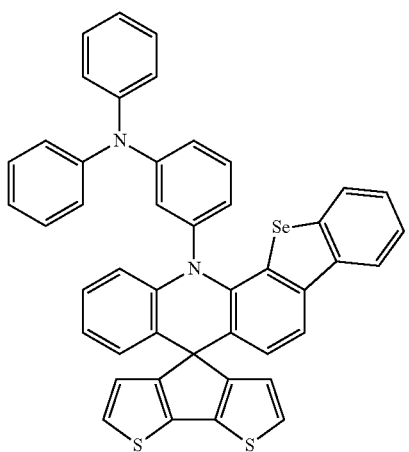 |

-continued
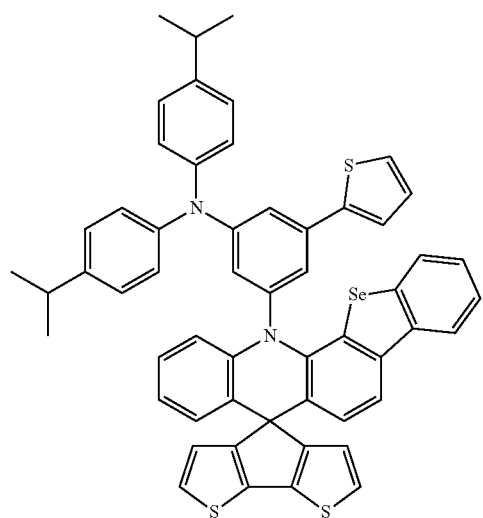
C98
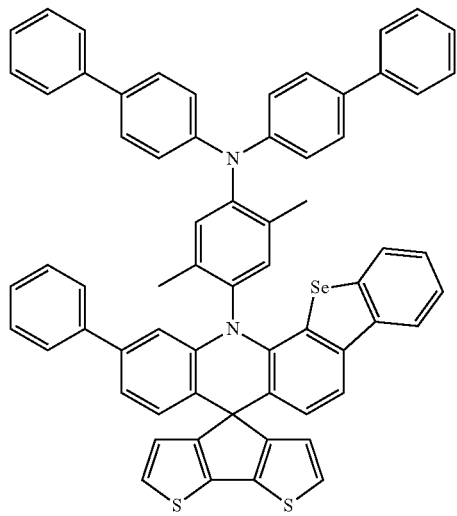
C99
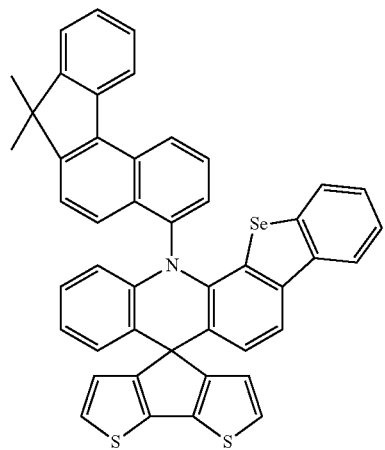
C100
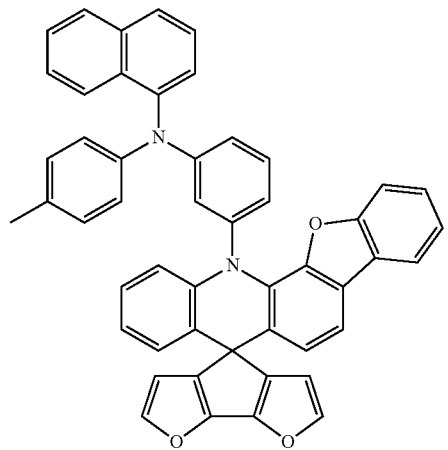
C101
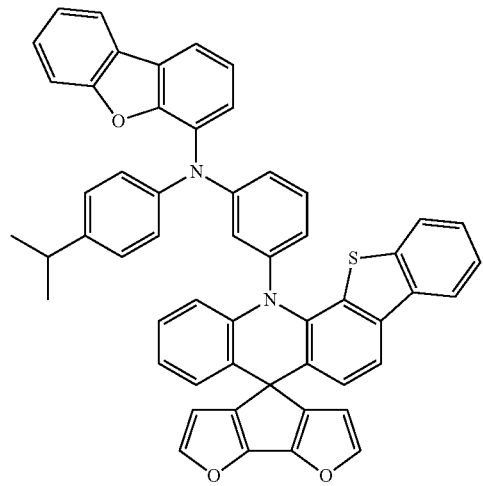
C102
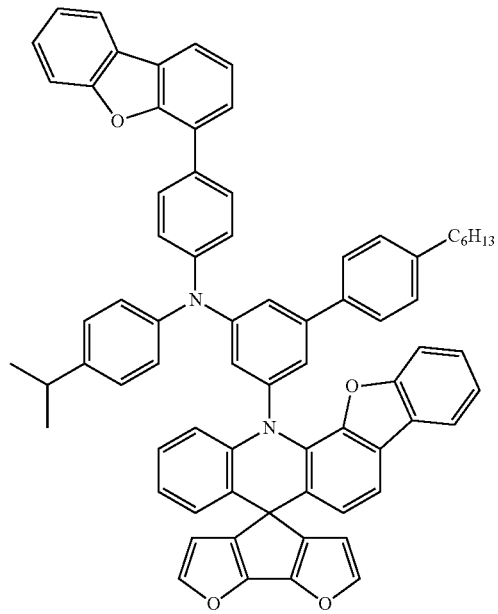
C103

-continued
C104
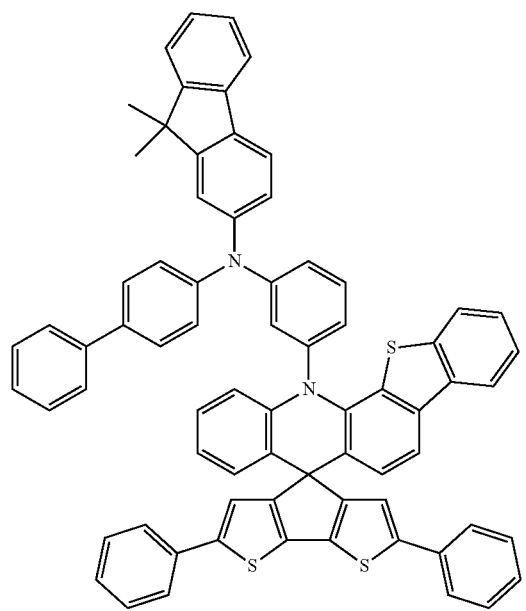
C105
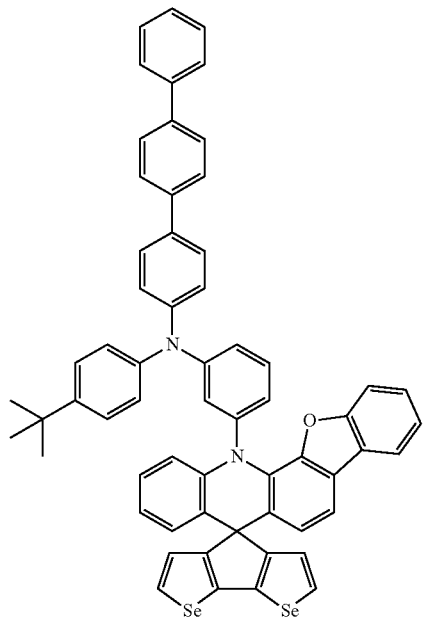
C106
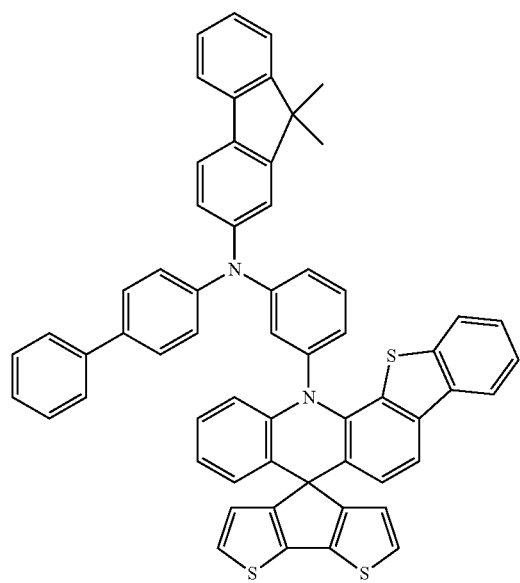

-continued
C107
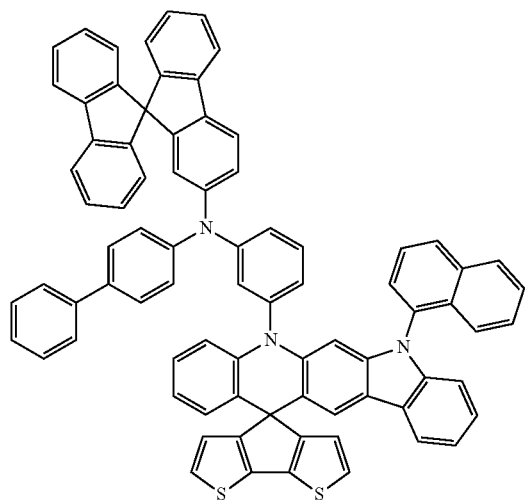
C108
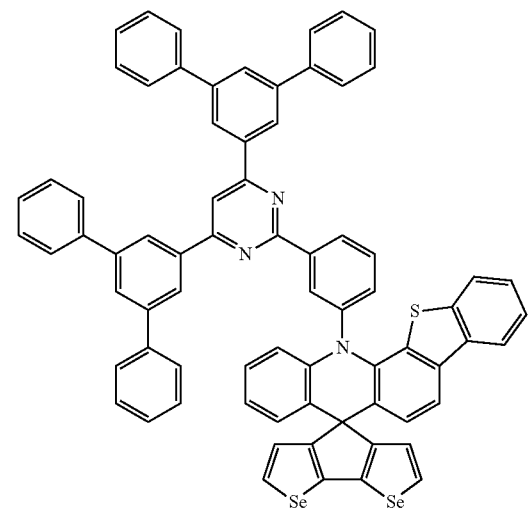
C109
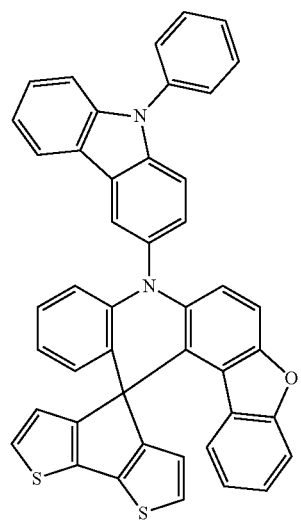
C110
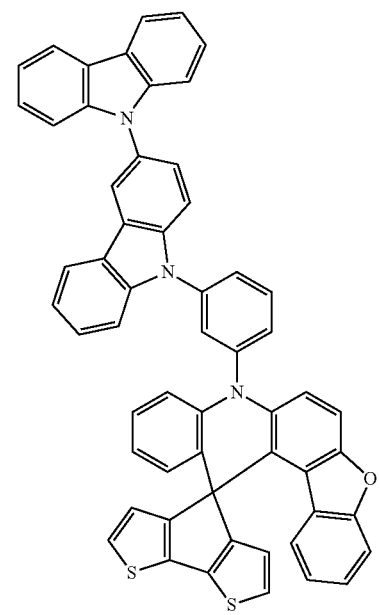
C111
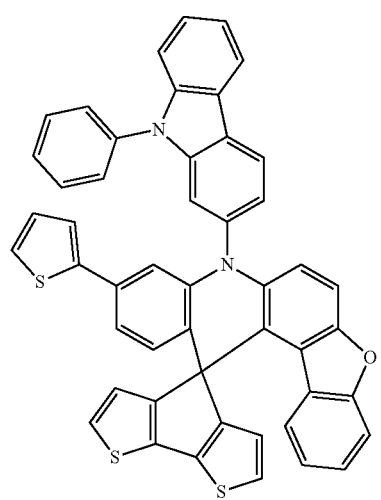

C112
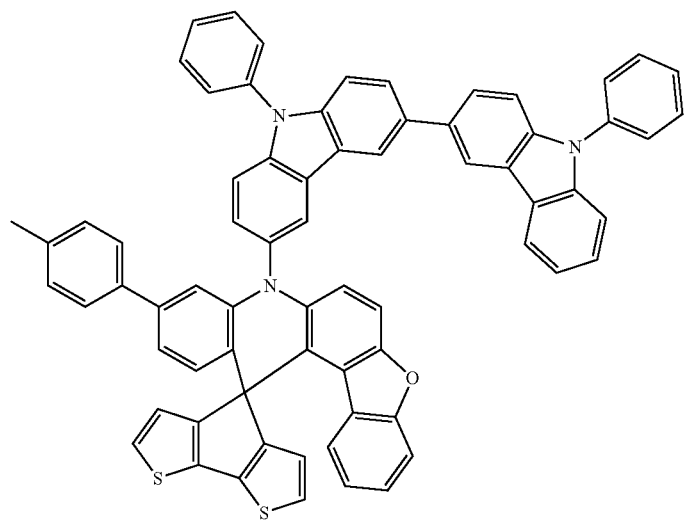
C113
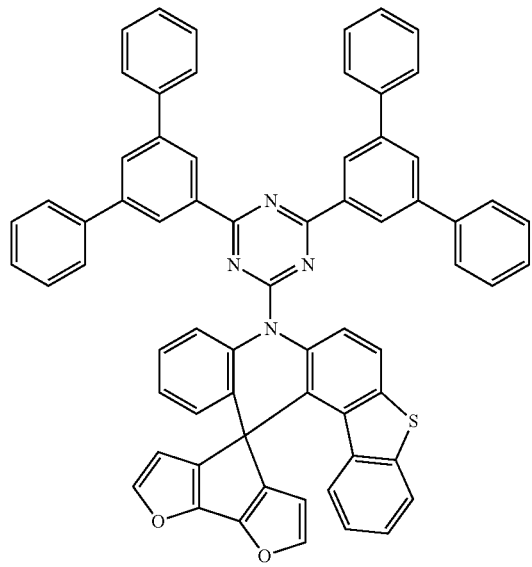
C114
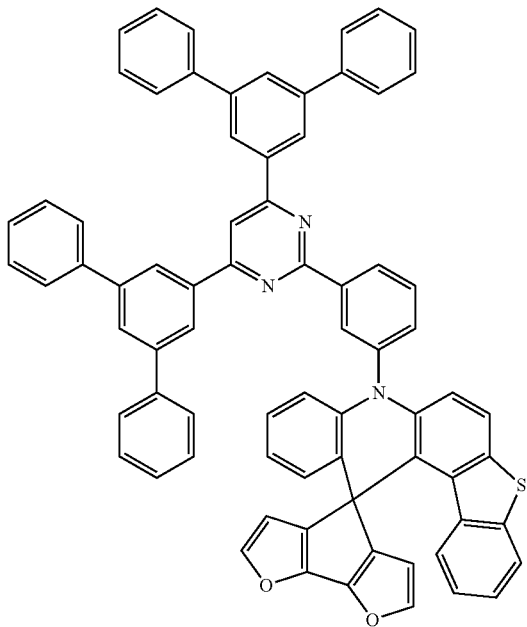
C115
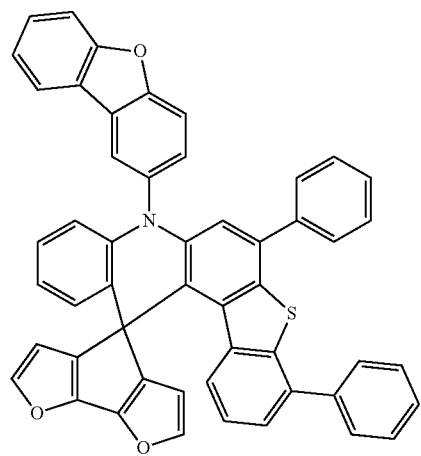
C116
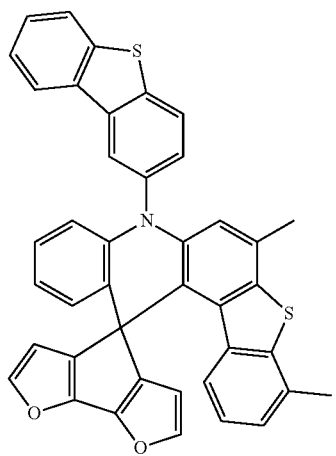

-continued
C117 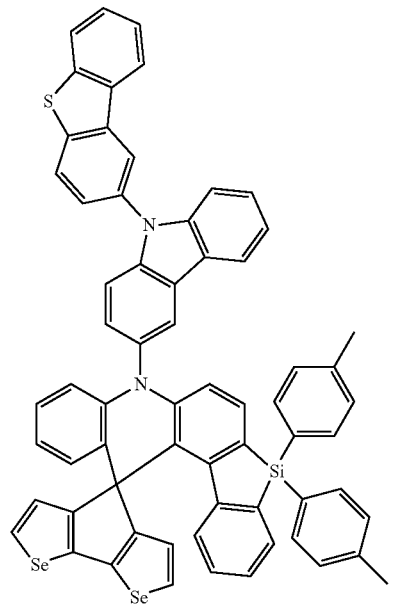
C118 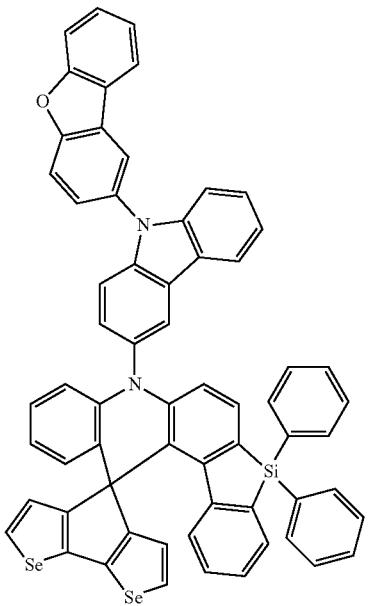
C119 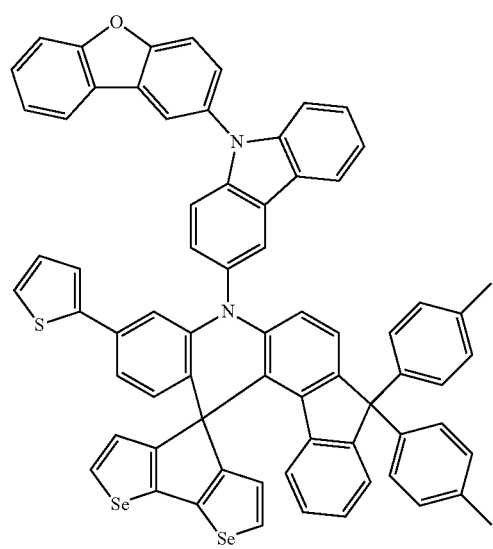
C120 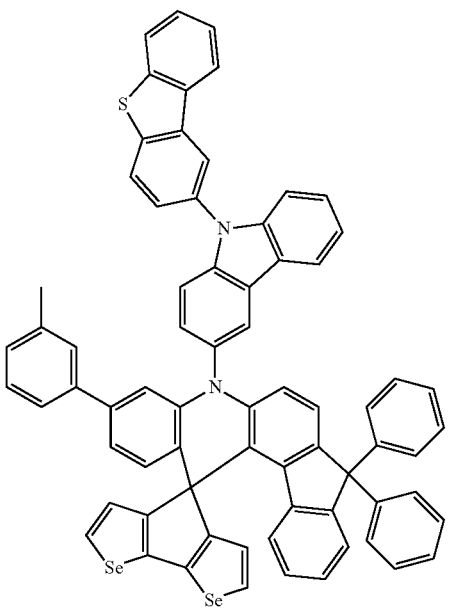
C121 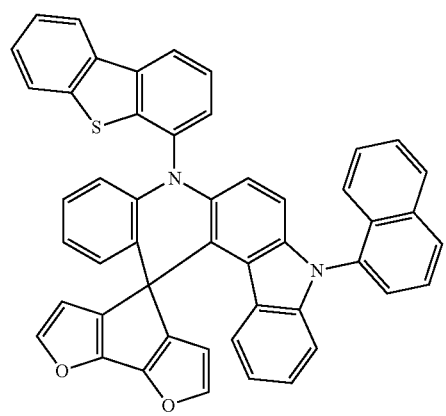
C122 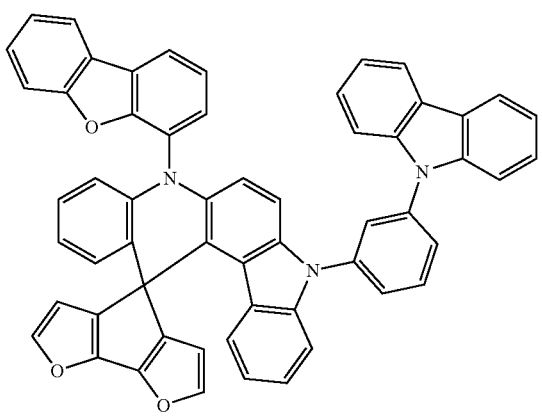

-continued
C123
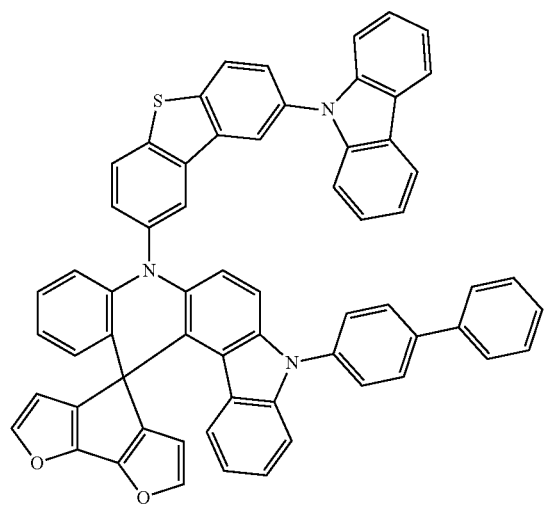
C124
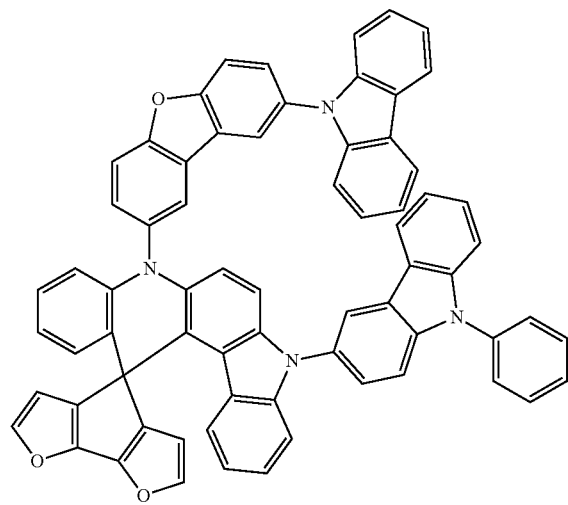
C125
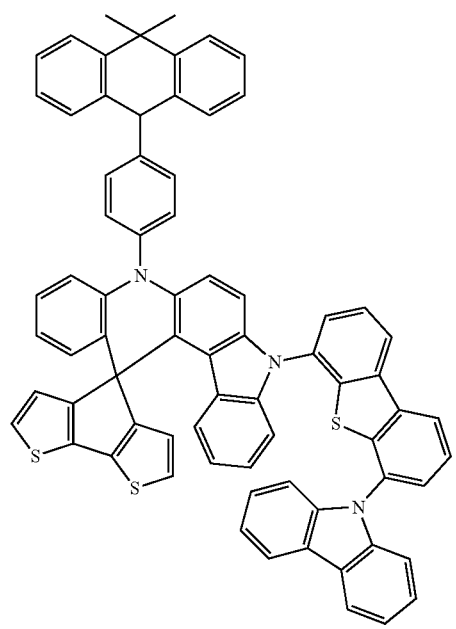
C126
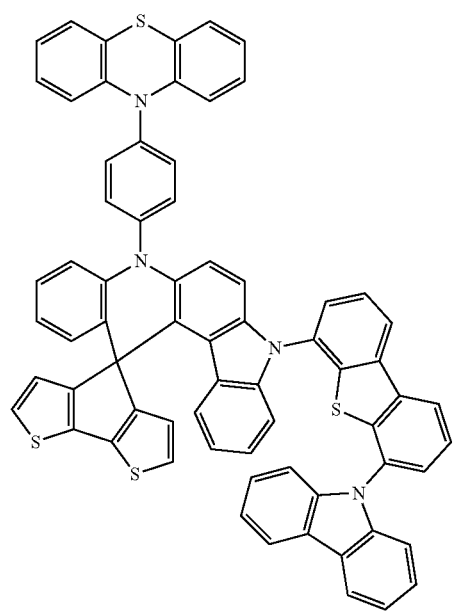

-continued
C127
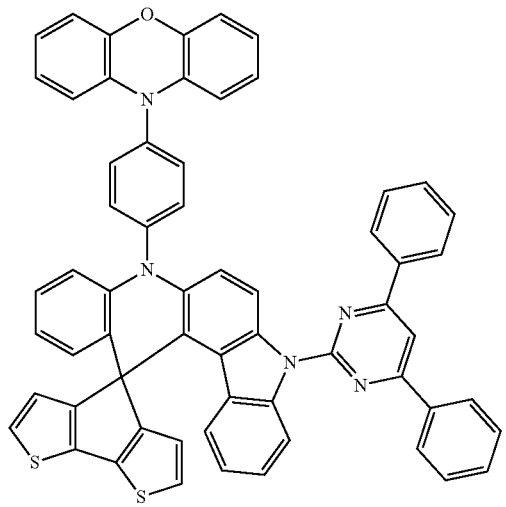
C128
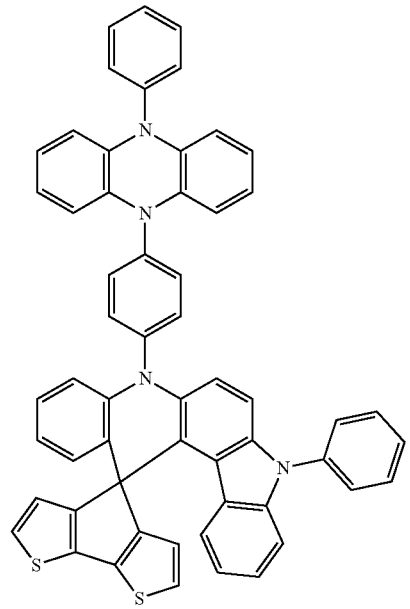
C129
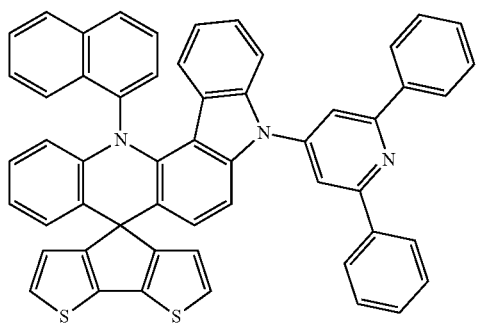
C130
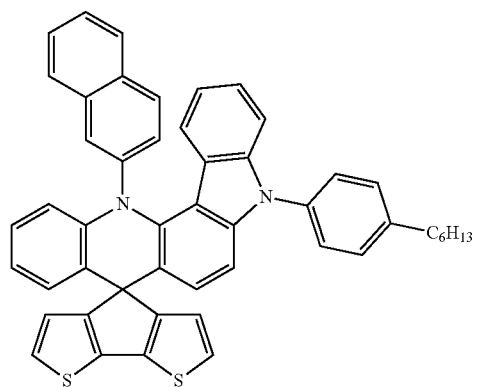
C131
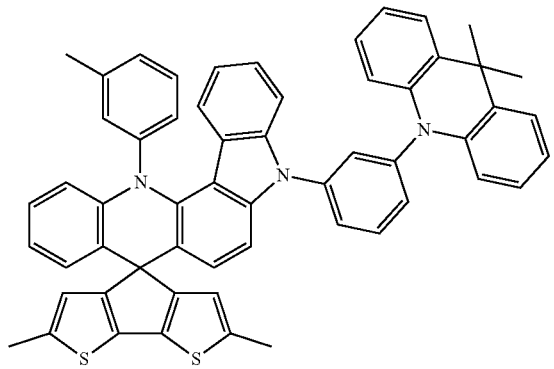
C132
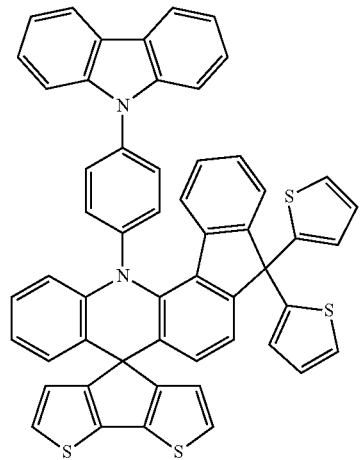

-continued
C133
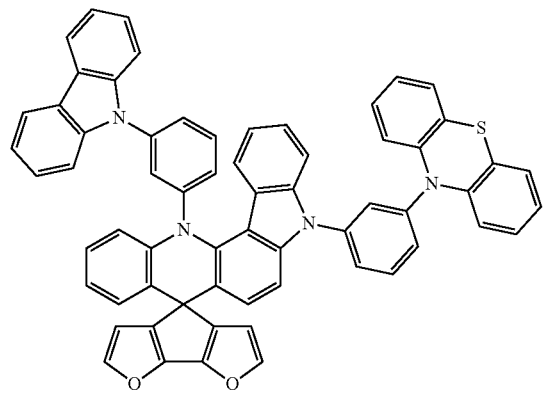
C134
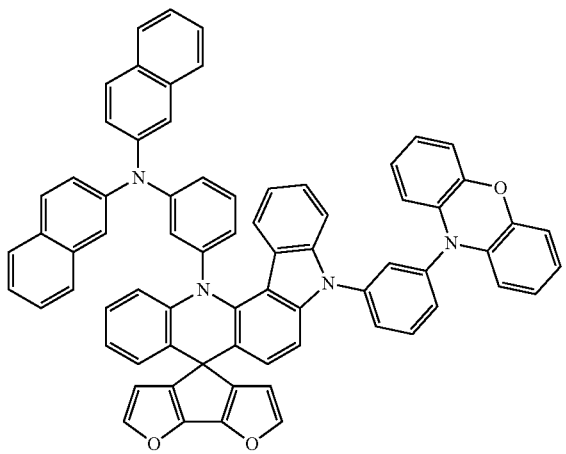
C135
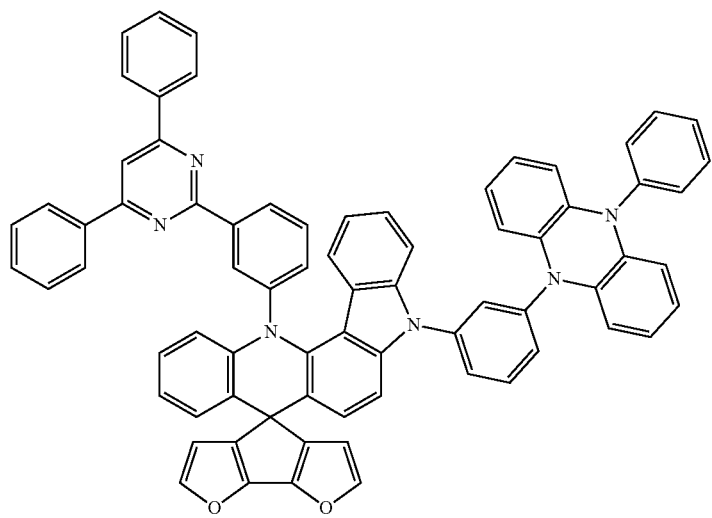
C136
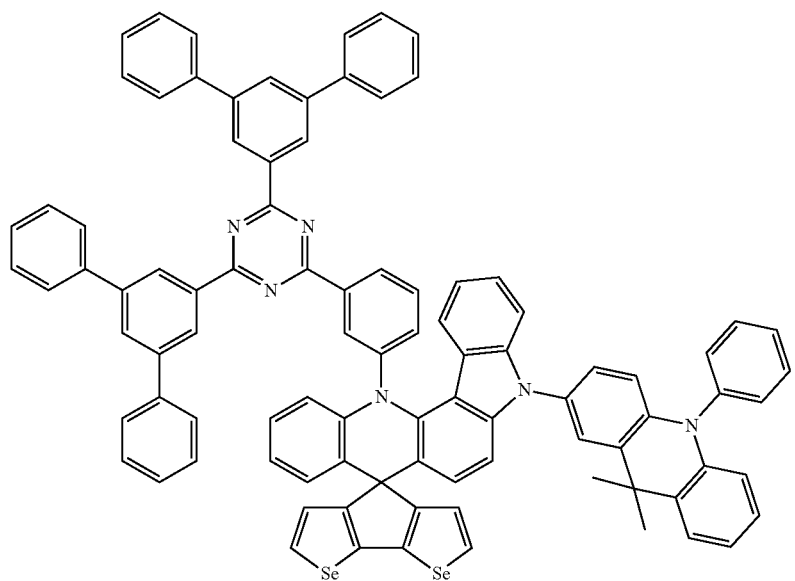

-continued
C137
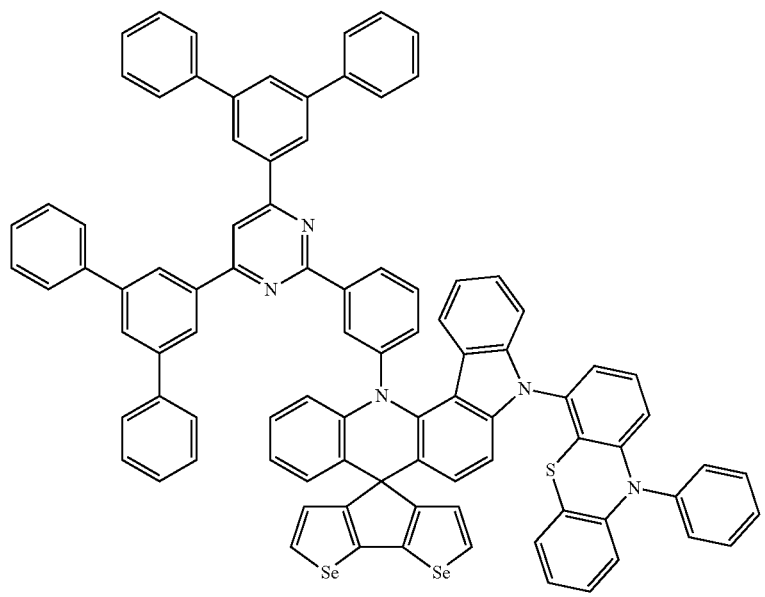
C138
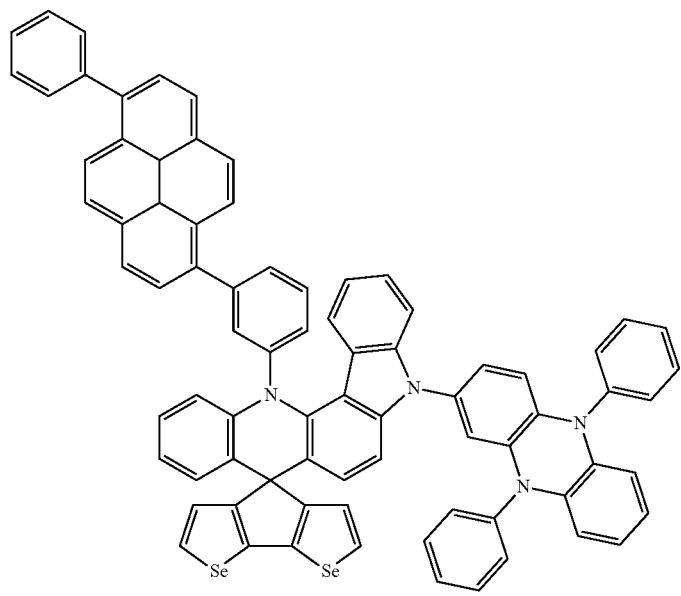
C139
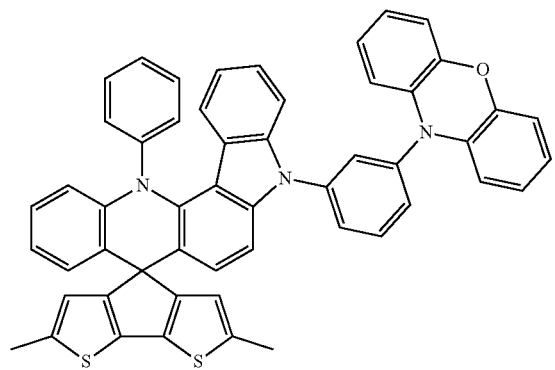

-continued
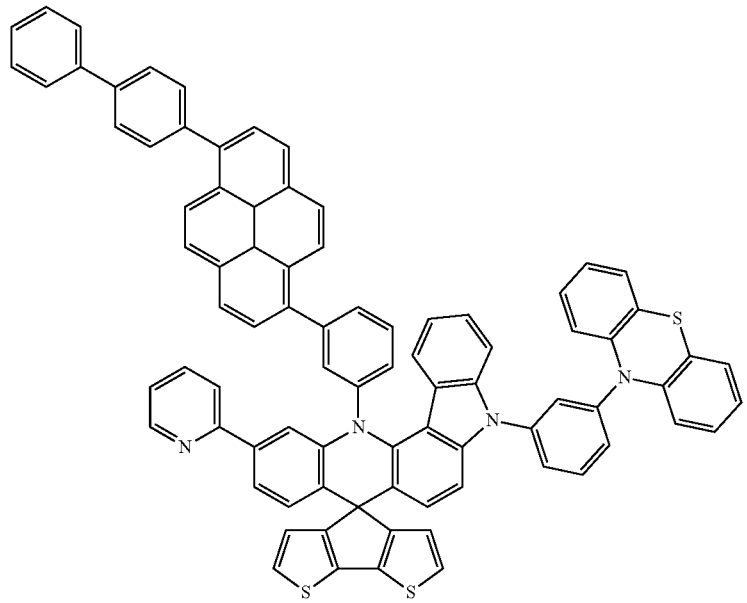
C140
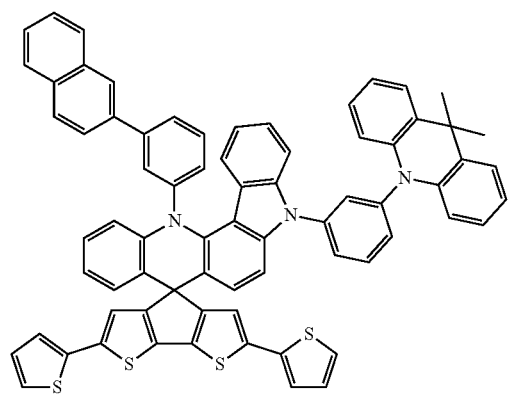
C141
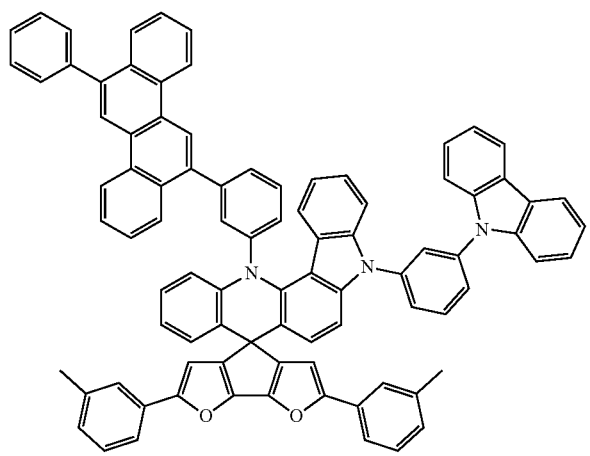
C142
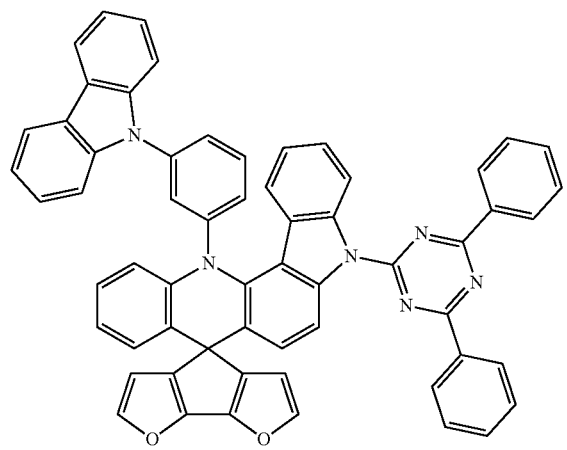
C143
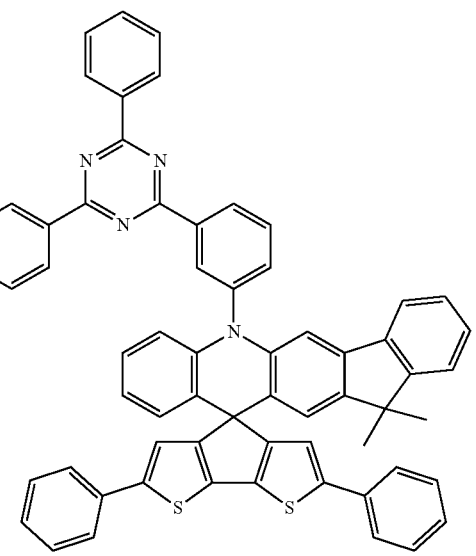
C144

-continued
C145
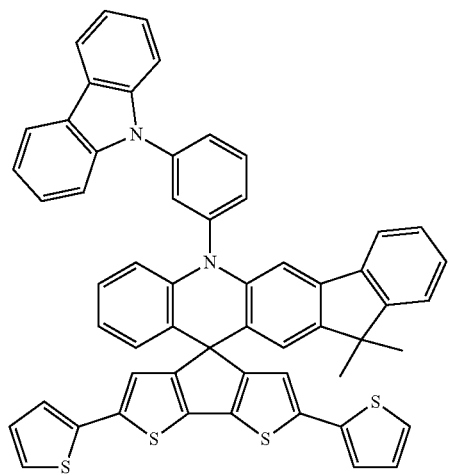
C146
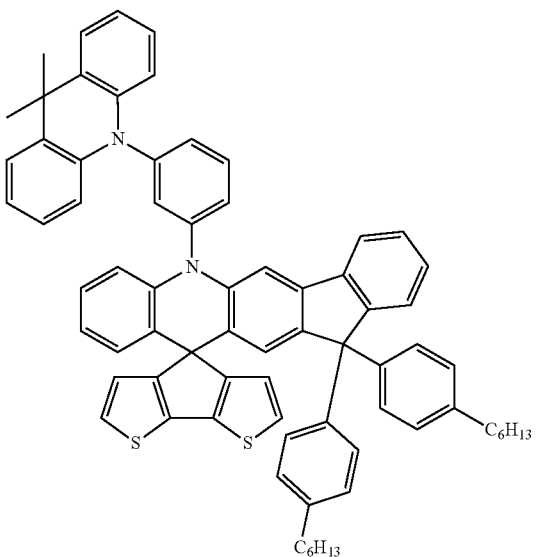
C147
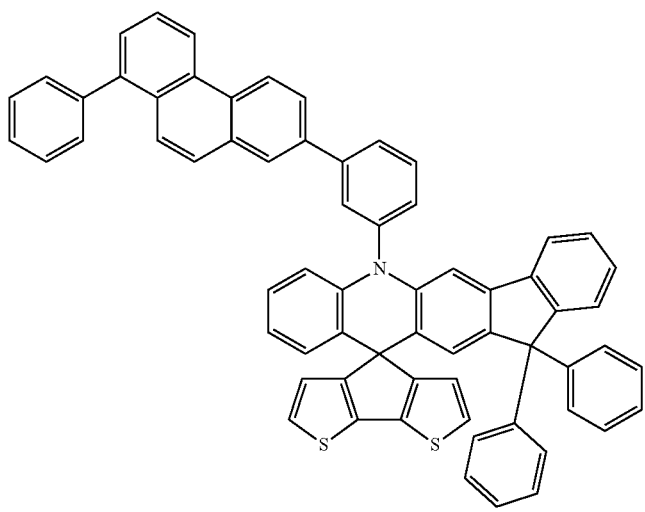
C148
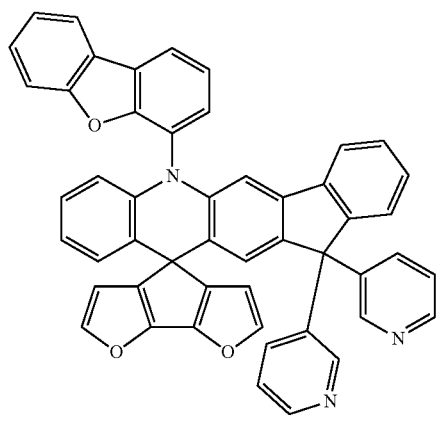
C149
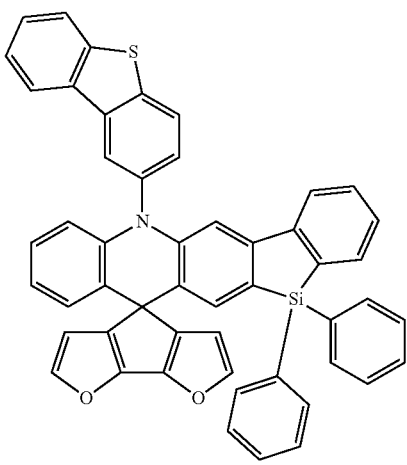

-continued
C150
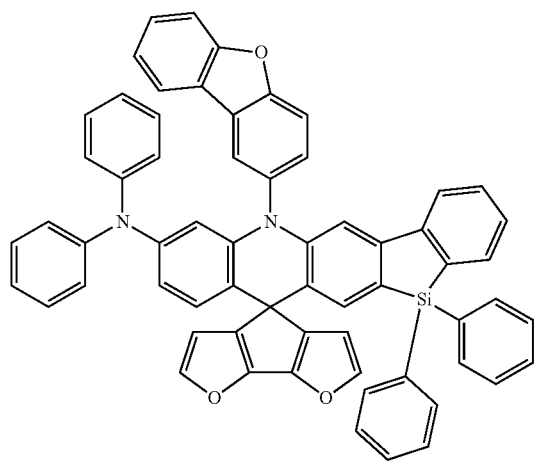
C151
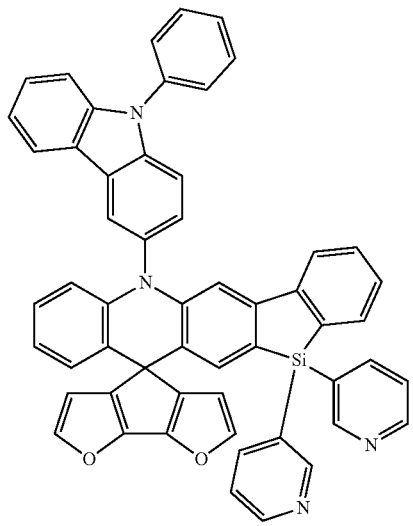
C152
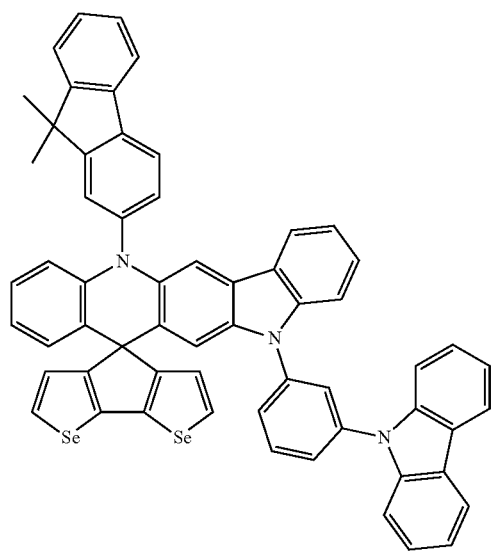
C153
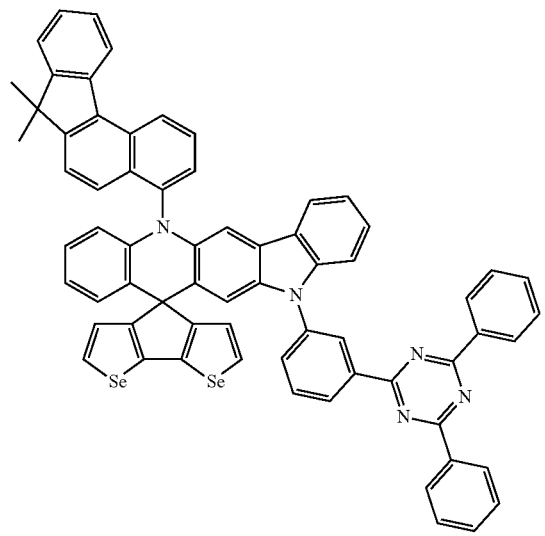
C154
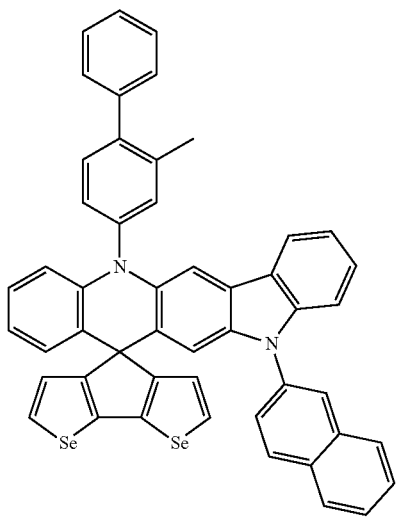

-continued
C155
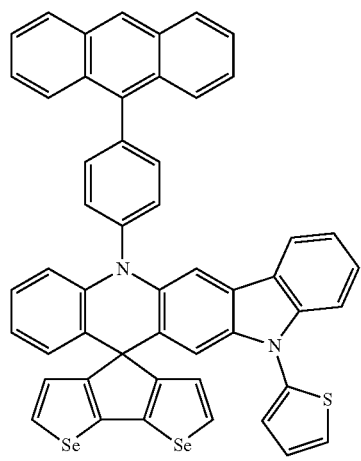
C156
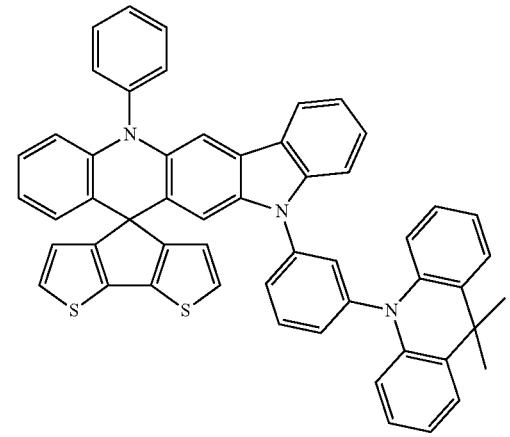
C157
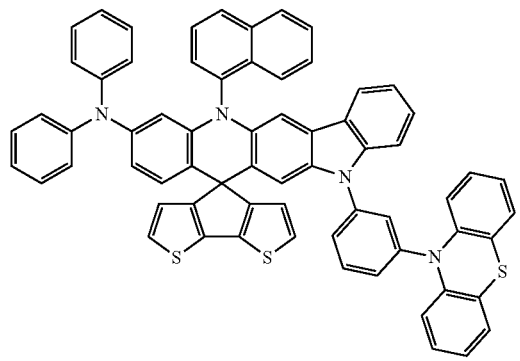
C158
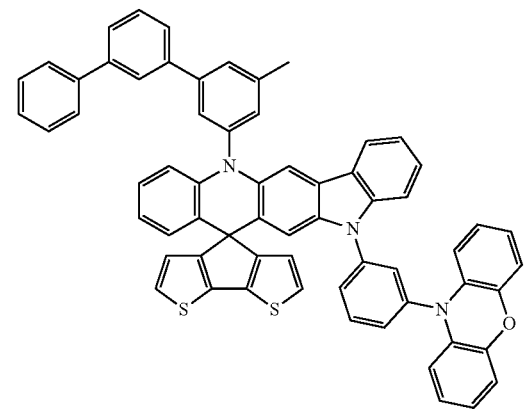
C159
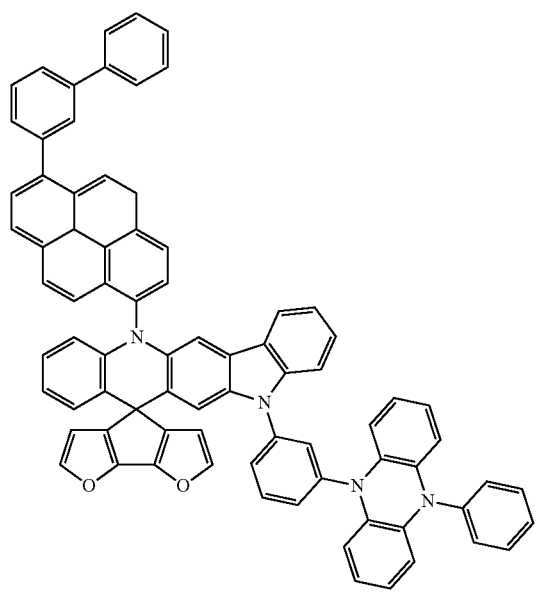
C160
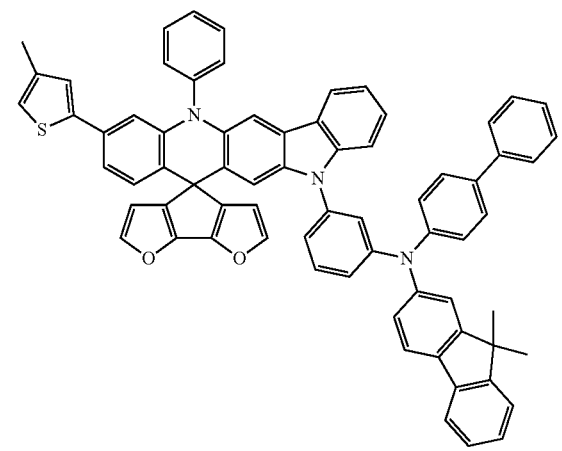

-continued
C161
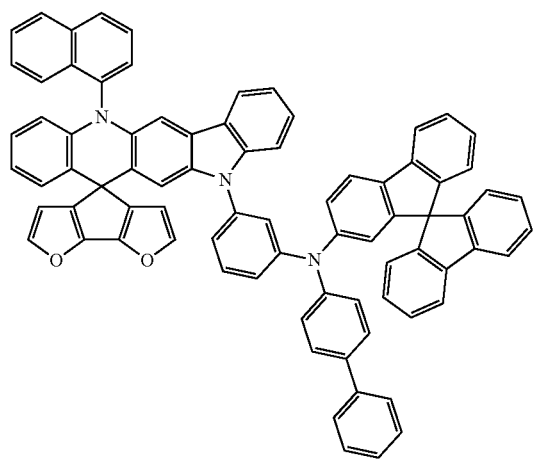
C162
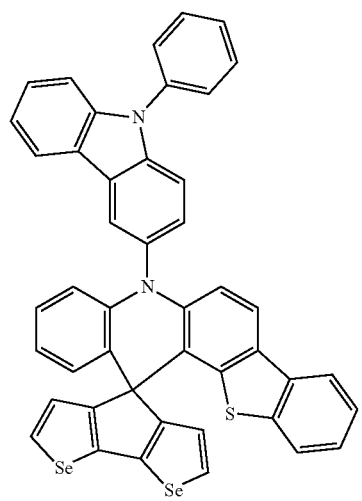
C163
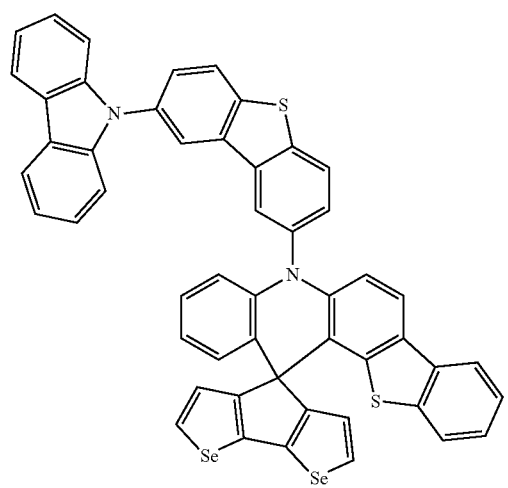
C164
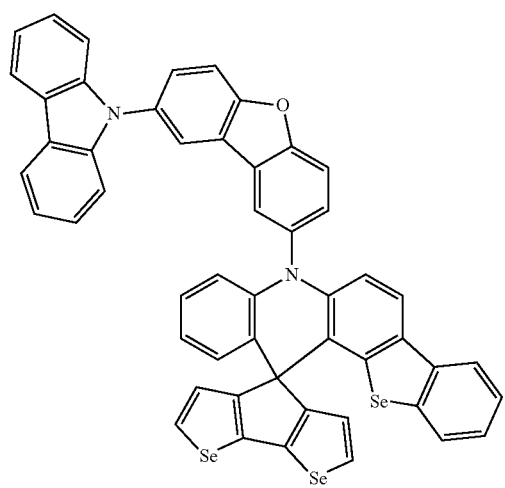
C165
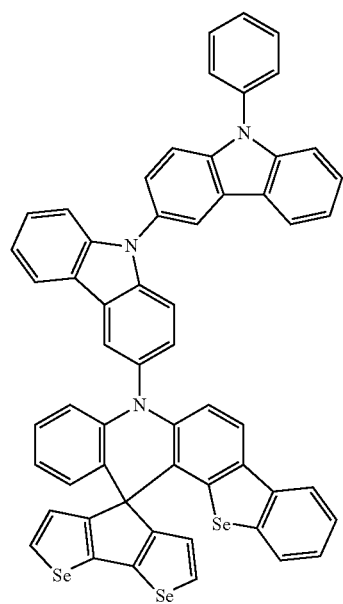
C166
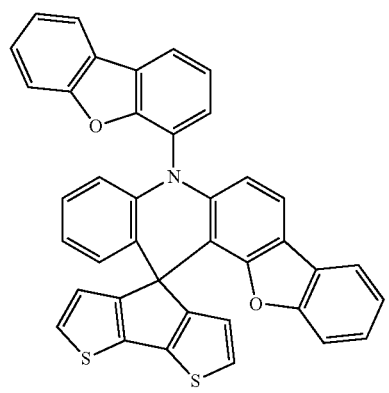

-continued
C167
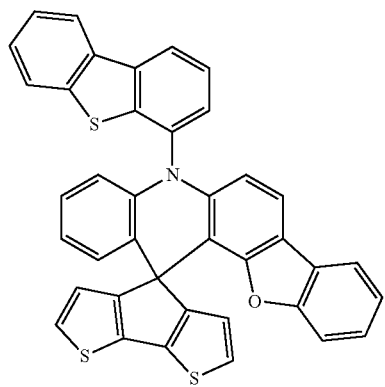
C168
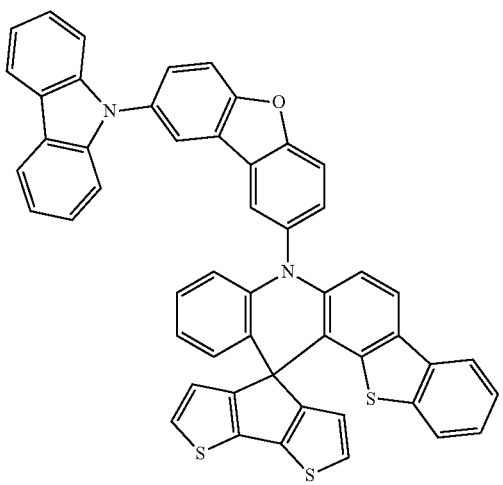
C169
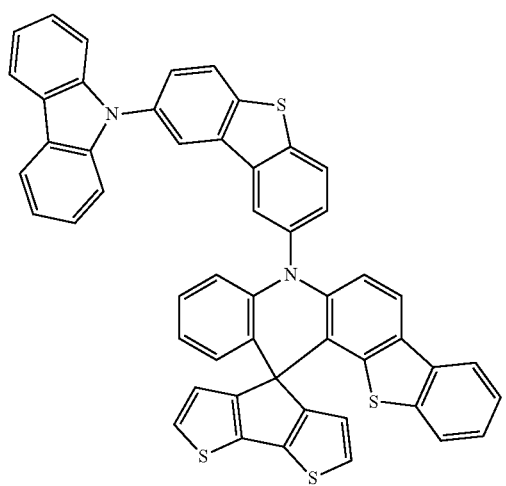
C170
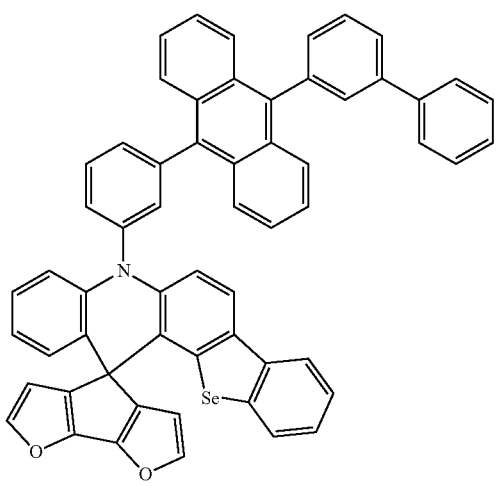
C171
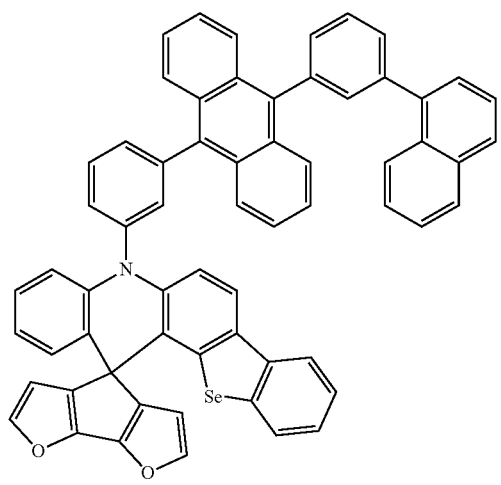
C172
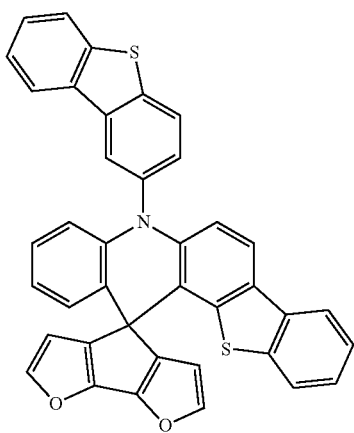

-continued
C173
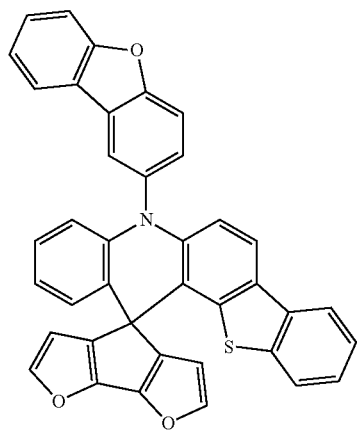
C174
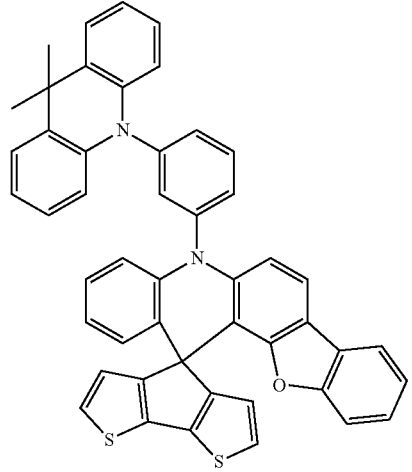
C175
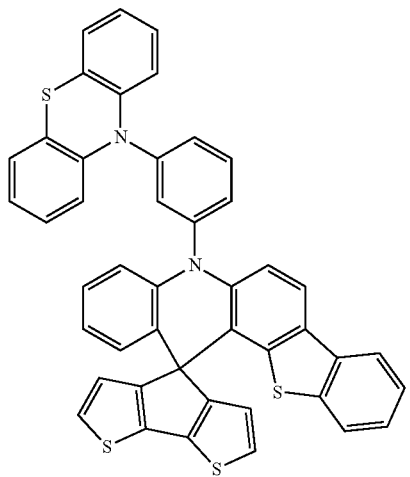
C176
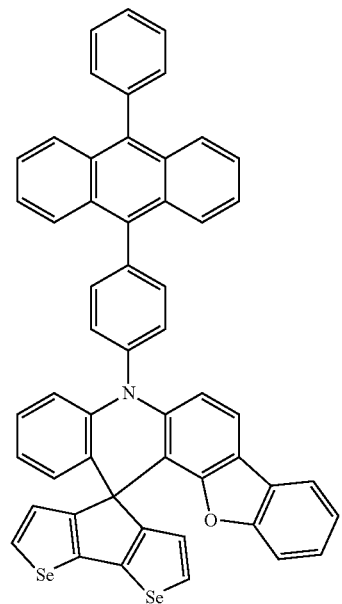
C177
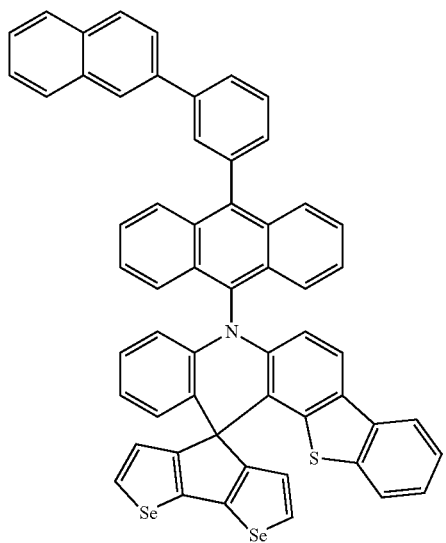
C178
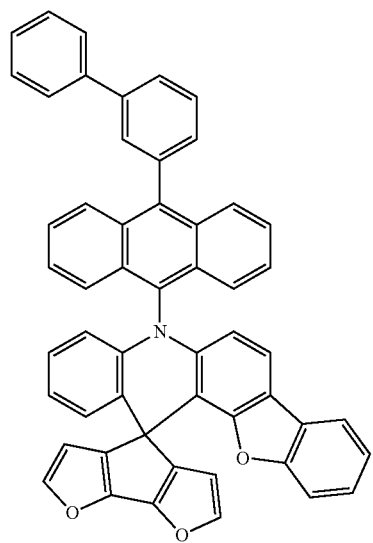

-continued
C179
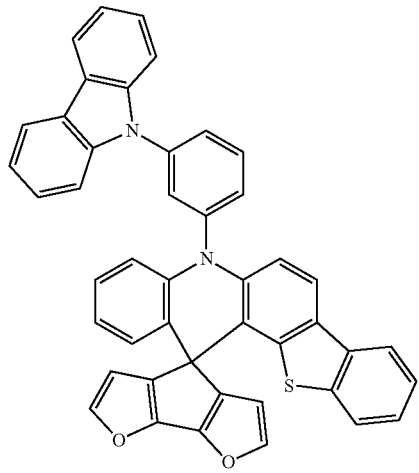
C180
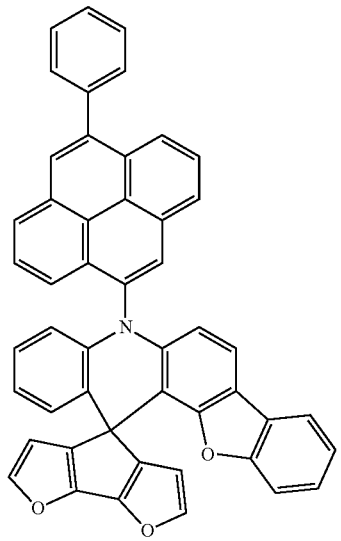
C181
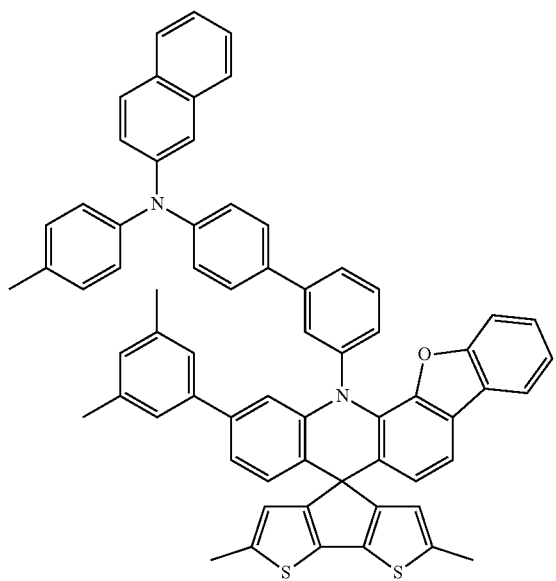
C182
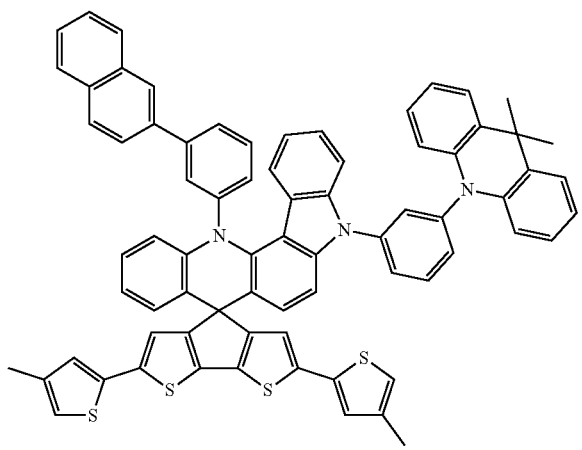

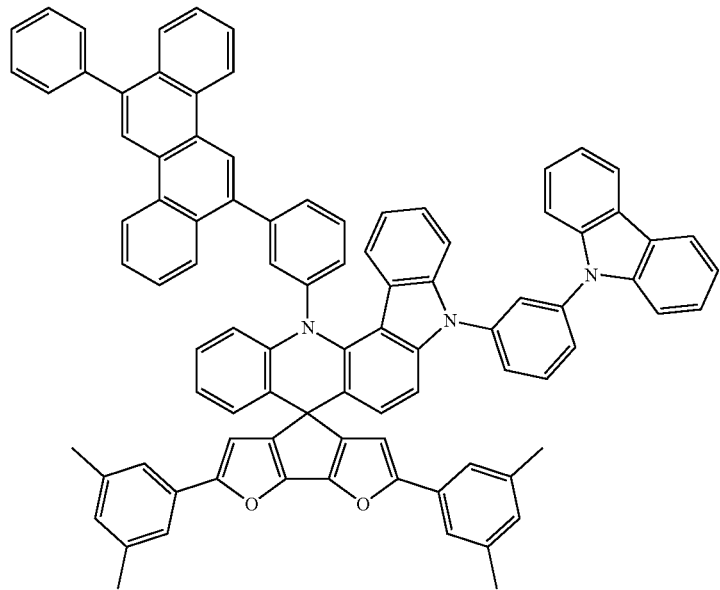
C183
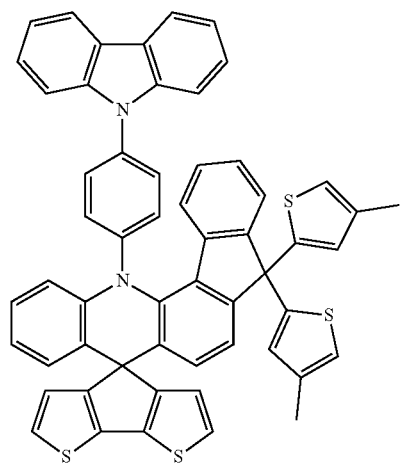
C184
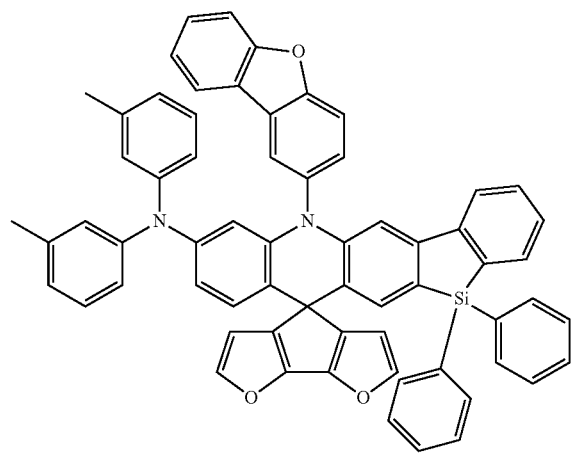
C185

-continued
C186
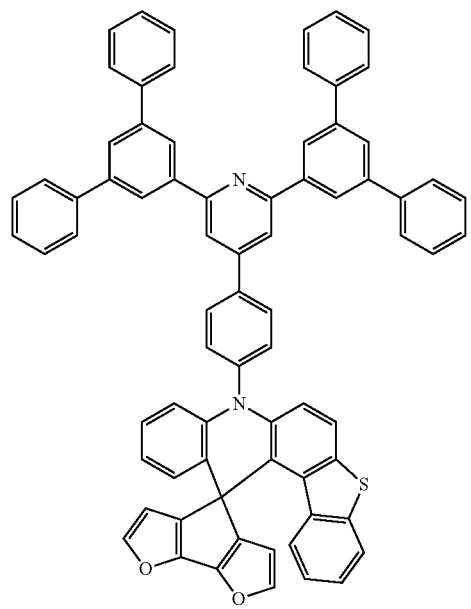
C187
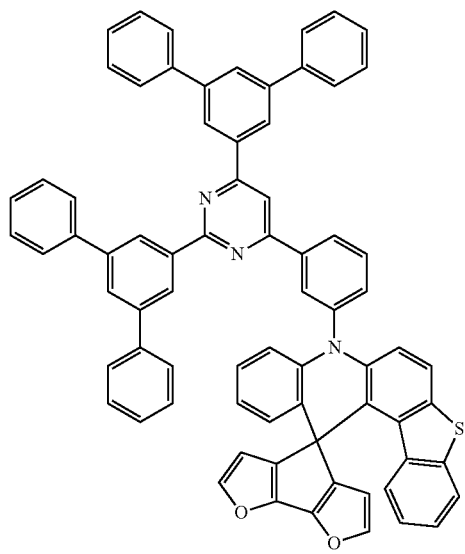
C188
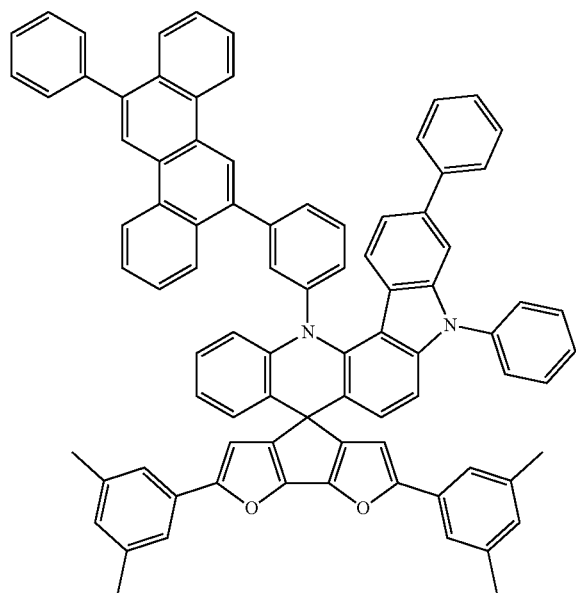
C189
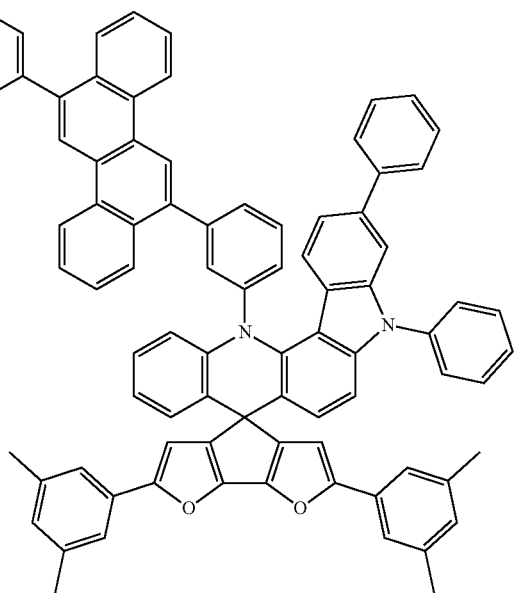

-continued
C190
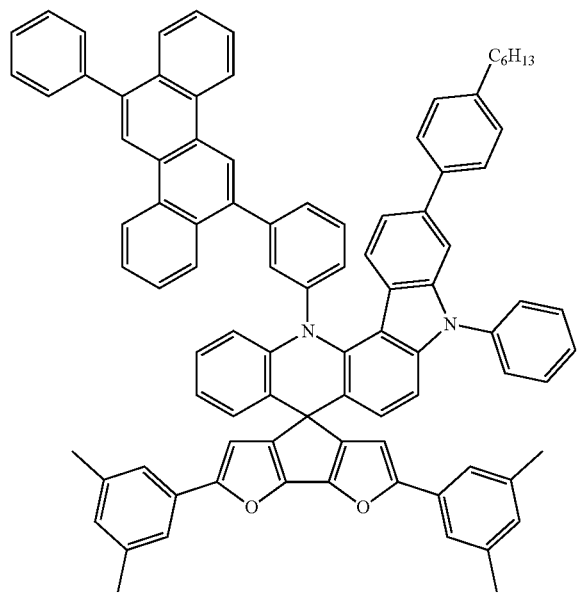
C191
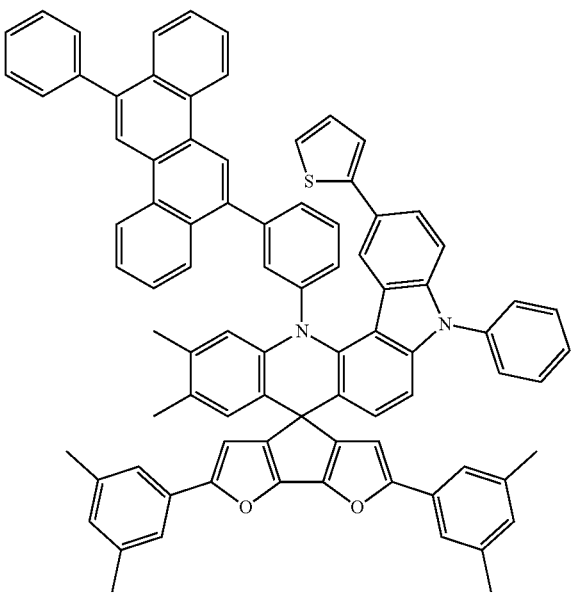
C192
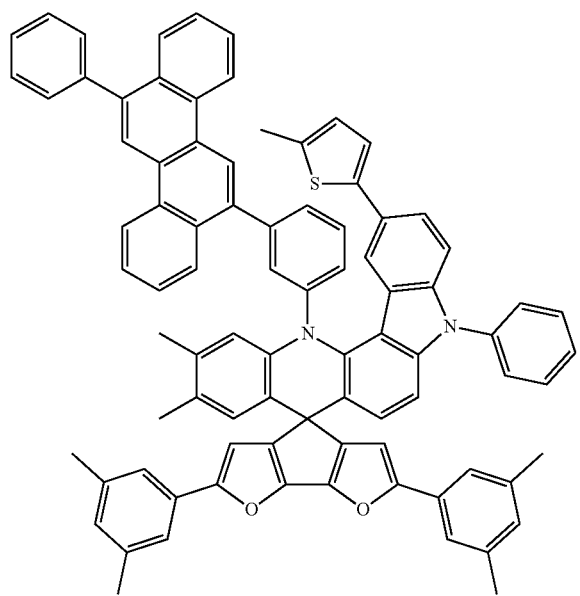
C193
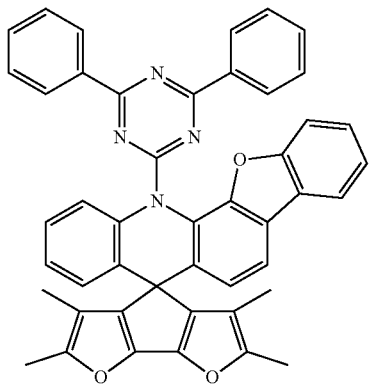

-continued
C194
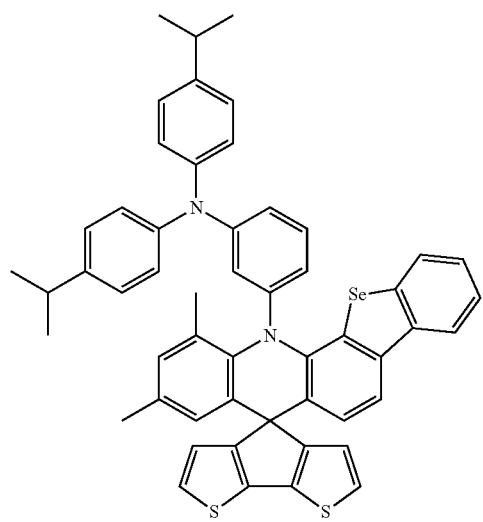
C195
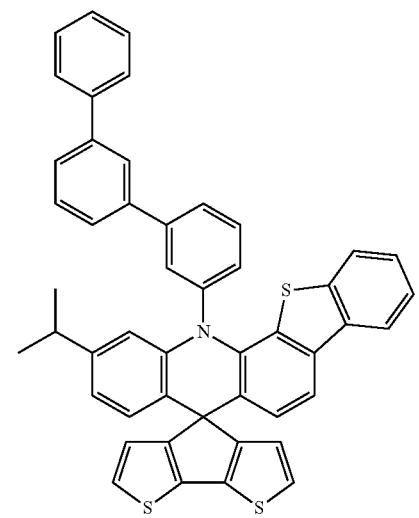
C196
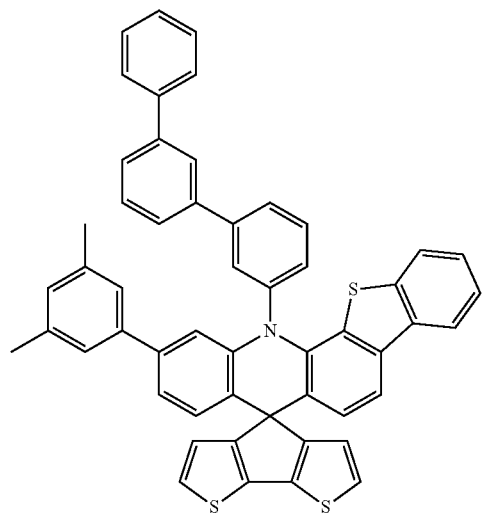
C197
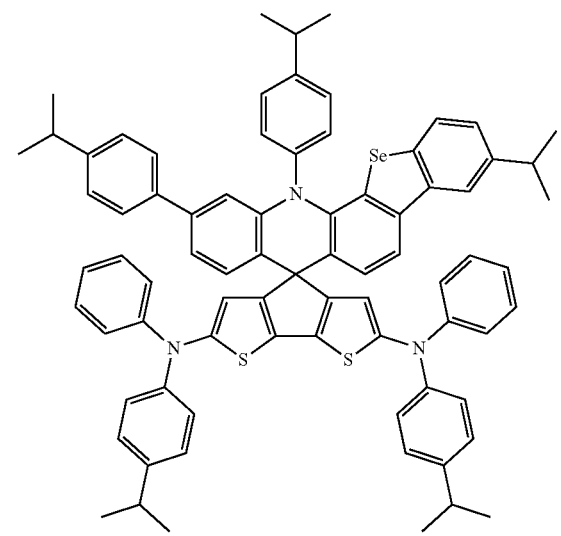
C198
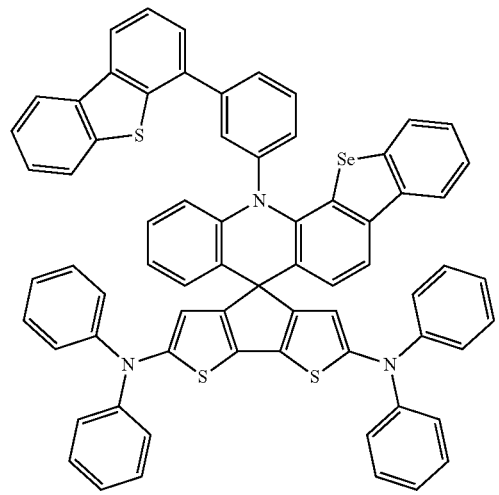
C199
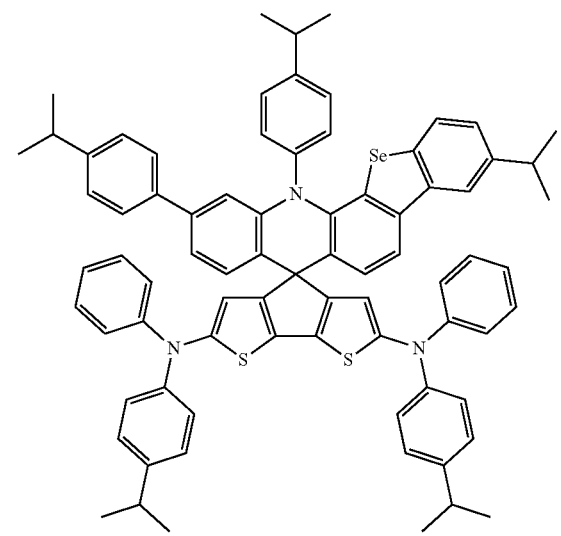

C200

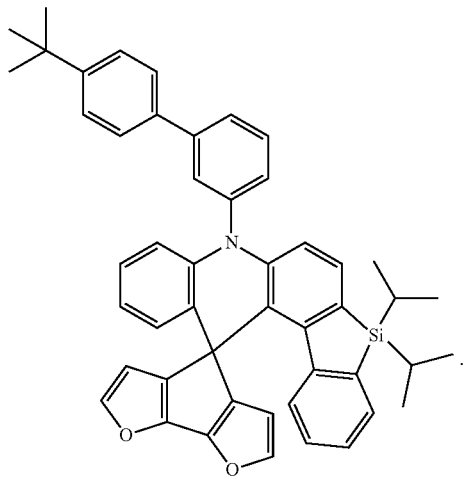

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. At least one of the light emitting layer and the organic thin film layer comprises the polyheteroaromatic compound of formula (1).

In some embodiments, the light emitting layer comprising the polyheteroaromatic compound of formula (1) is a host material. The host material may be a phosphorescent host material or a fluorescenct host material. In certain embodiments, the light emitting layer comprising the polyheteroaromatic compound of formula (1) is used as a fluorescent dopant. material.

In some embodiments, the light emitting layer comprising the polyheteroaromatic compound of formula (1) is a thermally activated delayed fluorescence host material. In other embodiments, the light emitting layer comprising the polyheteroaromatic compound of formula (1) is used as a thermally activated delayed fluorescence dopant material. In some embodiments, the organic thin film layer comprising the polyheteroaromatic compound of formula (1) is an electron transporting layer.

In a further embodiment of the present invention, the organic electroluminescence device is a lighting panel. In other embodiment of the present invention, the organic electroluminescence device is a backlight panel.

Detailed preparation of the polyheteroaromatic compounds of the present invention will be clarified by exemplary embodiments below, but the present invention is not limited thereto. EXAMPLES 1 to 6 show the preparation of the polyheteroaromatic compounds of the present invention, and EXAMPLE 7 shows the fabrication and test report of the organic EL device.

EXAMPLE 1

Synthesis of N-(2-bromophenyl)-9,9-dimethyl-9H-fluoren-2-amine

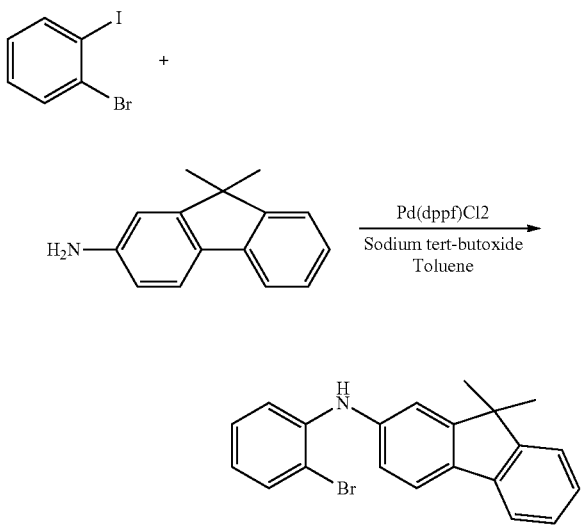

A mixture of 10 g (35.3 mmol) of 1-bromo-2-iodobenzene, 7.4 g (35.3 mmol) of 9,9-dimethyl-9H-fluoren-2-amine, 0.52 g (0.7 mmol) of Pd(dppf)Cl$_2$, 6.8 g (70.6 mmol) of sodium tert-butoxide, and 60 ml of toluene was degassed and placed under nitrogen, and then heated at 100° C. for 2 h. After the reaction was finished, the mixture was allowed to cool to room temperature and then filtered to remove the solvent. The crude product was purified by column chromatography, yielding 9.4 g of yellow solid (73%). $^1$H NMR (CDCl3, 400 MHz): chemical shift (ppm) 8.11 (d, 1H), 7.65 (d, 1H), 7.55 (d, 2H), 7.43 (m, 1H), 7.31 (m, 1H), 7.18 (m, 2H), 6.68-6.74 (m, 2H), 6.50-6.56 (m, 2H) , 4.11 (s, 1H), 1.68 (s, 6H).

Synthesis of 7',7'-dimethyl-5',7'-dihydrospiro[cyclopenta-[1,2-b:5,4-b']dithiophene-4,13'-indeno[1,2-b]acridine]

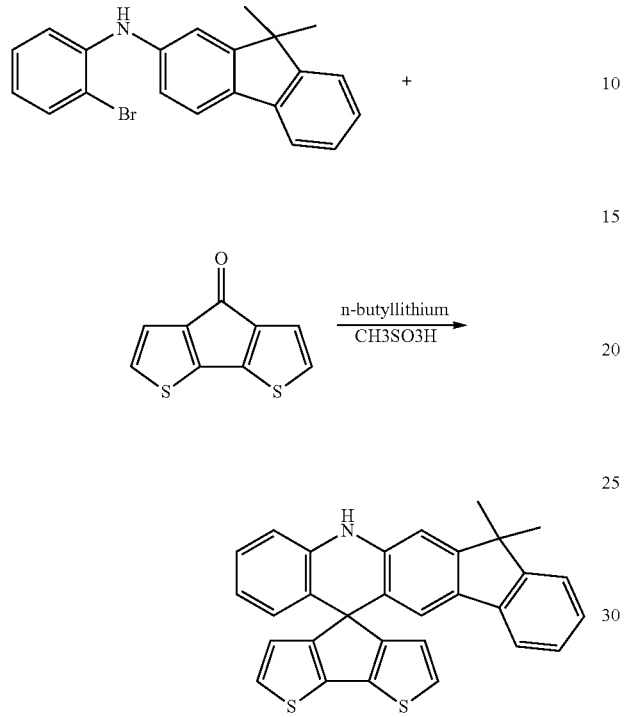

A mixture of 5 g (13.7 mmol) of N-(2-bromophenyl)-9,9-dimethyl-9H-fluoren-2-amine and 100 ml of THF was cooled in a dry ice bath, and then 8.2 ml of n-butyllithium (2.5 M in Hexane, 20.6 mmol) was added dropwisely thereto and then stirred for 1 h in a dry ice bath. Afterwards, 2.9 g of 4H-cyclopenta[1,2-b:5,4-b']-dithiophen-4-one dissolved in 20 ml of THF was added dropwisely and stirred for 1 h at the room temperature, and then heated at 70° C. for 12 h. The solvent was removed from the resulting mixture under reduced pressure. Subsequently, 1.58 g of methanesulfonic acid and 50 ml of CHCl₃ were added and then stirred at 60° C. for 2 h. After the reaction was finished, the mixture was allowed to cool to room temperature and the solvent was removed. The crude product was purified by column chromatography, yielding 1.64 g of brown solid (26%). ¹H NMR (CDCl3, 400 MHz): chemical shift (ppm) 8.05 (d, 1H), 7.61 (m, 3H), 7.44 (d, 2H), 7.27-7.33 (m, 1H), 6.92 -7.01 (m, 4H), 6.64-6.68 (m, 2H),6.48 (d, H),4.13 (s, 1H), 1.66 (s, 6H).

Synthesis of compound C3

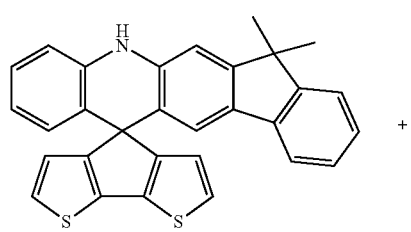 +

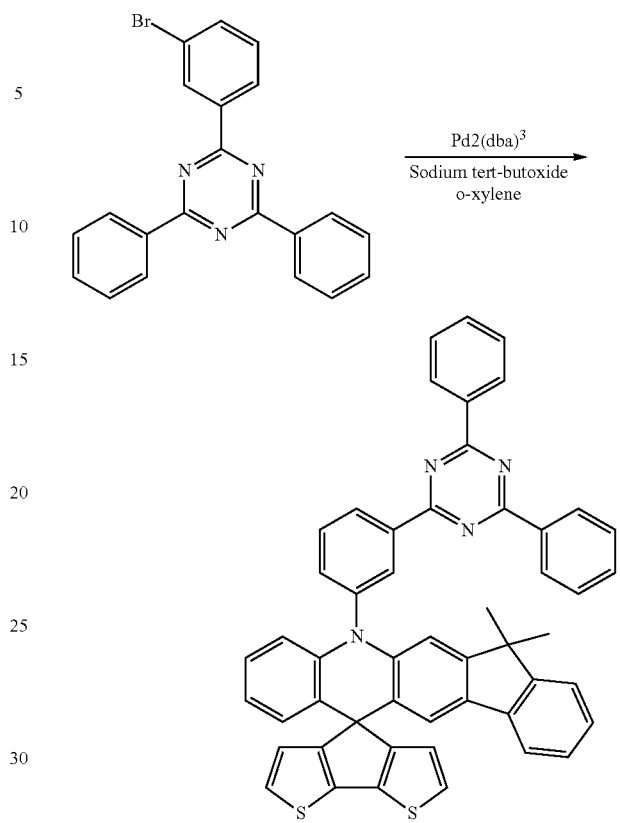

A mixture of 1 g (2.18 mmol) of 7',7'-dimethyl-5',7'-dihydrospiro-[cyclopenta-[2-b:5,4-b']dithiophene-4,13'-indeno[1,2-b]acridine], 0.93 g (2.39 mmol) of 2-(3-bromophenyl)-4,6-diphenyl-1,3,5-triazine, 0.04 g (0.04 mmol) of Pd₂(dba)₃, and 30 ml of o-xylene was degassed and placed under nitrogen, and then heated at 120° C. for 3 h. After the reaction was finished, the mixture was allowed to cool to room temperature. Subsequently, 50 ml of methanol was added to the mixture, which was then filtered and washed by methanol, yielding 1.13 g of yellow solid (68%). ¹H NMR (CDCl3, 400 MHz): chemical shift (ppm) 8.35 (d, 4H), 7.93 (d, 1H),7.69 (d, 1H), 7.52-7.59 (m, 7H), 7.34-7.42 (m, 6H), 7.26 (m, 1H), 6.96-7.02 (m, 3H), 6.86 (d, 1H), 6.61-6.67 (d, 3H), 6.52 (d, 1H), 1.69 (s, 6H). MS (m/z, EI⁺): 766.7.

EXAMPLE 2

Synthesis of Compound C12

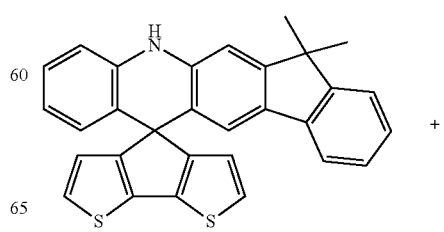 +

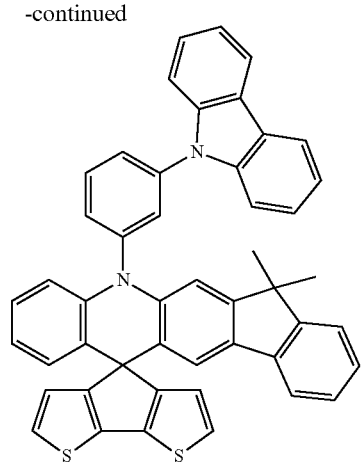

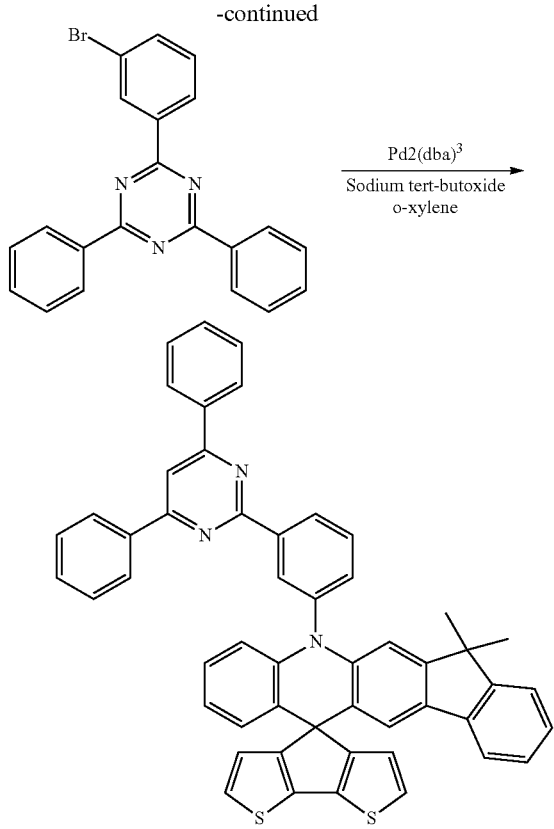

The same synthesis procedure as in EXAMPLE 1 was used, except that 12-(3-bromophenyl)-4,6-diphenylpyrimidine was used instead of 2-(3-bromophenyl)-4,6-diphenyl-1,3,5-triazine to obtain the compound of 5'-(3-(4,6-diphenylpyrimidin-2-yl)phenyl)-7',7'-dimethyl-5',7'-dihydrospiro[cyclopenta[1,2-b:5,4-b']dithiophene-4,13'-indeno[1,2-b]acridine]. MS (m/z, EI+): 765.6.

EXAMPLE 3

Synthesis of Compound C5

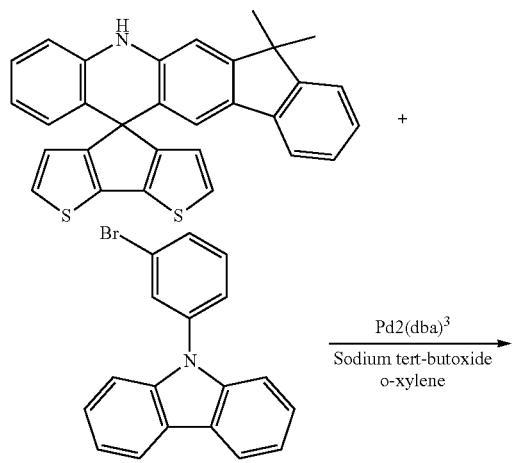

The same synthesis procedure as in EXAMPLE 1 was used, except that 9-(3-bromophenyl)-9H-carbazole was used instead of 2-(3-bromophenyl)-4,6-diphenyl-1,3,5-triazine to obtain the desired compound of 5'-(3-(9H-carbazol-9-yl)phenyl)-7',7'-dimethyl-5',7'-dihydrospiro[cyclopenta[1, 2-b:5,4-b']dithiophene-4,13'-indeno[1,2-b]acridine]. MS (m/z, EI+):700.6.

EXAMPLE 4

Synthesis of Compound C7

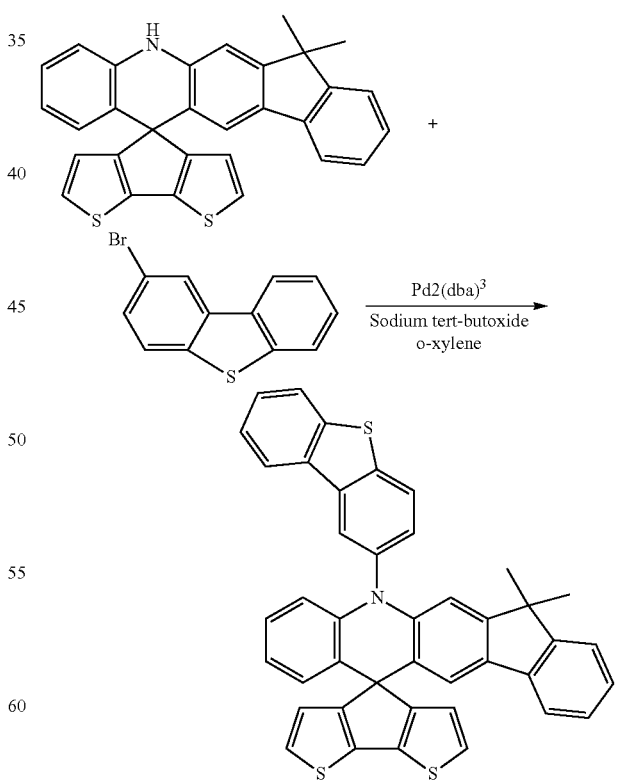

The same synthesis procedure as in EXAMPLE 1 was used, except that 2-bromodibenzo[b,d]thiophene was used instead of 2-(3-bromophenyl)-4,6-diphenyl-1,3,5-triazine to obtain the desired compound of 5'-(dibenzo[b,d]thiophen-2-yl)-7',7'-dimethyl-5',7'-dihydrospiro[cyclopenta[1,2-b:5,4-b']dithiophene-4,13'-indeno[1,2-b]acridine]. MS (m/z, EI+): 641.5.

EXAMPLE 5

Synthesis of Compound C8

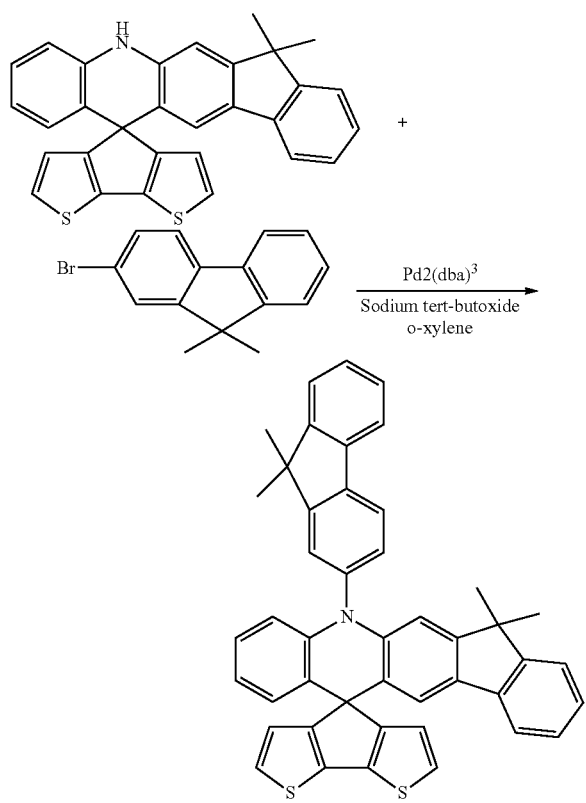

The same synthesis procedure as in EXAMPLE 1 was used, except that 2-bromo-9,9-dimethyl-9H-fluorene was used instead of 2-(3-bromophenyl)-4,6-diphenyl-1,3,5-triazine to obtain the desired compound of 5'-(9,9-dimethyl-9H-fluoren-2-yl)-7',7'-dimethyl-5',7'-dihydrospiro[cyclopenta[1,2-b:5,4-b']dithiophene-4,13'-indeno[1,2-b]acridine]. MS (m/z, EI+): 651.6.

EXAMPLE 6

Synthesis of Compound C6

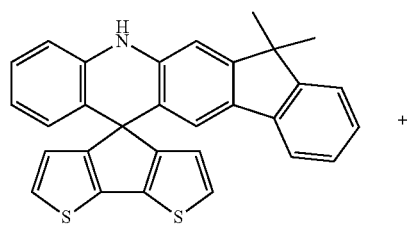

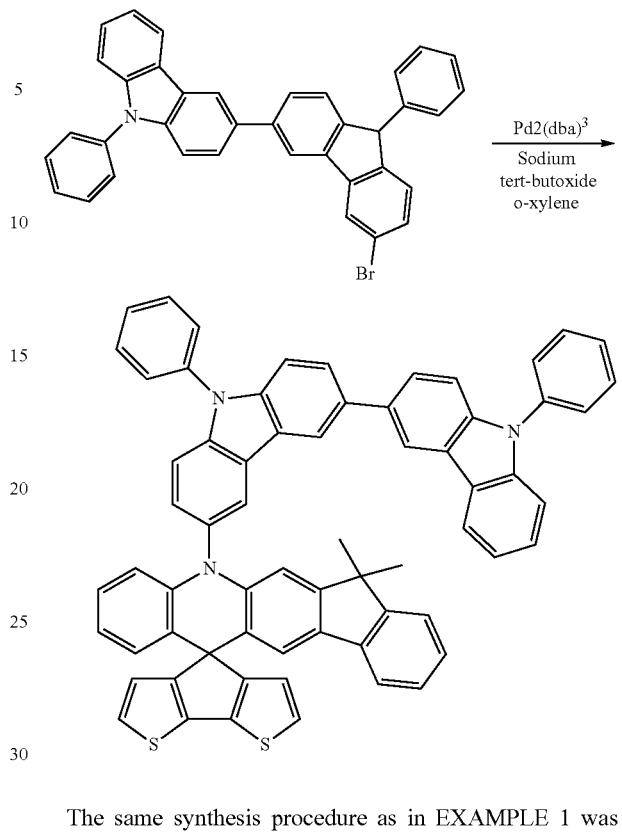

The same synthesis procedure as in EXAMPLE 1 was used, except that 6-bromo-9,9'-diphenyl-9H,9'H-3,3'-bicarbazole was used instead of 2-(3-bromophenyl)-4,6-diphenyl-1,3,5-triazine to obtain the desired compound of 5'-(9,9'-diphenyl-9H,9'H-[3,3'-bicarbazol]-6-yl)-7',7'-dimethyl-5',7'-dihydrospiro[cyclopenta[1,2-b:5,4-b']dithiophene-4,13'-indeno[1,2-b]-acridine]. MS (m/z, EI+): 942.1.

EXAMPLE 7

Synthesis of Compound C1

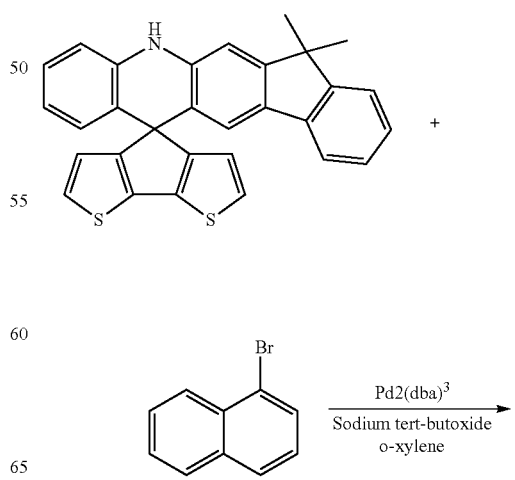

-continued

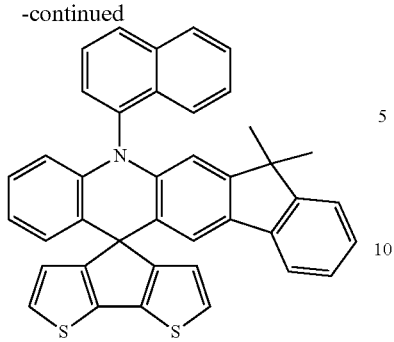

The same synthesis procedure as in EXAMPLE 1 was used, except that 1-bromanaphthalene was used instead of 2-(3-bromophenyl)-4,6-diphenyl-1,3,5-triazine to obtain the desired compound of 7',7'-dimethyl-5'-(naphthalen-1-yl)-5',7'-dihydrospiro-[cyclopenta[1,2-b:5,4-b']dithiophene-4,13'-indeno[1,2-b[acridine]. MS (m/z, EI⁺): 585.6.

General Method of Producing Organic EL Device

ITO-coated glasses with 9~12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the polyheteroaromatic compounds of the present invention are thermally stable.

Dipyrazino[2,3-f:2,3-]quinoxaline-2,3,6,7,10,11-hexacarbonitrile (HAT-CN) is used to form the hole injection layer of the organic EL device. N,N-bis(naphthalene-1-yl)-N,N-bis(phenyl)-benzidine (NPB) is used to form the hole transporting layer. Bis(2-phenylpyridinato)(2,4-diphenylpyridinato)-iridium(III) (D1) is used as the phosphorescent dopant and 3-(9,9-dimethyl-acridin-10(9H)-yl)-9H-xanthen-9-one (D2) is used as the fluorescent dopant. 4-(10,10-dimethyl-10H-indeno[2,1-b]triphenylen-13-yl)dibenzo[b,d]thiophene (H1) is used as the phosphorescent host material, and dibenzo[b,d]thiophene-2,8-diylbis(diphenylphosphine oxide) (H2) is used as the fluorescent host material and TADF host material. 2-(10,10-dimethyl-10H-indeno[2,1-b]triphenylen-13-yl)-9-phenyl-1,10-phenanthroline (ET1) is used as the electron transporting material. Compound C12 is used as fluorescent dopant material to compare with compound D2, and compound C3 is used as TADF dopant material to compare with compound A. Compound C5 and C7 are used as phosphorescent host materials to compare with compound H1. Compound C8 is used as fluorescent host material to compare with compound H2, and compound C6 is used as TADF host material to compare with compound H2. Compound C 1 is used as electron transporting material to compare with compound ET1. The chemical structures of conventional OLED materials and the exemplary polyheteroaromatic compounds of the present invention for producing control and exemplary organic EL devices in this invention are shown as follows:

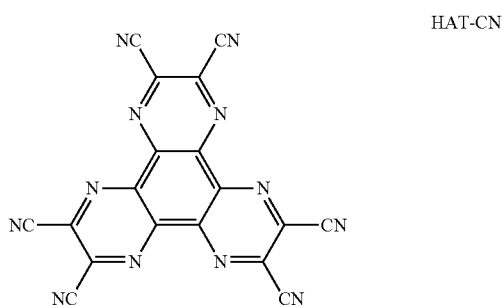
HAT-CN

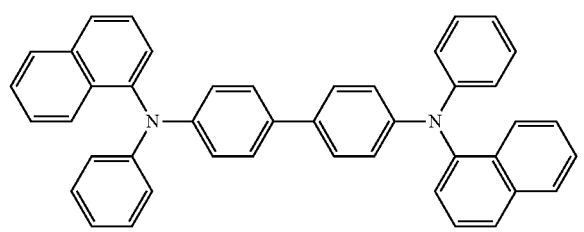
NPB

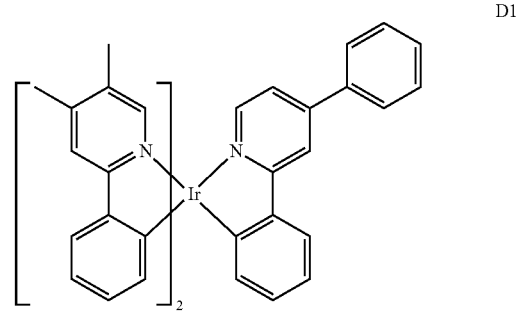
D1

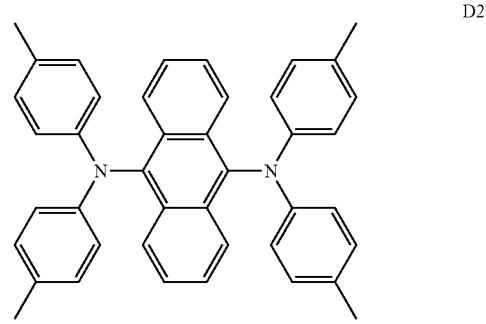
D2

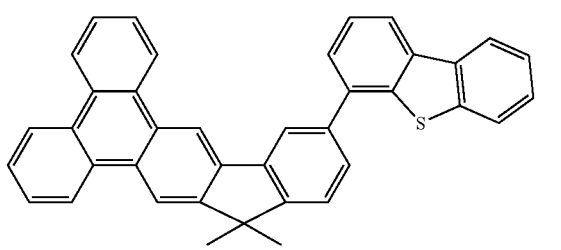
H1

H2
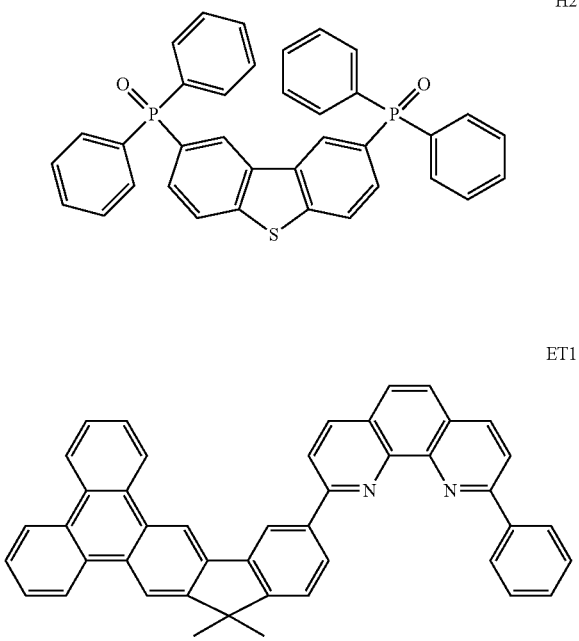
ET1
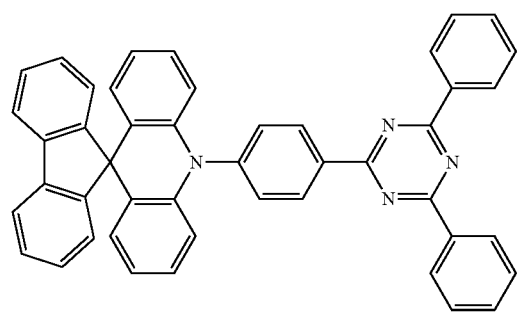
Compound A
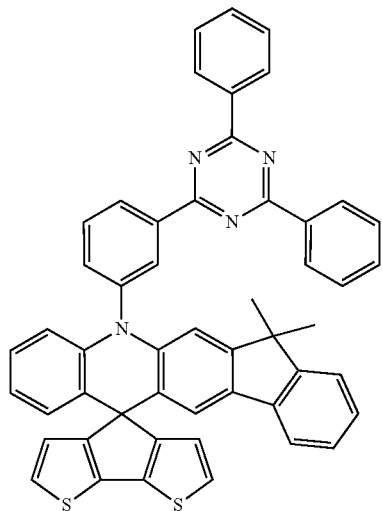
Compound C3
Compound C12
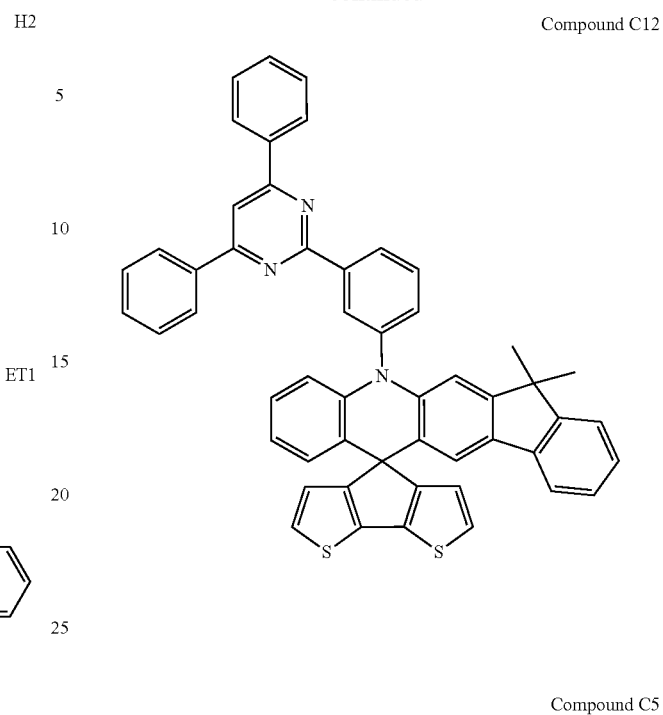
Compound C5
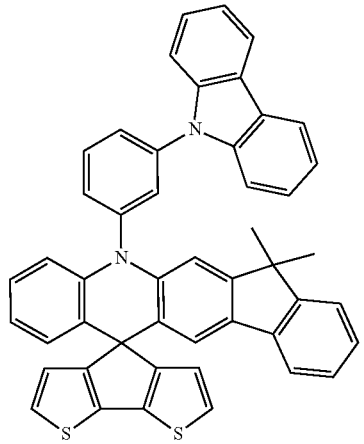
Compound C7
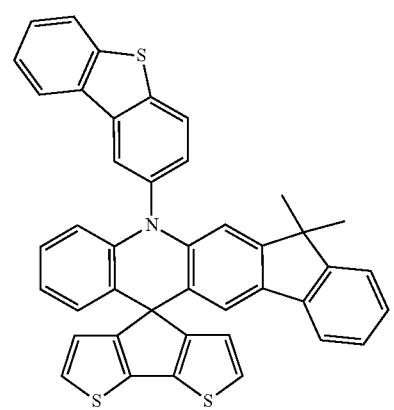

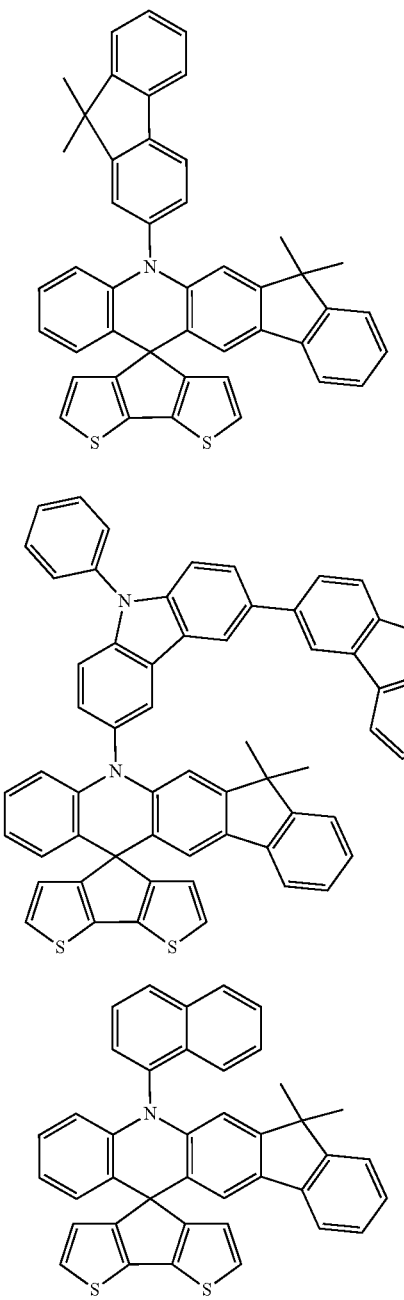

Compound C8

Compound C6

Compound C1

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ (as shown below), MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

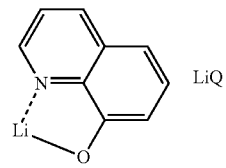

LiQ

EXAMPLE 7

Using a procedure analogous to the above mentioned general method, organic EL devices emitting green light and having the following device structure as shown in the FIGURE were produced: ITO/HAT-CN (20 nm)/NPB (130 nm)/Host doped with Dopant (30 nm)/ETM/LiQ/Al (160 nm). The I-V-B (at 1000 nits) test reports of these organic EL devices are summarized in Table 1 below.

TABLE 1

| Dopant (%) | Host | ETM | Voltage (V) | Efficiency (cd/A) |
|---|---|---|---|---|
| D1 (8%) | H1 | ET1 | 4.9 | 14 |
| D1 (8%) | C5 | ET1 | 4.6 | 20 |
| D1 (8%) | C7 | ET1 | 4.8 | 16 |
| D2 (20%) | H2 | ET1 | 5.1 | 11 |
| D2 (20%) | C8 | ET1 | 4.7 | 13 |
| C12 (20%) | H2 | ET1 | 4.9 | 15 |
| A (20%) | H2 | ET1 | 5 | 10 |
| A (20%) | C6 | ET1 | 4.8 | 13 |
| C3 (20%) | H2 | ET1 | 4.7 | 22 |
| C3 (20%) | H2 | C1 | 4.5 | 25 |

From the above test report summary of the organic EL devices, it is obvious that the polyheteroaromatic compound of formula (1) used as the fluorescenct or TADF dopant material, the phosphorescent, fluorescenct or TADF host material, or the electron transfer material of the organic EL device exhibits better performance than the prior art materials. In particular, the organic EL devices of the present invention employing the polyheteroaromatic compound of formula (1) as the dopant material, the host material, or the electron transfer material to collocate with the host material H2 or the dopant material D1, D2, or compound A have lower power consumption and higher luminous efficiency.

To sum up, the present invention discloses a polyheteroaromatic compound, which can be used as the host material, the fluorescent dopant material, the thermally activated delayed fluorescence host material, or the thermally activated delayed fluorescence dopant material of the light emitting layer, or the electron transporting material in organic EL devices. The mentioned polyheteroaromatic compound is represented by the following formula (1):

What is claimed is:

1. A polyheteroaromatic compound of formula (1) below:

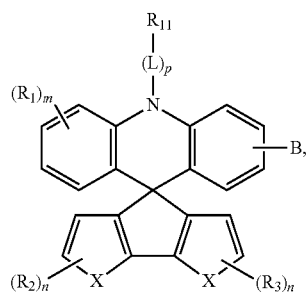

formula (1)

wherein X is O, S, or Se; each n and p is independently an integer of 0 to 2; L represents formula (2) below:

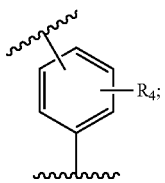

formula (2)

and B represents formula (3) below:

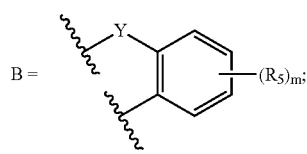

formula (3)

wherein m is an integer of 0 to 4; Y is O, S, Se, $CR_6R_7$, $NR_8$, or $SiR_9R_{10}$; and $R_1$ to $R_{11}$ are independently selected from the group consisting of a hydrogen atom, a halide, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, and a substituted or unsubstituted arylamine group having 6 to 60 carbon atoms.

2. The polyheteroaromatic compound according to claim 1, wherein $R_8$ or $R_{11}$ represents one of the following substituents:

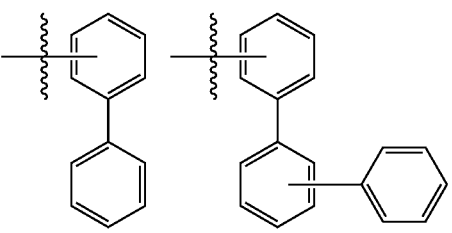

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

-continued
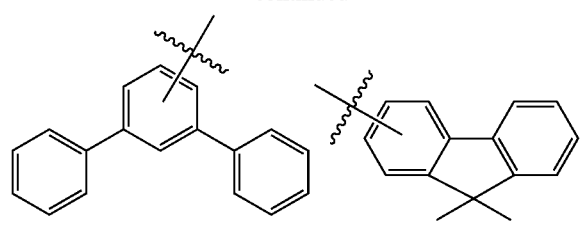
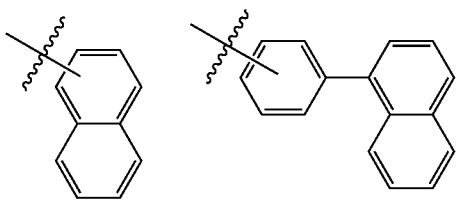
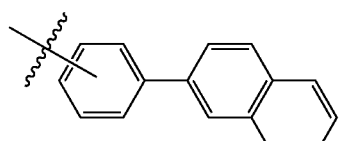
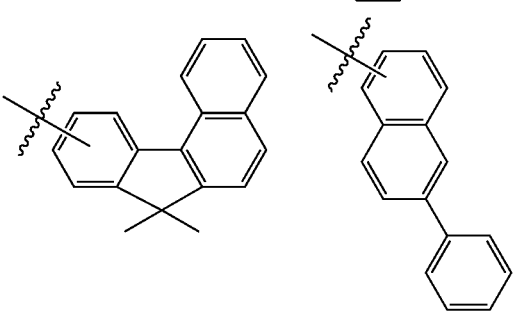
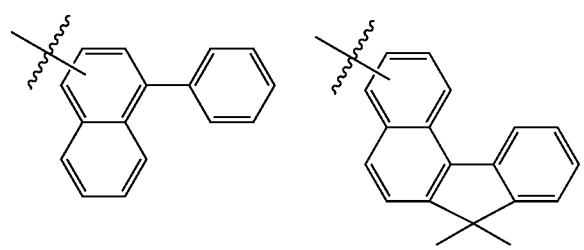
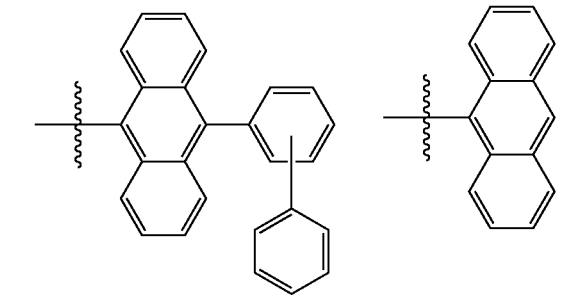
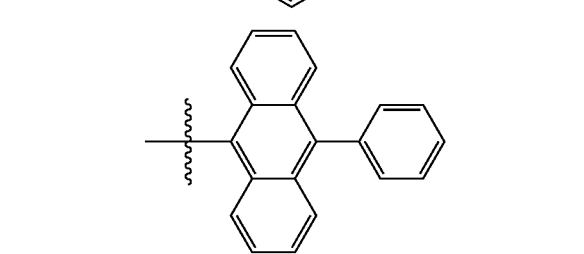
-continued
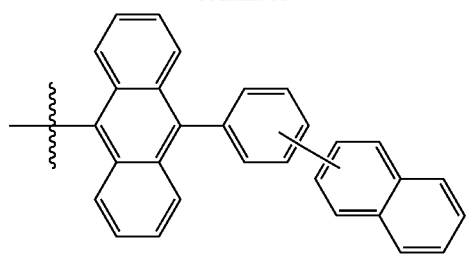
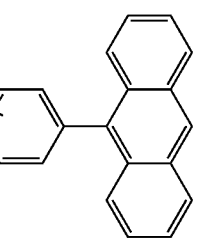
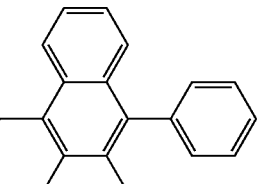
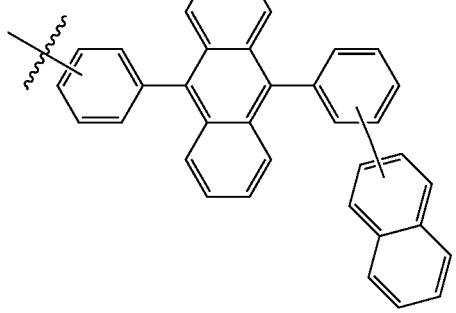
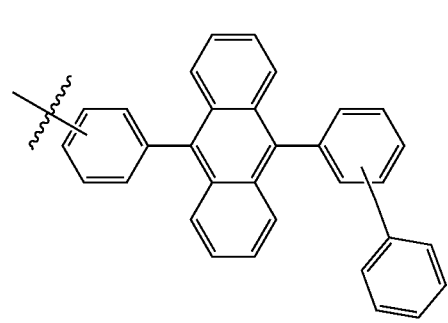
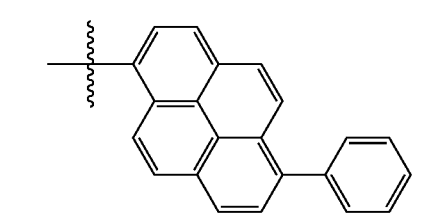

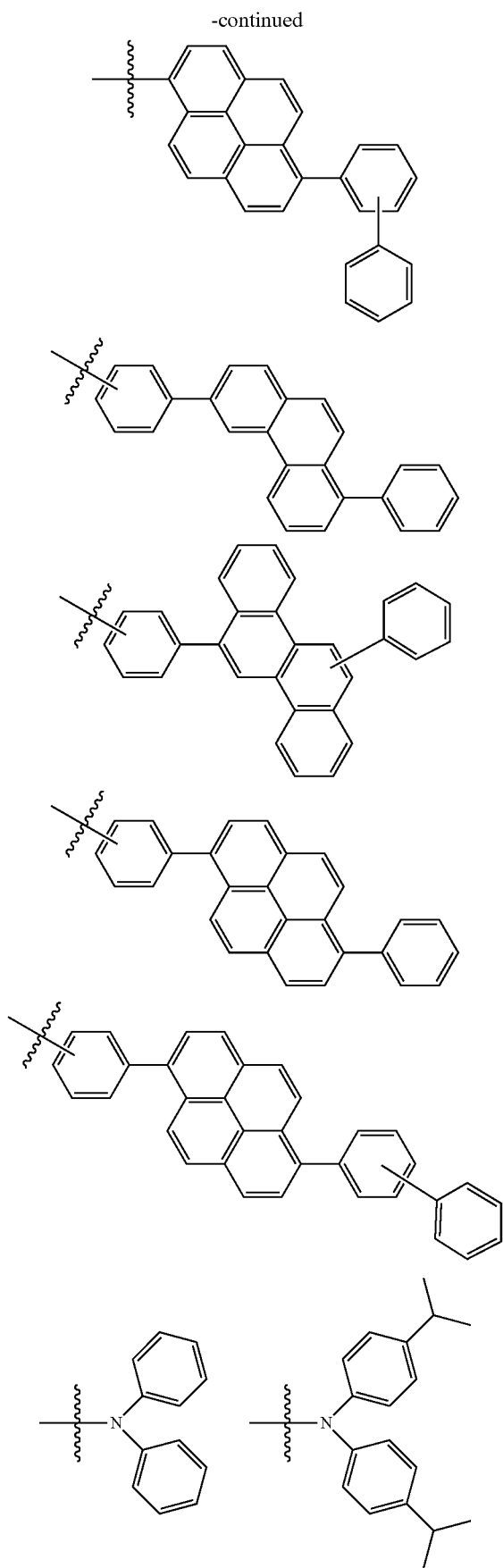
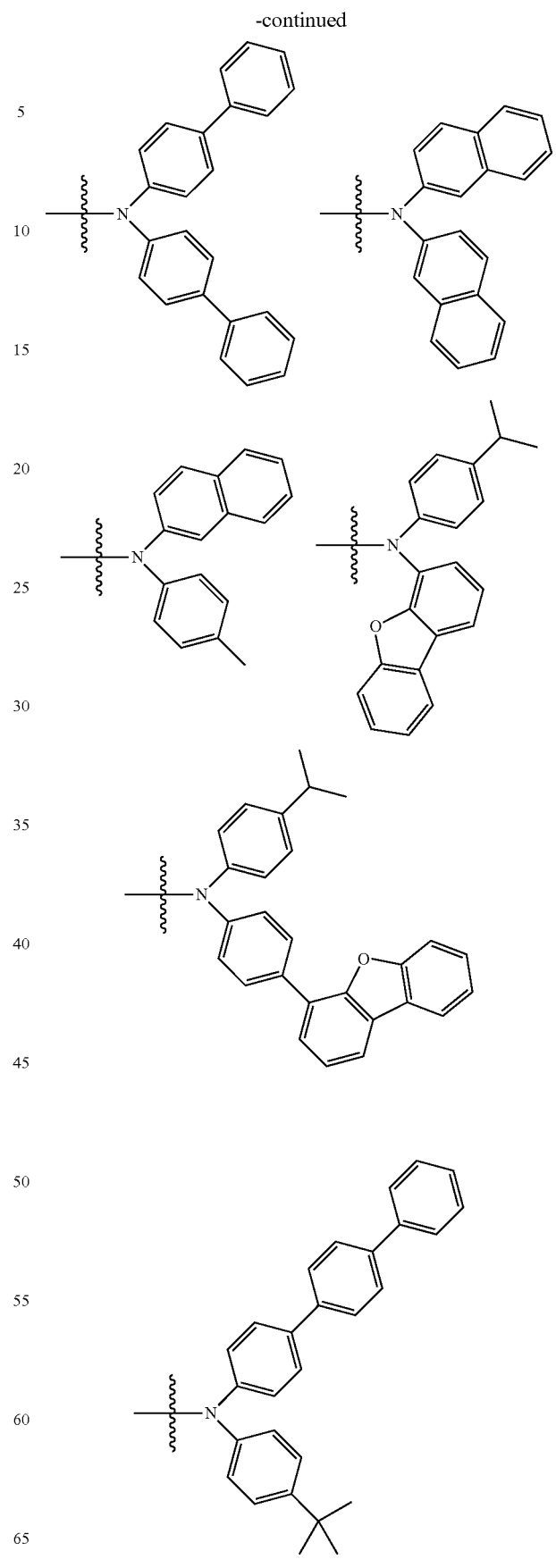

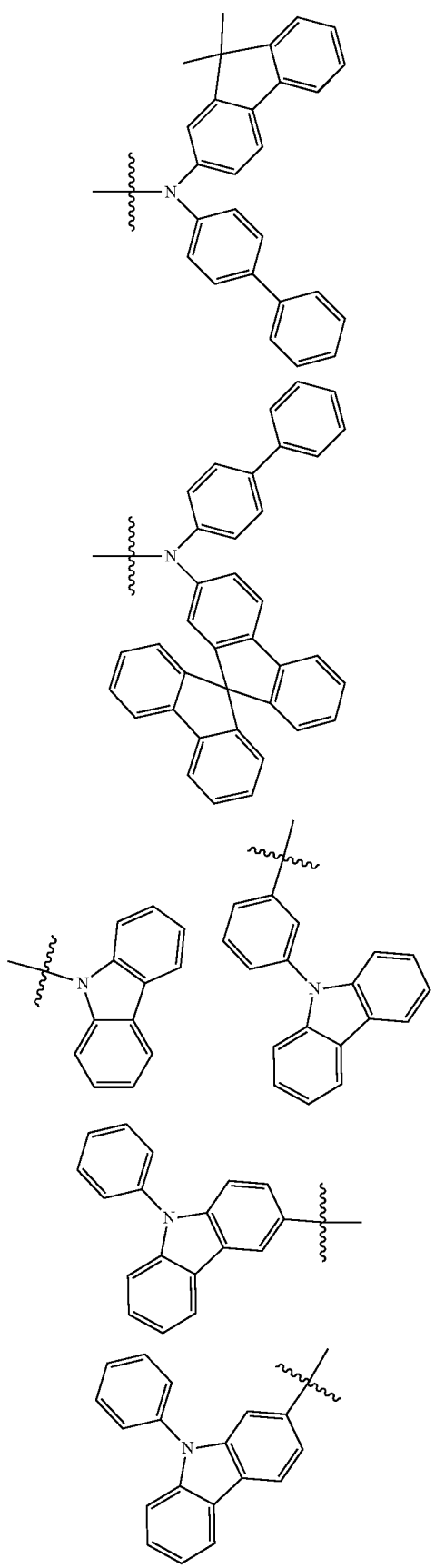
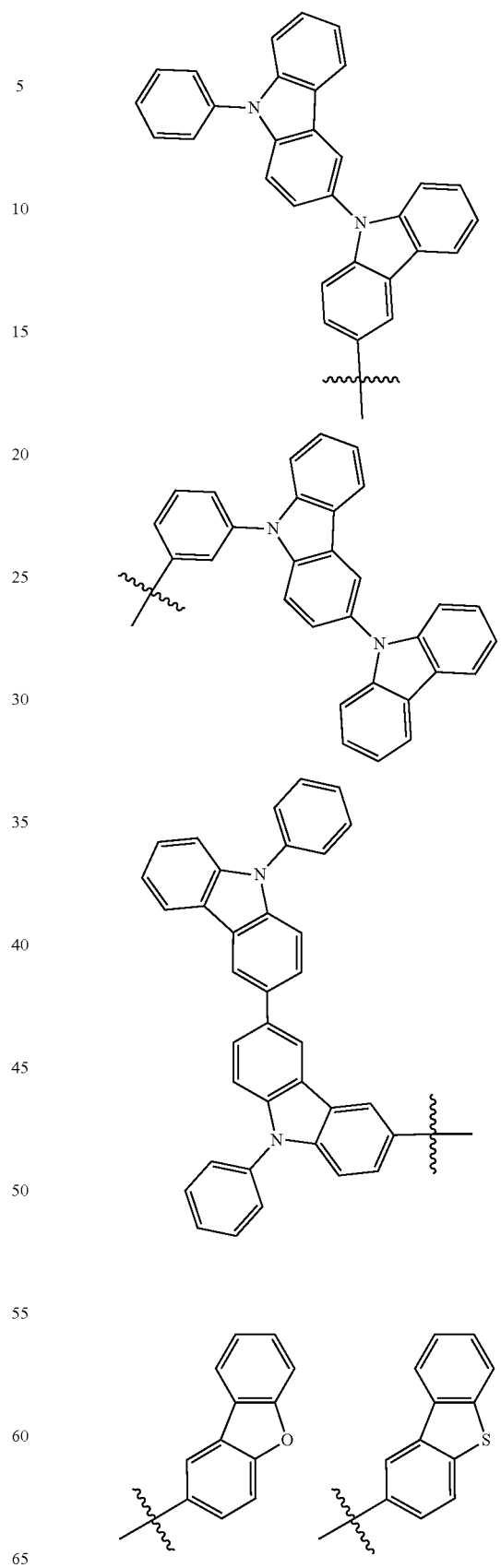

119
-continued
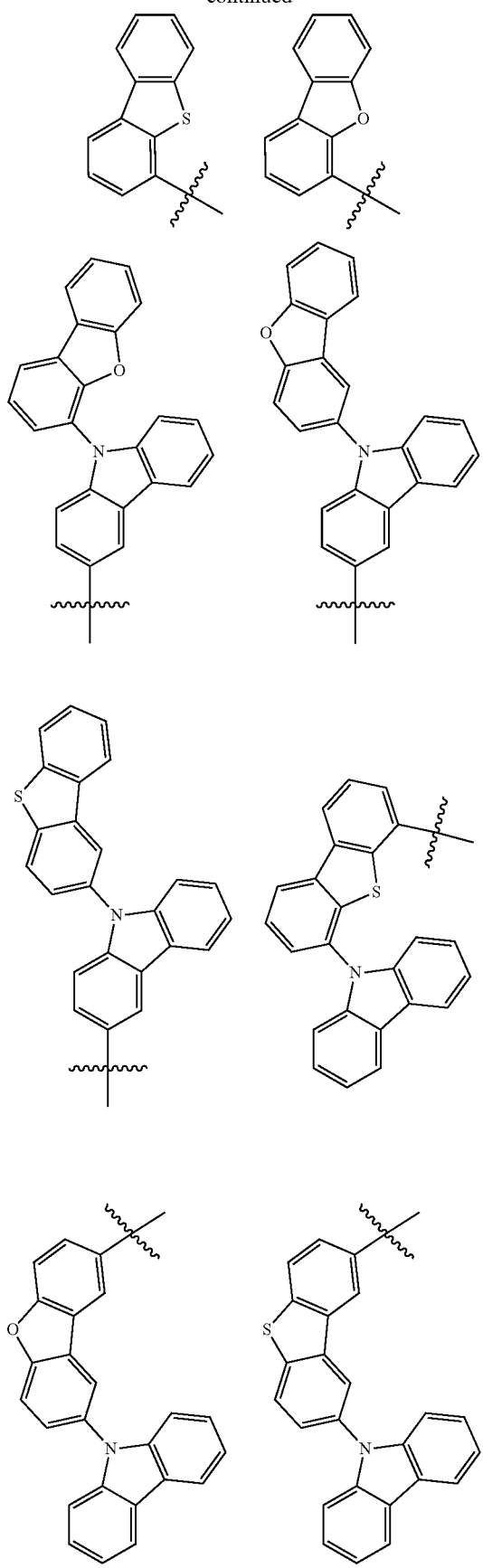
120
-continued
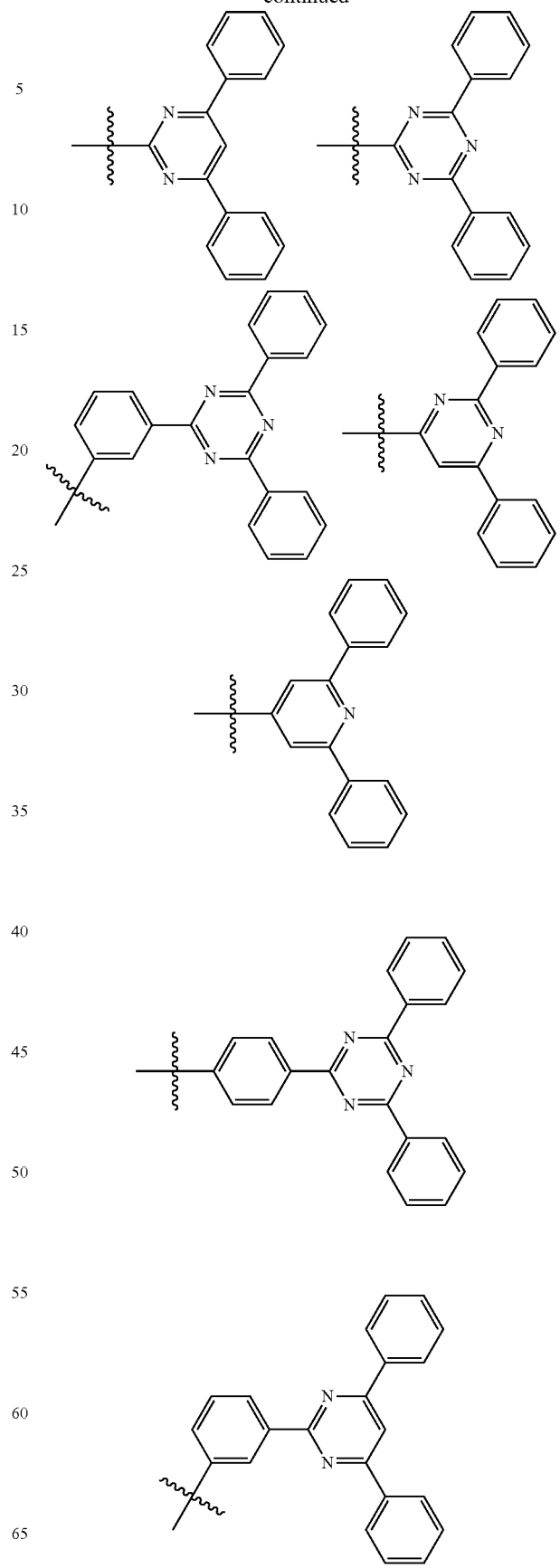

121
-continued
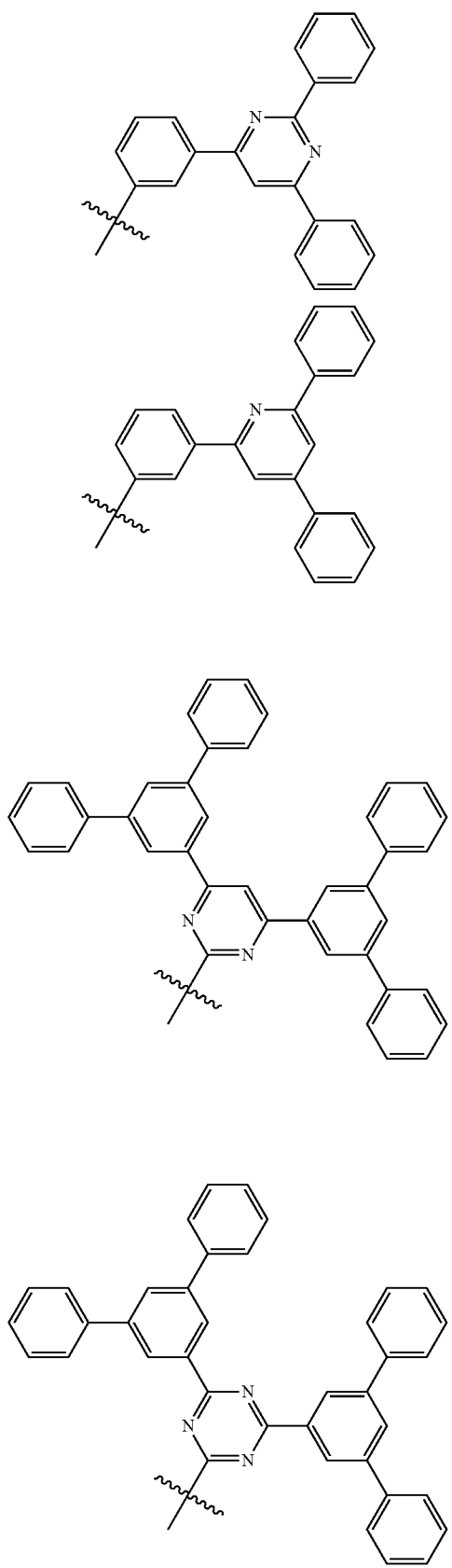
122
-continued
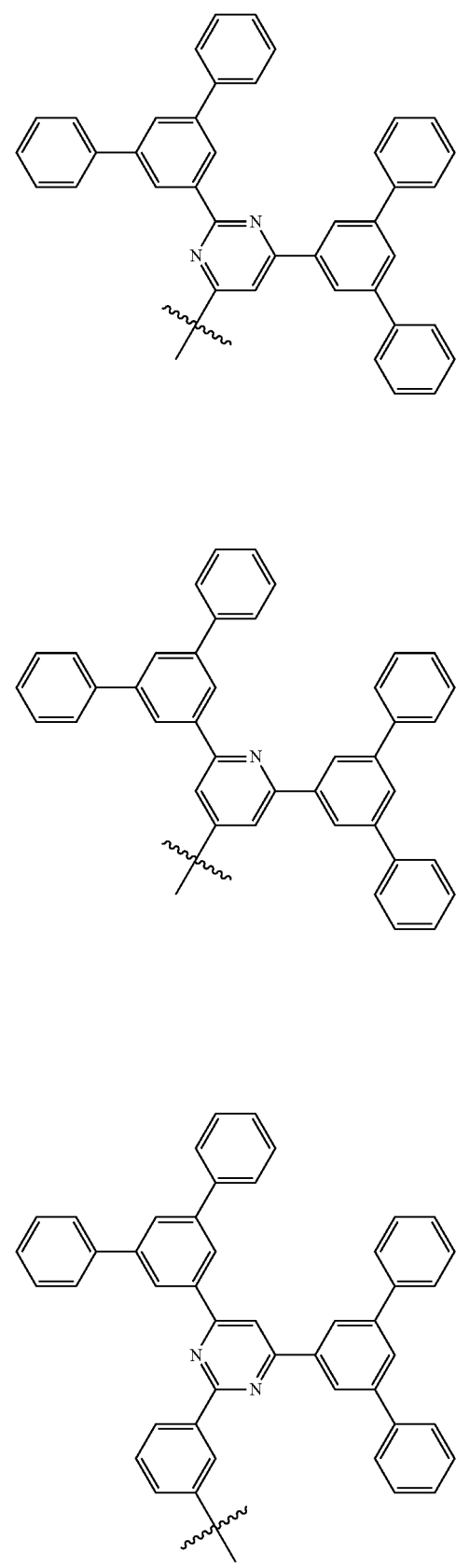

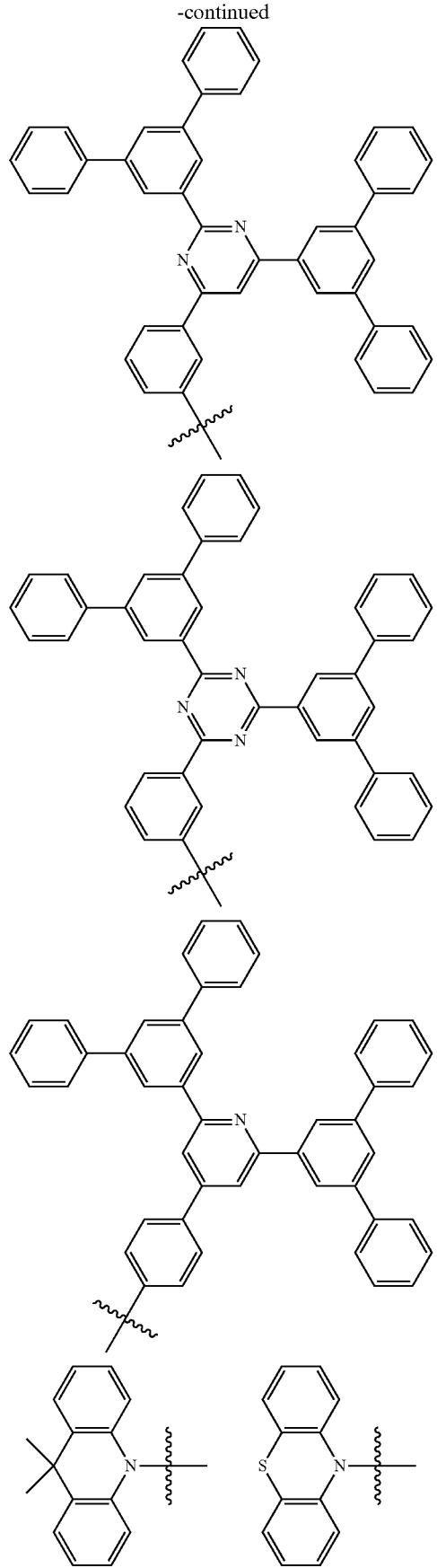
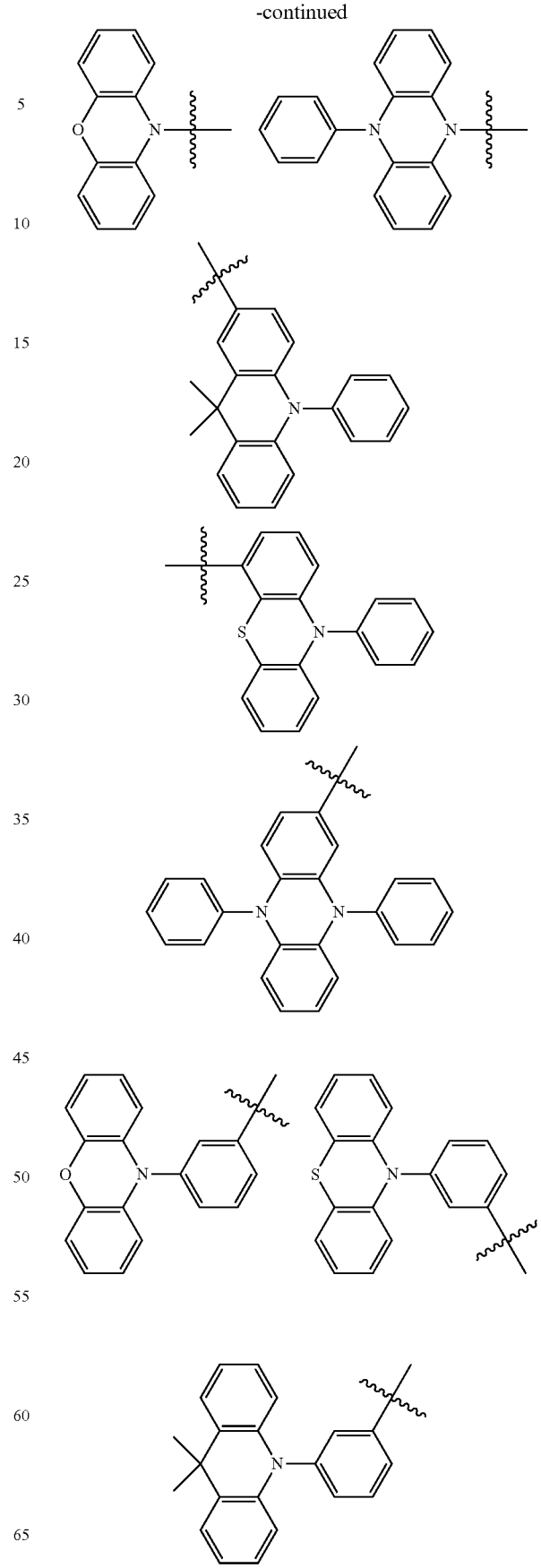

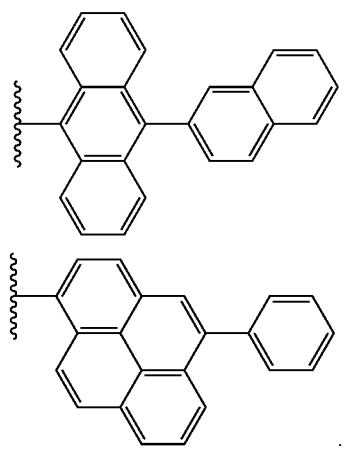

3. The polyheteroaromatic compound according to claim 1, wherein the polyheteroaromatic compound is represented by one of the following formula (4) to formula (9):

formula (4)
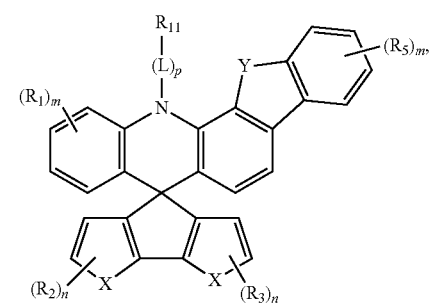

formula (5)
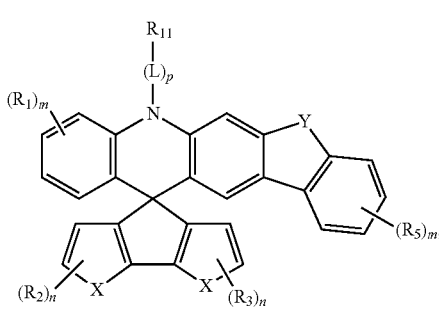

formula (6)
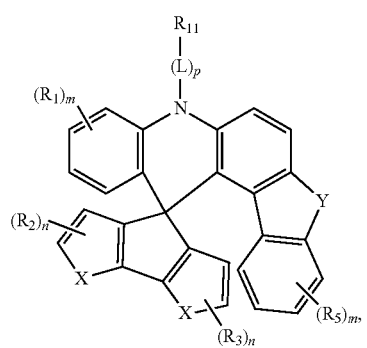

formula (7)
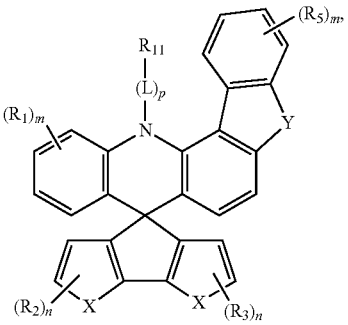

formula (8)
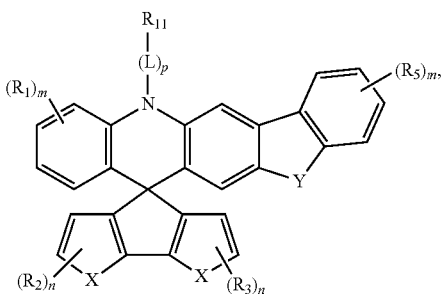

formula (9)
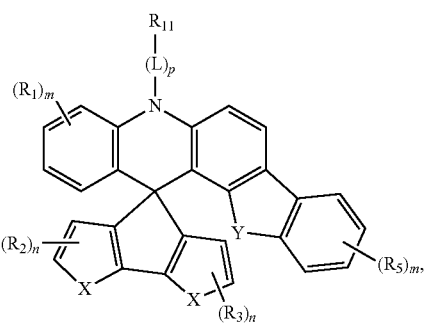

wherein X, n, p, L, m, Y and $R_1$ to $R_{11}$ have the same meaning as defined in claim 1.

4. The polyheteroaromatic compound according to claim 3, wherein $R_8$ or $R_{11}$ represents one of the following substituents:

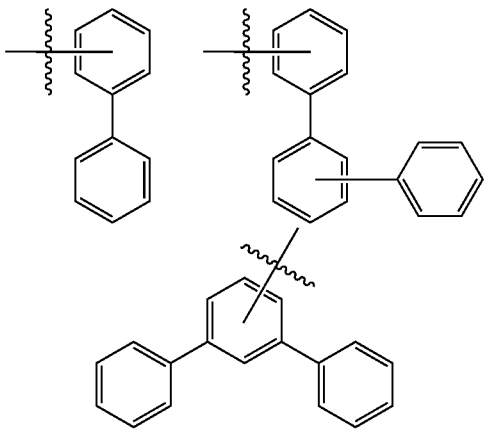

127
-continued
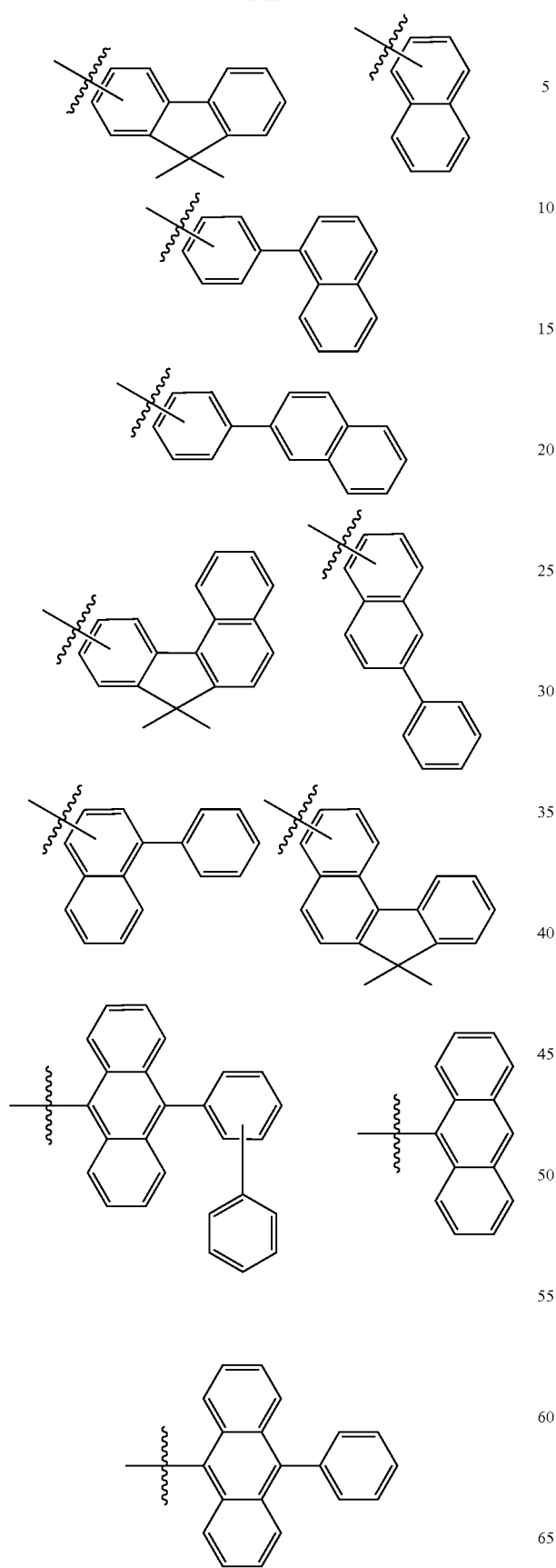
128
-continued
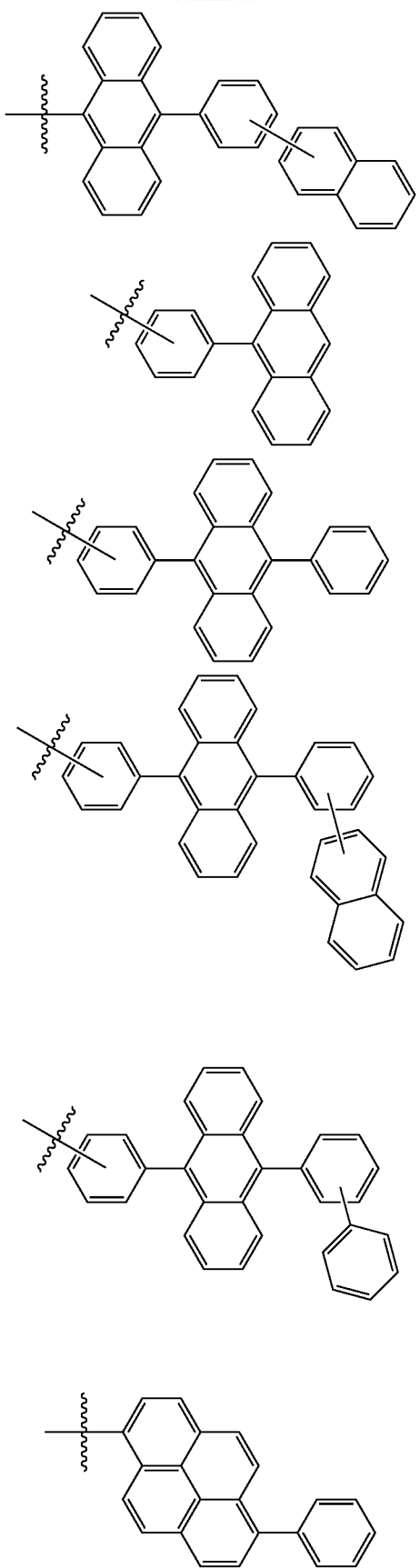

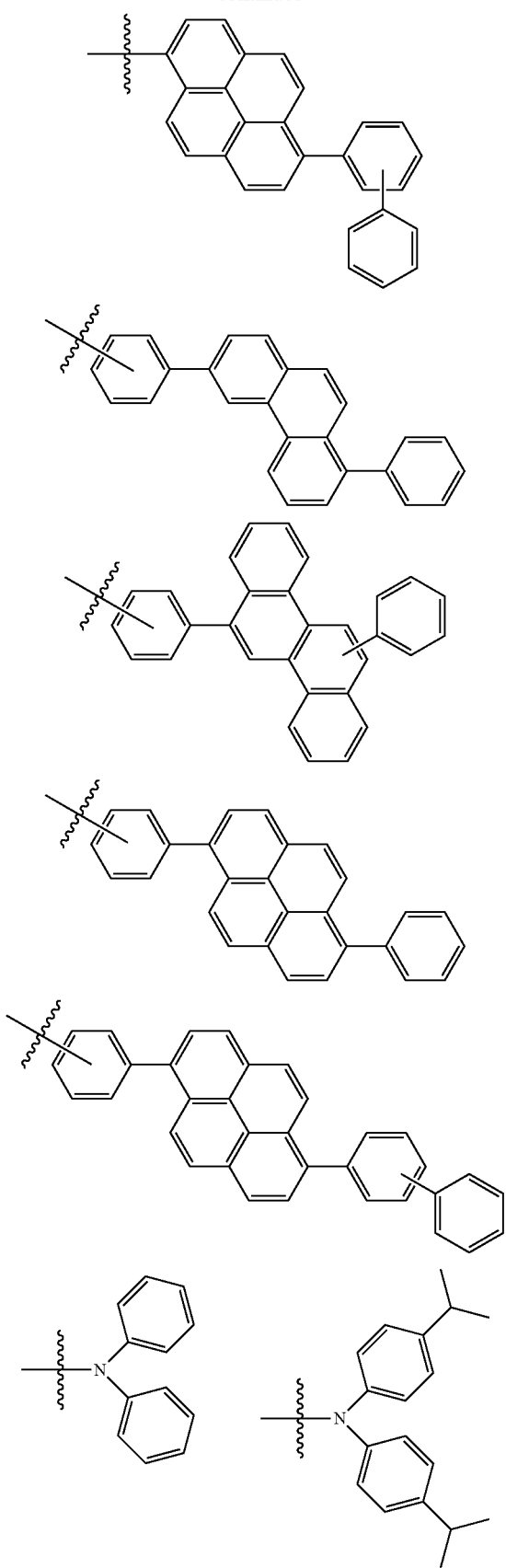
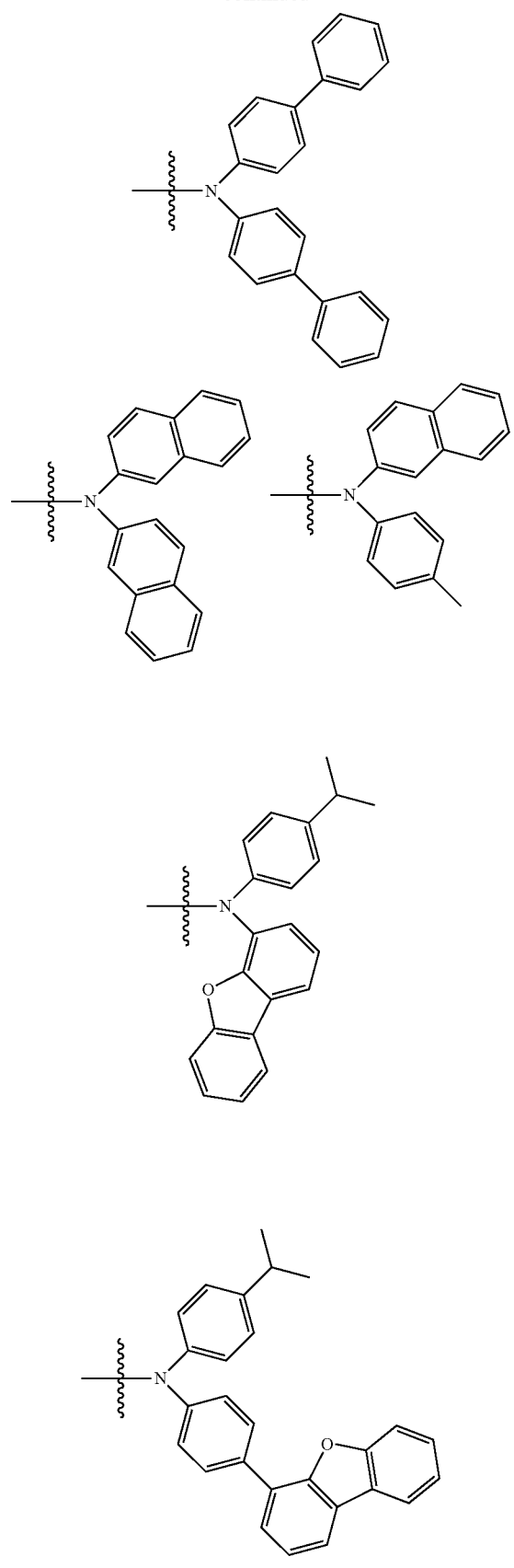

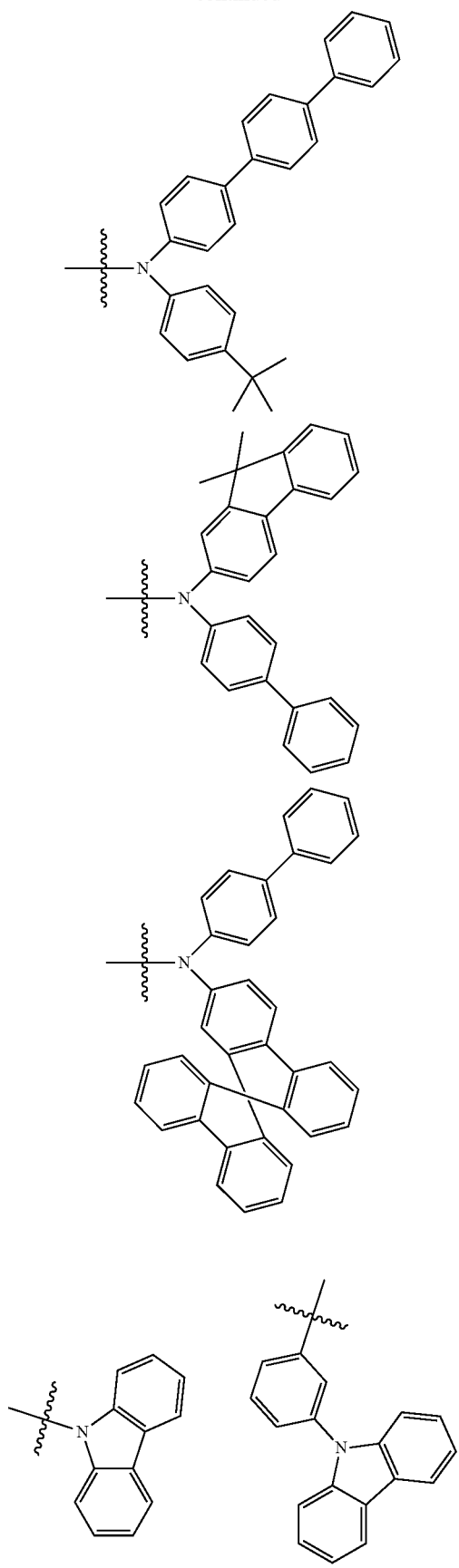
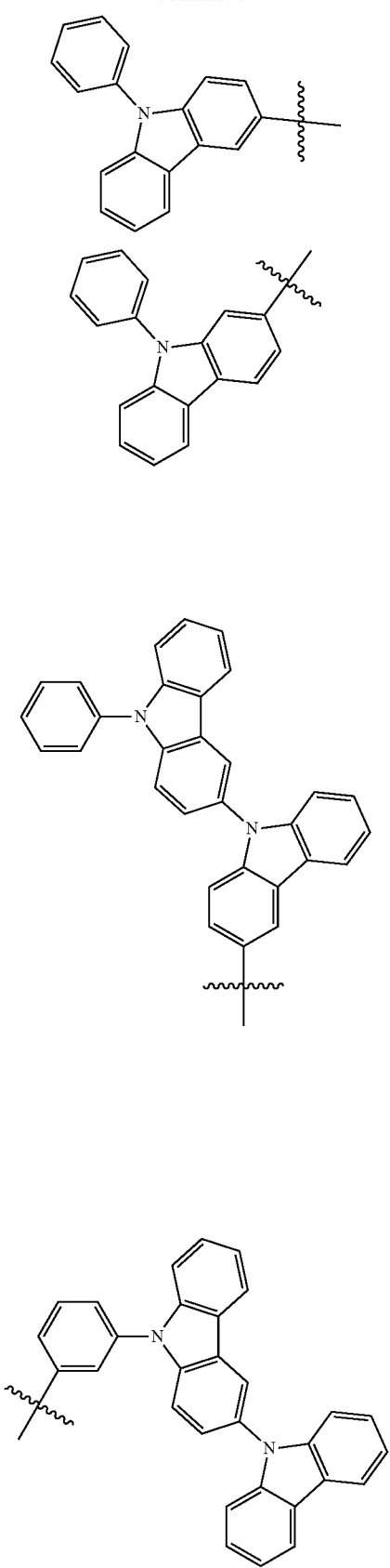

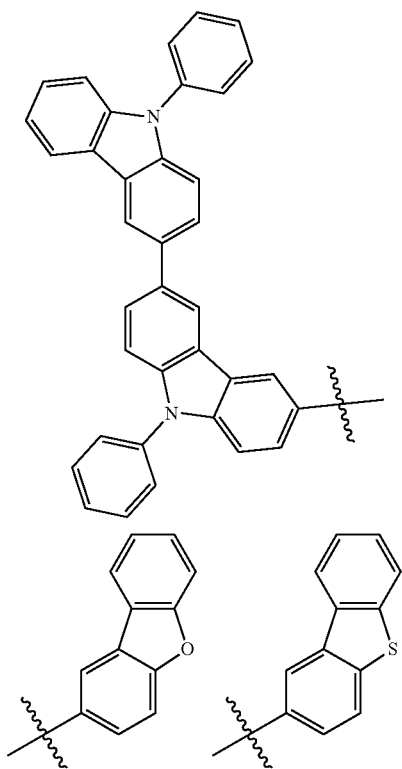
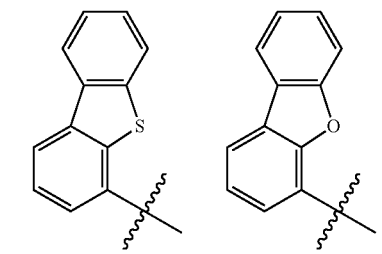
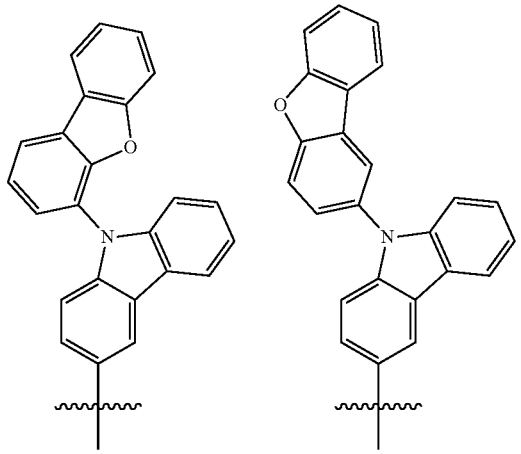
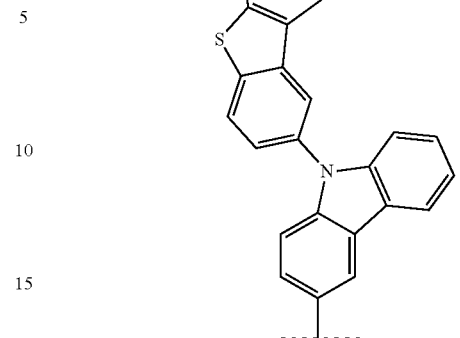
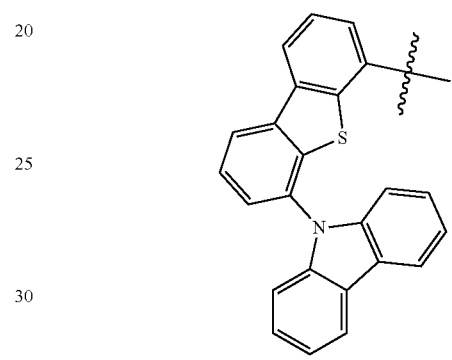
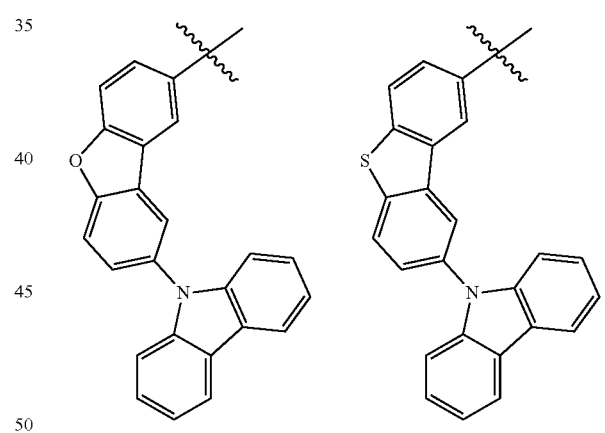
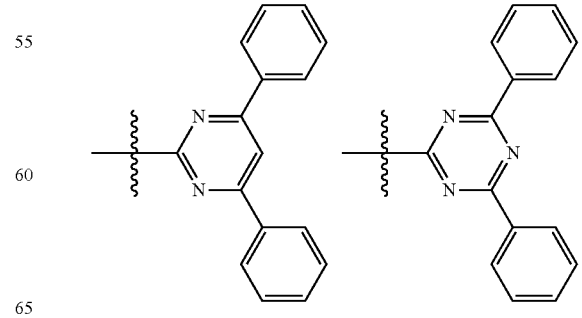

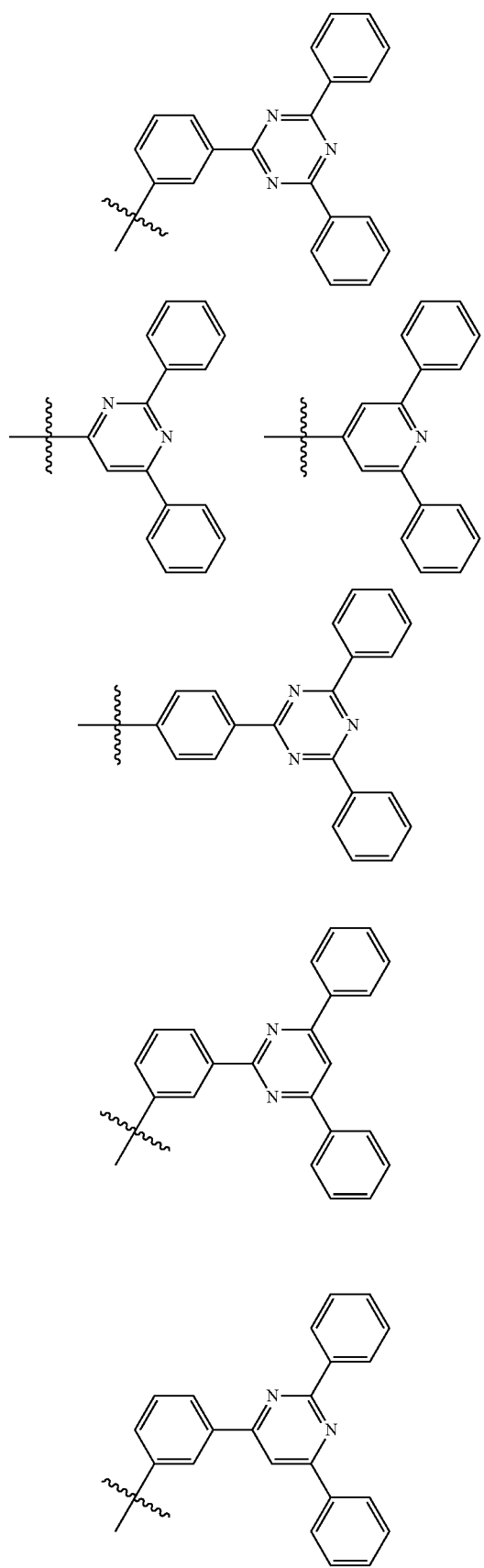
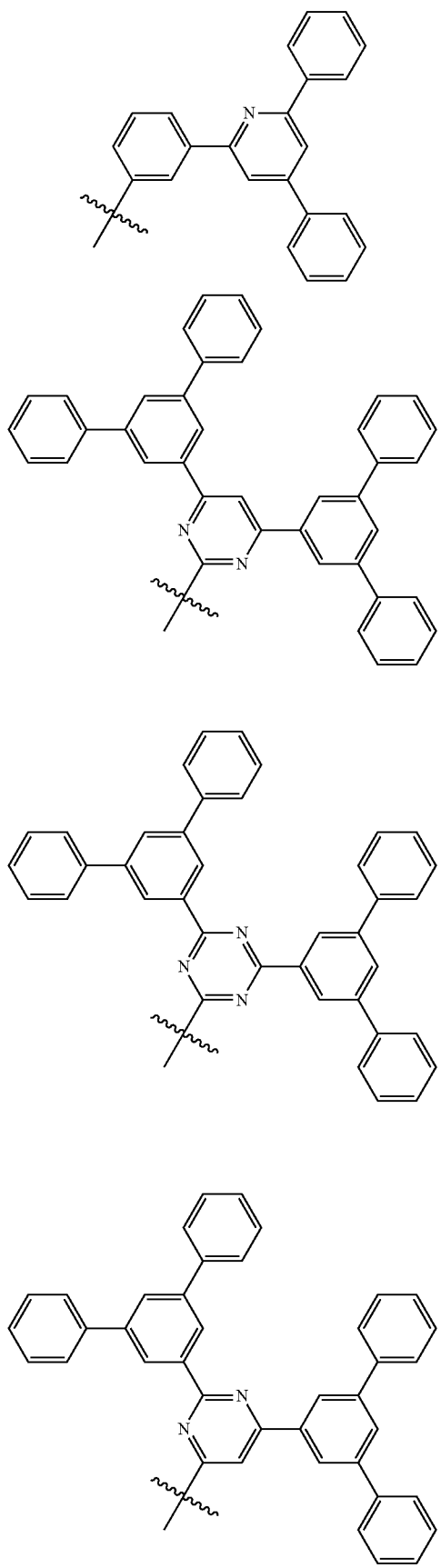

137
-continued
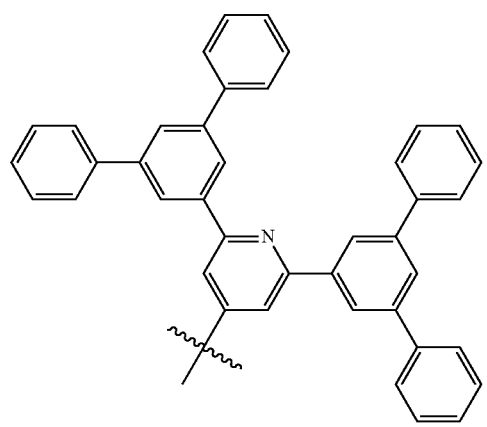
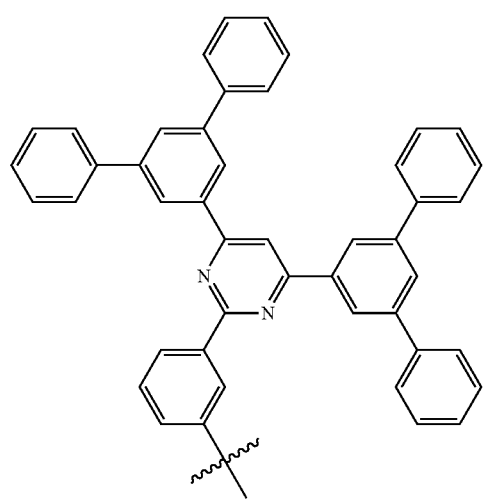
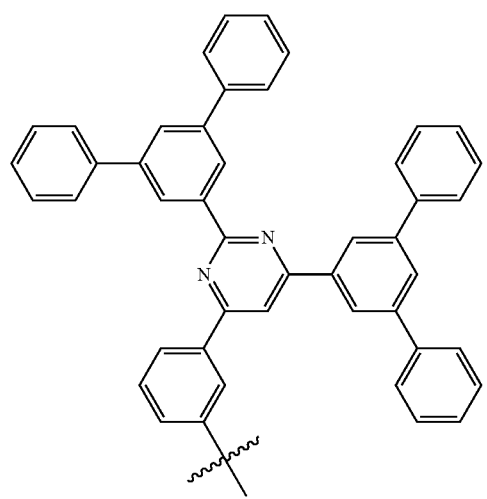
138
-continued
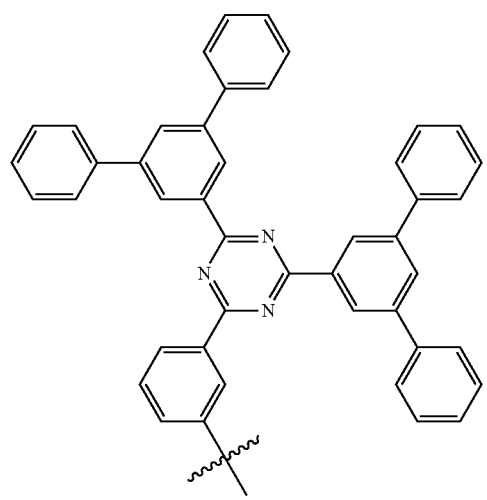
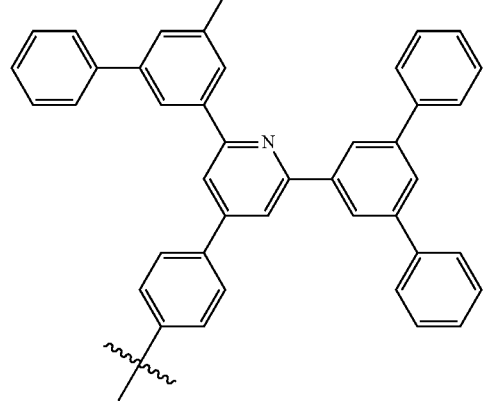
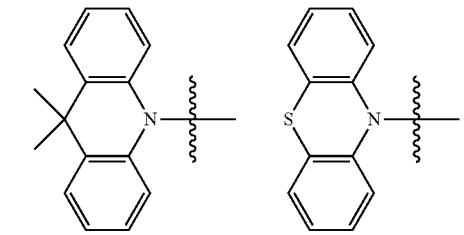
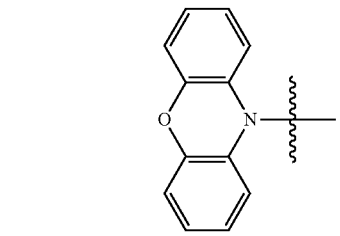
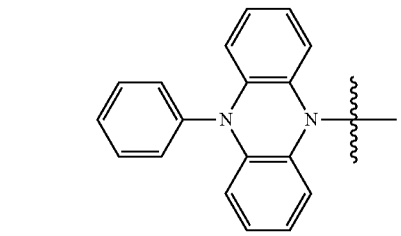

-continued
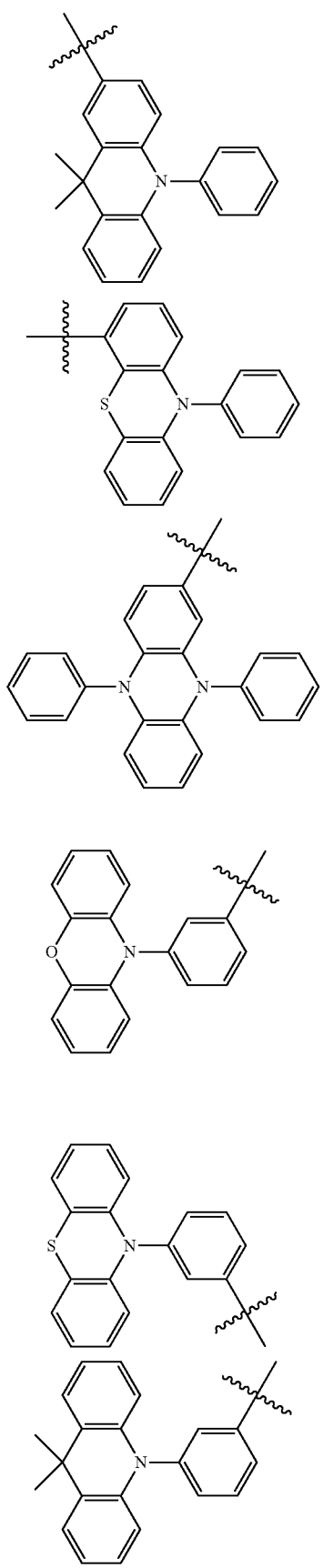
-continued
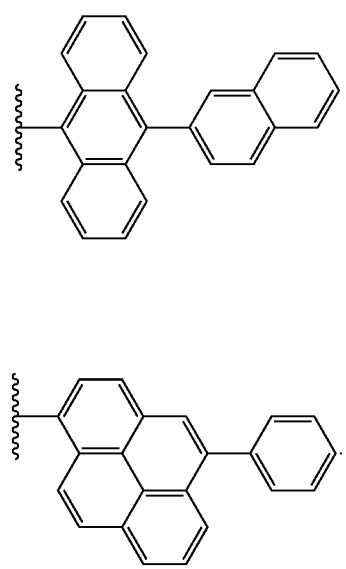
5. The polyheteroaromatic compound according to claim 1, wherein the polyheteroaromatic compound is one of the following compounds:
C1
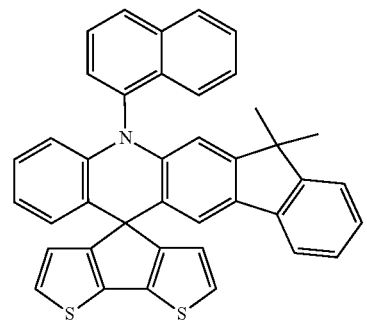
C2
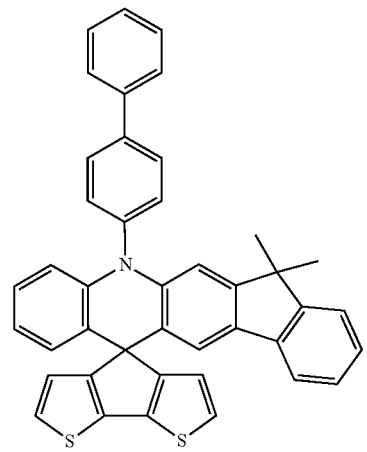

141
-continued
C3
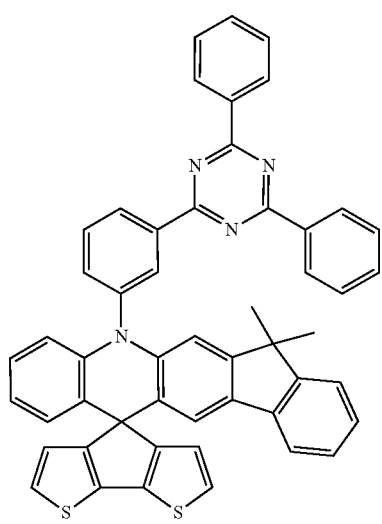
C4
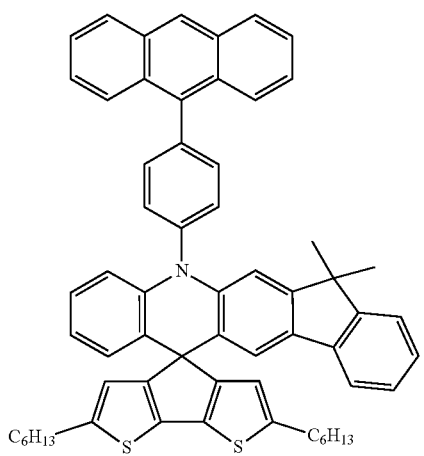
C5
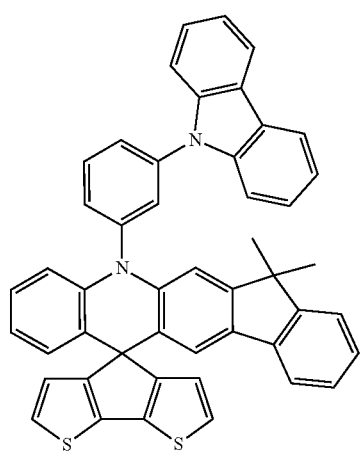
142
-continued
C6
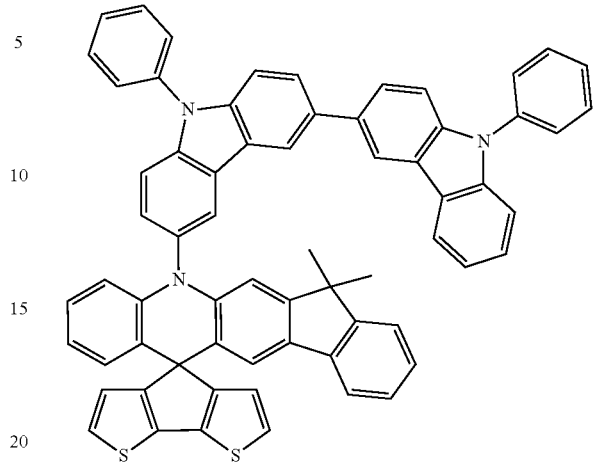
C7
C8

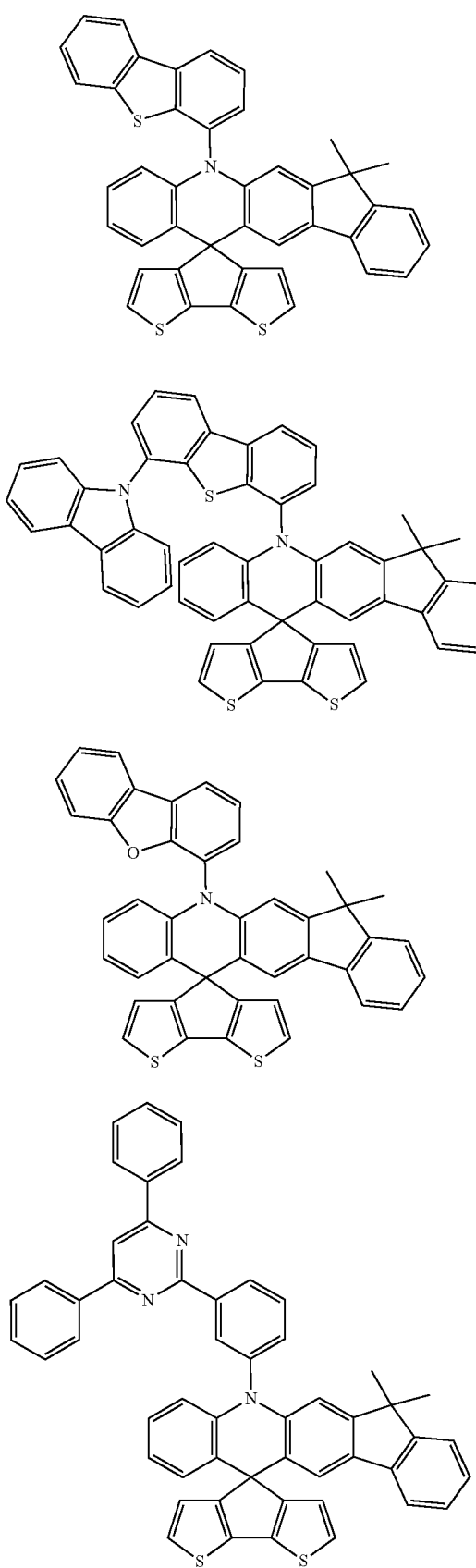
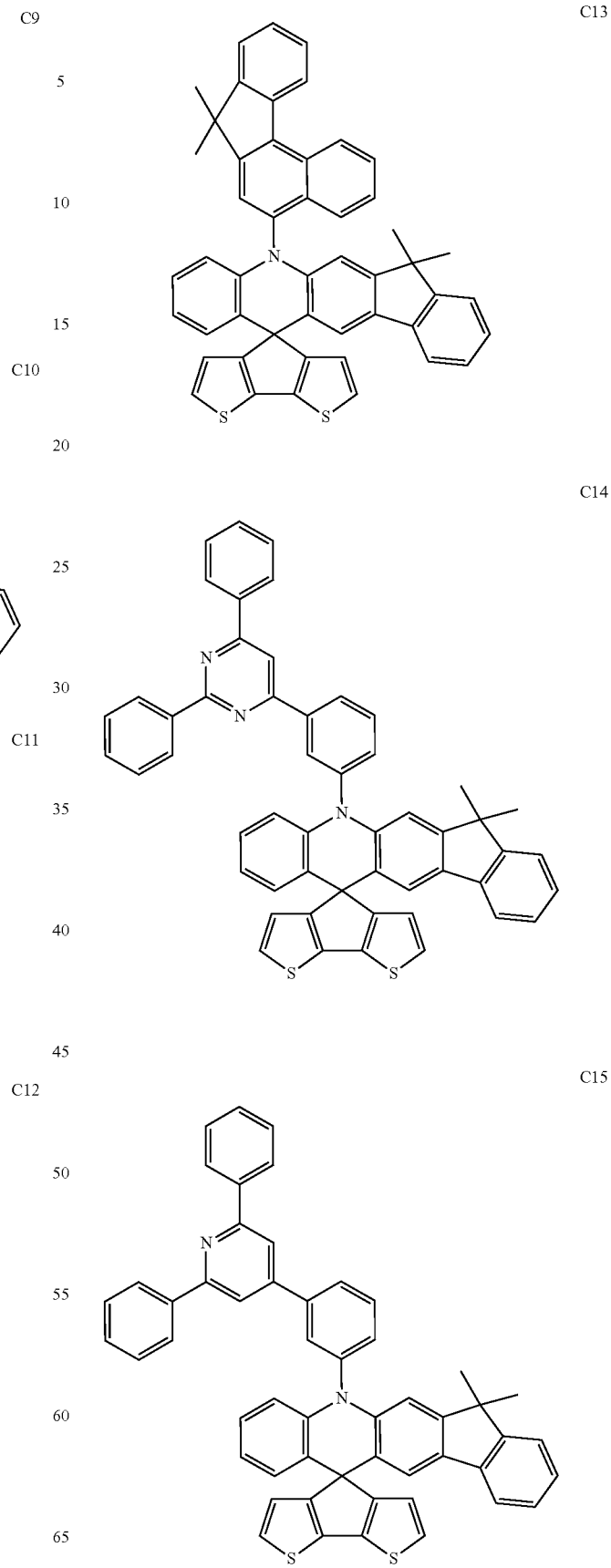

-continued
C16
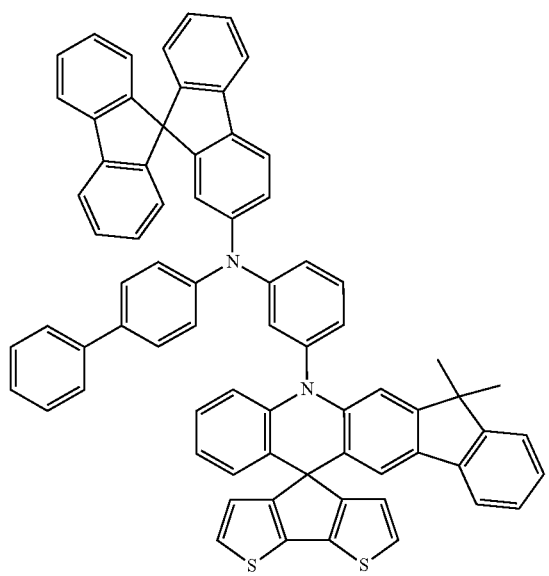
C17
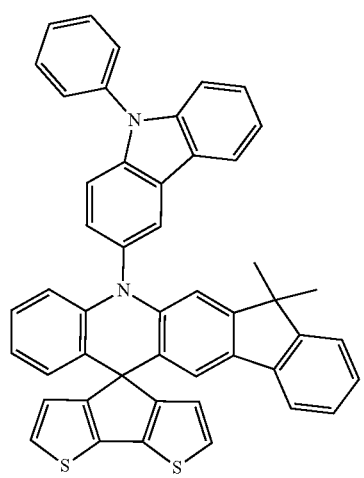
C18
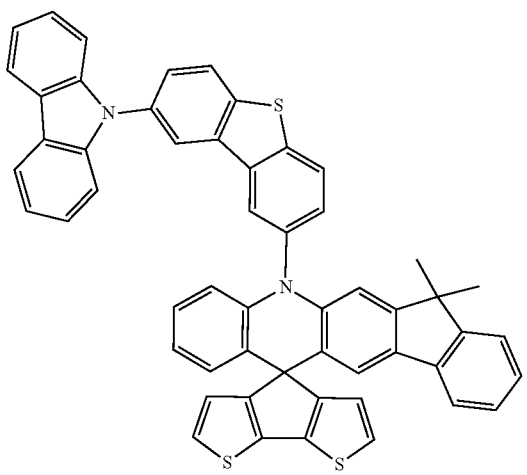
-continued
C19
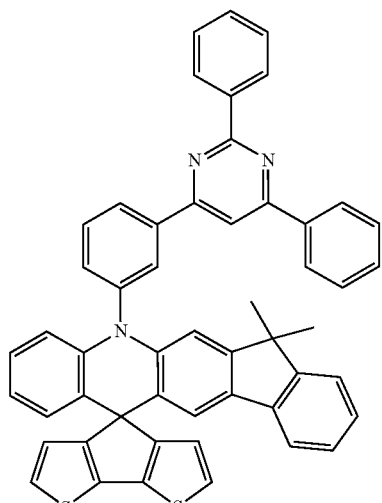
C20
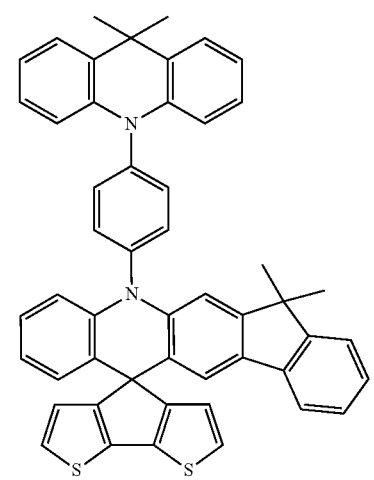
C21
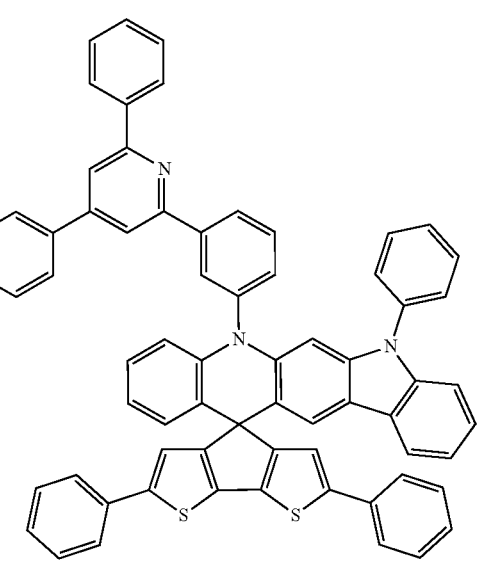

C22
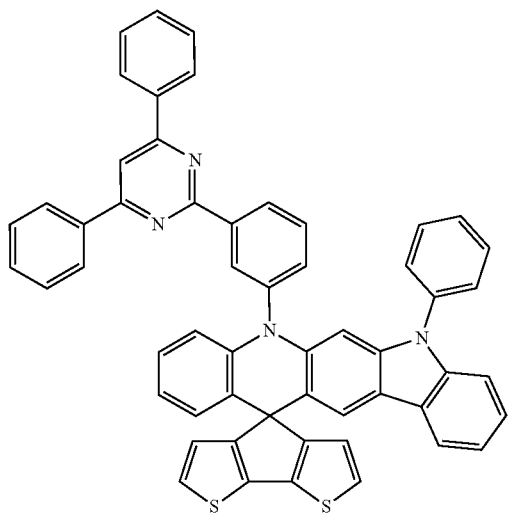
C23
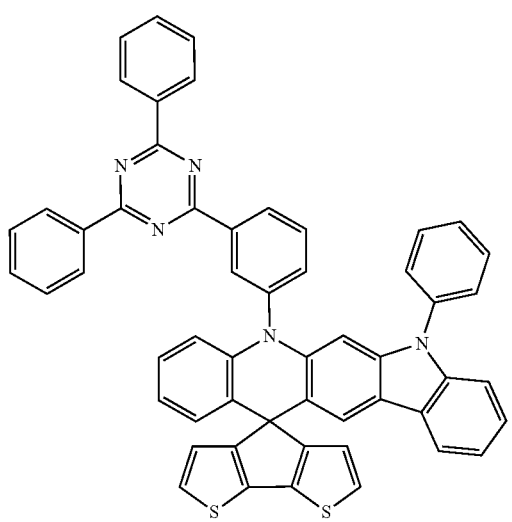
C24
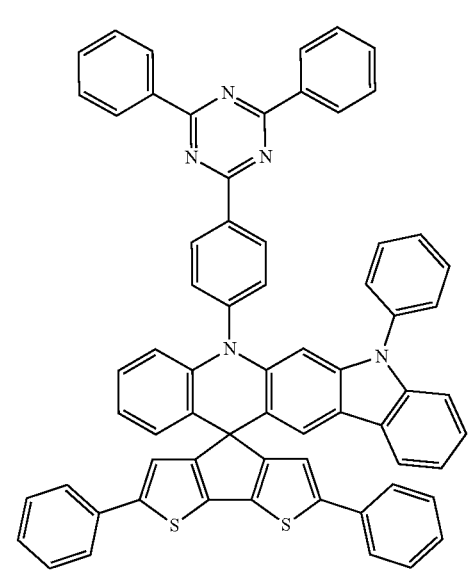
C25
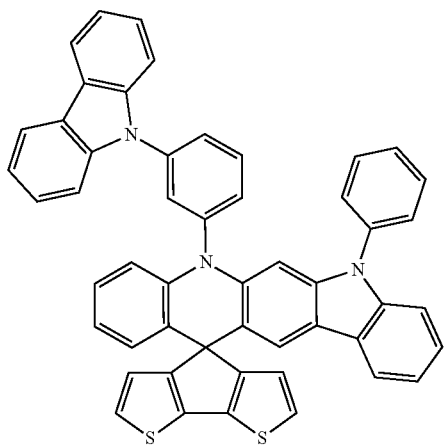
C26
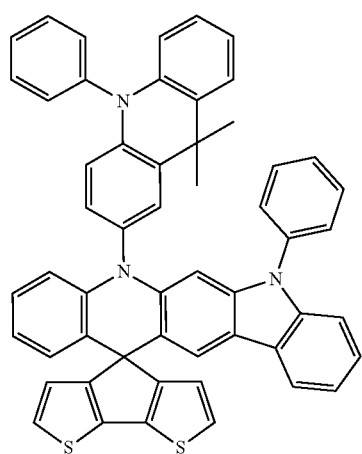
C27
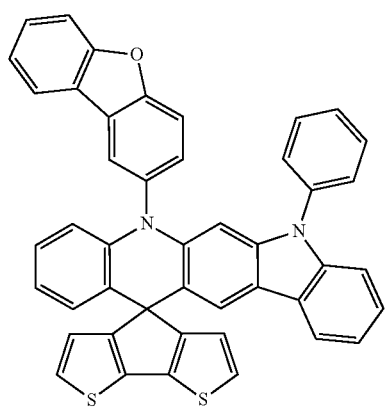

C28
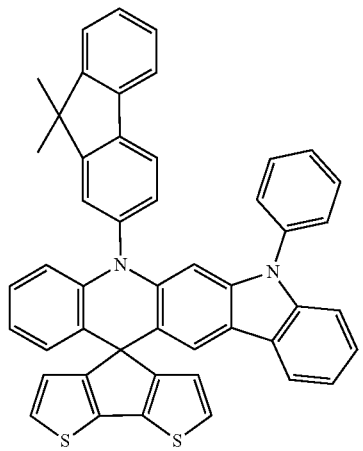
C29
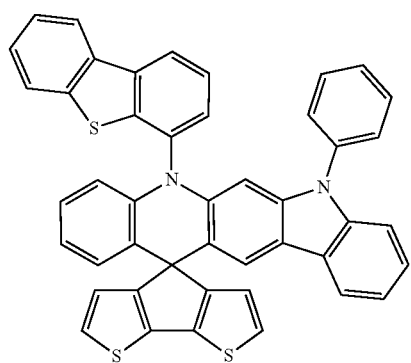
C30
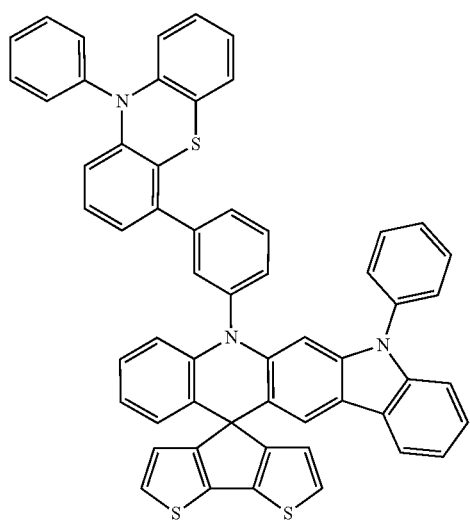
C31
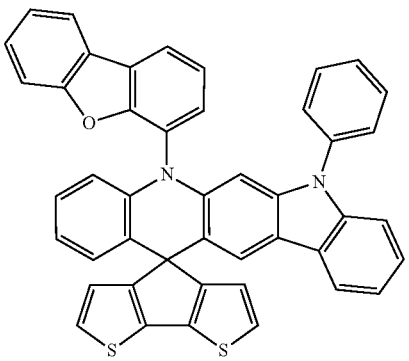
C32
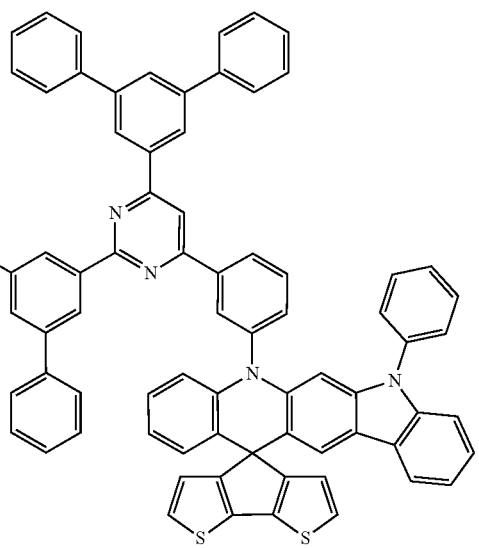
C33
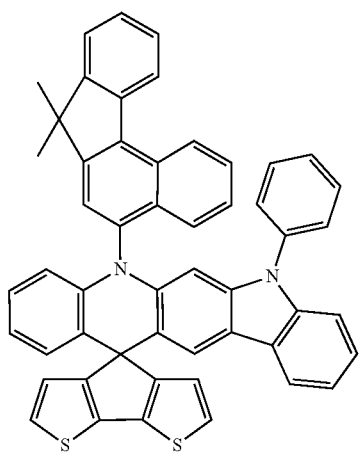

151
-continued
C34
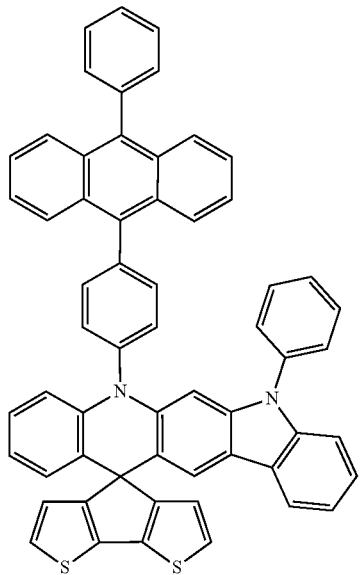
C35
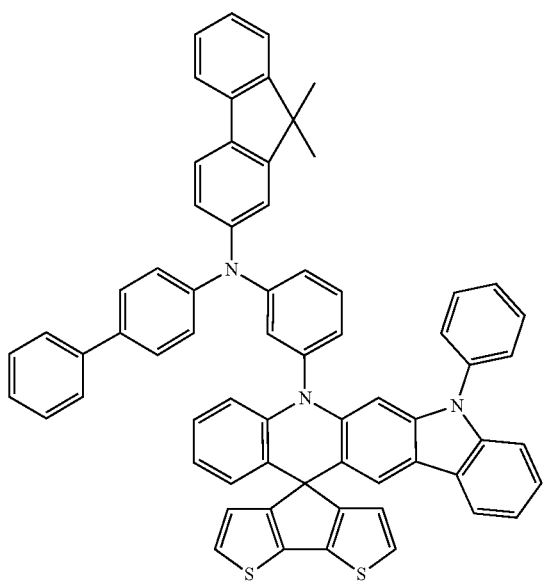
152
-continued
C36
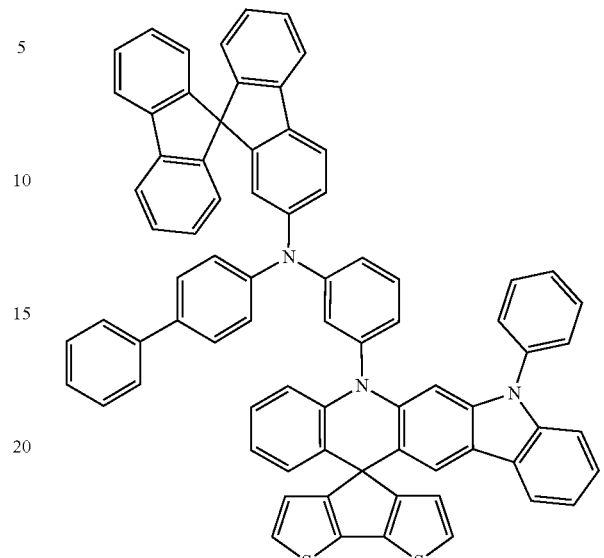
C37
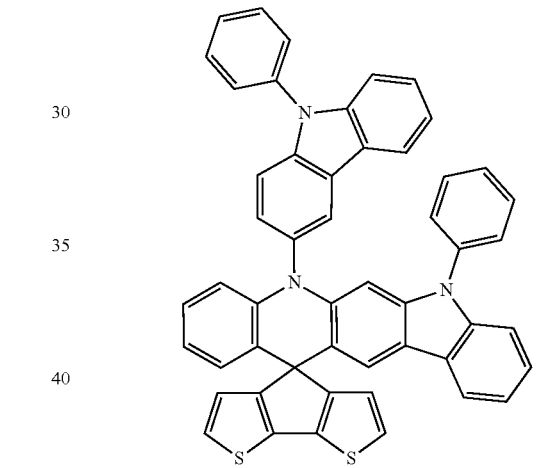
C38
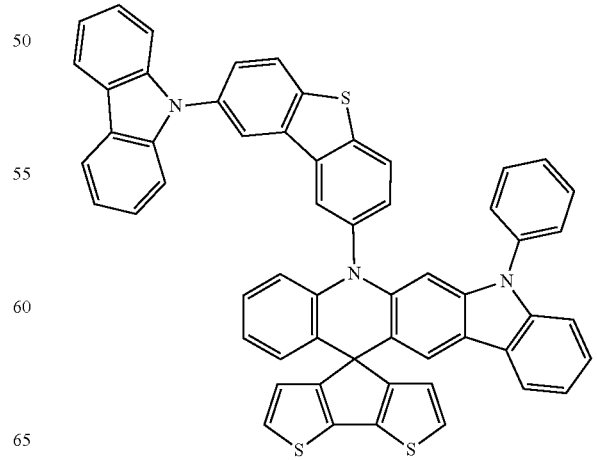

C39
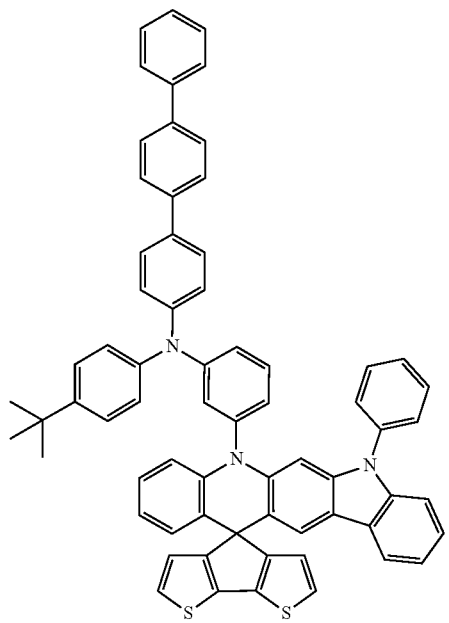
C40
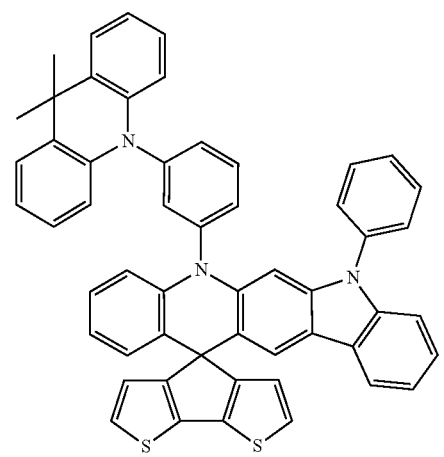
C41
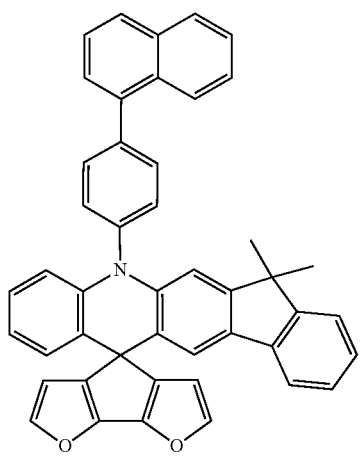
C42
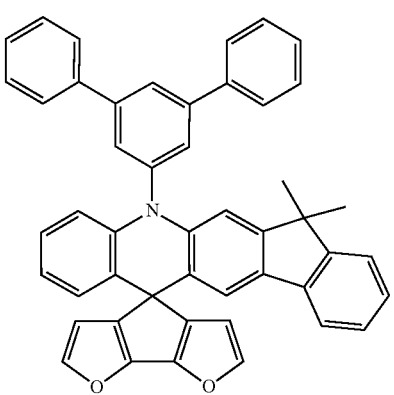
C43
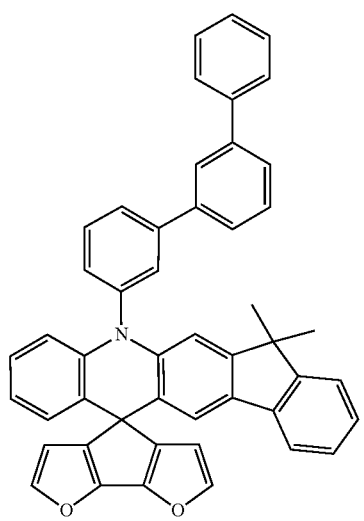
C44
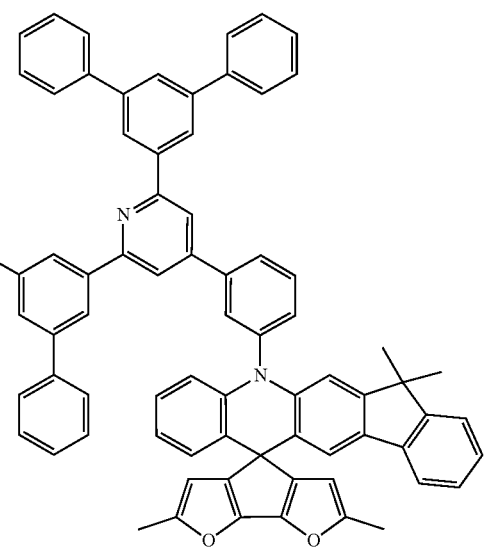

C45
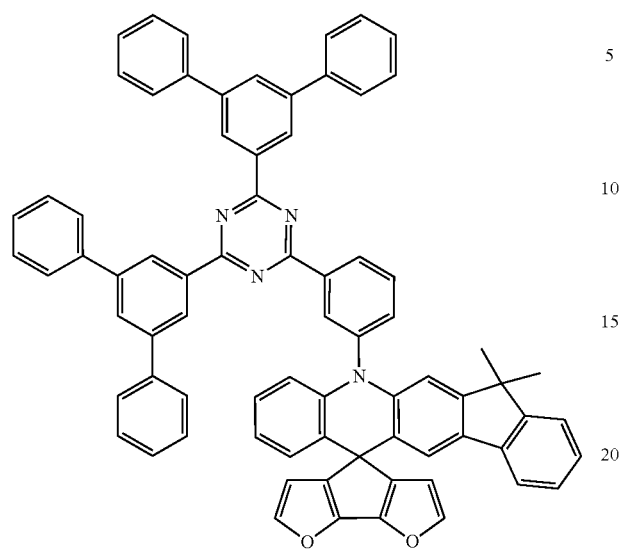
C46
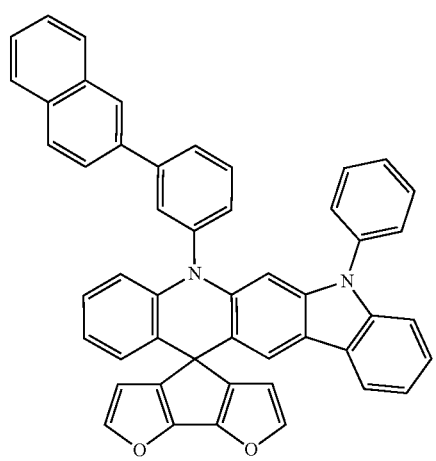
C47
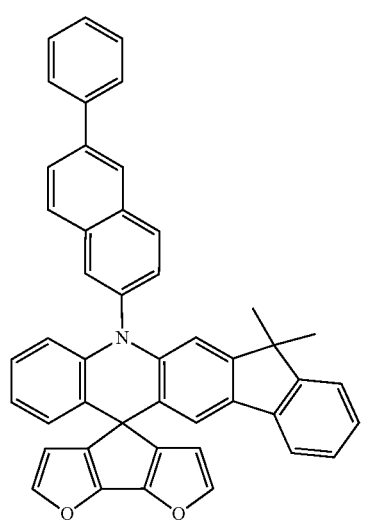
C48
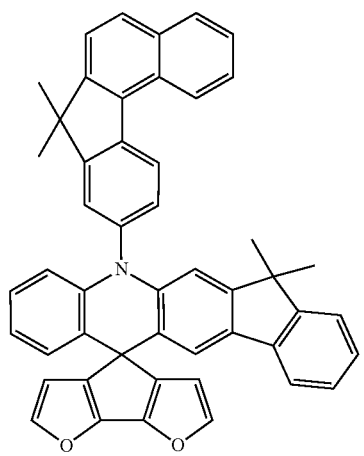
C49
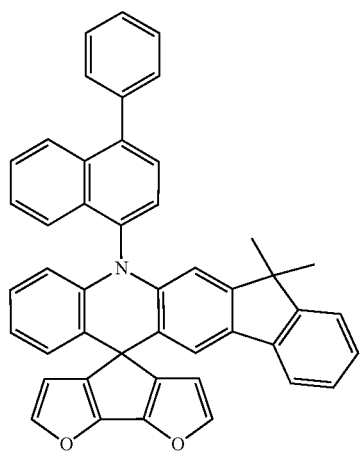
C50
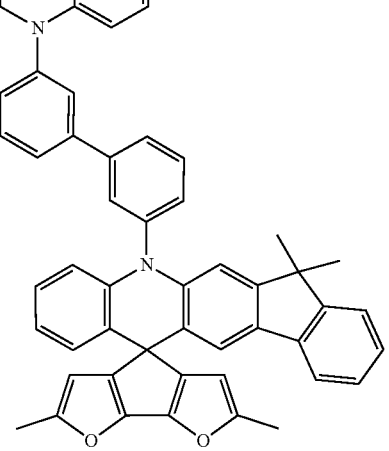

C51
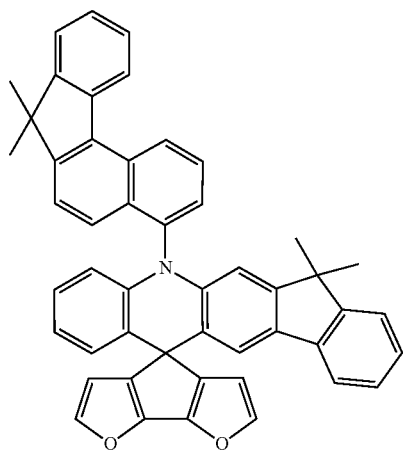
C52
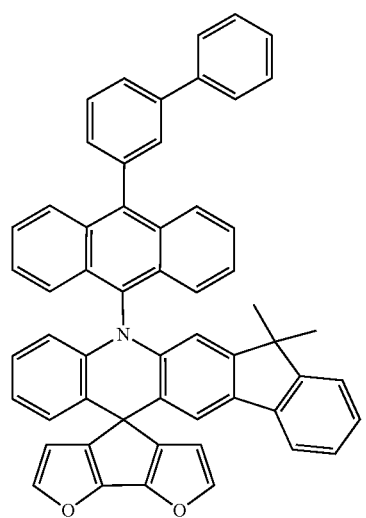
C53
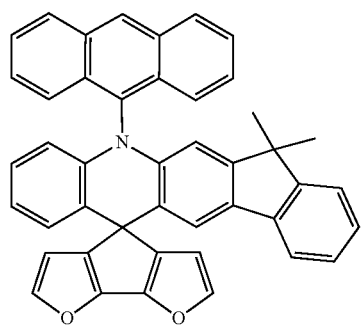
C54
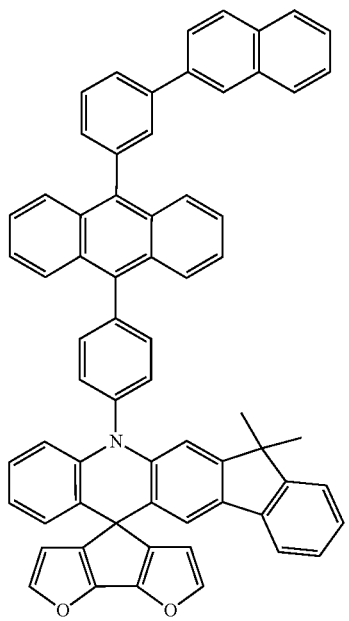
C55
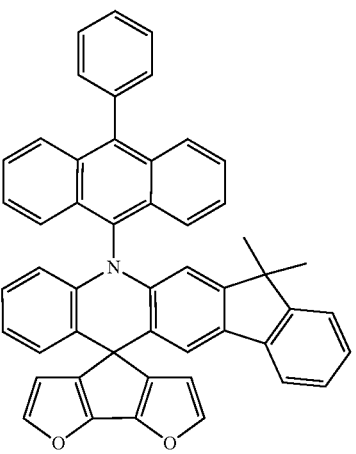
C56
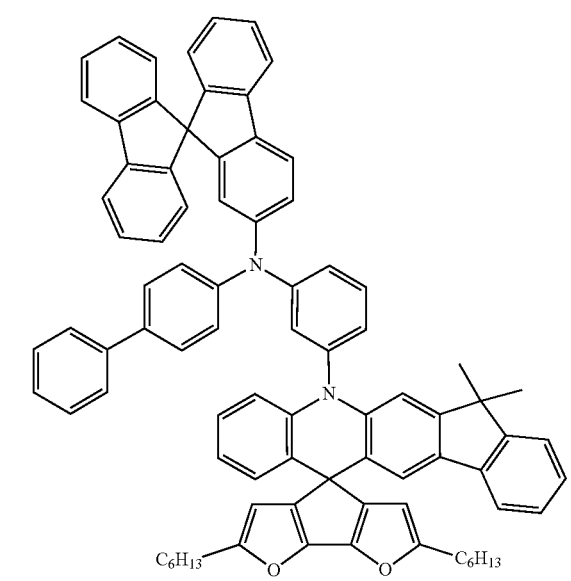

C57
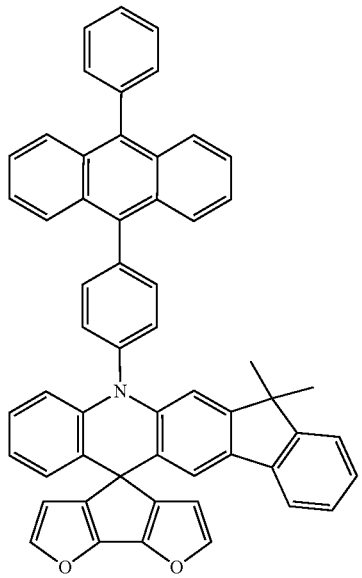
C58
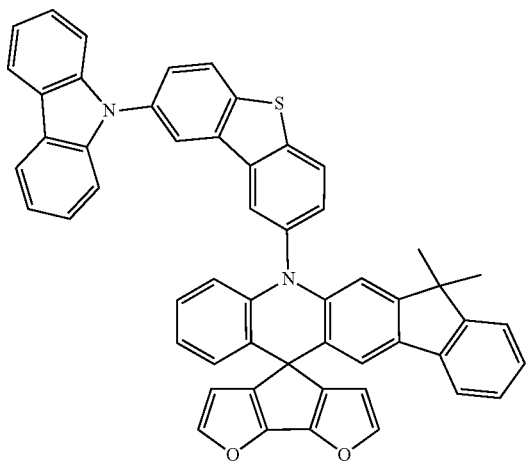
C59
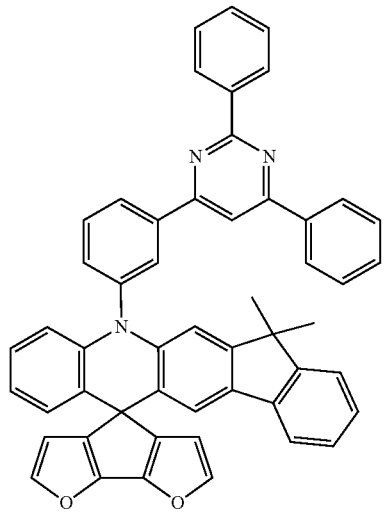
C60
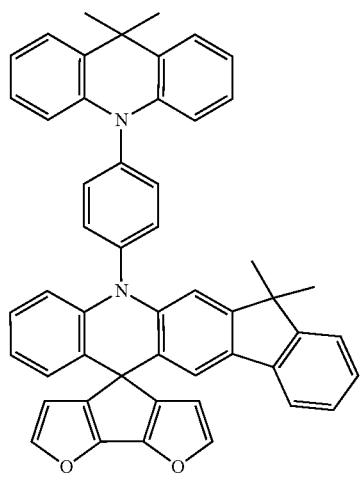
C61
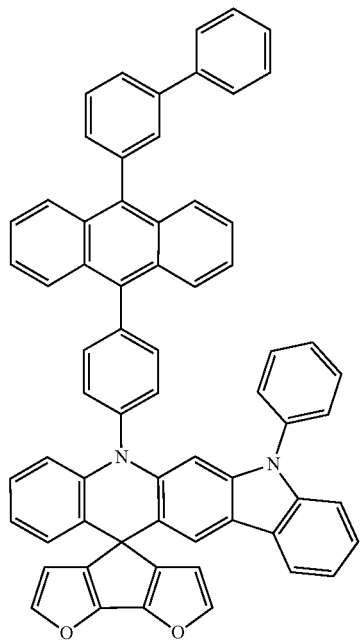

C62
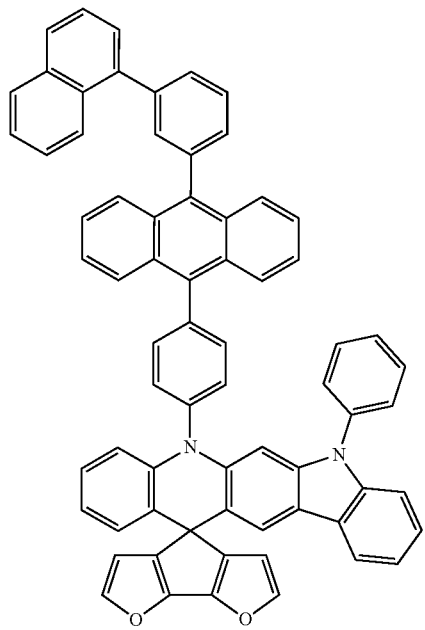
C63
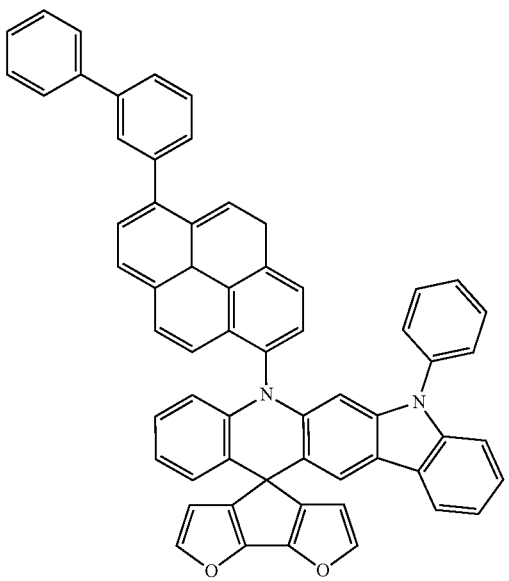
C64
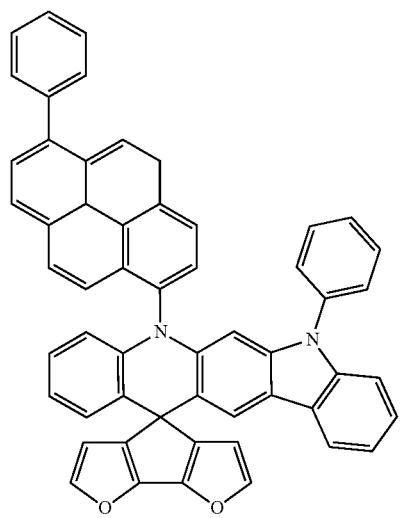
C65
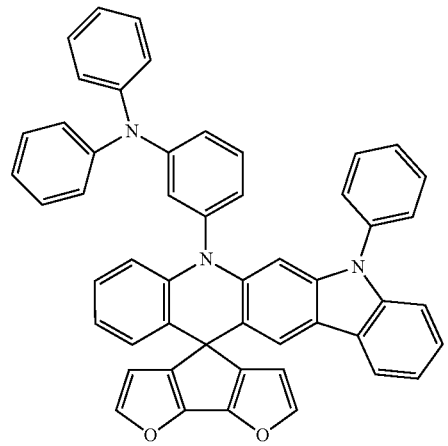
C66
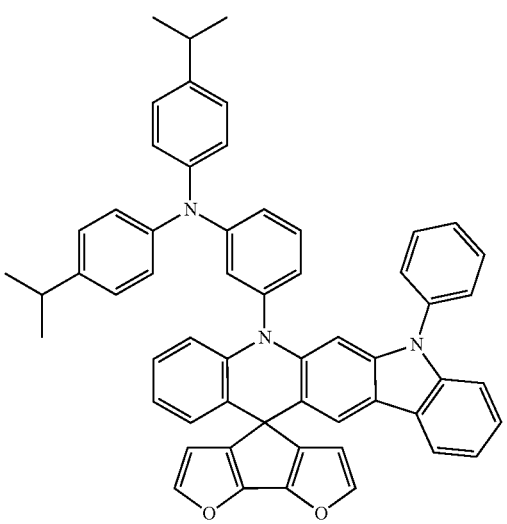

-continued
C67
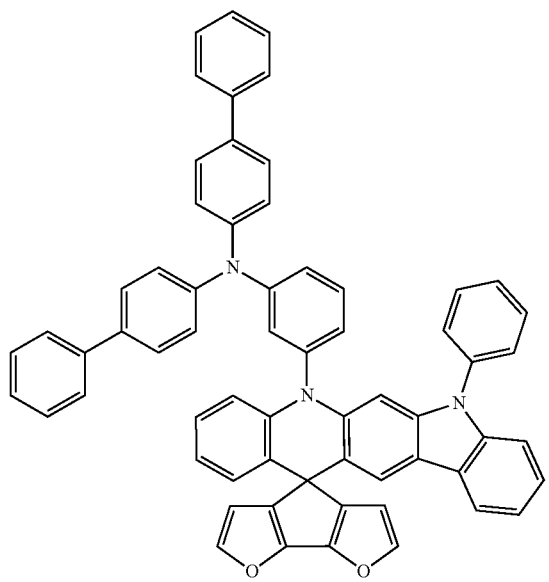
C68
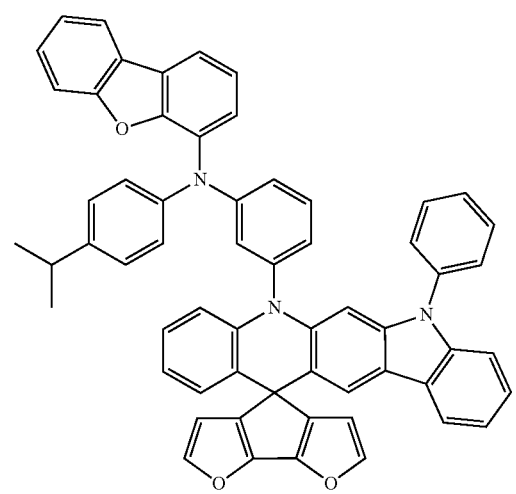
C69
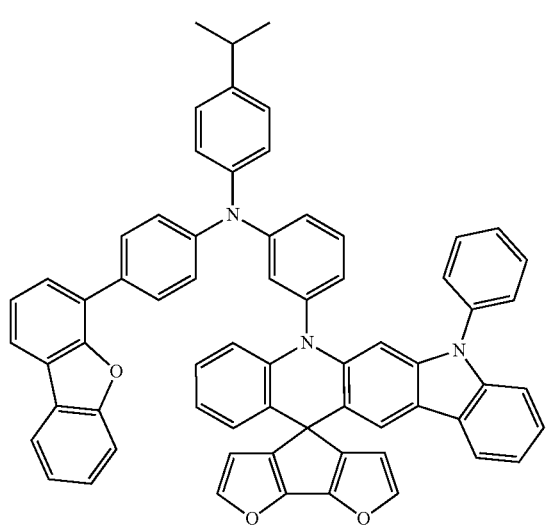
-continued
C70
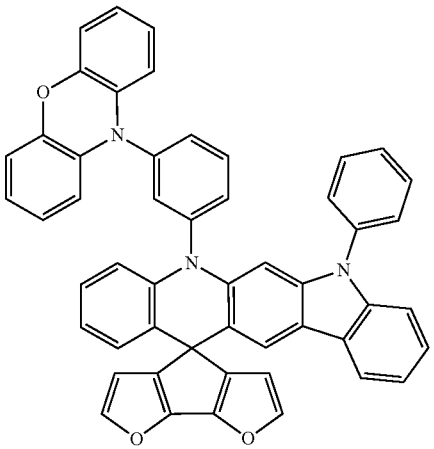
C71
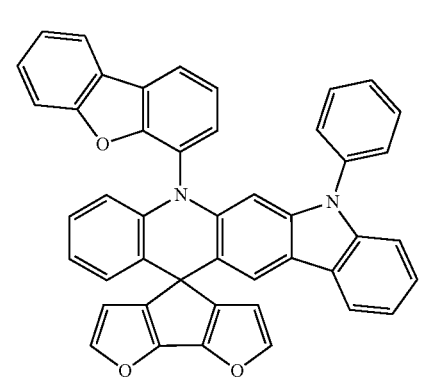
C72
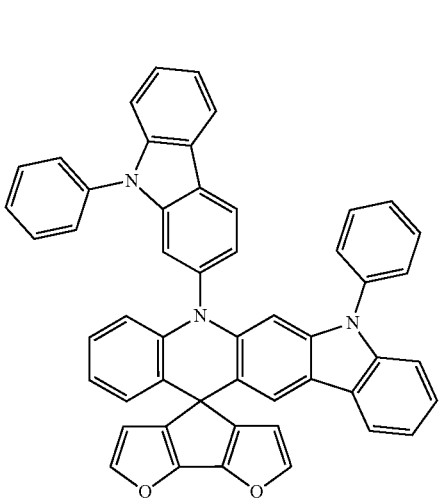

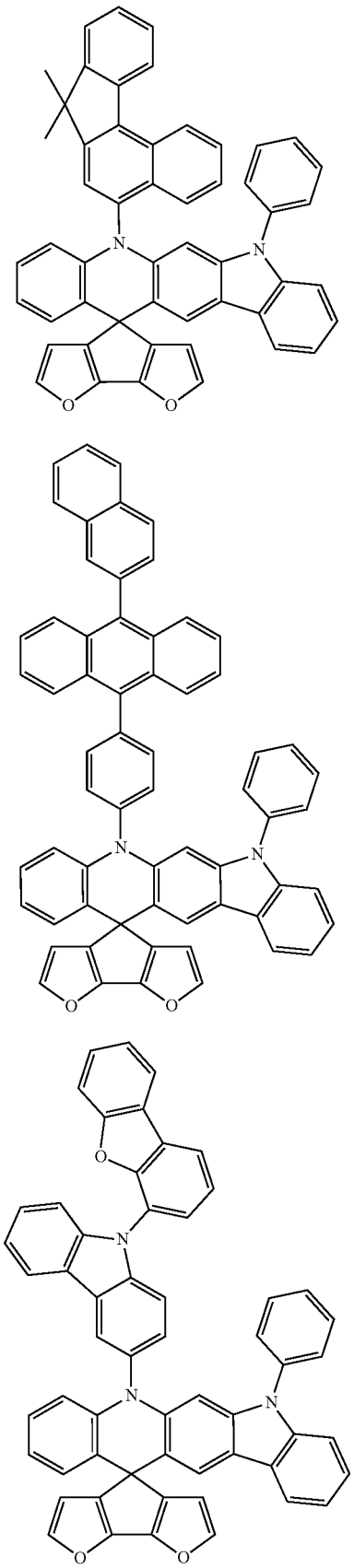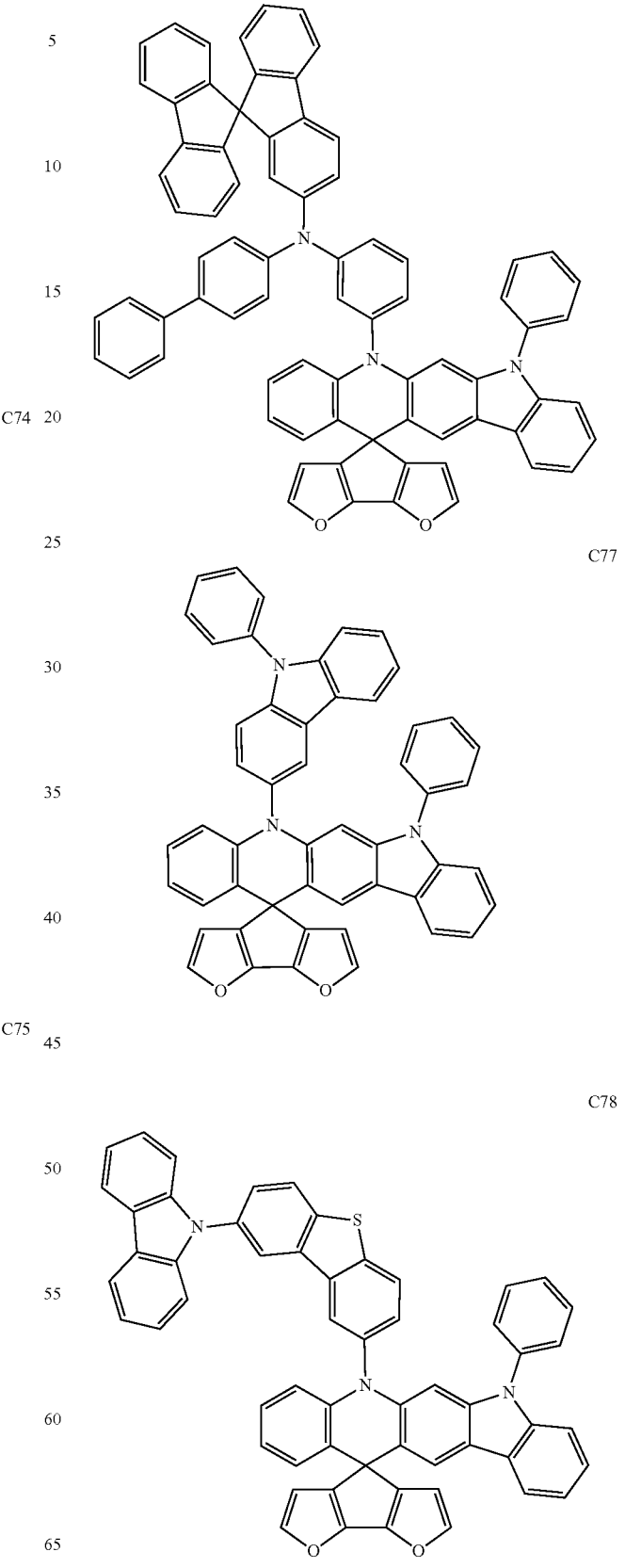

167
-continued
C79
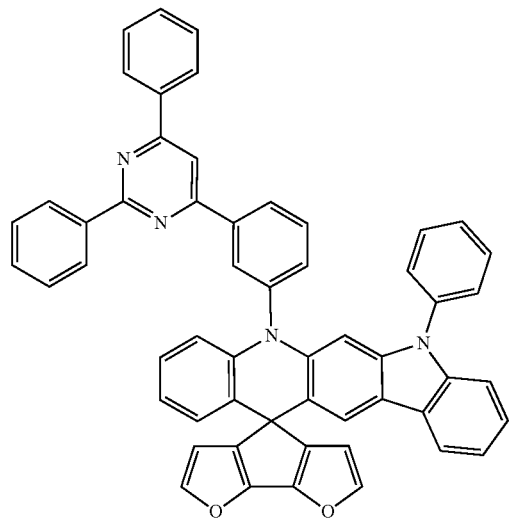
C80
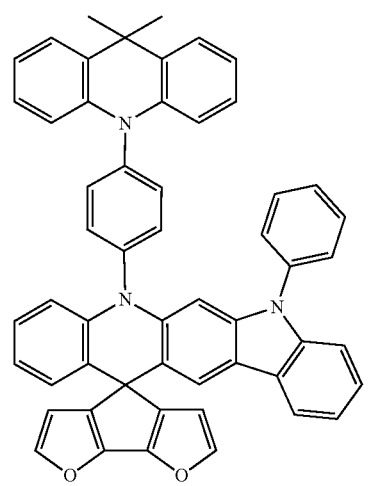
C81
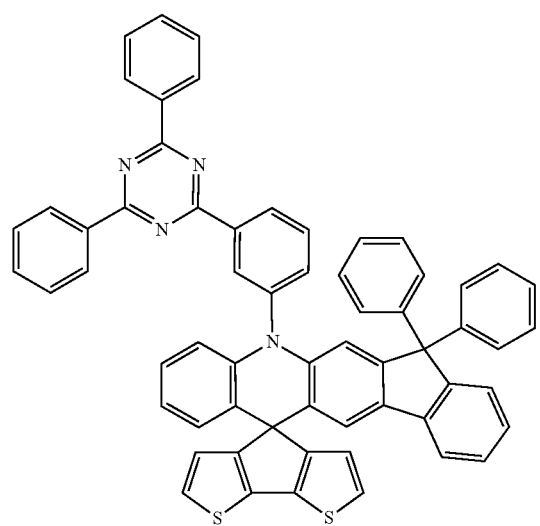
168
-continued
C82
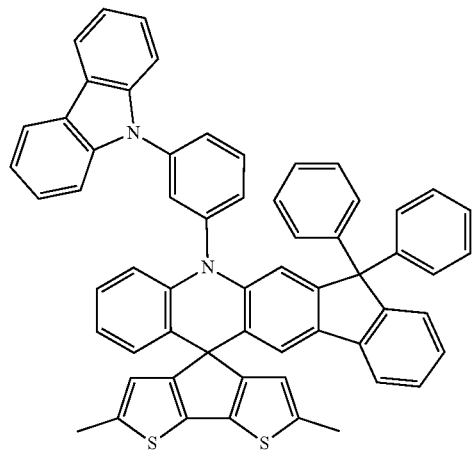
C83
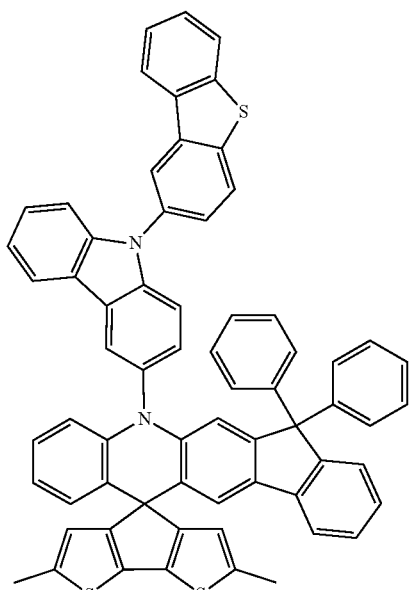
C84
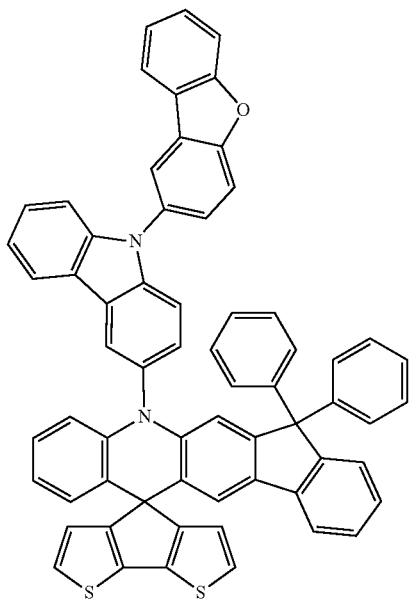

C85
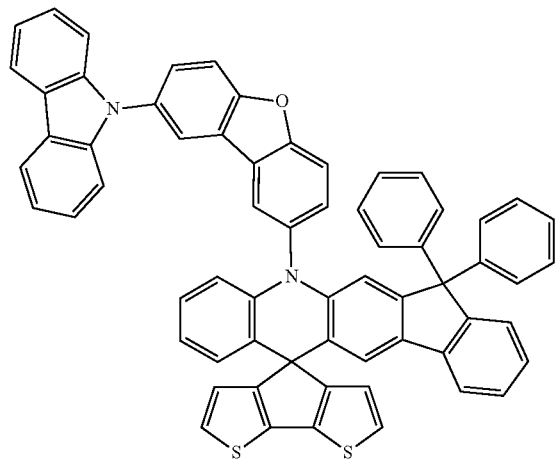
C86
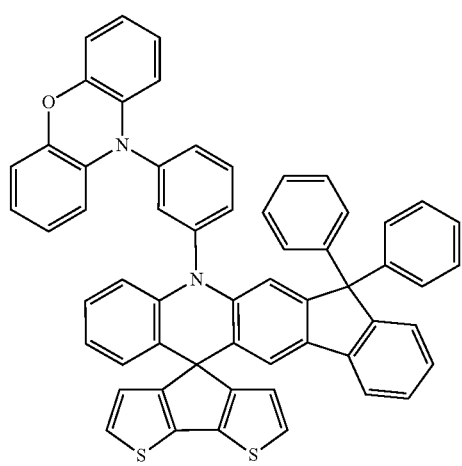
C87
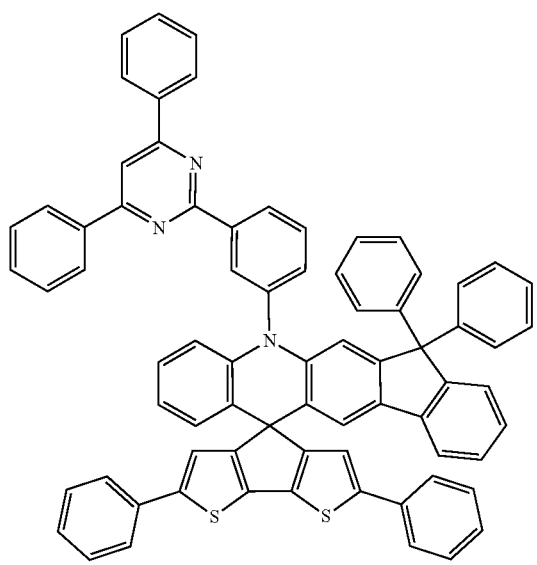
C88
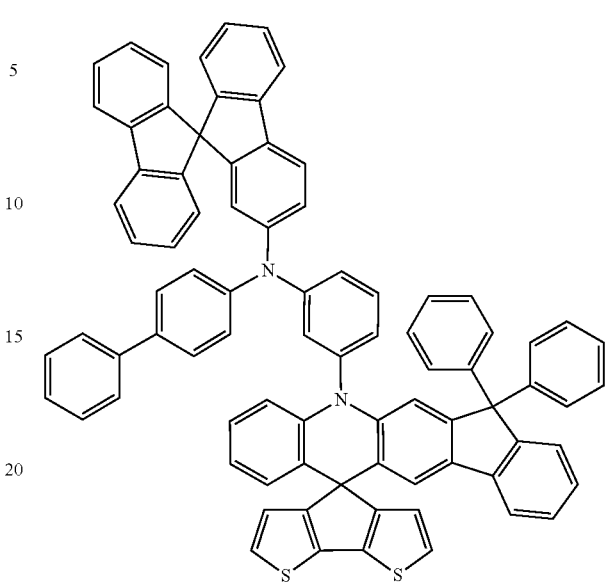
C89
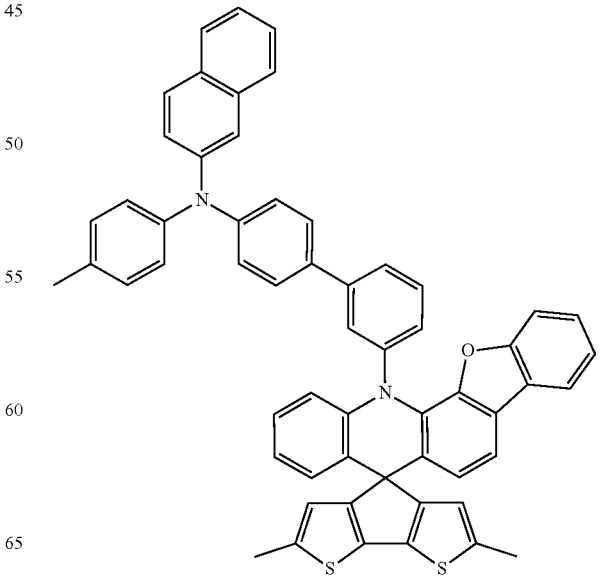

-continued
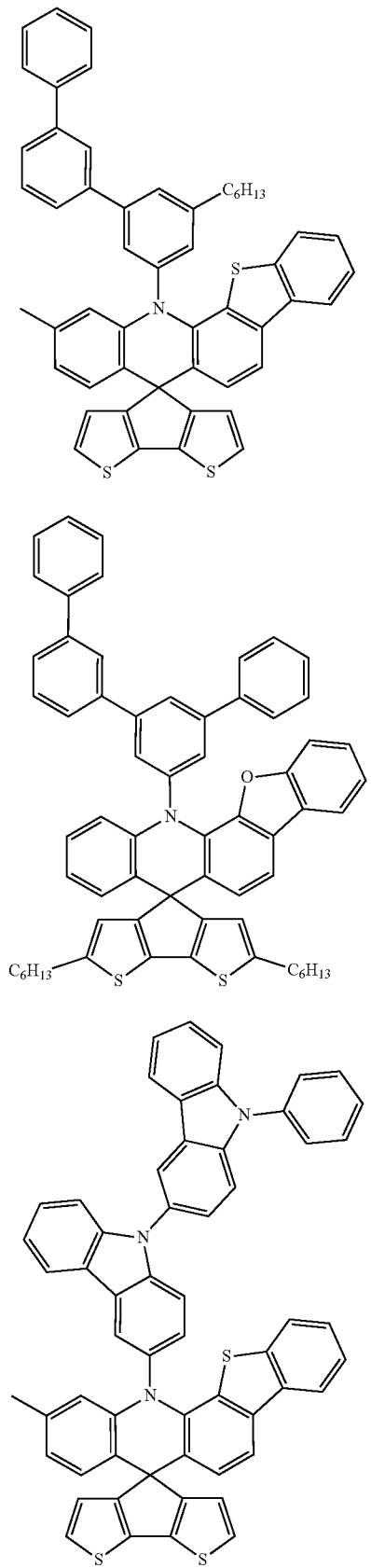
C90
C91
C92
-continued
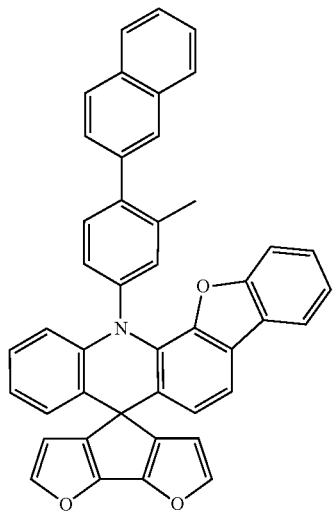
C93
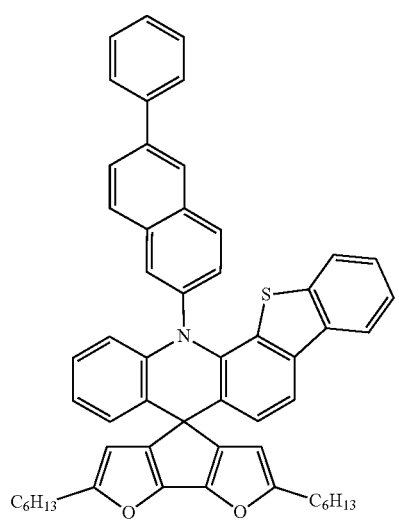
C94
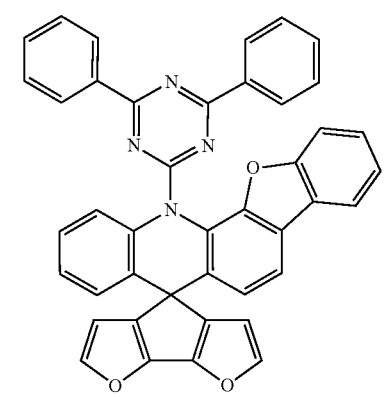
C95

C96
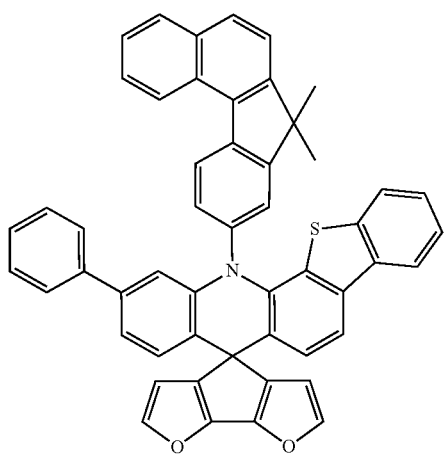
C97
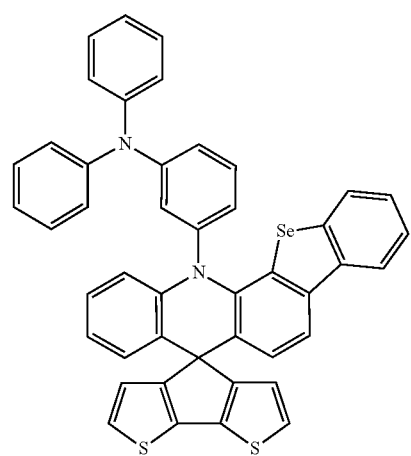
C98
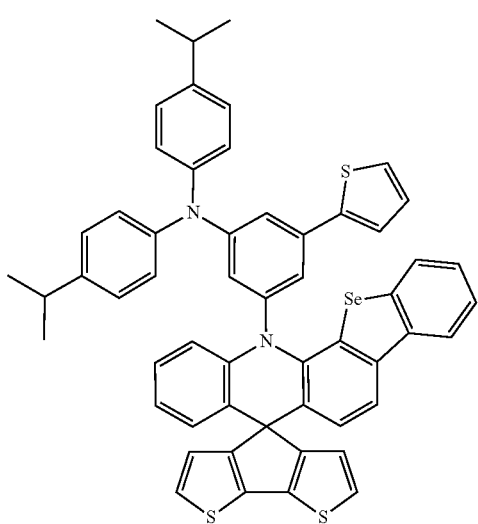
C99
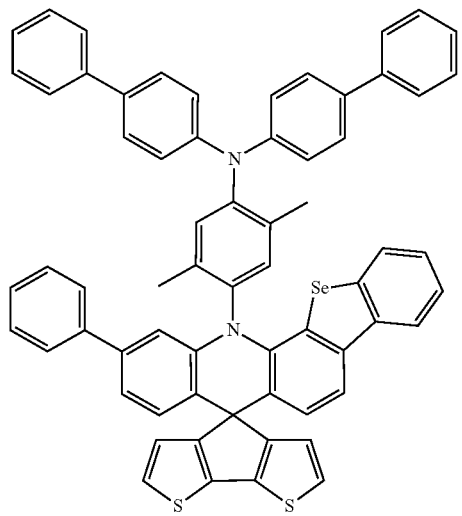
C100
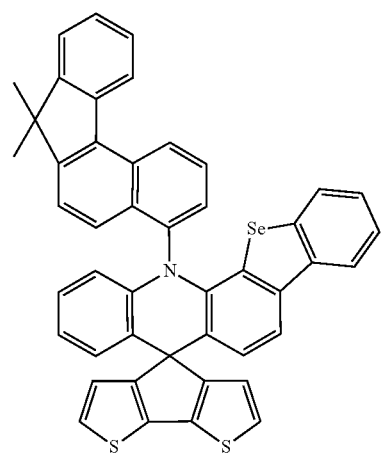
C101
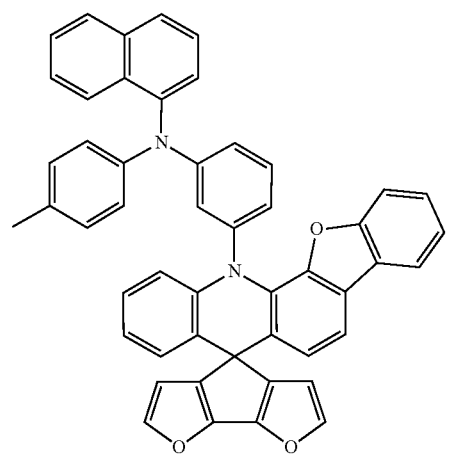

C102
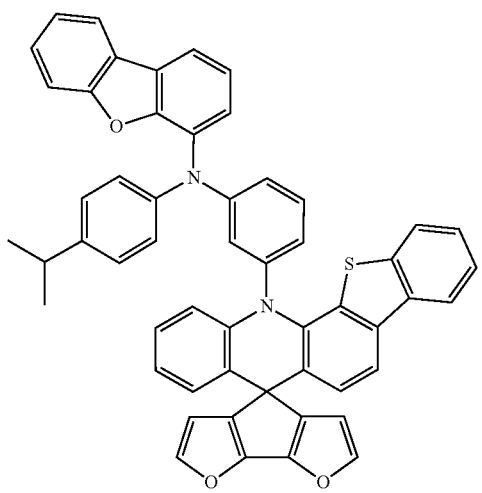
C104
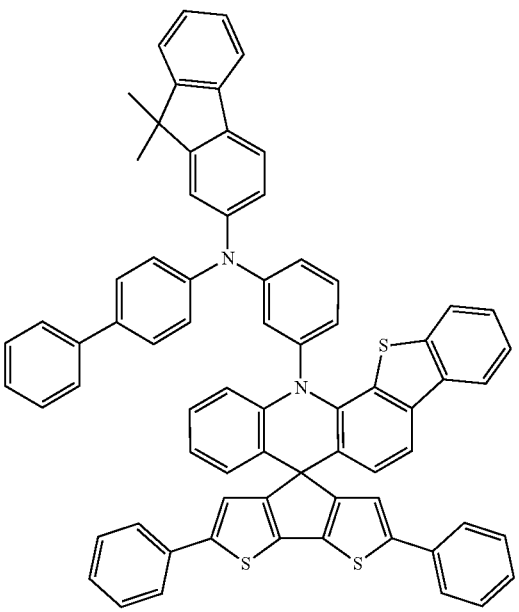
C103
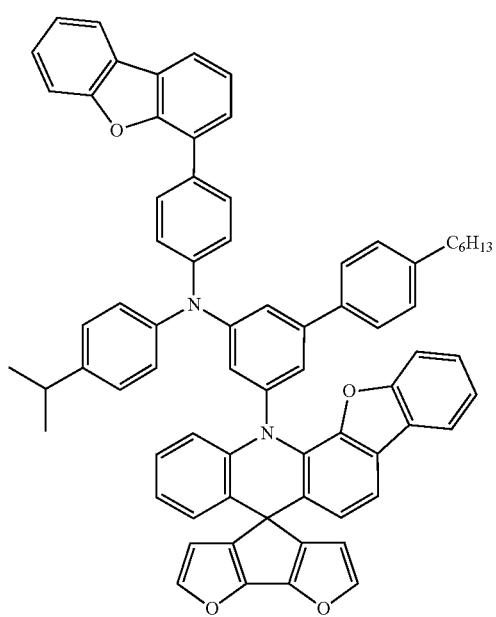
C105
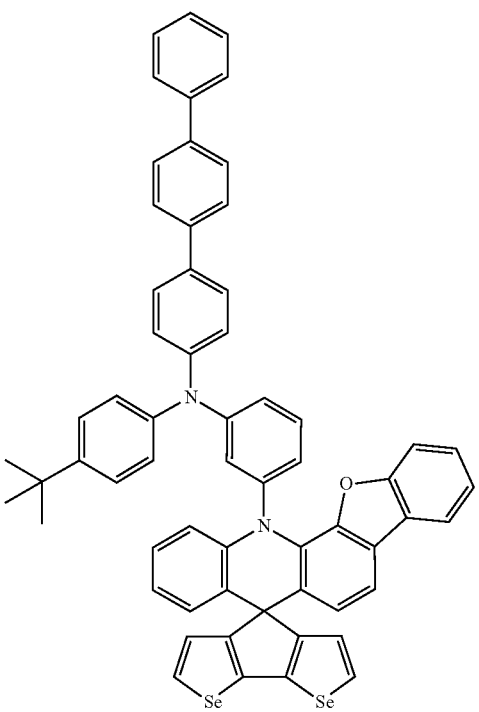

C106
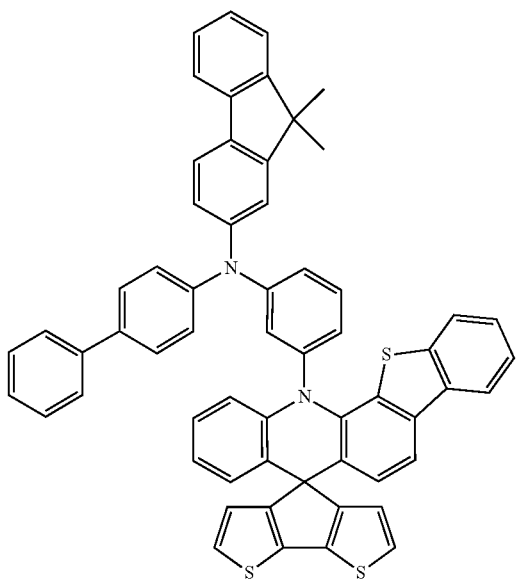
C108
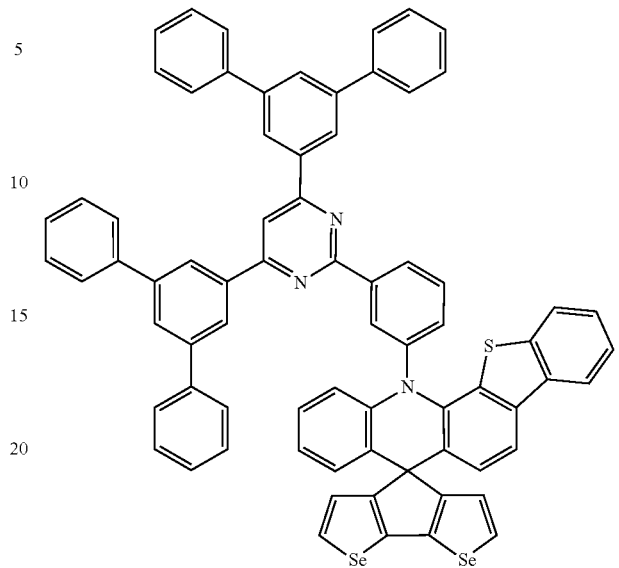
C107
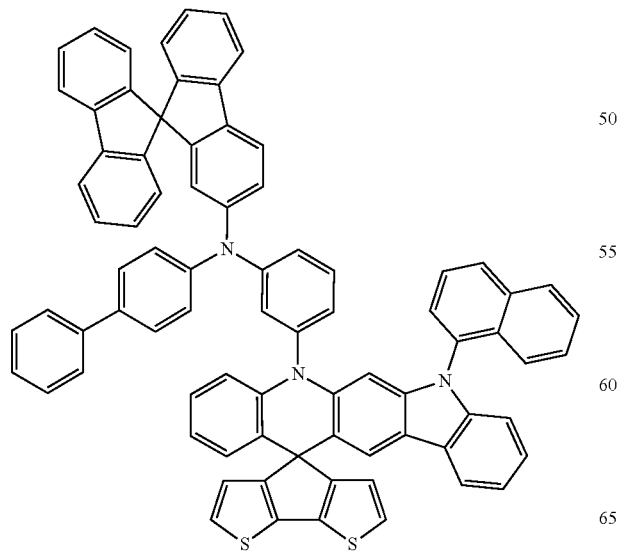
C109
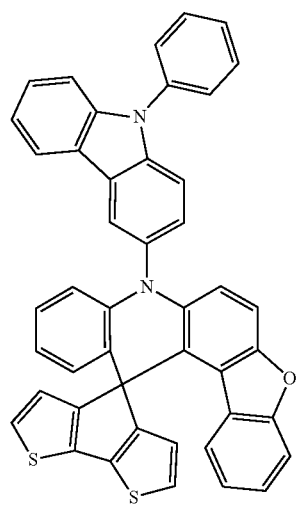

C110
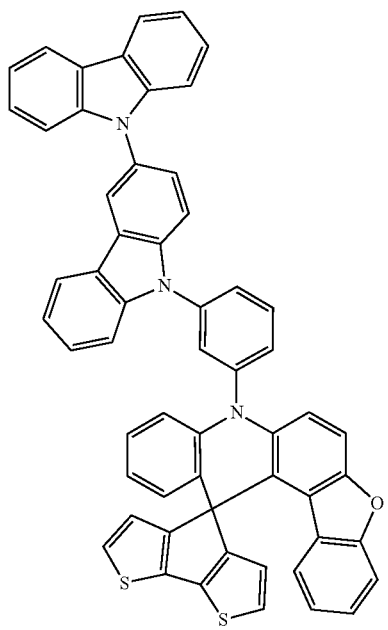
C111
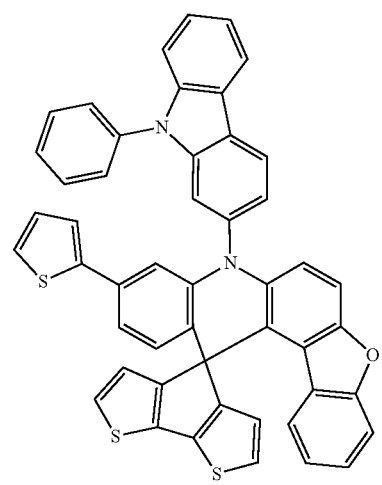
C112
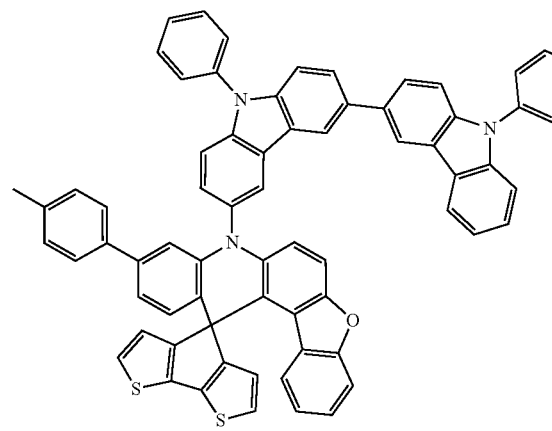
C113
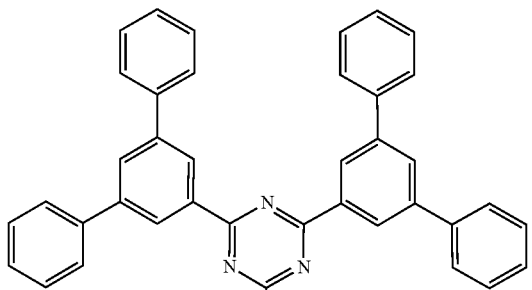
C114
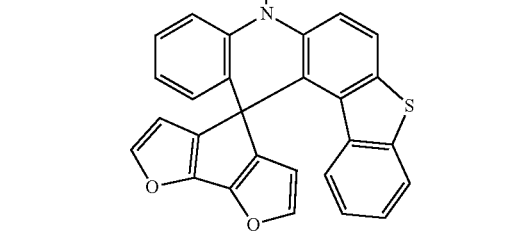
C115
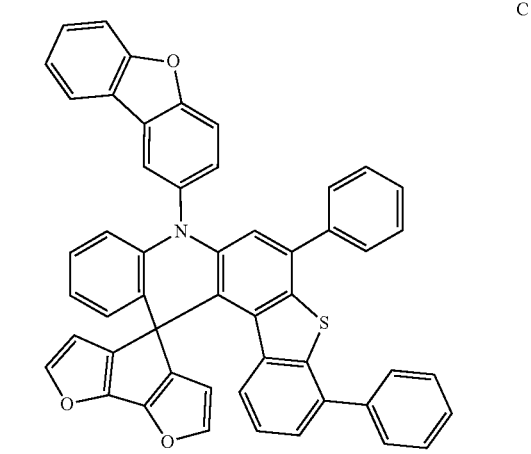
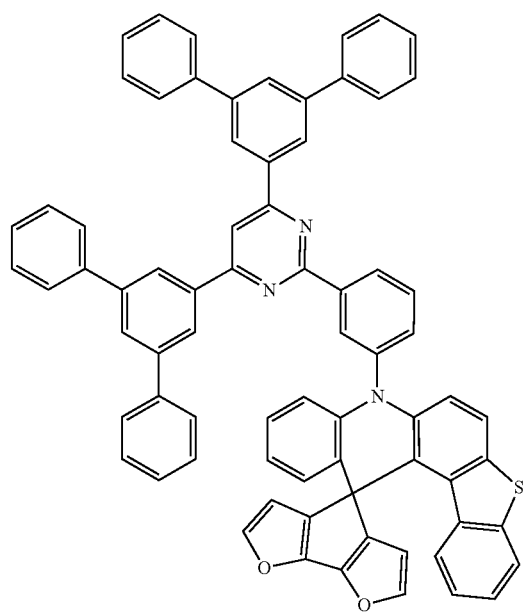

C116
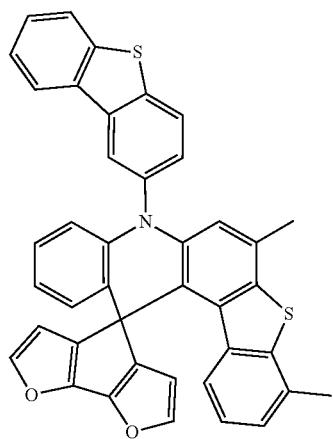
C117
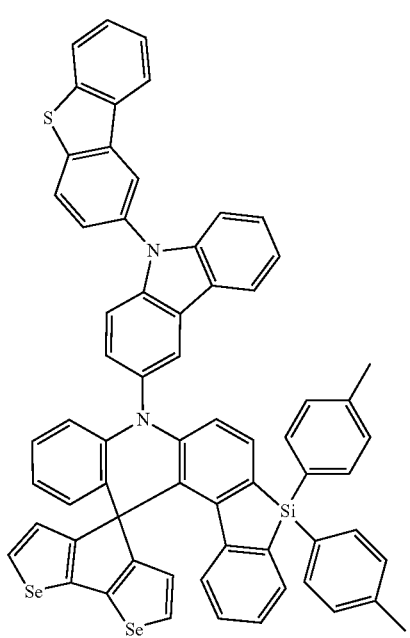
C118
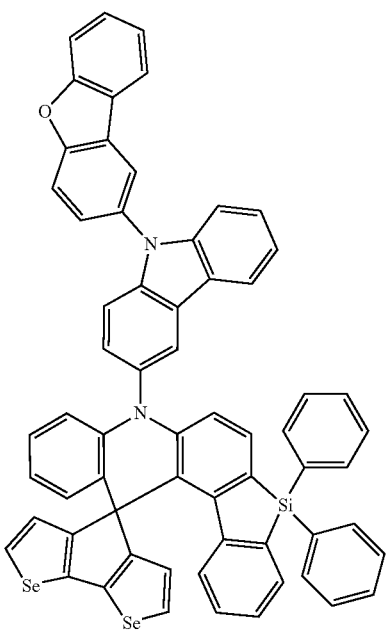
C119
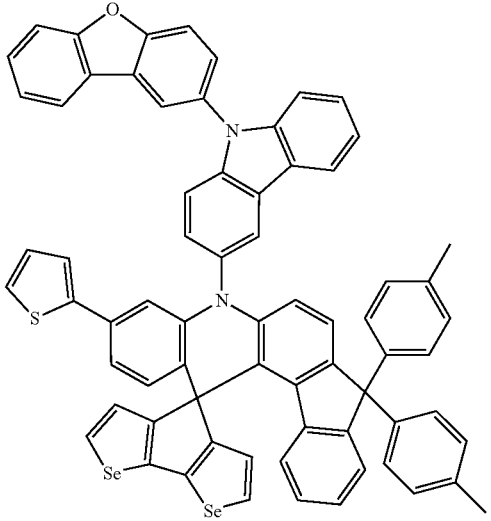

183
-continued
C120
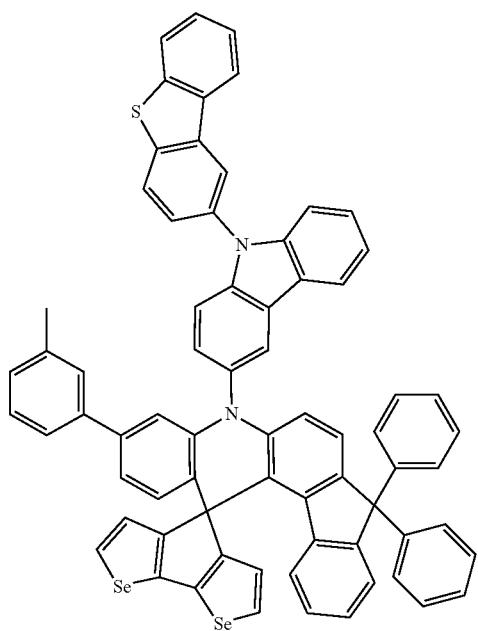
C121
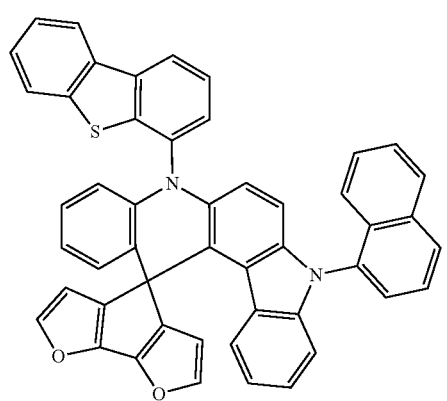
C122
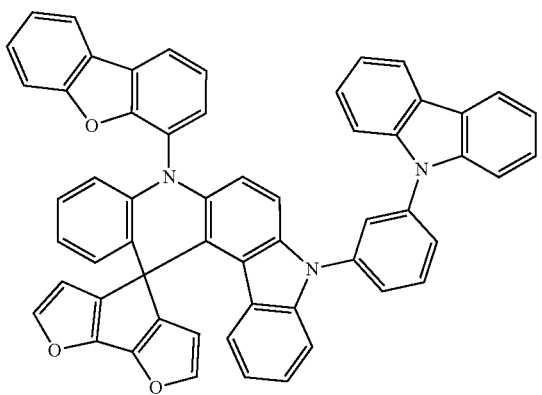
184
-continued
C123
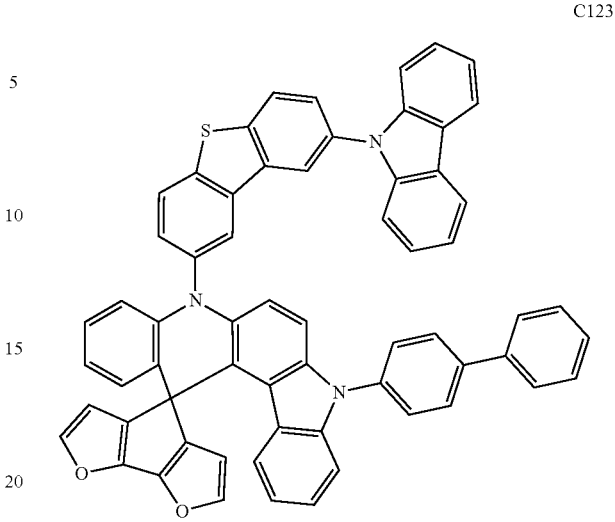
C124
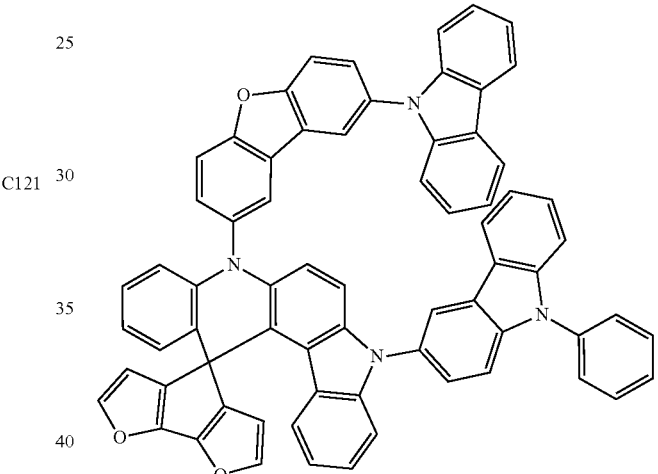
C125
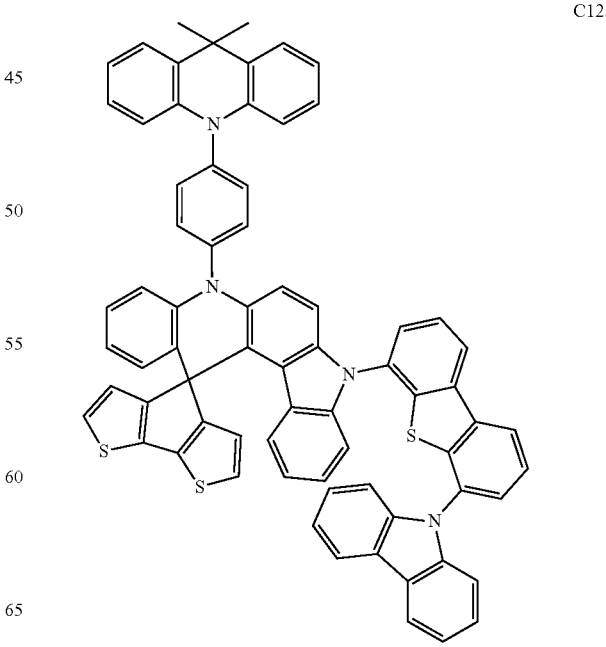

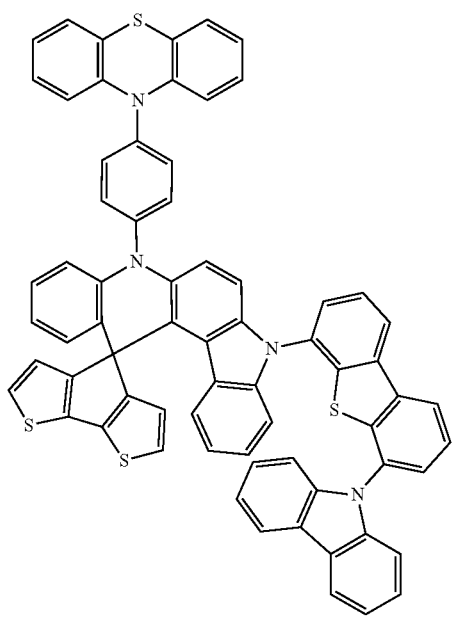
C126
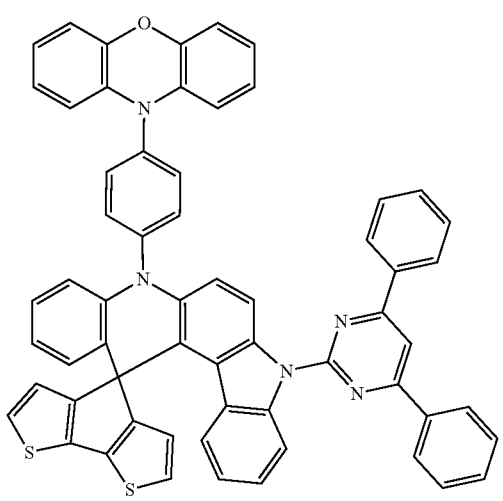
C127
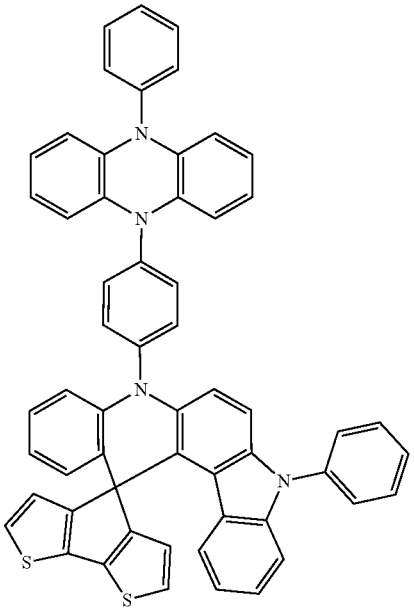
C128
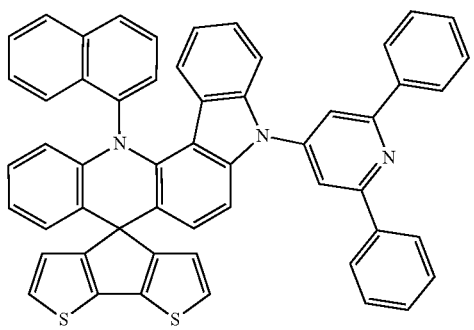
C129
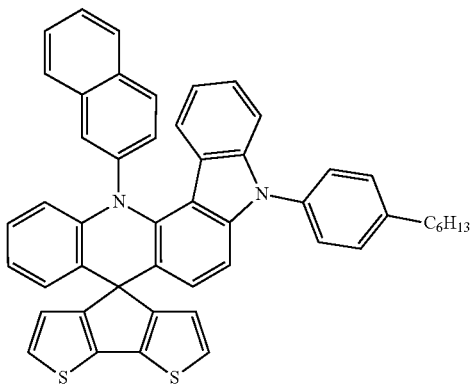
C130

C131
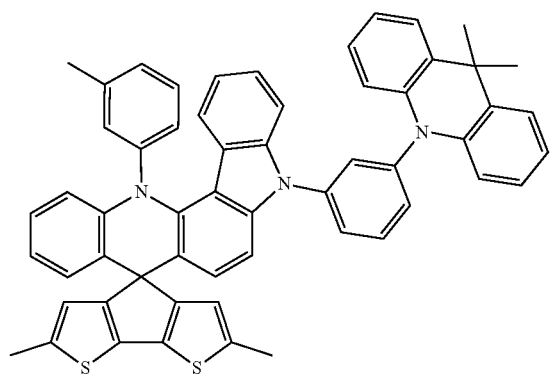
C132
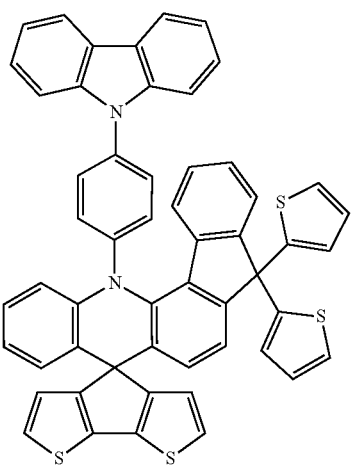
C133
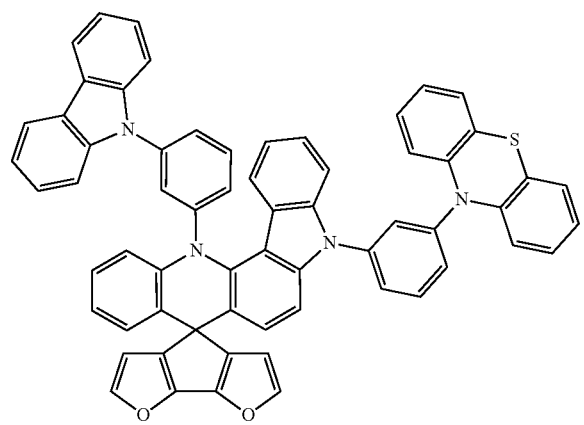
C134
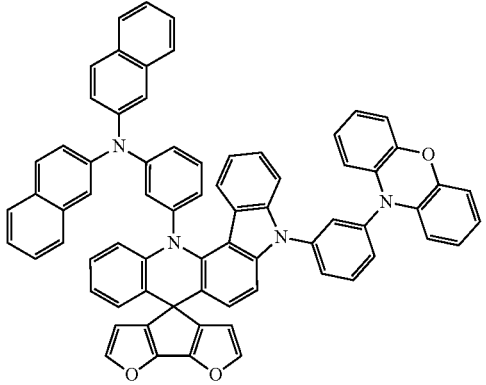
C135
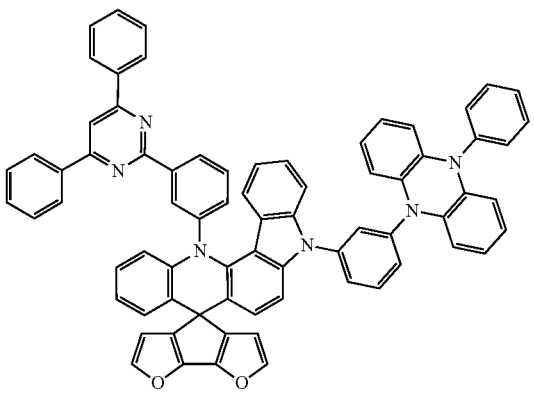
C136
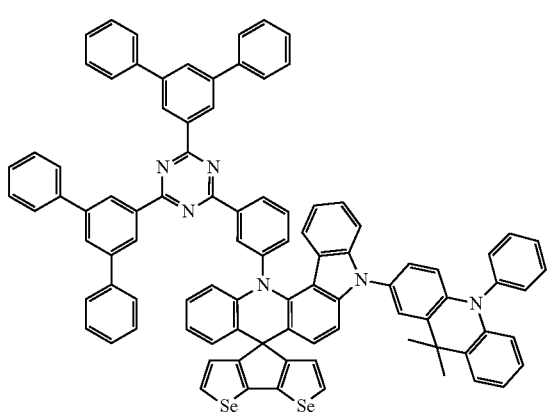

C137
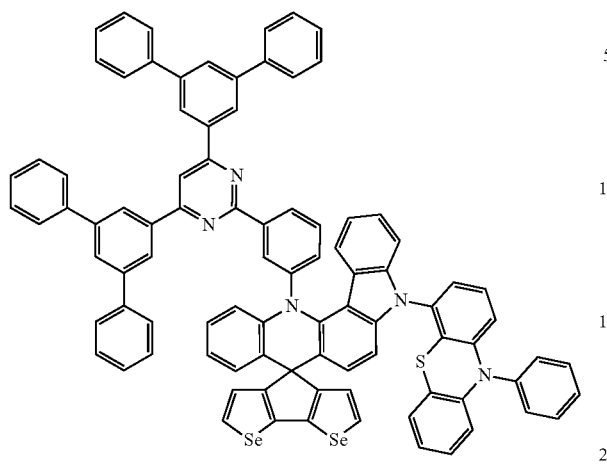
C138
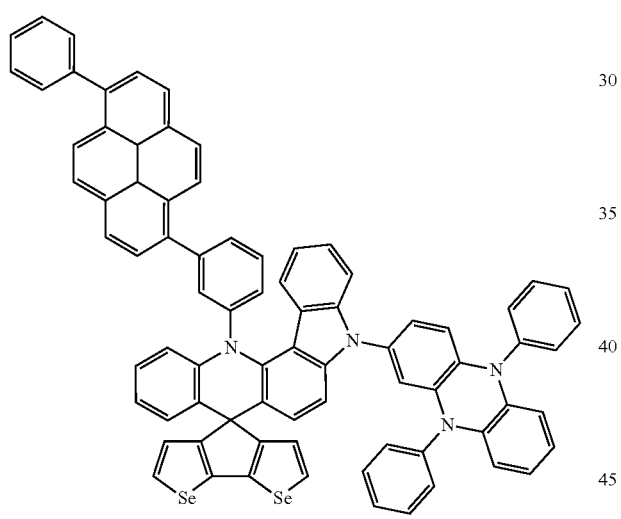
C139
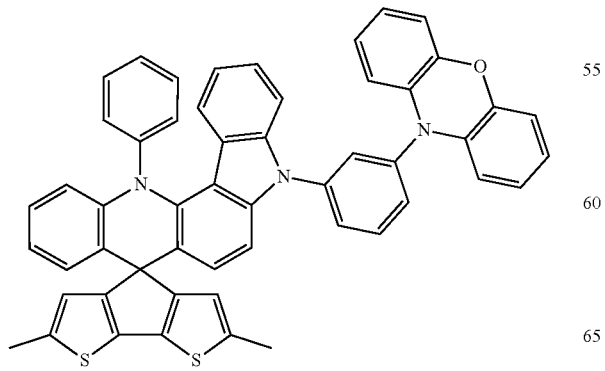
C140
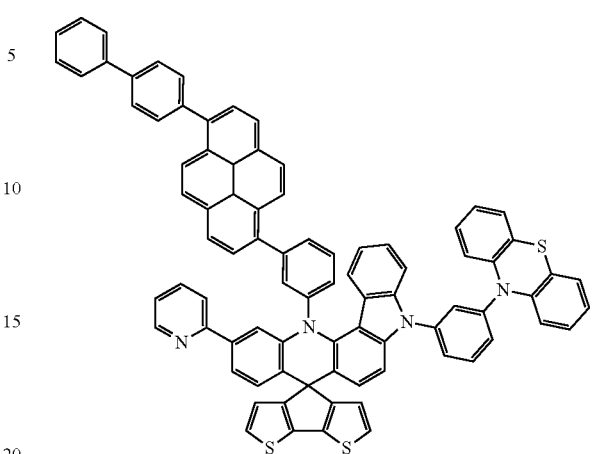
C141
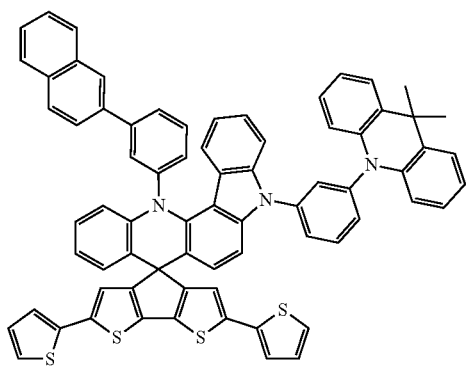
C142
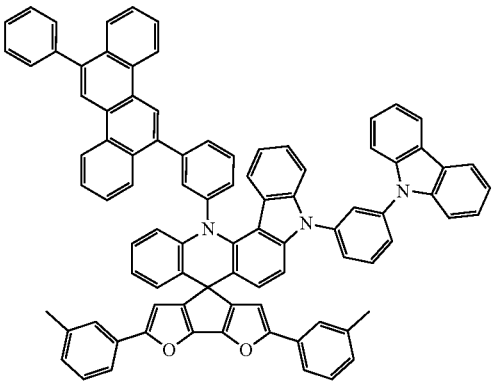

C143
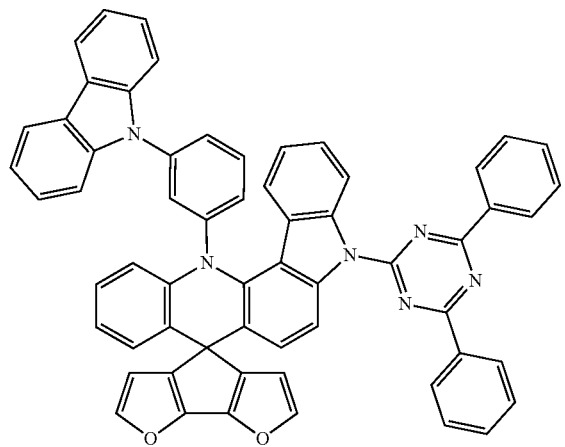
C144
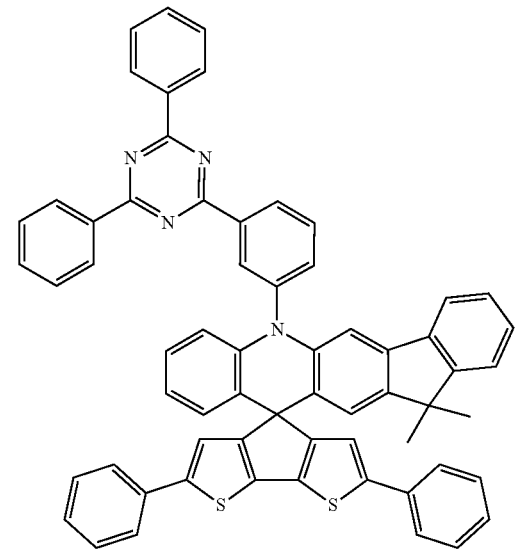
C145
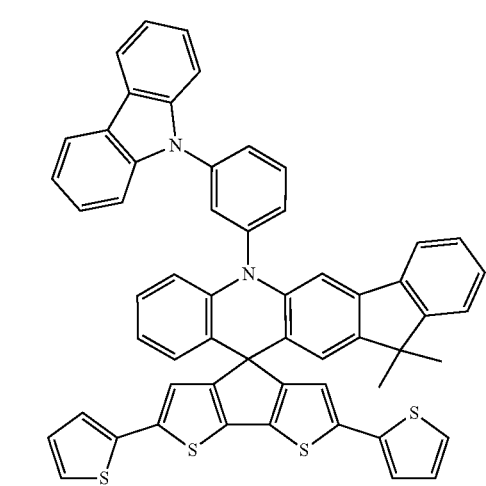
C146
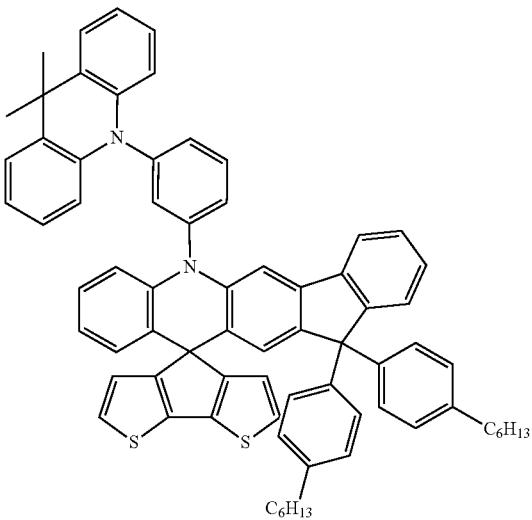
C147
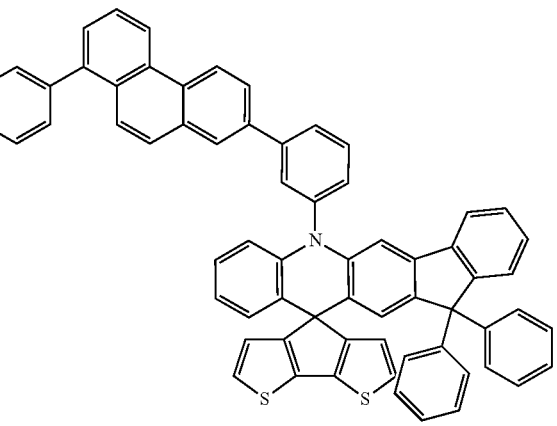
C148
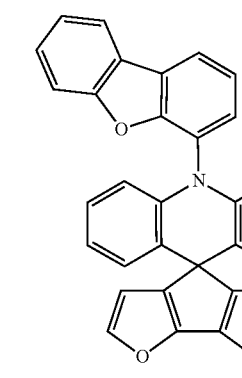

C149
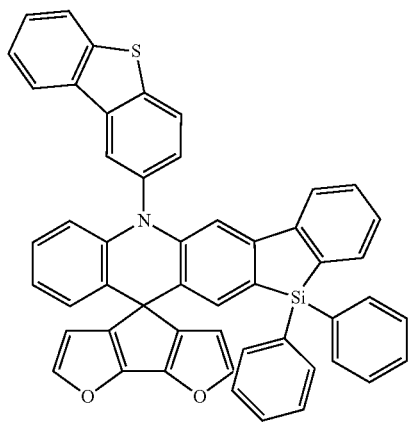
C150
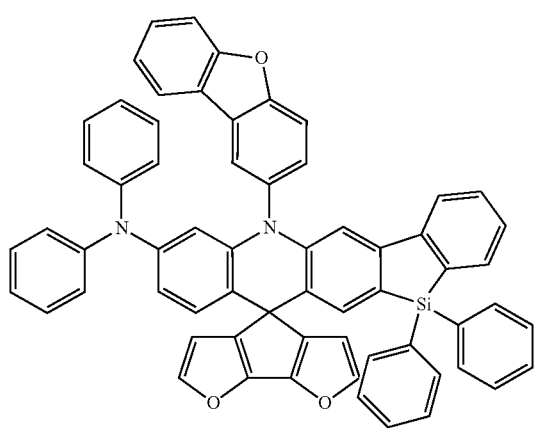
C151
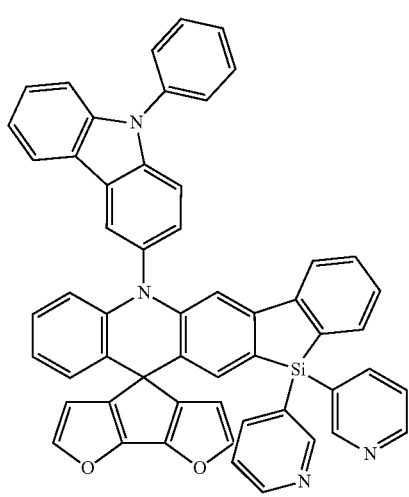
C152
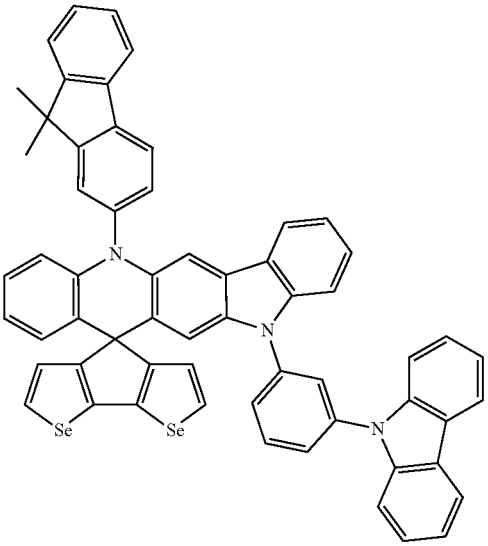
C153
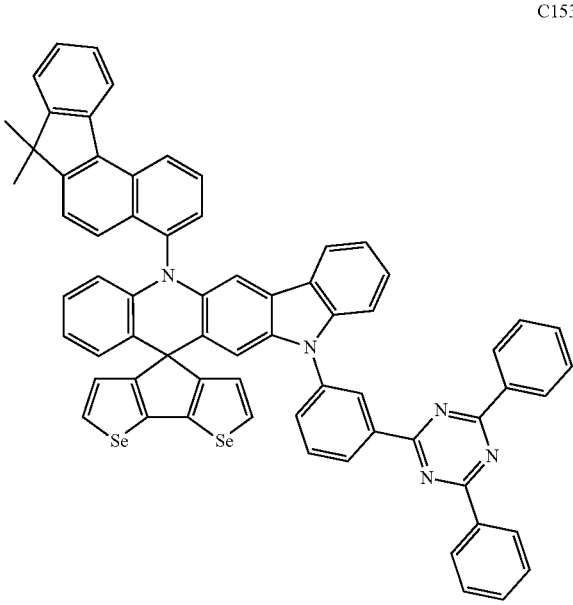
C154

C155
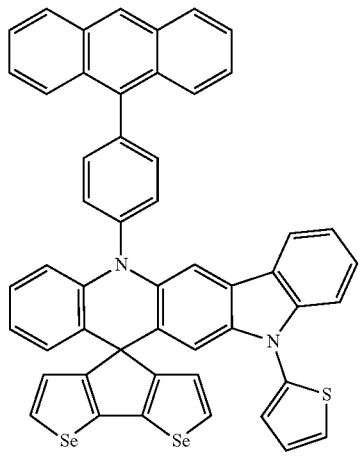
C156
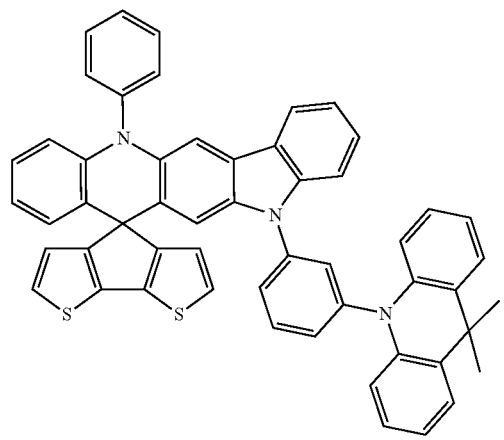
C157
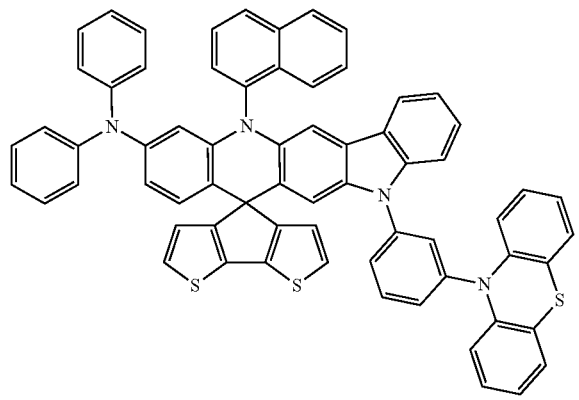
C158
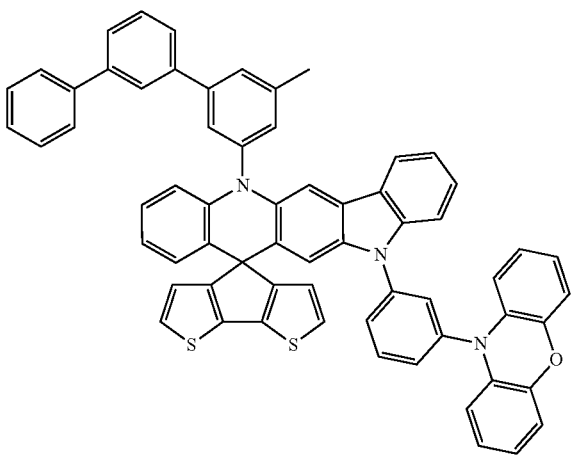
C159
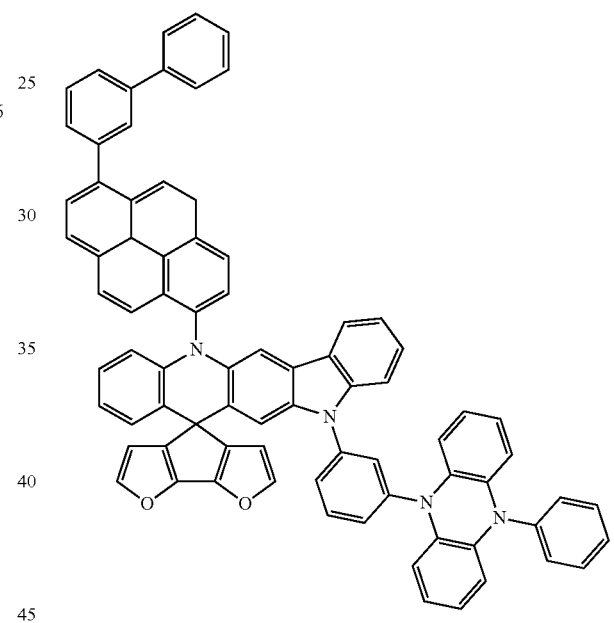
C160
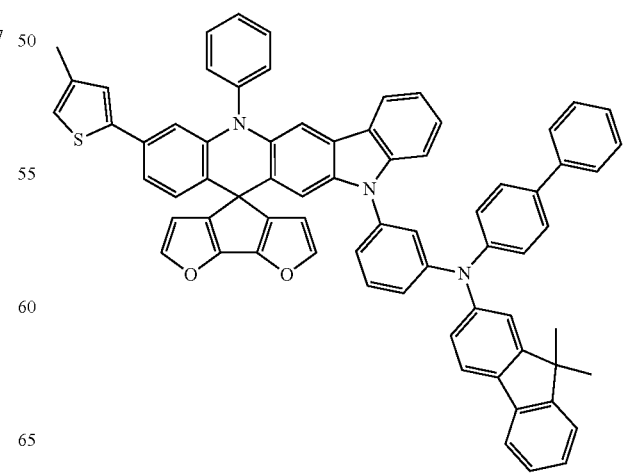

C161
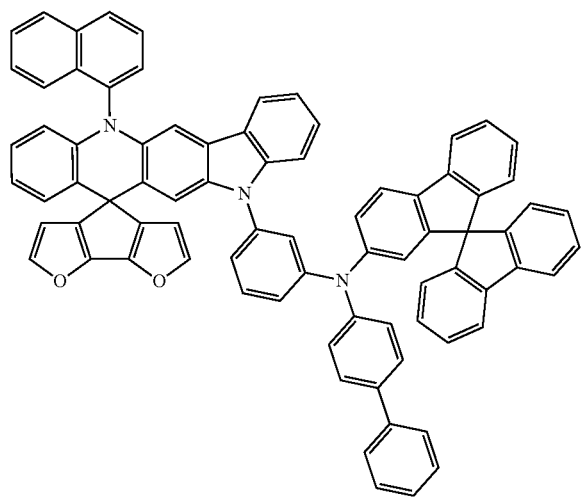
C164
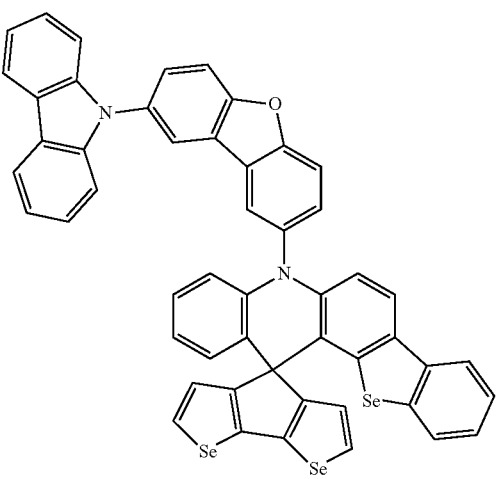
C162
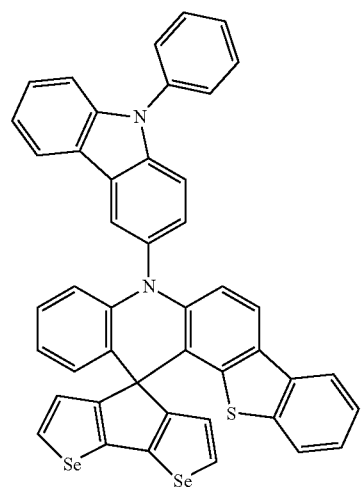
C165
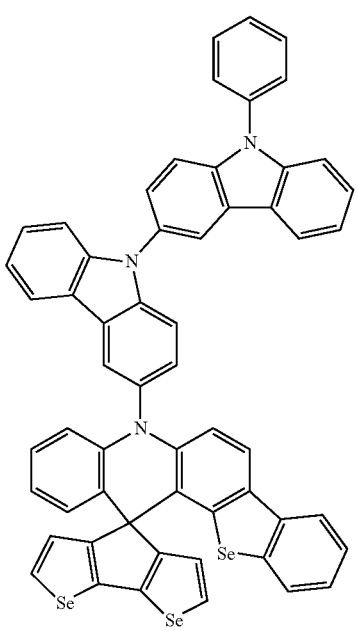
C163
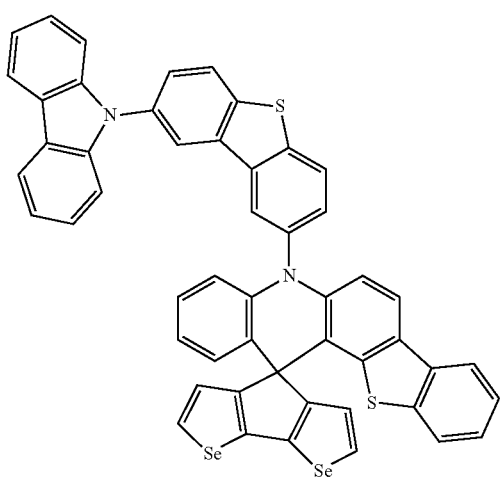
C166
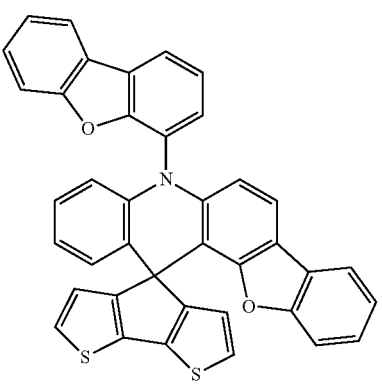

-continued
C167
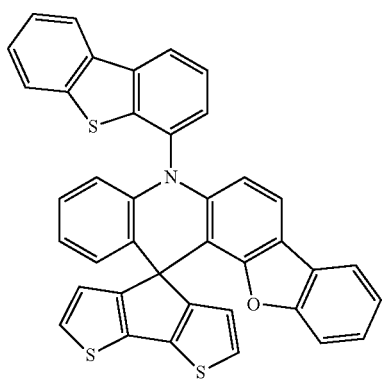
C168
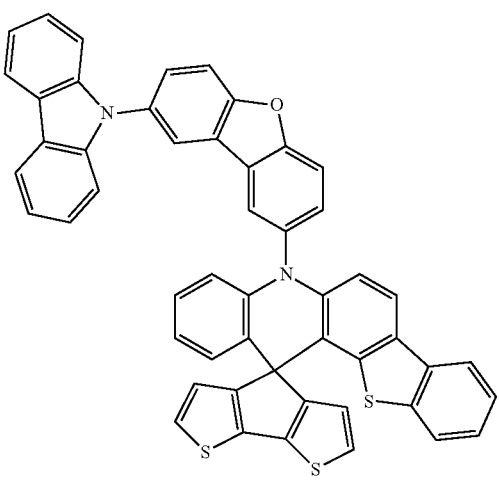
C169
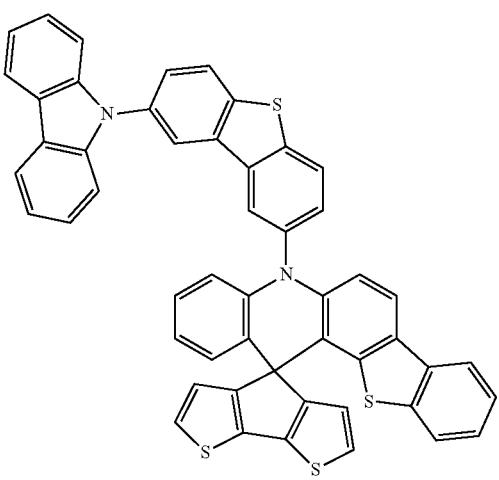
-continued
C170
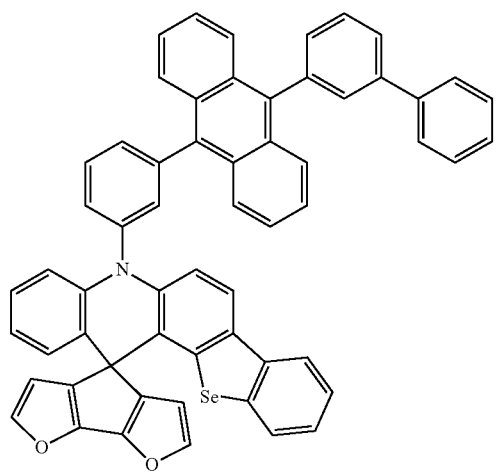
C171
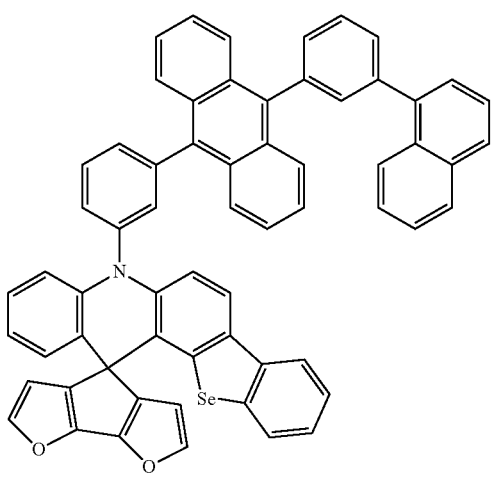
C172
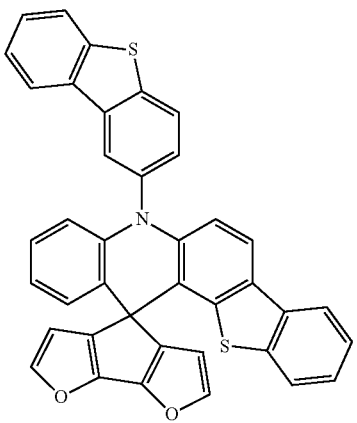

201
-continued
C173
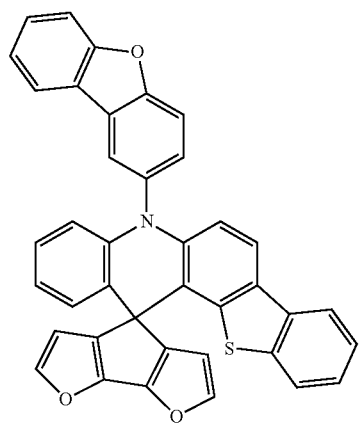
C174
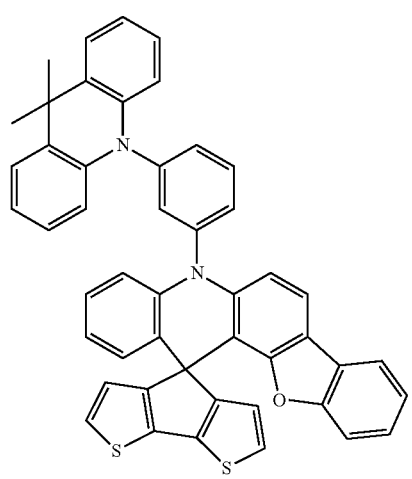
C175
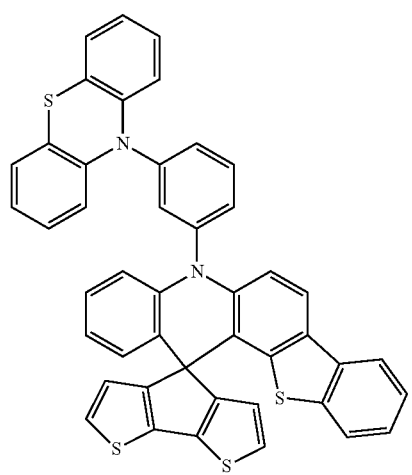
202
-continued
C176
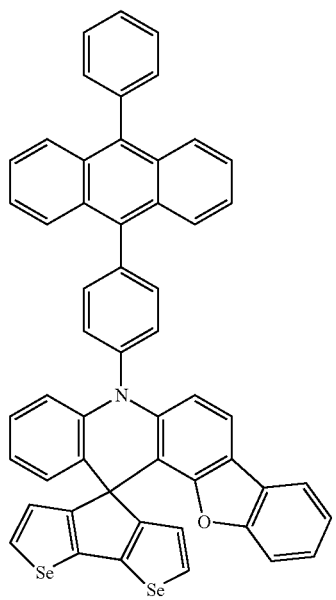
C177
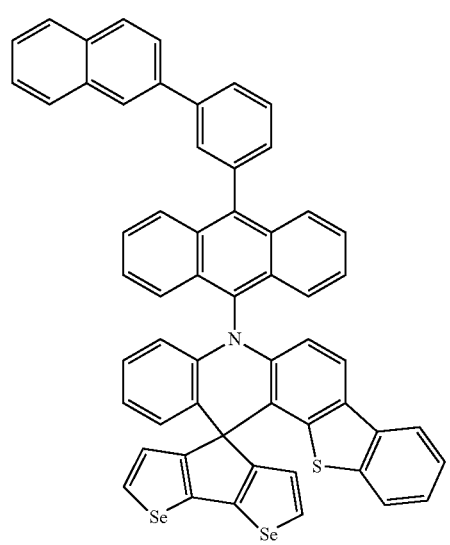
C178
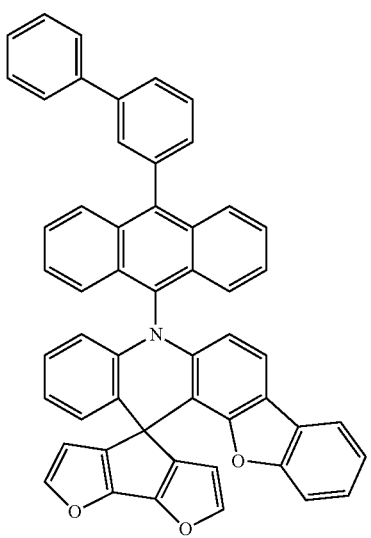

-continued
C179
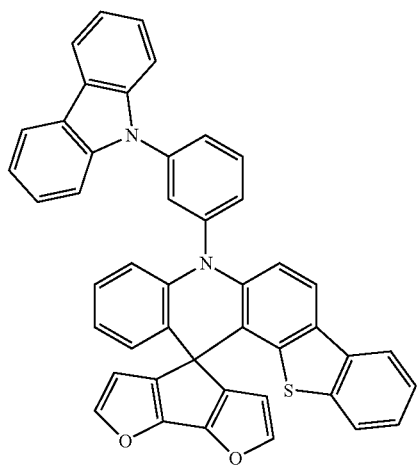
C180
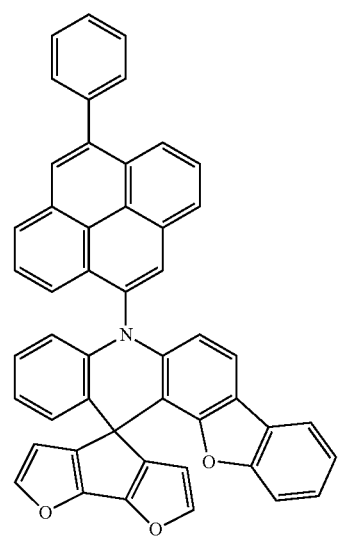
C181
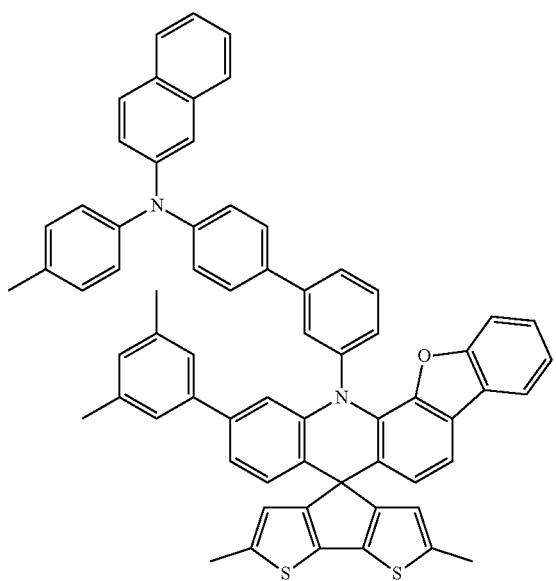
-continued
C182
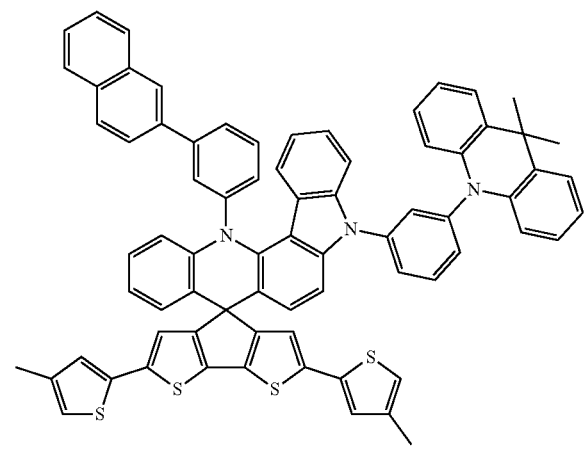
C183
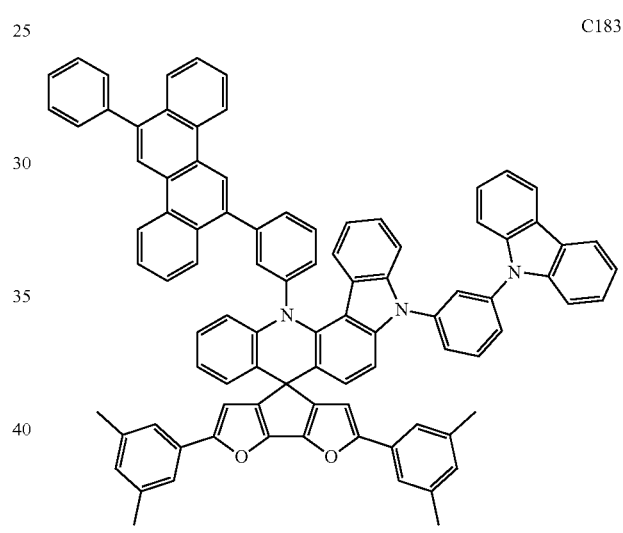
C184
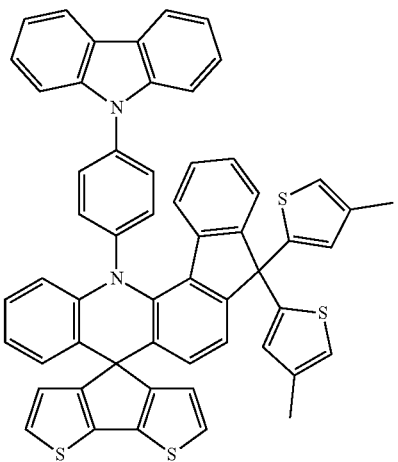

C185
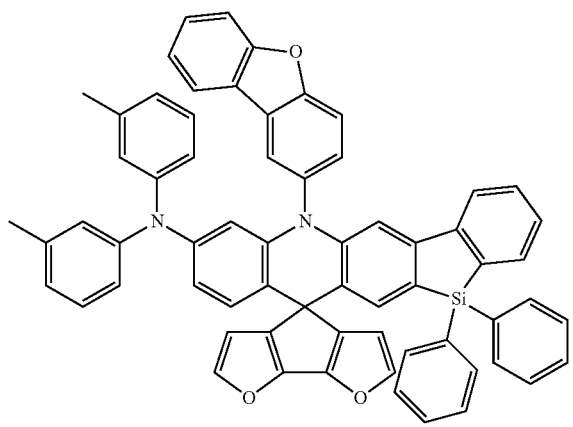
C186
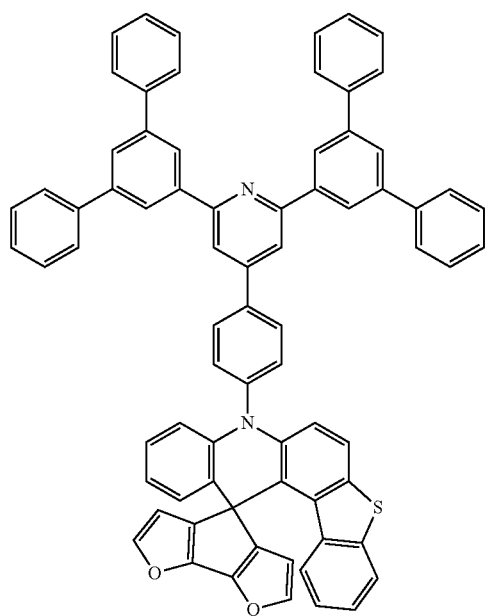
C187
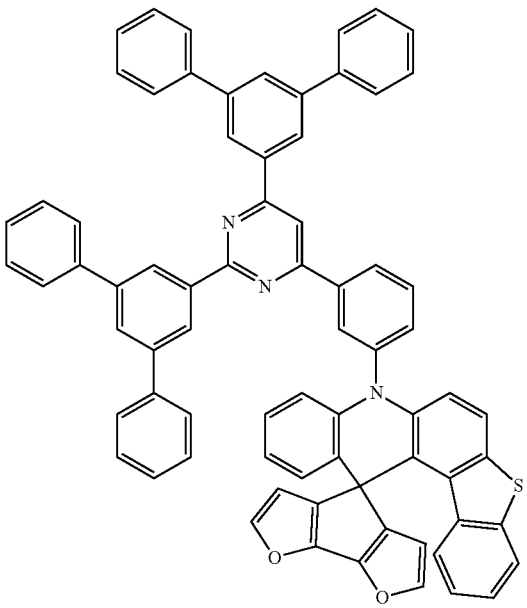
C188
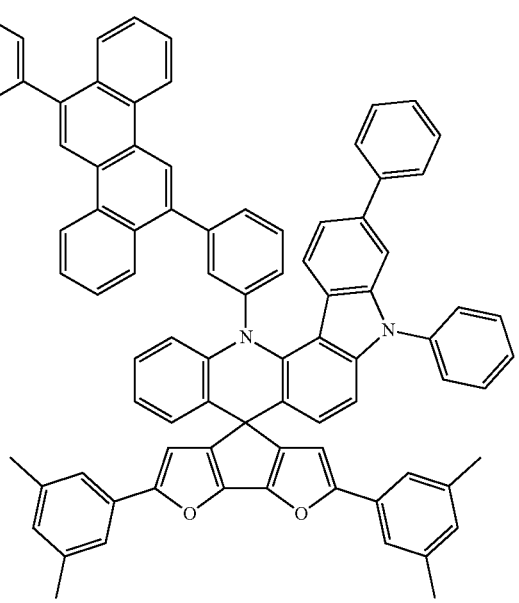

C189
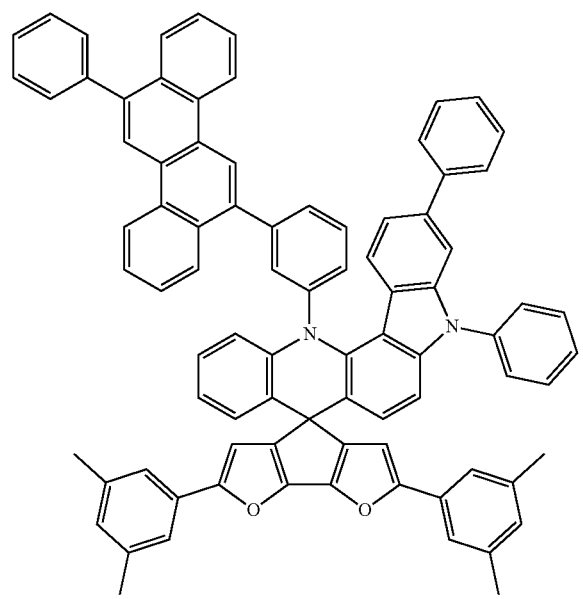
C190
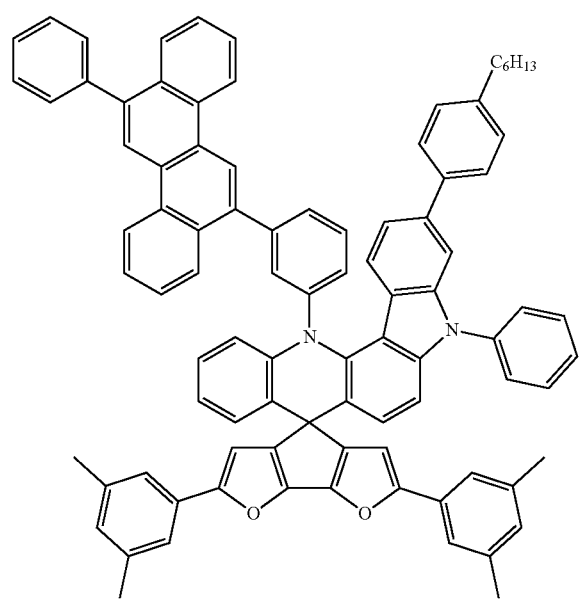
C191
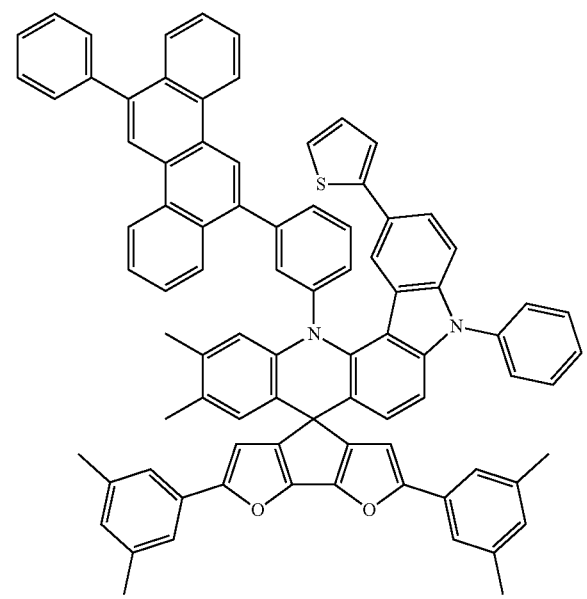
C192
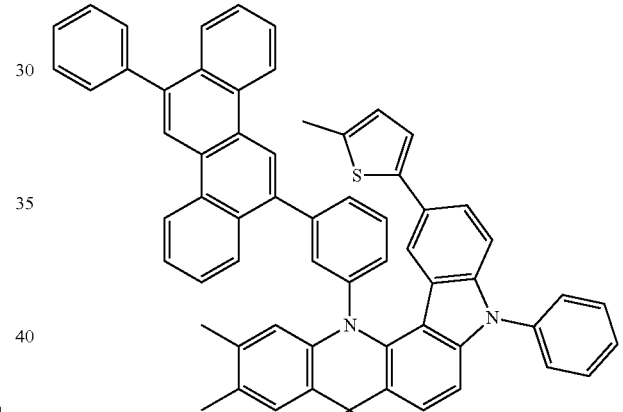
C193
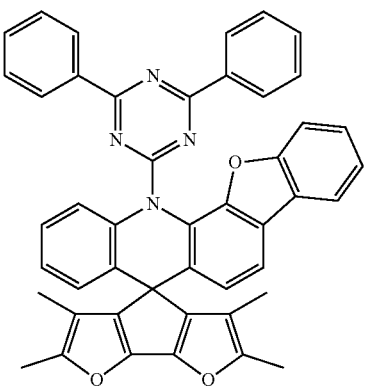

C194
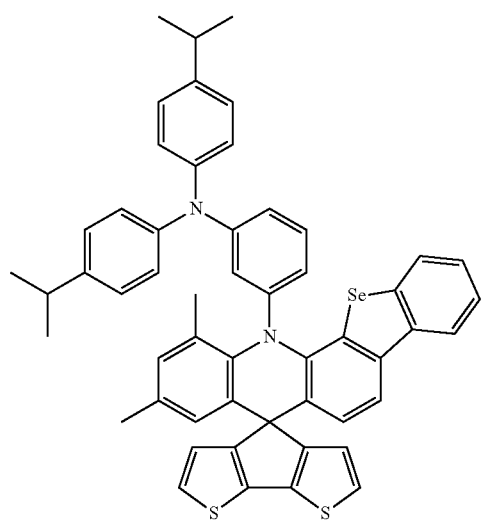
C195
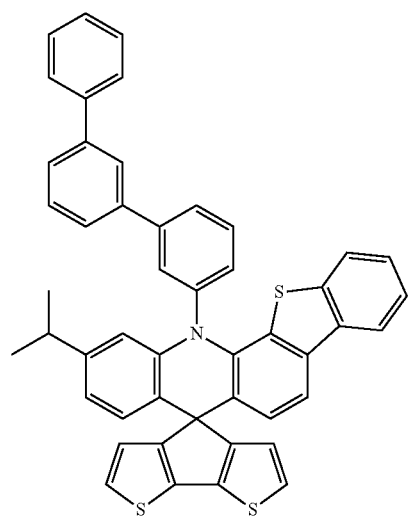
C196
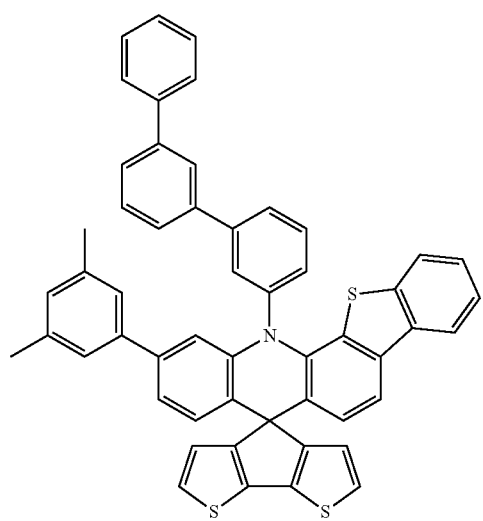
C197
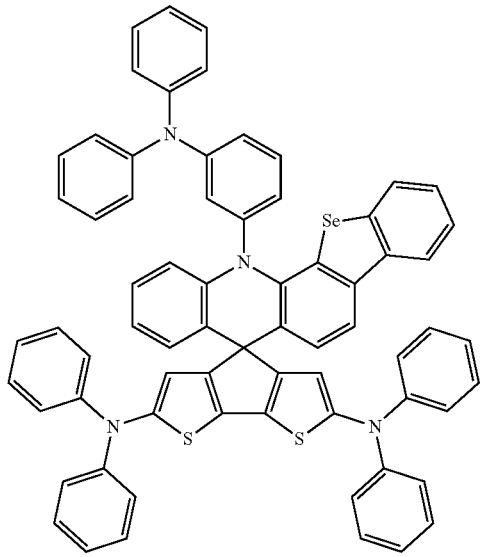
C198
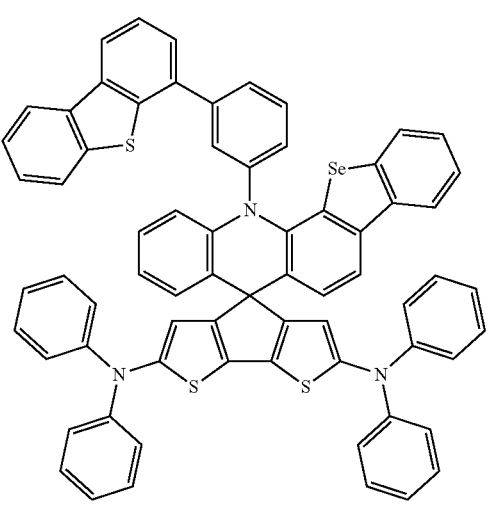
C199
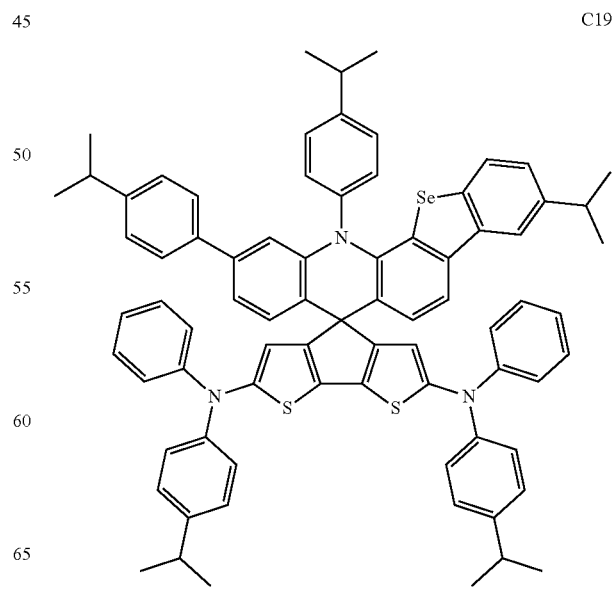

-continued

C200

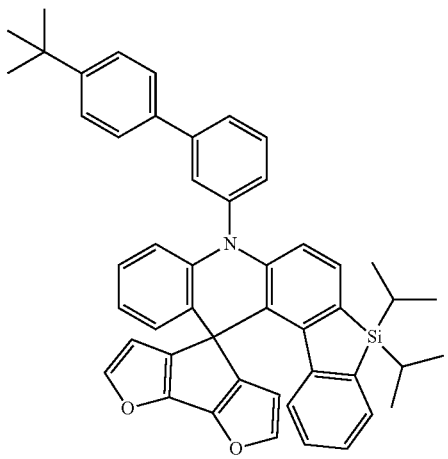

6. An organic electroluminescence device, comprising a pair of electrodes composed of a cathode and an anode, and a light emitting layer and one or more organic thin film layers between the pair of electrodes, wherein at least one of the light emitting layer and the organic thin film layer comprises the polyheteroaromatic compound according to claim 1.

7. The organic electroluminescence device according to claim 6, wherein the light emitting layer comprising the polyheteroaromatic compound of formula (1) is a host material.

8. The organic electroluminescence device according to claim 6, wherein the light emitting layer comprising the polyheteroaromatic compound of formula (1) is a fluorescent dopant material.

9. The organic electroluminescence device according to claim 6, wherein the light emitting layer comprising the polyheteroaromatic compound of formula (1) is a thermally activated delayed fluorescence host material.

10. The organic electroluminescence device according to claim 6, wherein the light emitting layer comprising the polyheteroaromatic compound of formula (1) is a thermally activated delayed fluorescence dopant material.

11. The organic electroluminescence device according to claim 6, wherein the organic thin film layer comprising the polyheteroaromatic compound of formula (1) is an electron transporting layer.

12. The organic electroluminescence device according to claim 6, wherein the organic electroluminescence device is a lighting panel.

13. The organic electroluminescence device according to claim 6, wherein the organic electroluminescence device is a backlight panel.

* * * * *